(12) United States Patent
Saito et al.

(10) Patent No.: US 11,446,386 B2
(45) Date of Patent: Sep. 20, 2022

(54) ANTI-CDH6 ANTIBODY AND METHOD OF PRODUCING AN ANTI-CDH6 ANTIBODY-DRUG CONJUGATE

(71) Applicant: DAIICHI SANKYO COMPANY, LIMITED, Tokyo (JP)

(72) Inventors: Atsuko Saito, Tokyo (JP); Tsuyoshi Hirata, Tokyo (JP); Kensuke Nakamura, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 233 days.

(21) Appl. No.: 16/613,203

(22) PCT Filed: May 14, 2018

(86) PCT No.: PCT/JP2018/018572
§ 371 (c)(1),
(2) Date: Nov. 13, 2019

(87) PCT Pub. No.: WO2018/212136
PCT Pub. Date: Nov. 22, 2018

(65) Prior Publication Data
US 2020/0171163 A1 Jun. 4, 2020

(30) Foreign Application Priority Data
May 15, 2017 (JP) .............................. JP2017-096749

(51) Int. Cl.
| A61K 47/68 | (2017.01) |
| C07K 16/28 | (2006.01) |
| A61P 35/00 | (2006.01) |
| A61K 31/4745 | (2006.01) |

(52) U.S. Cl.
CPC ...... *A61K 47/6803* (2017.08); *A61K 31/4745* (2013.01); *A61K 47/6849* (2017.08); *A61P 35/00* (2018.01); *C07K 16/28* (2013.01); *C07K 2317/24* (2013.01); *C07K 2317/40* (2013.01); *C07K 2317/41* (2013.01); *C07K 2317/565* (2013.01); *C07K 2317/732* (2013.01); *C07K 2317/76* (2013.01); *C07K 2317/77* (2013.01)

(58) Field of Classification Search
CPC ............ A61K 47/6803; A61K 47/6849; A61K 31/4745; A61P 35/00; C07K 16/28; C07K 2317/24; C07K 2317/40; C07K 2317/41; C07K 2317/565; C07K 2317/732; C07K 2317/76; C07K 2317/77
See application file for complete search history.

(56) References Cited

U.S. PATENT DOCUMENTS

| 5,480,968 | A | 1/1996 | Kraus et al. |
| 5,677,171 | A | 10/1997 | Hudziak et al. |
| 5,821,337 | A | 10/1998 | Carter et al. |
| 5,834,476 | A | 11/1998 | Terasawa et al. |
| 5,837,673 | A | 11/1998 | Tsujihara et al. |
| 5,892,043 | A | 4/1999 | Tsujihara et al. |
| 5,968,511 | A | 10/1999 | Akita et al. |
| 6,214,345 | B1 | 4/2001 | Firestone et al. |
| 6,291,671 | B1 | 9/2001 | Inoue et al. |
| 6,835,807 | B1 | 12/2004 | Susaki et al. |
| 7,449,184 | B2 | 11/2008 | Allison et al. |
| 7,585,491 | B2 | 9/2009 | Govindan |
| 7,833,979 | B2 | 11/2010 | Sullivan et al. |
| 7,837,980 | B2 | 11/2010 | Alley et al. |
| 7,999,083 | B2 | 8/2011 | Govindan et al. |
| 8,226,945 | B2 | 7/2012 | Ebens et al. |
| 8,268,319 | B2 | 9/2012 | Govindan |
| 8,394,607 | B2 | 3/2013 | Ebens et al. |
| 8,425,912 | B2 | 4/2013 | Govindan |
| 8,524,865 | B2 | 9/2013 | Ebens et al. |
| 8,741,291 | B2 | 6/2014 | Bhat et al. |
| 8,802,820 | B2 | 8/2014 | Chamberlain et al. |
| 8,907,071 | B2 | 12/2014 | Sullivan et al. |
| 8,968,741 | B2 | 3/2015 | Ebens et al. |
| 9,808,537 | B2 | 11/2017 | Masuda et al. |
| 9,850,312 | B2 | 12/2017 | Agatsuma et al. |
| 9,872,924 | B2 | 1/2018 | Naito et al. |

(Continued)

FOREIGN PATENT DOCUMENTS

| CA | 2927832 A1 | 11/2011 |
| CA | 2815154 A1 | 2/2012 |

(Continued)

OTHER PUBLICATIONS

Dunne E, et al. Arterioscler (Jul. 2012) Thromb Vase Biol. 32(7):1724-1731. (doi: 10.1161/ATVBAHA.112.250464).*
Shimazui T, et al. (2000) Eur Urol. 38:331-338.*
Cho EA, et al. (Mar. 1998) Development.125(5):803-12.*
Carl U. Bialucha et al: "Discovery and Optimization of HKT288, a Cadherin-6-Targeting ADC for the Treatment of Ovarian and Renal Cancers", Cancer Discovery, vol. 7, No. 9, Sep. 1, 2017 (Sep. 1, 2017), pp. 1030-1045, XP055484340.
Corada M et al: "Monoclonal antibodies directed to different regions of vascular endothelial cadherin extracellular domain affect adhesion and clustering of the protein and modulate endothelial permeability", Blood, the American Society of Hematology, US, vol. 97, No. 6, Mar. 15, 2001 (Mar. 15, 2001), pp. 1679-1684, XP002187985.

(Continued)

*Primary Examiner* — Robert S Landsman
(74) *Attorney, Agent, or Firm* — Foley & Lardner LLP

(57) ABSTRACT

It is an object of the present invention to provide an antibody binding to CDH6 and having internalization activity, an antibody-drug conjugate of the antibody and a drug having antitumor activity, a pharmaceutical product comprising the antibody-drug conjugate and having therapeutic effects on a tumor, a method for treating a tumor using the antibody, the antibody-drug conjugate or the pharmaceutical product, and the like. The present invention provides an anti-CDH6 antibody having internalization activity, an antibody-drug conjugate of the antibody and a drug having antitumor activity, a pharmaceutical product comprising the antibody or the antibody-drug conjugate, and a method for treating a tumor.

18 Claims, 29 Drawing Sheets

Specification includes a Sequence Listing.

(56) References Cited

U.S. PATENT DOCUMENTS

| | | | |
|---|---|---|---|
| 9,982,045 B2* | 5/2018 | Bialucha | A61K 31/537 |
| 10,195,288 B2 | 2/2019 | Masuda et al. | |
| 10,227,417 B2 | 3/2019 | Agatsuma et al. | |
| 10,383,878 B2 | 8/2019 | Hettmann et al. | |
| 2003/0148931 A1 | 8/2003 | Takahashi et al. | |
| 2003/0166513 A1 | 9/2003 | Imura et al. | |
| 2004/0185053 A1 | 9/2004 | Govindan | |
| 2005/0123536 A1 | 6/2005 | Law et al. | |
| 2005/0228007 A1 | 10/2005 | Jagtap et al. | |
| 2005/0271671 A1 | 12/2005 | Griffiths | |
| 2005/0276812 A1 | 12/2005 | Ebens, Jr. et al. | |
| 2006/0018899 A1 | 1/2006 | Kao et al. | |
| 2006/0193865 A1 | 8/2006 | Govindan | |
| 2007/0071764 A1 | 3/2007 | Sullivan et al. | |
| 2008/0050310 A1 | 2/2008 | Ebens et al. | |
| 2008/0131363 A1 | 6/2008 | Govindan et al. | |
| 2008/0161245 A1 | 7/2008 | Kratz et al. | |
| 2008/0305044 A1 | 12/2008 | McDonagh et al. | |
| 2009/0274713 A1 | 11/2009 | Chari et al. | |
| 2009/0286258 A1 | 11/2009 | Kaur et al. | |
| 2009/0291093 A1 | 11/2009 | Govindan | |
| 2010/0068181 A1 | 3/2010 | Paliwal et al. | |
| 2010/0120816 A1 | 5/2010 | Fontana et al. | |
| 2011/0045587 A1 | 2/2011 | Sullivan et al. | |
| 2011/0059076 A1 | 3/2011 | McDonagh et al. | |
| 2011/0070248 A1 | 3/2011 | Ichikawa et al. | |
| 2011/0229406 A1 | 9/2011 | Hettmann et al. | |
| 2011/0293513 A1 | 12/2011 | Govindan et al. | |
| 2012/0121615 A1 | 5/2012 | Flygare et al. | |
| 2012/0171201 A1 | 7/2012 | Sapra | |
| 2012/0201809 A1 | 8/2012 | Bhat et al. | |
| 2012/0328634 A1 | 12/2012 | Govindan | |
| 2013/0089872 A1 | 4/2013 | Nakamura et al. | |
| 2013/0123178 A1 | 5/2013 | Dimarchi et al. | |
| 2013/0216561 A1 | 8/2013 | Govindan | |
| 2014/0004078 A1 | 1/2014 | Govindan | |
| 2015/0297748 A1 | 10/2015 | Masuda et al. | |
| 2015/0352224 A1 | 12/2015 | Naito et al. | |
| 2016/0046711 A1 | 2/2016 | Bialucha et al. | |
| 2016/0279259 A1 | 9/2016 | Masuda et al. | |
| 2016/0287722 A1 | 10/2016 | Govindan | |
| 2016/0297890 A1 | 10/2016 | Agatsuma et al. | |
| 2017/0021031 A1 | 1/2017 | Hettmann et al. | |
| 2019/0151328 A1 | 5/2019 | Hettmann et al. | |

FOREIGN PATENT DOCUMENTS

| | | |
|---|---|---|
| CA | 2859255 A1 | 6/2013 |
| CN | 1227499 A | 9/1999 |
| CN | 1764478 A | 4/2006 |
| CN | 101023100 A | 8/2007 |
| CN | 101490087 A | 7/2009 |
| CN | 102481364 A | 5/2012 |
| CO | 2017001191 A2 | 4/2017 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 2 594 589 A1 | 5/2013 |
| EP | 2 799 452 A1 | 11/2014 |
| EP | 2 907 824 A1 | 8/2015 |
| EP | 2 910 573 A1 | 8/2015 |
| JP | H05-059061 A | 3/1993 |
| JP | H08-337584 A | 12/1996 |
| JP | H10-095802 A | 4/1998 |
| JP | H1171280 A | 3/1999 |
| JP | H11-092405 A | 4/1999 |
| JP | 2002-060351 A | 2/2002 |
| JP | 2005-511627 A | 4/2005 |
| JP | 2006-511526 A | 4/2006 |
| JP | 2007-527872 A | 10/2007 |
| JP | 2008-521828 A | 6/2008 |
| JP | 2009-538629 A | 11/2009 |
| JP | 2010-513524 A | 4/2010 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-534535 A | 9/2012 |
| JP | 2013-500253 A | 1/2013 |
| JP | 2013-534906 A | 9/2013 |
| JP | 2017-503784 A | 2/2017 |
| KR | 1020010052385 A | 6/2001 |
| KR | 1020110044808 A | 4/2011 |
| RU | 2404810 C2 | 7/2008 |
| RU | 2450008 C2 | 5/2012 |
| TW | 1232930 | 5/2005 |
| TW | 200817434 A | 4/2008 |
| TW | 201613643 A | 4/2016 |
| WO | WO-97/46260 A1 | 12/1997 |
| WO | WO-00/25825 A1 | 5/2000 |
| WO | WO-01/00244 A2 | 1/2001 |
| WO | WO-02/00734 A1 | 1/2002 |
| WO | WO-03/013602 A1 | 2/2003 |
| WO | WO-03/015826 A1 | 2/2003 |
| WO | WO-03/043583 A2 | 5/2003 |
| WO | WO-2005/112919 A2 | 12/2005 |
| WO | WO-2006/065533 A2 | 6/2006 |
| WO | WO-2006/092230 A2 | 9/2006 |
| WO | WO-2007/077028 A2 | 7/2007 |
| WO | WO-2008/100624 A2 | 8/2008 |
| WO | WO-2008/116219 A2 | 9/2008 |
| WO | WO-2008/144891 A1 | 12/2008 |
| WO | WO-2011/011474 A1 | 1/2011 |
| WO | WO-2011/021397 A1 | 2/2011 |
| WO | WO-2011/068845 A1 | 6/2011 |
| WO | WO-2011/145744 A1 | 11/2011 |
| WO | WO-2011/155579 A1 | 12/2011 |
| WO | WO-2012/019024 A2 | 2/2012 |
| WO | WO-2012/064733 A2 | 5/2012 |
| WO | WO-2013/068946 A2 | 5/2013 |
| WO | WO-2013/077458 A1 | 5/2013 |
| WO | WO-2013/163229 A1 | 10/2013 |
| WO | WO-2013/188740 A1 | 12/2013 |
| WO | WO-2014/057687 A1 | 4/2014 |
| WO | WO-2014/061277 A1 | 4/2014 |
| WO | WO-2014/107024 A1 | 7/2014 |
| WO | WO-2015/098099 A1 | 7/2015 |
| WO | WO-2015/155998 A1 | 10/2015 |
| WO | 2016024195 * | 2/2016 |
| WO | WO-2016/024195 A1 | 2/2016 |
| WO | WO-2018/185618 A1 | 10/2018 |
| WO | WO-2018/212136 A1 | 11/2018 |

OTHER PUBLICATIONS

Extended European Search Report dated Jan. 19, 2021 for corresponding European Patent Application No. 18802536.5.
Office Action dated Oct. 7, 2020 for corresponding Japanese Patent Application No. 2019-518773.
International Searching Authority, "International Search Report," issued in connection with International Patent Application No. PCT/JP2018/018572, dated Aug. 7, 2018.
International Searching Authority, "Written Opinion," issued in connection with International Patent Application No. PCT/JP2018/018572, dated Aug. 7, 2018.
Shimoyama et al., "Isolation and Sequence Analysis of Human Cadherin-6 Complementary DNA for the Full Coding Sequence and Its Expression in Human Carcinoma Cells," Cancer Research, vol. 55, May 15, 1995, pp. 2206-2211.
Inoue et al., "Cadherin-6 Expression Transiently Delineates Specific Rhombomeres, Other Neural Tube Subdivisions, and Neural Crest Subpopulations in Mouse Embryos," Developmental Biology, vol. 183, 1997, pp. 183-194.
Osterhout et al., "Cadherin-6 Mediates Axon-Target Matching in a Non-Image-Forming Visual Circuit," Neuron Report, vol. 71, Aug. 25, 2011, pp. 632-639.
Cho et al., "Differential expression and function of cadherin-6 during renal epithelium development," Development, vol. 125, 1998, pp. 803-812.
Mah et al., "Kidney Development in Cadherin-6 Mutants: Delayed Mesenchyme-to-Epithelial Conversion and Loss of Nephrons," Developmental Biology, vol. 223, 2000, pp. 38-53.

(56) References Cited

OTHER PUBLICATIONS

Paul et al., "Cadherin-6, a Cell Adhesion Molecule Specifically Expressed in the Proximal Renal Tubule and Renal Cell Carcinoma," Cancer Research, vol. 57, Jul. 1, 1997, pp. 2741-2748.
Shimazui et al., "The Level of Cadherin-6 mRNA in Peripheral Blood is Associated with the Site of Metastasis and with the Subsequent Occurrence of Metastases in Renal Cell Carcinoma," Cancer, vol. 101, No. 5, Sep. 1, 2004, pp. 963-968.
Koebel et al., "Ovarian Carcinoma Subtypes Are Different Diseases: Implications for Biomarker Studies," PLoS Medicine, vol. 5, Issue 12, e232, Dec. 2008, pp. 1749-1760.
Gugnoni et al., "Cadherin-6 promotes EMT and cancer metastasis by restraining autophagy," Oncogene, vol. 36, 2017, pp. 667-677.
Polakis, Paul, "Antibody Drug Conjugates for Cancer Therapy," Pharmacological Reviews, vol. 68, Jan. 2016, pp. 3-19.
Peters et al., "Antibody-drug conjugates as novel anti-cancer chemotherapeutics," Bioscience Reports, vol. 35, Issue 4, Aug. 2015, pp. 1-20.
Goeppert et al., "Cadherin-6 is a putative tumor suppressor and target of epigenetically dysregulated miR-429 in cholangiocarcinoma," Epigenetics, vol. 11, No. 11, 2016, pp. 780-790.
Yokoi et al., "A Novel Target Gene, SKP2, within the 5p13 Amplicon That Is Frequently Detected in Small Cell Lung Cancers," The American Journal of Pathology, vol. 161, Issue 1, Jul. 2002, pp. 207-216.
Acchione et al, Impact of linker and conjugation chemistry on antigen binding, Fc receptor binding and thermal stability of model antibody-drug conjugates, mAbs, 2012, pp. 362-372—(12 pages).
Adams et al., "Humanization of a recombinant monoclonal antibody to produce a therapeutic HER dimerization inhibitor, pertuzumab," Cancer Immunol. Immunother. 55:717-727 (2006).
Alimandi et al., "Cooperative signaling of ErbB3 and ErbB2 in neoplastic transformation and human mammary carcinomas," Oncogene 10:1813-1821 (1995)—9 Pages.
Alley et al., "Antibody-drug conjugates: targeted drug delivery for cancer," Current Opinion in Chemical Biology 14:529-537 (2010)—9 Pages.
Allowance dated Jul. 4, 2017, in Japanese Patent Application No. 2016-117096.
Allowance issued in connection with Taiwanese Patent Application No. 104103127, dated Apr. 11, 2018.
Australian Intellectual Property Office, "Examination Report No. 2 for Standard Patent Application," Australian Patent Application No. 2014371934, dated Sep. 13, 2019.
Barginear et al., "Trastuzumab-DM1: A Review of the Novel Immuno-Conjugate for HER2-Overexpressing Breast Cancer," The Open Breast Cancer Journal 1:25-30 (2009).
Barok et al, Trastuzumab-DM1 is highly effective in preclinical models of HER2-positive gastric cancer, Cancer Letters, 2011, vol. 306, No. 2, pp. 172-179 (9 pages).
Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncol. 14(3):737-744 (Mar. 1996).
Basu et al., "The Epithelial/Carcinoma Antigen EGP-1 Recognized by Monoclonal Antibody RS7-3G11, is Phosphorylated on Serine 303," Int. J. Cancer 62(4):472-479 (1995).
Beck, Alain, "The Next Generation of Antibody-drug Conjugates Comes of Age," Discovery Medicine 10(53):329-339 (Oct. 16, 2010)—8 Pages.
Behrens et al., Methods for site-specific drug conjugation to antibodies, mAbs, 2014, vol. 6, No. 1, pp. 46-53.
Blok et al., "Cytoplasmic Overexpression of HER2: a Key Factor in Colorectal Cancer", Clinical Insights: Oncology, vol. 7, 2013 pp. 41-51.
Burke, Patrick J et al. Design, Synthesis, and Biological Evaluation of Antibody—Drug Conjugates Comprised of Potent Campothetchin Analogues, Bioconjugate Chemistry, Jun. 17, 2009. vol. 20 No. 6 pp. 1242-1250.

Calabrese et al., "Assignment of TACSTD1 (alias TROP1, M4S1) to human chromosome 2p21 and refinement of mapping of TACSTD2 (alias TROP2, M1S1) to human chromosome 1p32 by in situ hybridization," Cytogenet Cell Genet. 92(1-2):164-165 (2001).
Canadian Examiner's Interview Summary issued in Canadian Patent Application No. 2885800 dated Mar. 28, 2017.
Canadian Office Action dated Apr. 13, 2018 in corresponding application No. 2939802.
Chinese Office Action dated Nov. 1, 2016 in corresponding application No. 201380053256.2.
Chinese Office Action dated Nov. 8, 2019 for corresponding Application No. 201580019138.9—4 pages.
Chinese Office Action issued to corresponding App. No. 201480071134.0—dated Aug. 20, 2019 (5 pages).
Chinese Search Report dated Jun. 24, 2020 for corresponding Application No. 108114649.
Colombian Reconsideration Petition dated Mar. 15, 2018 in corresponding application No. NC2016/0000187—36 pages.
Coussens et al., "Tyrosine Kinase Receptor with Extensive Homology to EGF Receptor Shares Chromosomal Location with neu Oncogene," Science 230(4730):1132-1139 (Dec. 1985).
D. Loo et al: "Development of an Fc-Enhanced Anti-B7-H3 Monoclonal Antibody with Potent Antitumor Activity", Clinical Cancer Research, vol. 18, No. 14, Jul. 15, 2012 (Jul. 15, 2012), pp. 3834-3845, XP055092714, ISSN: 1078-0432, DOI: 10.1158/1078-0432.CCR-12-0715.
Damle, Nitin K., "Tumour-targeted chemotherapy with immunoconjugates of calicheamicin," Expert Opin. Biol. Ther. 4(9):1445-1452 (2004)—8 Pages.
De Jager et al., "DX-8951f: Summary of Phase I Clinical Trials," Ann. N.Y. Acad. Sci. 922:260-273 (2000)—16 Pages.
Defazio et al., "Expression of c-erbB Receptors, Heregulin and Oestrogen Receptor in Human Breast Cell Lines," Int. J. Cancer 87:487-498 (2000)—12 Pages.
Di Fiore et al., "erbB-2 Is a Potent Oncogene When Overexpressed in NIH/3T3 Cells," Science 237:178-182 (Jul. 1987).
Dosio et al., "Antibody-targeted leucinostatin A", Journal of Controlled Release, No. 32, (1994), pp. 37-44.
Ducry et al., "Antibody—Drug Conjugates: Linking Cytotoxic Payloads to Monoclonal Antibodies,"Bioconjugate Chem. 21:5-13 (2010)—9 Pages.
El Sewedy et al., "Cloning of the Murine Trop2 Gene: Conservation of a PIP2-Binding Sequence in the Cytoplasmic Domain of Trop-2," Int. J. Cancer 75(2):324-330 (1998).
International Search Report issued in International Patent Application No. PCT/JP2015/002020 dated Jul. 20, 2015.
Esteva et al., A Phase II Study of Intravenous Exatecan Mesylate (DX-8951f) Administered Daily for 5 Days Every 3 Weeks to Patients with Metastatic Breast Carcinoma, American Cancer Society, 2003, 900-907.
European Search Report issued in corresponding application No. 15743738.5 dated Aug. 9, 2017.
Extended European Search Report dated Feb. 4, 2020 for corresponding Application No. 19206764.3.
Extended European Search Report dated May 10, 2017 in European Patent Application No. 14874745.4.
Extended European Search Report dated May 13, 2016, in European patent Application No. 13847461.4.
Extended European Search Report dated May 6, 2016, in European Patent Application No. 13845596.9.
Extended European Search Report issued in European Patent Application No. 15776810.2 dated Aug. 11, 2017.
Faulk et al., "Antigens of human trophoblasts: A working hypothesis for their role in normal and abnormal pregnancies," Proc. Natl. Acad. Sci. USA 75(4):1947-1951 (1978).
Fendly et al., "Characterization of Murine Monoclonal Antibodies Reactive to Either the Human Epidermal Growth Factor Receptor or HER2/neu Gene Product," Cancer Research 50:1550-1558 (1990).
Final Office Action issued in U.S. Appl. No. 15/221,851 dated Nov. 13, 2017.
Fong et al., "High expression of TROP2 correlates with poor prognosis in pancreatic cancer," Br. J. Cancer 99(8):1290-1295 (2008).

(56) References Cited

OTHER PUBLICATIONS

Fong et al., "TROP2: a novel prognostic marker in squamous cell carcinoma of the oral cavity," Mod. Pathol. 21(2):186-191 (2008).
Fornaro et al., "Cloning of the Gene Encoding Trop-2, a Cell-Surface Glycoprotein Expressed by Human Carcinomas," Int. J. Cancer 62(5):610-618 (1995).
Fukushige et al., "Localization of a Novel v-erbB-Related Gene, c-erbB-2, on Human Chromosome 17 and Its Amplification in a Gastric Cancer Cell Line," Mol. Cell. Biol. 6(3):955-958 (1986).
Gomez-Monterrey et al., "Design, Synthesis, and Cytotoxic Evaluation of Acyl Derivatives of 3-Aminonaphtho[2,3-b]thiophene-4,9-dione, a Quinone-Based System," Journal of Medicinal Chemistry, 2011, 54(12):4077-4091, abstract.
Graus-Porta et al., "ERbB-2, the preferred heterodimerization partner of all ErbB receptors, is a mediator of lateral signaling," EMBO J. 16(7):1647-1655 (1997).
Gravalos et al., "HER2 in gastric cancer: a new prognostic factor and a novel therapeutic target," Ann. Oncol. 19:1523-1529 (2008).
Hardwick et al., "Immunohistochemical detection of p53 and c-erbB-2 in oesophageal carcinoma; no correlation with prognosis," Eur. J. Surg. Oncol. 23:30-35 (1997).
Hudis, M.D., Clifford A., "Trastuzumab—Mechanism of Action and Use in Clinical Practice," N. Engl. J. Med. 357(1):39-51 (2007).
Hudziak et al., "Increased expression of the putative growth factor receptor p185HER2 causes transformation and tumorigenesis of NIH 3T3 cells," Proc. Natl. Acad. Sci. USA 84:7159-7163 (1987).
I. Sullivan, et al. "Osimertinib in the treatment of patients with epidermal growth factor receptor T790Mmutation-positive metastatic non-small cell lung cancer: clinical trial evidence and experience", Therapeutic Advances in Respiratory Disease, vol. 10(6), pp. 549-565, 2016 (17 pages).
IN Office Action issued in the corresponding Indian Patent Application Ser. No. 201647013640, dated Jul. 19, 2019.
Inoue et al., "CM-Dextran-Polyalcohol-Camptothecin Conjugate: DE-310 with A Novel Carrier System and Its Preclinical Data," Polymer Drugs in the Clinical Stage, 145-153 (2003)—9 Pages.
International Search Report and Written Opinion for correspondence Application No. PCT/JP2018/007152 dated Apr. 24, 2018.
International Search Report for corresponding Application No. PCT/JP2014/006421 dated Mar. 17, 2015.
International Search Report for PCT/JP2013/006069, dated Dec. 17, 2013.
International Search Report for PCT/JP2013/006178, dated Dec. 17, 2013.
International Search Report issued in International Patent Application No. PCT/JP2015/000355 dated Apr. 21, 2015.
Japanese Notice Of Allowance dated Oct. 18, 2016 in corresponding application No. 2016-166850.
Japanese Office Action dated Dec. 6, 2016 in corresponding application No. 2016-540705.
Joto et al., "DX-8951F, A Water-Soluble Camptothecin Analog, Exhibits Potent Antitumor Activity Against a Human Lung Cancer Cell Line and its SN-38-Resistant Variant," Int. J. Cancer 72:680-686 (1997)—7 Pages.
K. Yonesaka, et al., "Anti-HER3 monoclonal antibody patritumab sensitizes refractory non-small cell lung cancer to the epidermal growth factor receptor inhibitor erlotinib",Oncogene vol. 35, pp. 878-886, 2016 (10 pages).
Kang et al, Engineering multivalent antibodies to target heregulin-induced HER3 signaling in breast cancer cells, mAbs, 2013, vol. 64, No. 1, pp. 15-29.
Kaptain et al., "Her-2/neu and Breast Cancer," Diagn. Mol. Pathol. 10(3):139-152 (2001).
Karunagaran et al., "ErbB-2 is a common auxiliary subunit of NDF and EGF receptors: implications for breast cancer," EMBO J. 15(2):254-264 (1996).
Kawakami et al—"The anti-HER3 antibody patritumab abrogates cetuximab resistance mediated by heregulin in colorectal cancer cells", Oncotarget, vol. 5, No. 23, Dec.-May 2014, 11847-11856— 10 pages.

Kimio Yonesaka, "Anti-HER3 Antibody Patritumab Overcomes Resistance to EGFR Inhibitor in Nonsmall Cell Lung Cancer", The Japan Lung Cancer Society, vol. 55, pp. 948-955, 2015 (8 pages).
Korean Office Action dated May 1, 2018 in corresponding application No. 10-2016-7015961.
Korkaya et al., "HER2 regulates the mammary stem/progenitor cell population driving tumorigenesis and invasion," Oncogene 27:6120-6130 (2008).
Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993)—5 Pages.
Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989)—5 pages.
Kumazawa et al., "Antitumor activity of DX-8951f: a new camptothecin derivative," Exp. Opin. Invest. Drugs 7(4):625-632 (1998)—8 Pages.
Kumazawa et al., "DE-310, a novel macromolecular carrier system for the camptothecin analog DX-8951f: Potent antitumor activities in various murine tumor models," Cancer Sci. 95(2):168-175 (Feb. 2004)—8 Pages.
Kumazawa et al., "Potent and broad antitumor effects of DX-8951f, a water-soluble camptothecin derivative, against various human tumors xenografted in nude mice," Cancer Chemother. Pharmacol. 42:210-220 (1998)—11 Pages.
Linnenbach et al., "Sequence investigation of the major gastrointestinal tumor-associated antigen gene family, GA733," Proc. Natl. Acad. Sci. 86(1):27-31 (Jan. 1989).
Lipinski et al., "Human trophoblast cell-surface antigens defined by monoclonal antibodies," Proc. Natl. Acad. Sci. 78(8):5147-5150 (Aug. 1981).
McDonagh et al., "Engineered antibody-drug conjugates with defined sites and stoichiometries of drug attachment," Protein Engineering, Design & Selection, 2006, 19(7):299-307.
Mitsui et al., "A New Water-soluble Camptothecin Derivative, DX-8951f, Exhibits Potent Antitumor Activity against Human Tumors in vitro and in vivo," Jpn. J. Cancer Res. 86:776-782 (Aug. 1995)—7 Pages.
Moghaddas et al., "Whether HER2-positive non-breast cancers are candidates for treatment with Ado-trastuzumab emtansine?", J. Res Parm Pract, vol. 5(4), 2016 pp. 227-233.
Mühlmann et al., "TROP2 expression as prognostic marker for gastric carcinoma," J. Clin. Pathol. 62(2):152-158 (2009).
N. Masabuchi, "Pharmacokinetics of DE-310, a novel macromolecular carrier system for the camptothecin analog DX-8951f, in tumor-bearing mice," Pharmazie 59: 374-377 (2004).
N.V. Sergina, et al. "Escape from HER-family tyrosine kinase inhibitor therapy by the kinase-inactive HER3", Nature, vol. 445, pp. 437-441, 2007 (6 pages).
Naidu et al., "Expression of c-erbB3 protein in primary breast carcinomas," British Journal of Cancer 78(10): 1385-1390 (1998)—6 Pages.
Nakada et al., "Novel antibody drug conjugates containing exatecan derivative-based cytotoxic payloads," Bioorganic & Medical Chemistry Letters 26(6):1542-1545 (2016)—4 Pages.
Ning et al., "TROP2 expression and its correlation with tumor proliferation and angiogenesis in human gliomas," Neurol. Sci. 34(10):1745-1750 (2013).
Non-Final Office Action issued in U.S. Appl. No. 14/435,114 dated Jul. 21, 2016.
Non-Final Office Action issued in U.S. Appl. No. 14/436,458 dated Jul. 19, 2016.
Non-Final Office Action issued in U.S. Appl. No. 15/180,203 dated Jul. 25, 2016.
Non-Final Office Action issued in U.S. Appl. No. 15/221,851 dated Jul. 7, 2017.
Non-Final Office Action issued in U.S. Appl. No. 15/821,662 dated Jan. 17, 2018.
Notice of Allowance issued in U.S. Appl. No. 15/221,851 dated Jun. 13, 2018.

(56) References Cited

OTHER PUBLICATIONS

Notice of Allowance issued in U.S. Appl. No. 15/821,662 dated Nov. 2, 2018.
Ochi et al, "A possible mechanism for the long-lasting antitumor effect of the macromolecular conjugate DE-310: mediation by cellular uptake and drug release of its active camptothecin analog DX-8951," Cancer Chemotherapy and Pharmacology 55(4): 323-332 (2004).
Office Action dated Nov. 21, 2017 in corresponding application No. PCT/JP2017/036215.
Office Action dated Apr. 22, 2016, in Singapore Patent Application No. 11201502887W.
Office Action issued in Colombian Application No. NC2016/0000187 dated May 9, 2017. An English translation is provided.
Office Action issued in U.S. Appl. No. 15/187,179 dated Oct. 21, 2016.
Office Action with Search Report dated Aug. 29, 2017, in RU 2015113767.
Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.
Ogitani et al., "DS-8201a, A Novel HER2-Targeting ADC with a Novel DNA Topoisomerase I inhibitor, Demonstrates a Promising Antitumor Efficacy with Differentiation from T-DM1," Clinical Cancer Research, vol. 22, No. 20, Oct. 15, 2016, pp. 5097-5108.
Ogitani et al., "Wide application of a novel topoisomerase I inhibitor-based drug conjugation technology," Bioorganic & Medicinal Chemistry Letters, vol. 26, 2016, 5069-5072.
Oguma et al, Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry, Biomedical Chromatography, 2005, vol. 19, No. 1, pp. 19-26—(8 pages).
Ohmachi et al., "Clinical Significance of TROP2 Expression in Colorectal Cancer," Clin. Cancer Res. 12(10):3057-3063 (May 15, 2006).
Opposition dated May 3, 2017, against corresponding Colombian Patent Application No. NC2016/0000187.
Otto Soepenberg, "chromatographic assays for DE-310, a novel camptothecin analog, and two major enzymatic products in human matrices," Journal of Chromatography B, 799, 15-22 (2004).
P. Janne, et al., "Phase 1 study of the Anti-HER3 Antibody Drug Conjugate U3-1402 in Metastic or Unresectable EGFR-mutant NSCLC.", Journal of Thoracic Oncology, vol. 12, No. 11, Supp. Supplement 2, pp. S2290, abstract No. P3.04-013, Nov. 2017 (3 pages).
Plowman et al., "Molecular cloning and expression of an additional epidermal growth factor receptor-related gene," Proc. Natl. Acad. Sci. USA 87:4905-4909 (Jul. 1990)—5 Pages.
Ripani et al., "Human Trop-2 is a Tumor-Associated Calcium Signal Transducer," Int. J. Cancer 76(5):671-676 (1998).
Rowinsky, Preclinical and Clinical Development of Exatecan(DX-8951f), Camptothecins in Cancer Therapy, 2005, pp. 317-318 (25 pages).
Russian Office Action dated Mar. 5, 2019 in corresponding application No. 2016143351.
Russian Office Action dated Oct. 11, 2018 in corresponding application No. 2016123597—13 pages.
Senter et al., "The discovery and development of brentuximab vedotin for use in relapsed Hodgkin lymphoma and systemic anaplastic large cell lymphoma," Nature Biotechnology 30(7):631-637 (Jul. 2012)—7 Pages.
Shen et al., Conjugation site modulates the in vivo stability and therapeutic activity of antibody-drug conjugates, Nature Biotechnology, 2012, vol. 30, pp. 184-189.
Shiose et al., "Systematic Research of Peptide Spacers Controlling Drug Release from Macromolecular Prodrug System, Carboxymethyldextran Polyalcohol-Peptide-Drug Conjugates," Bioconjugate Chem. 20(1):60-70(2009).
Shiose et al., "Relationship between Drug Release of DE-310, Macromolecular Prodrug of DX-8951f, and Cathepsins Activity in Several Tumors," Biol. Pharm. Bull., 2007, 30(12):2365-2370.
Sievers et al, Antibody-Drug Conjugates in Cancer Therapy, Annual Review of Medicine, 2013, vol. 64, No. 1, pp. 15-29.
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Sliwkowski et al., "Coexpression of erbB2 and erbB3 Proteins Reconstitutes a High Affinity Receptor for Heregulin." J. Biol. Chem. 269(20):14661-14665 (1994).
Sliwkowski et al., "Nonclinical Studies Addressing the Mechanism of Action of Trastuzumab (Herceptin)," Semin. Oncol. 26(4) Suppl. 12: 60-70 (Aug. 1999).
Soepenberg et al., "Phase I and Pharmacokinetic Study of DE-310 in Patients with Advanced Solid Tumors," Clin. Cancer Res. 11:703-711 (Jan. 15, 2005)—9 Pages.
Stepan et al., "Expression of Trop2 Cell Surface Glycoprotein in Normal and Tumor Tissues: Potential Implications as a Cancer Therapeutic Target," Journal of Histochemistry & Cytochemistry vol. 59, No. 7, pp. 701-710, (Jul. 2011).
Taiwanese Office Action dated Jul. 30, 2018 in corresponding application No. 104111534.
Taiwanese Office Action issued in Taiwanese Patent Application No. 102136742 dated May 15, 2017.
Takiguchi et al., "Antitumor Effect of DX-8951, a Novel Camptothecin Analog, on Human Pancreatic Tumor Cells and Their CPT-11-resistant Variants Cultured in vitro and Xeografted in Nude Mice," Jpn. J. Cancer Res. 88:760-769 (Aug. 1997)—10 Pages.
Thomas M. Cardillo, "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research 17(10): 3157-3169 (2011).
U.S. Notice of Allowance on U.S. Appl. No. 15/187,179 dated May 18, 2017.
U.S. Notice of Allowance on U.S. Appl. No. 15/187,179 dated Aug. 25, 2017.
Vogel et al., "Efficacy and Safety of Trastuzumab as a Single Agent in First-Line Treatment of HER2-Overexpressing Metastatic Breast Cancer," J. Clin. Oncol. 20(3):719-726 (Feb. 2002).
Wang et al., "Identification of Trop-2 as an oncogene and an attractive therapeutic target in colon cancers," Mol. Cancer Ther. 7(2):280-285 (Feb. 2008).
Wente et al., "DE-310, a macromolecular prodrug of the topoisomerase-1-inhibitor exatecan (DX-8951), in patients with operable solid tumors," Investigational New Drugs 23:339-347 (2005)—9 Pages.
Yano et al., "Comparison of HER2 gene amplification assessed by fluorescence in situ hybridization and HER2 protein expression assessed by immunohistochemistry in gastric cancer," Oncol. Rep. 15:65-71 (2006).
Colombian Patent Office, "Office Action," issued in connection with Colombian Patent Application No. NC2019/0013020, dated Nov. 29, 2021.
Colombian Patent Office, "Office Action," issued in connection with Colombian Patent Application No. NC2019/0013020, dated Aug. 9, 2021.
Japanese Patent Office, "Notice of Reason(s) for Refusal," issued in connection with Japanese Patent Application No. 2021-002874, dated Feb. 2, 2022.
Mexican Patent Office, "Office Action," issued in connection with Mexican Patent Application No. MX/a/2019/013597, dated Sep. 17, 2021.
Altshuler, E.P. et al., "Generation of Recombinant Antibodies and Means for Increasing Their Affinity," Advances in Chemistry, vol. 50, pp. 203-258.
Jarilin, A.A., Fundamentals of Immunology: Textbook—Publishing House "Meditisina," 1999, 608c., p. 171-173.
Office Action issued in corresponding Mexican Patent Application No. MX/a/2019/013597 dated Mar. 4, 2022.

(56) References Cited

OTHER PUBLICATIONS

Office Action issued in corresponding Russian Patent Application No. 2019141268 dated Feb. 22, 2022.
Singer, M. and Berg, P., Genes and Genomes: 2 volumes, vol. 1, translation from English M.: Mir, 1998.—373p., ill.; pp. 63-64.
UNIPROT: locus CADH9_MOUSE, access P70407, Nov. 25, 2002, Accessed via the Internet at: https://www.uniprot.org/uniprot/P70407.
Office Action and Search Report issued in corresponding Taiwanese Patent Application No. 107116035 dated May 10, 2022.

* cited by examiner

[Figure 1]
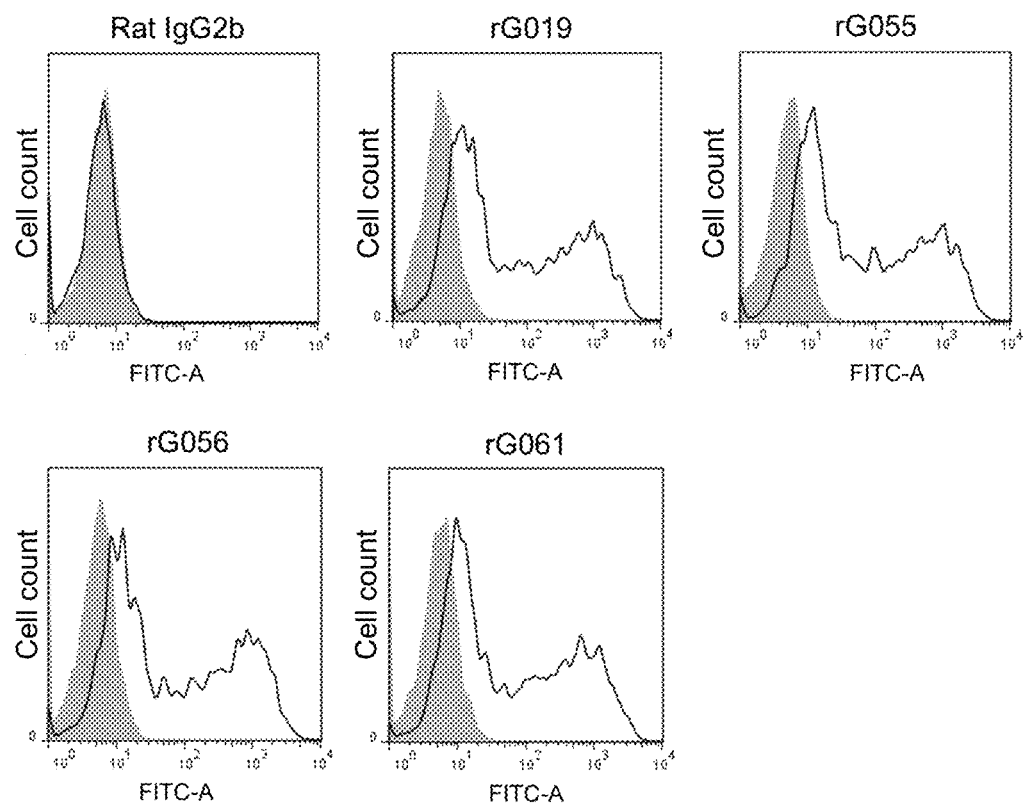

[Figure 2-1]
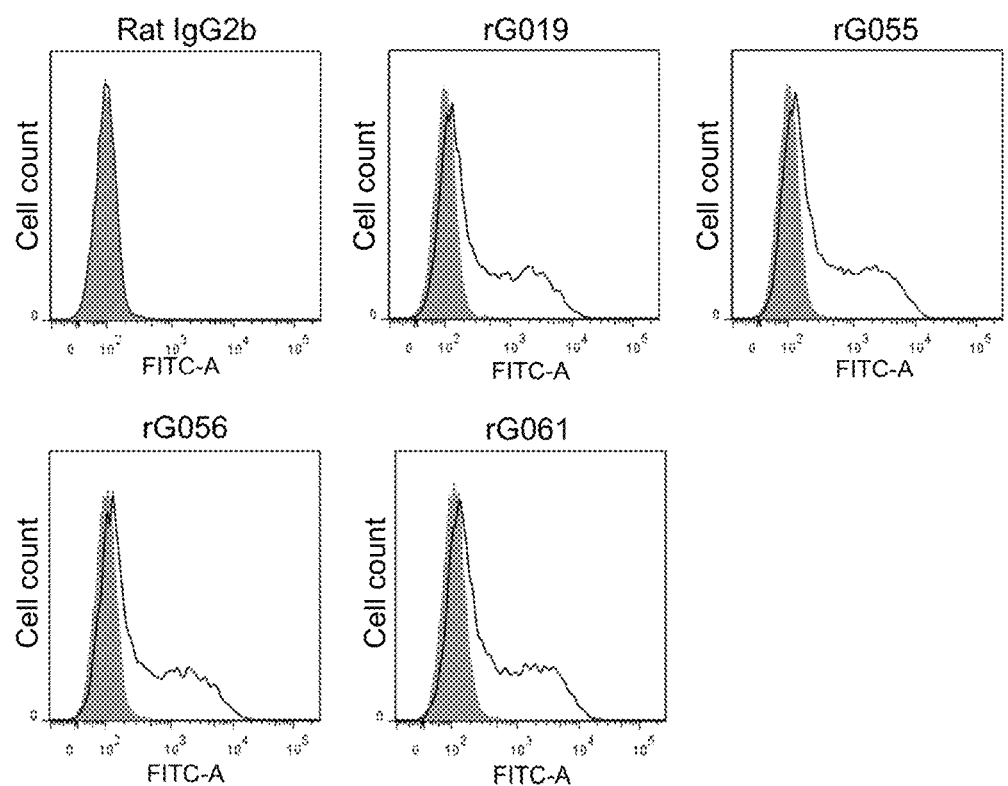

[Figure 2-2]
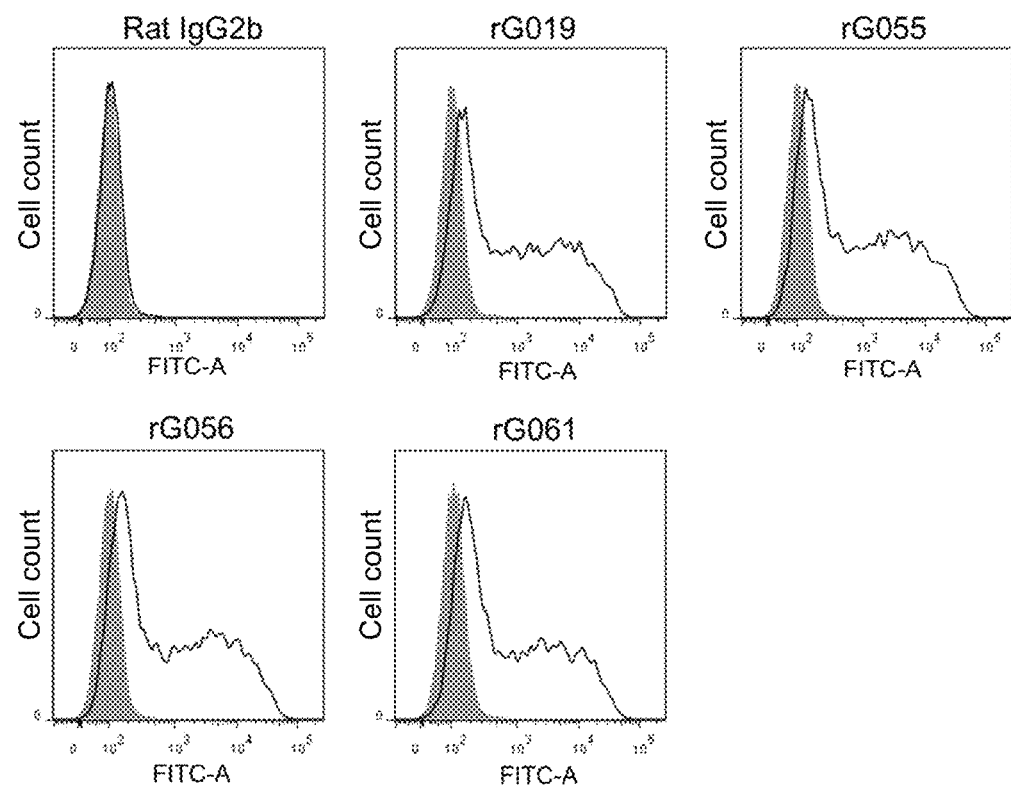

[Figure 2-3]
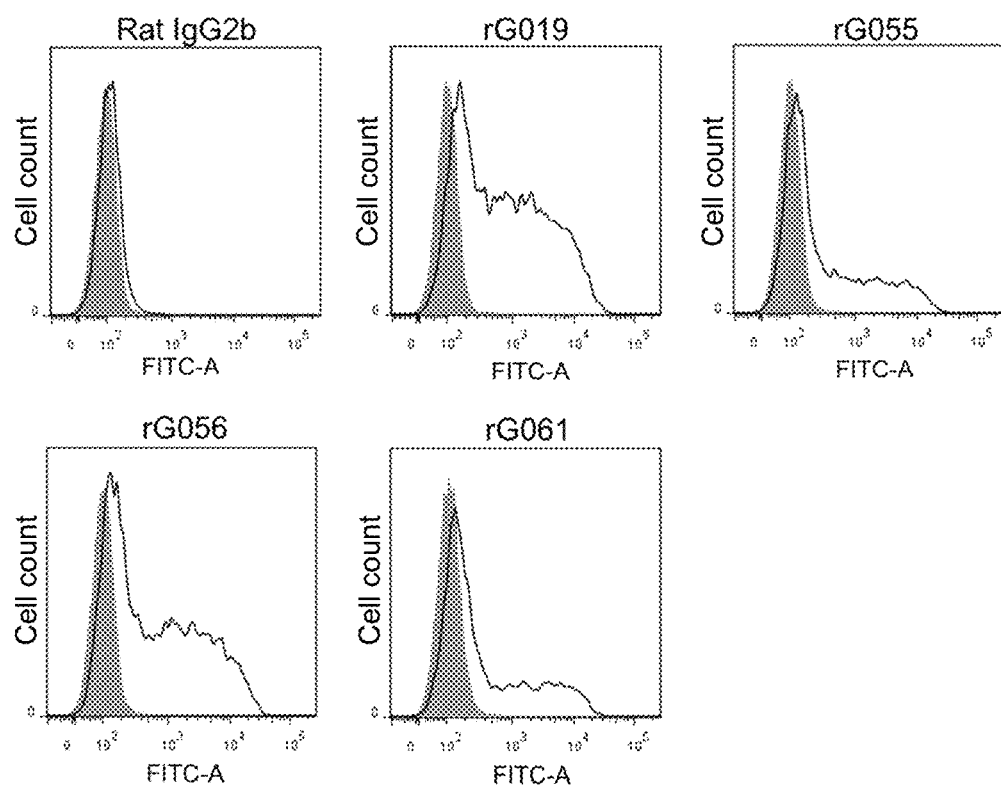

[Figure 2-4]
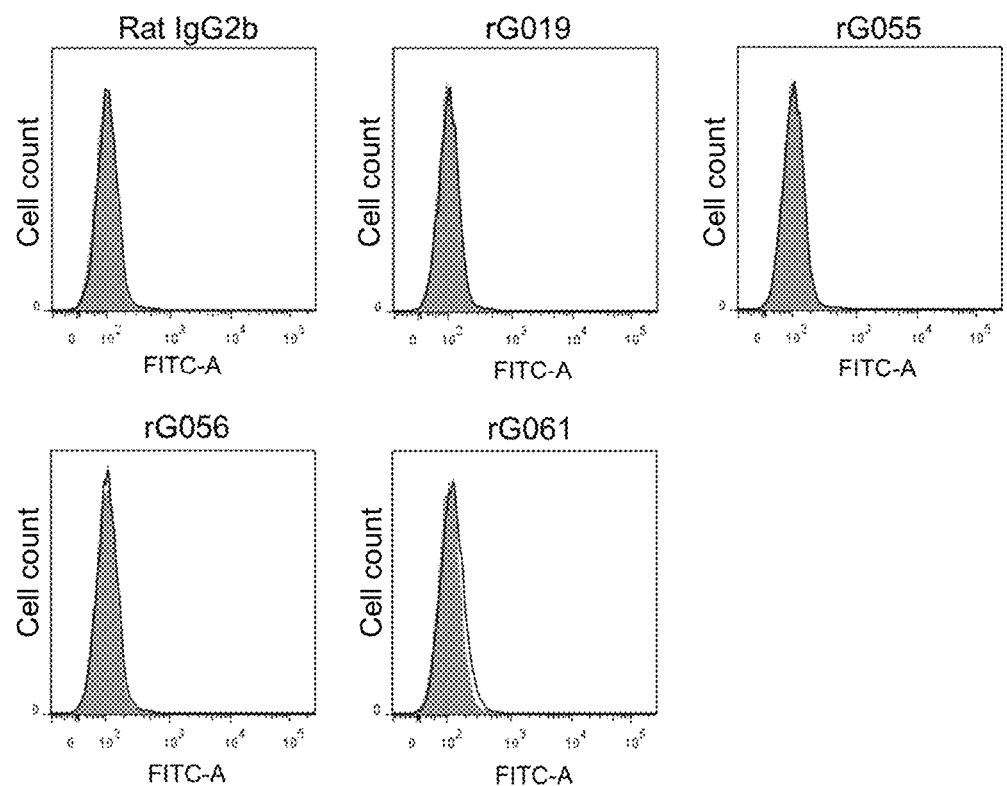

[Figure 2-5]
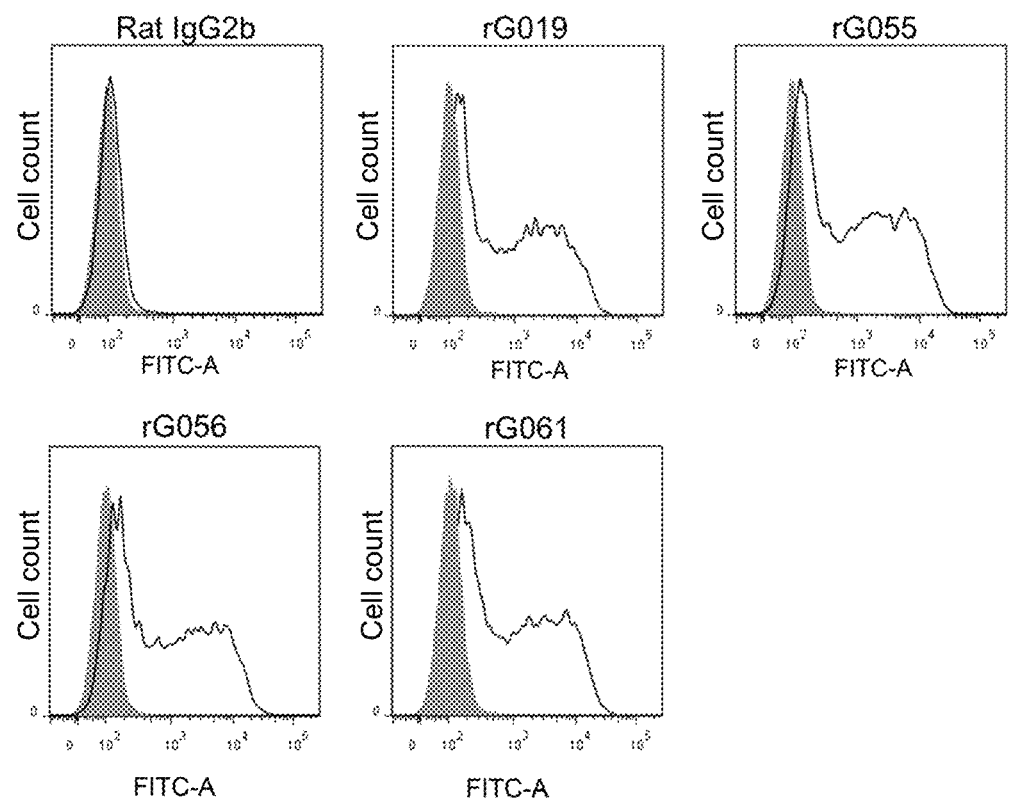

[Figure 2-6]
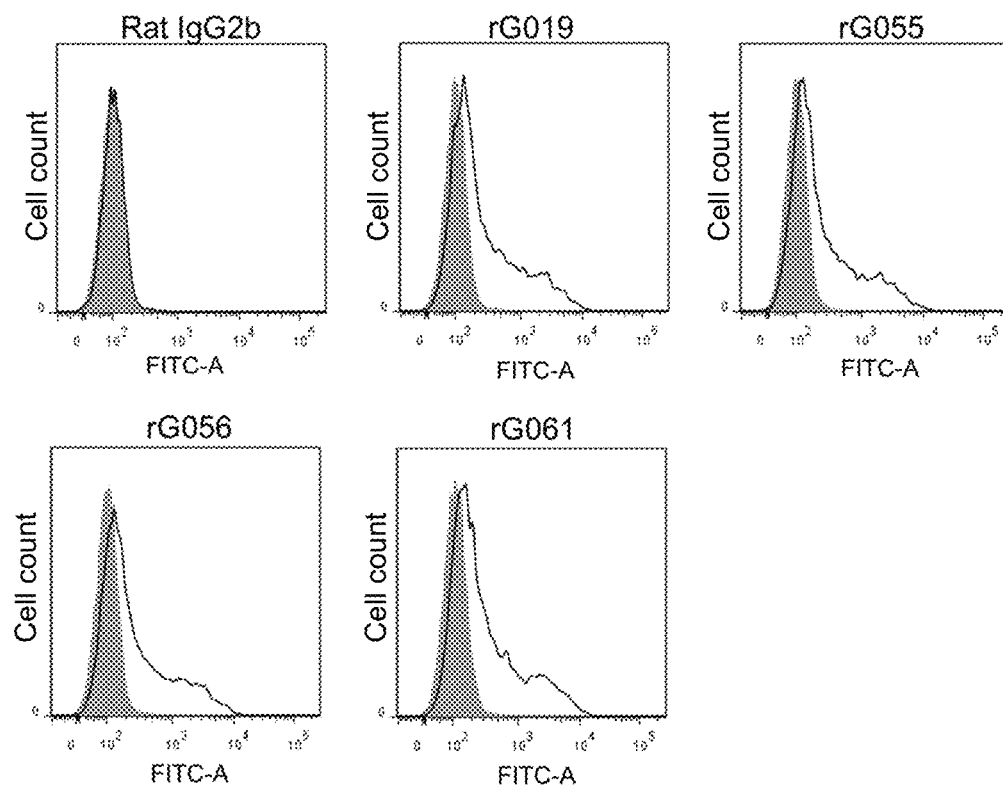

[Figure 3]
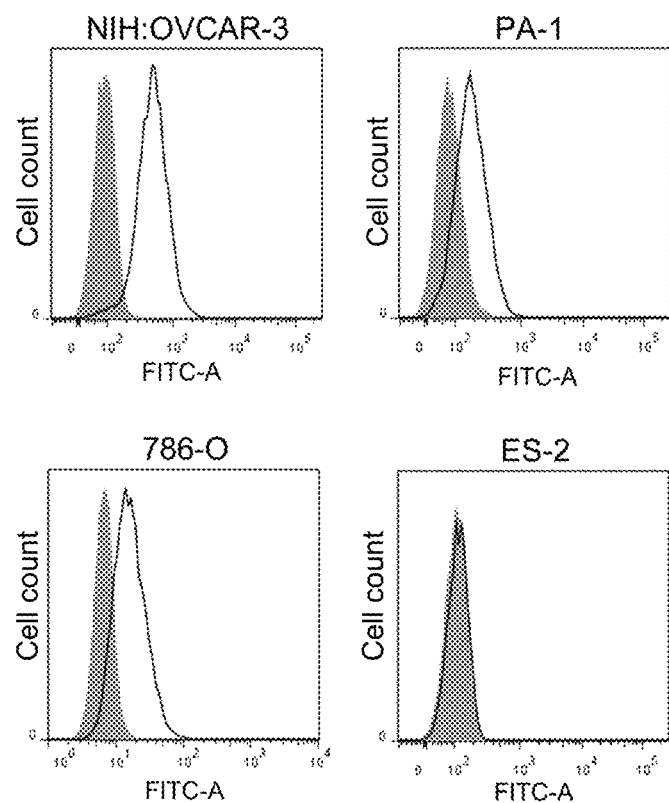

[Figure 4]
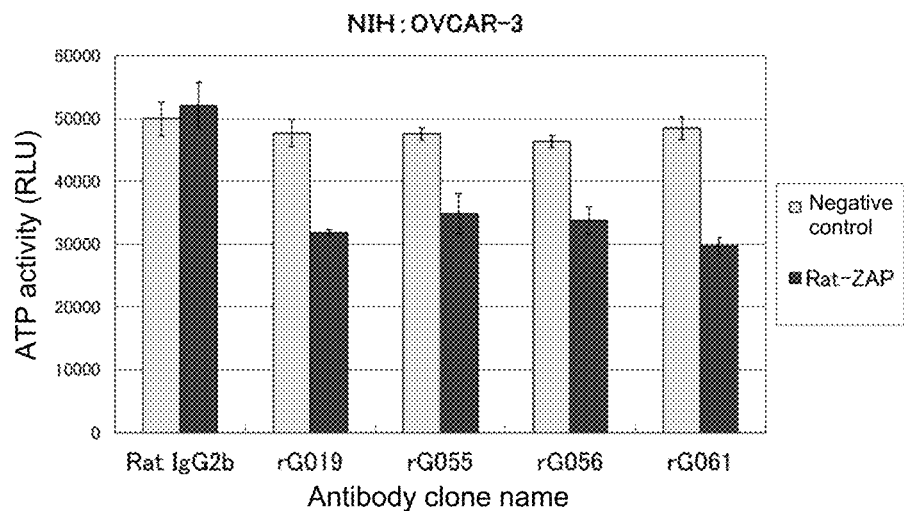
NIH:OVCAR-3 cell survival rate using Rat-ZAP (%)
| Rat IgG2b | rG019 | rG055 | rG056 | rG061 |
|---|---|---|---|---|
| 104.1 | 66.8 | 73.3 | 72.8 | 61.2 |
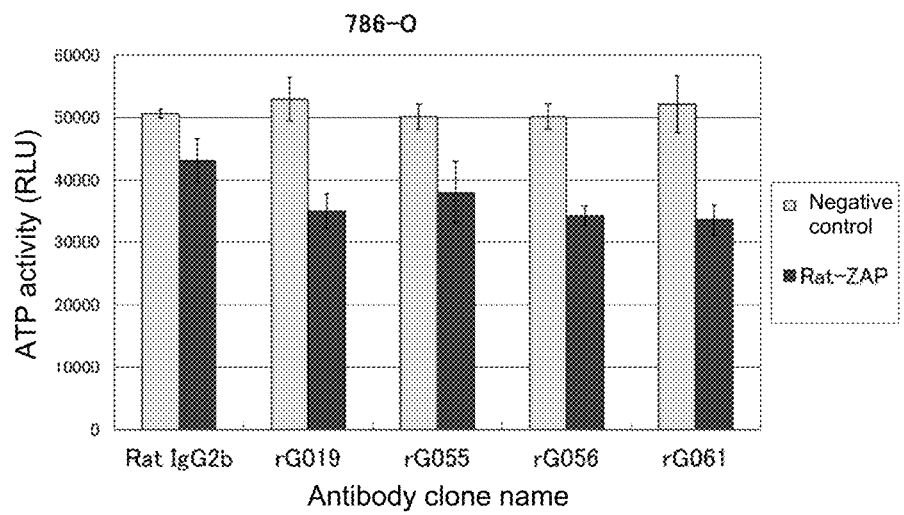
786-O cell survival rate using Rat-ZAP (%)
| Rat IgG2b | rG019 | rG055 | rG056 | rG061 |
|---|---|---|---|---|
| 85.2 | 66.1 | 75.7 | 68.1 | 64.2 |

[Figure 5]
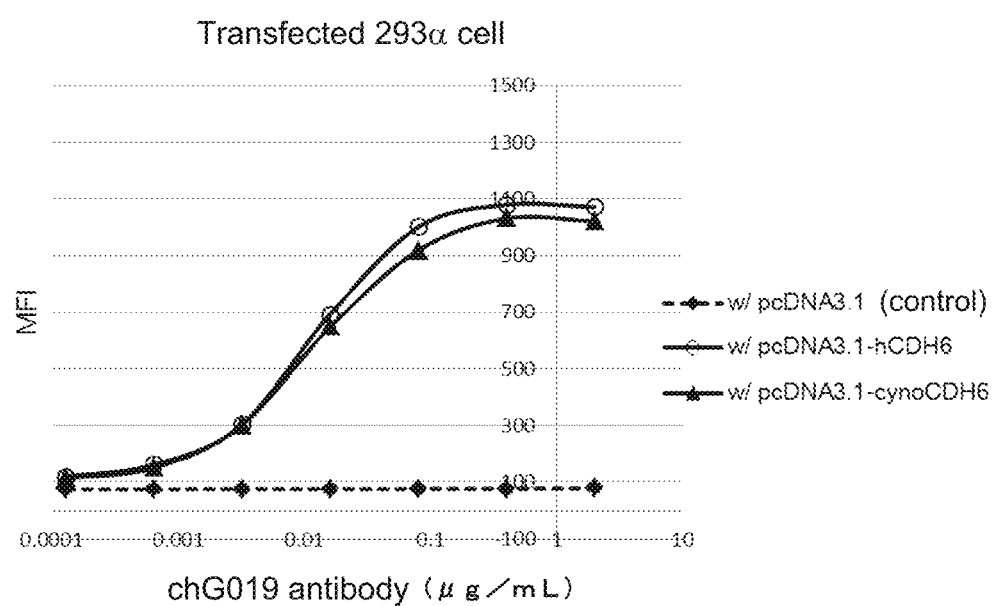

[Figure 6-1]
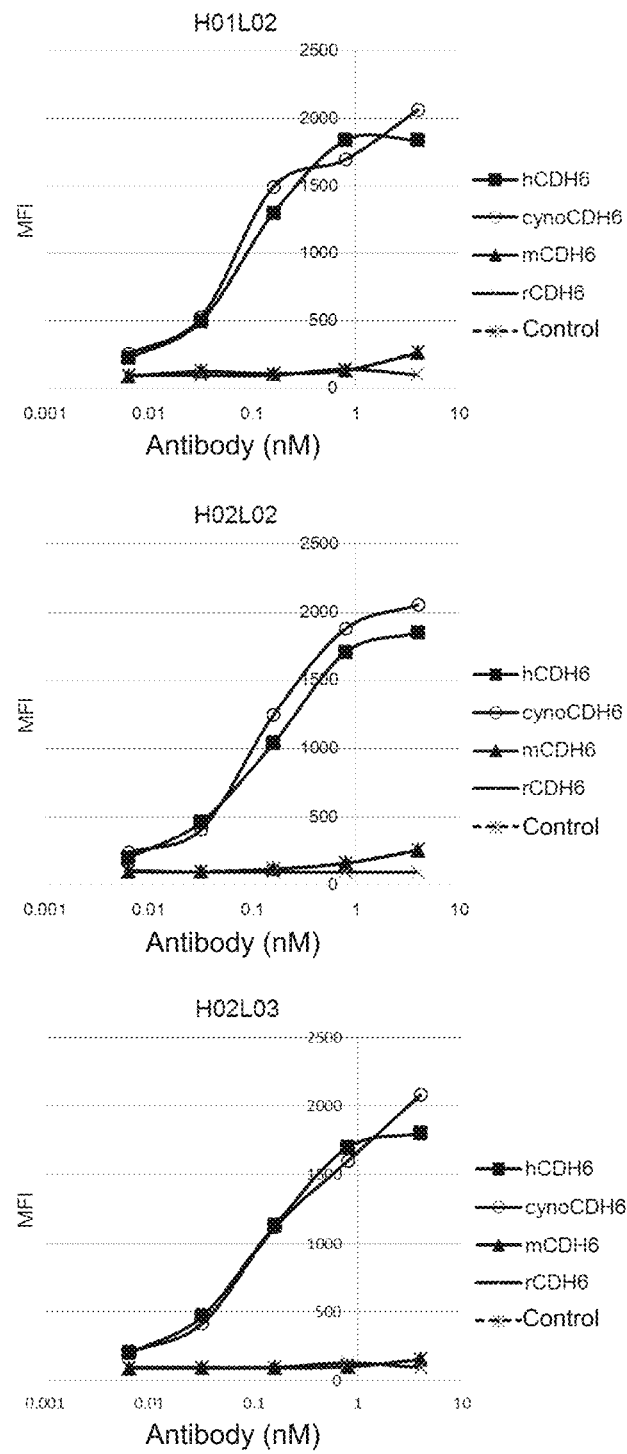

[Figure 6-2]
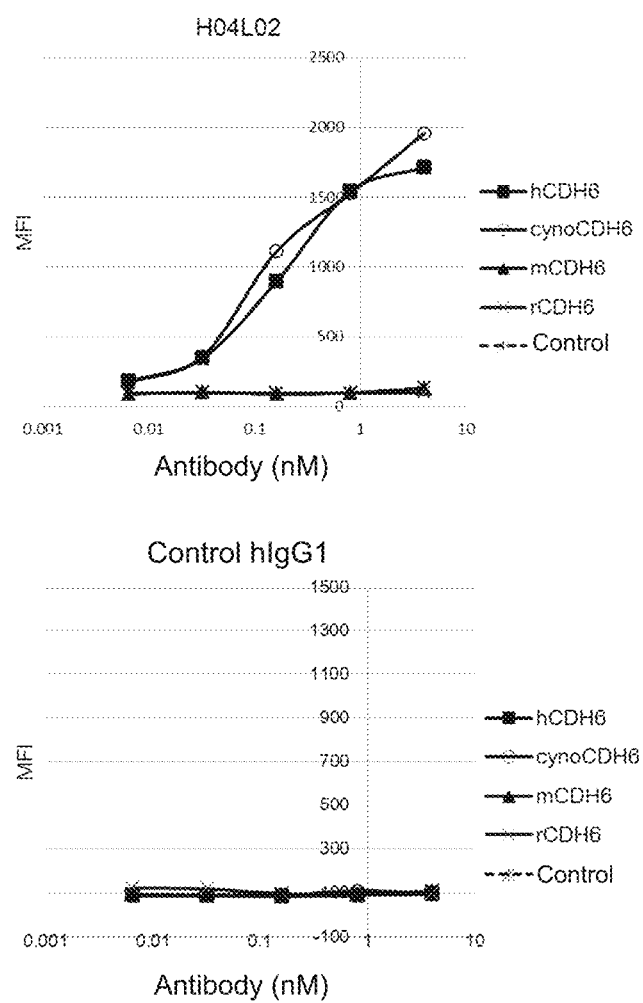

[Figure 7-1]
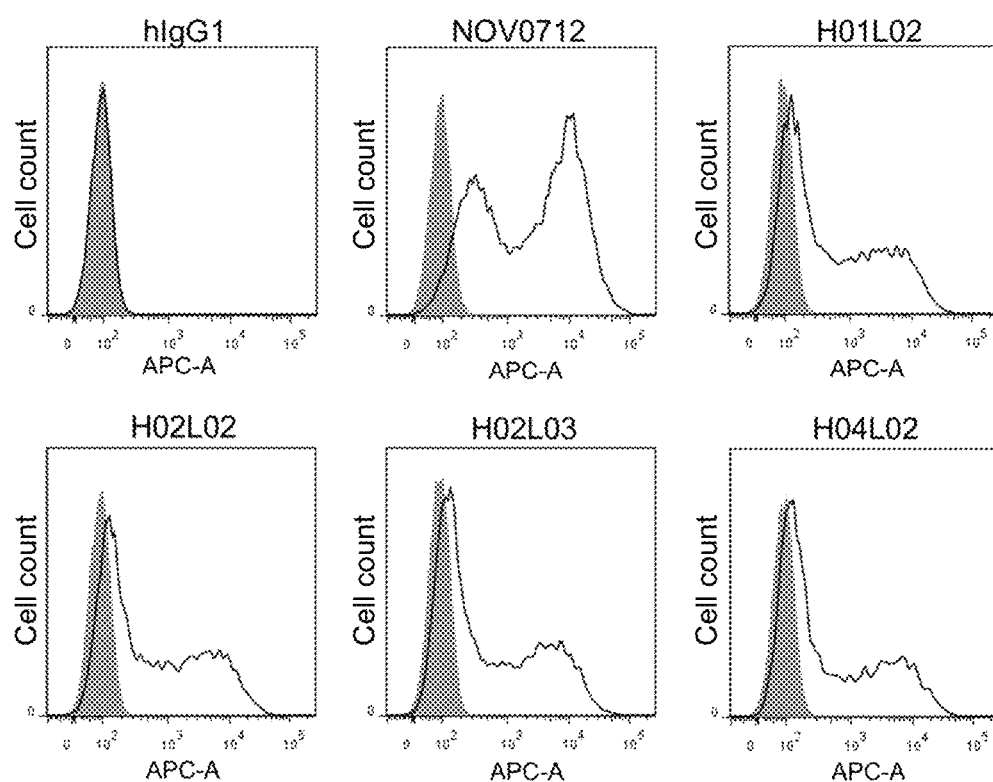

[Figure 7-2]
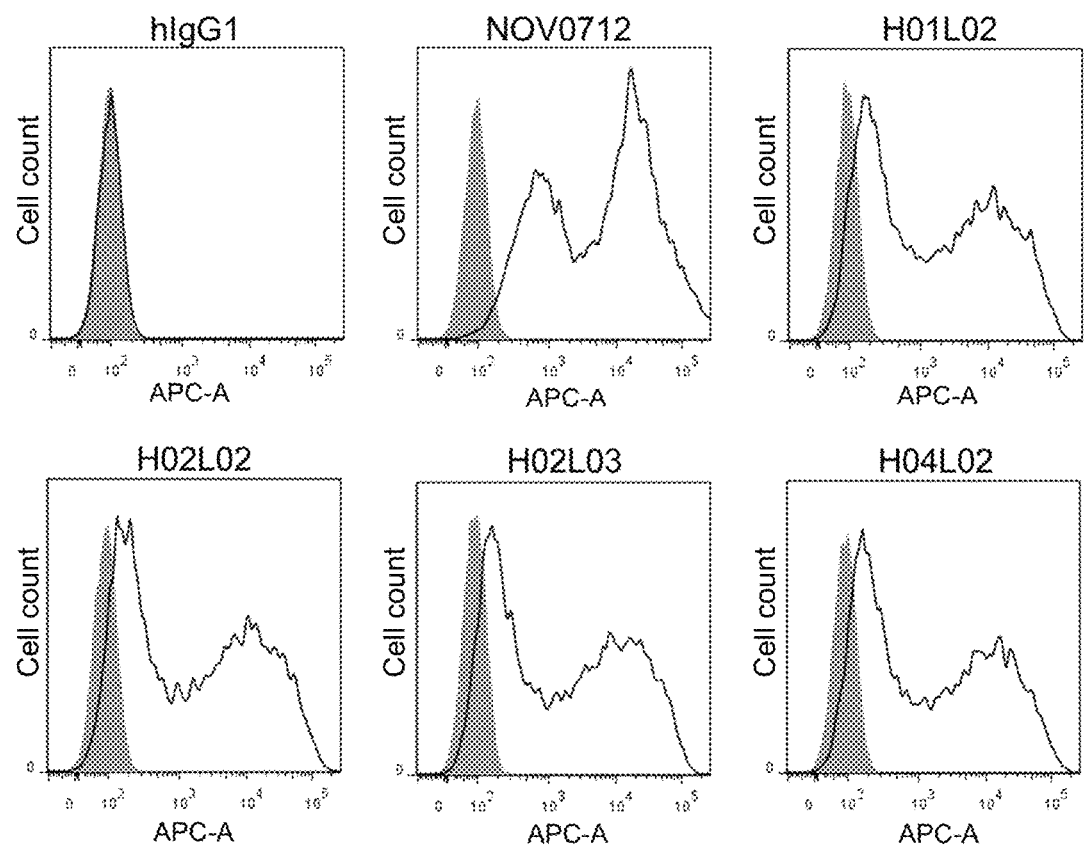

[Figure 7-3]
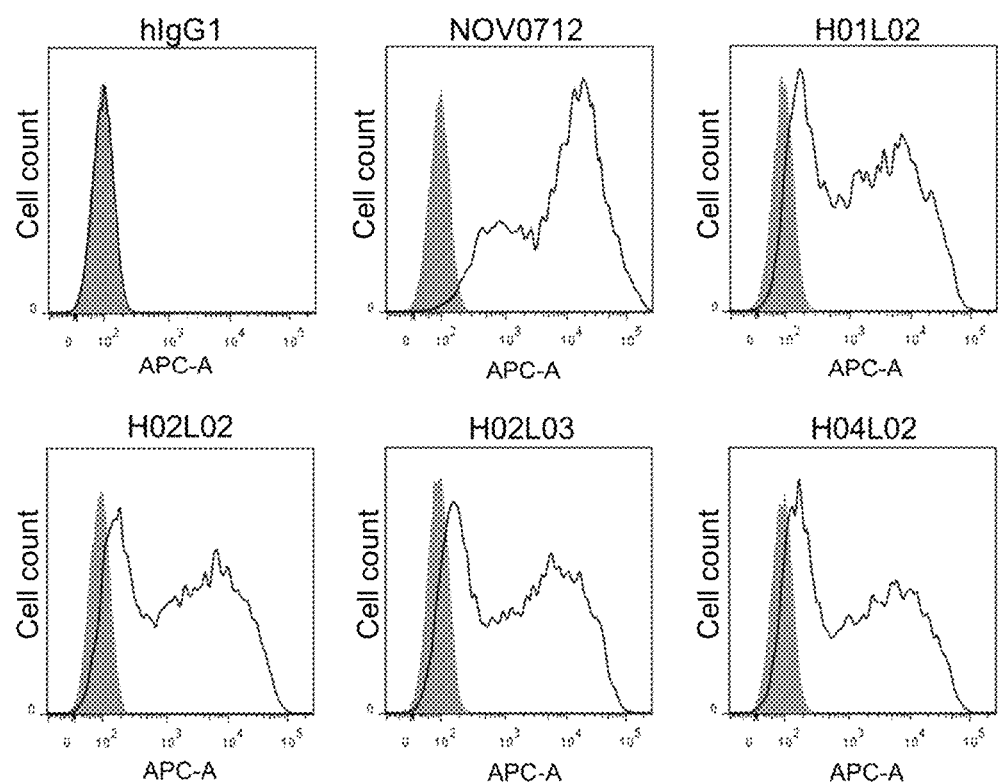

[Figure 7-4]
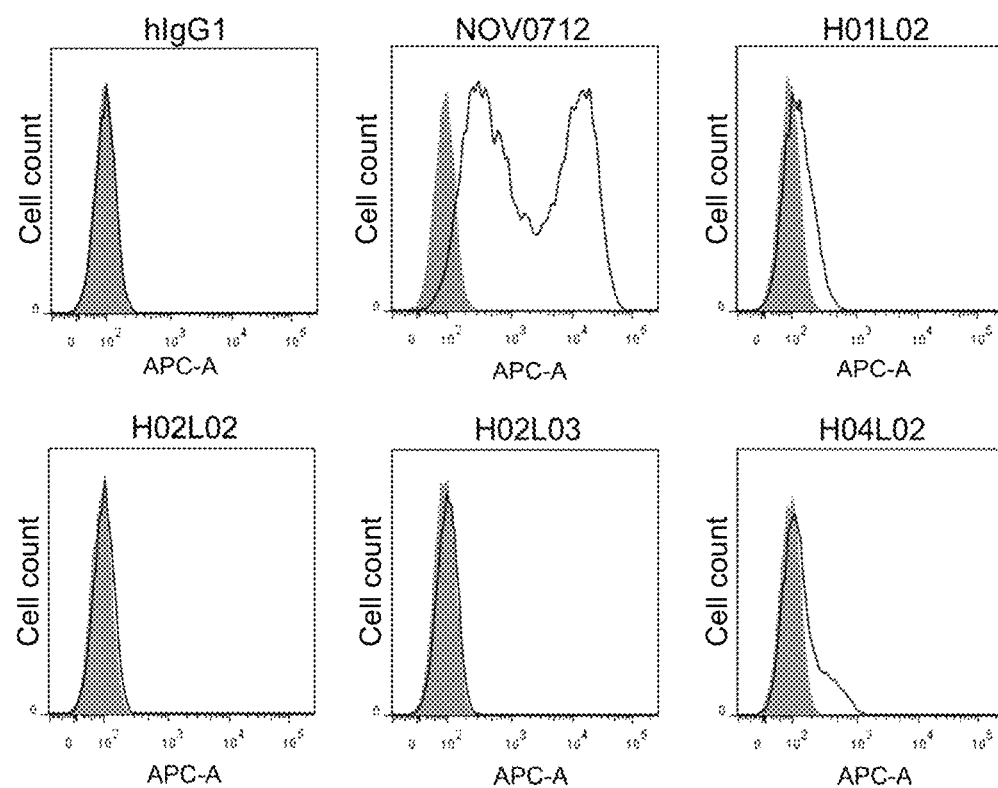

[Figure 7-5]
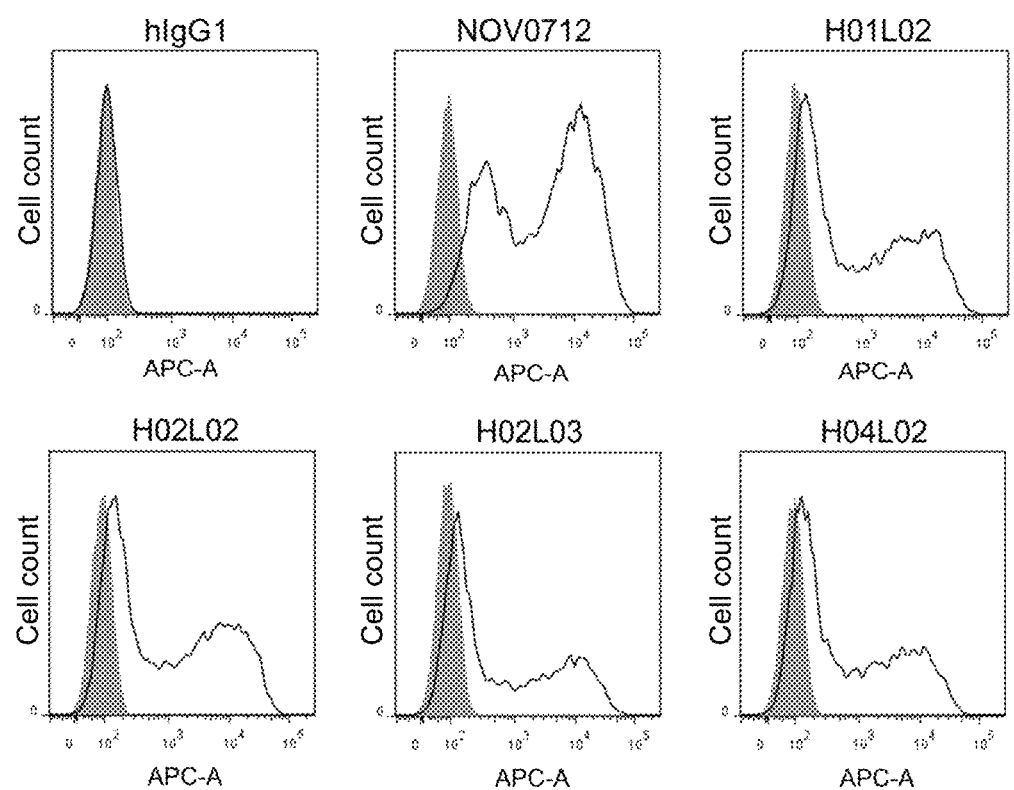

[Figure 7-6]
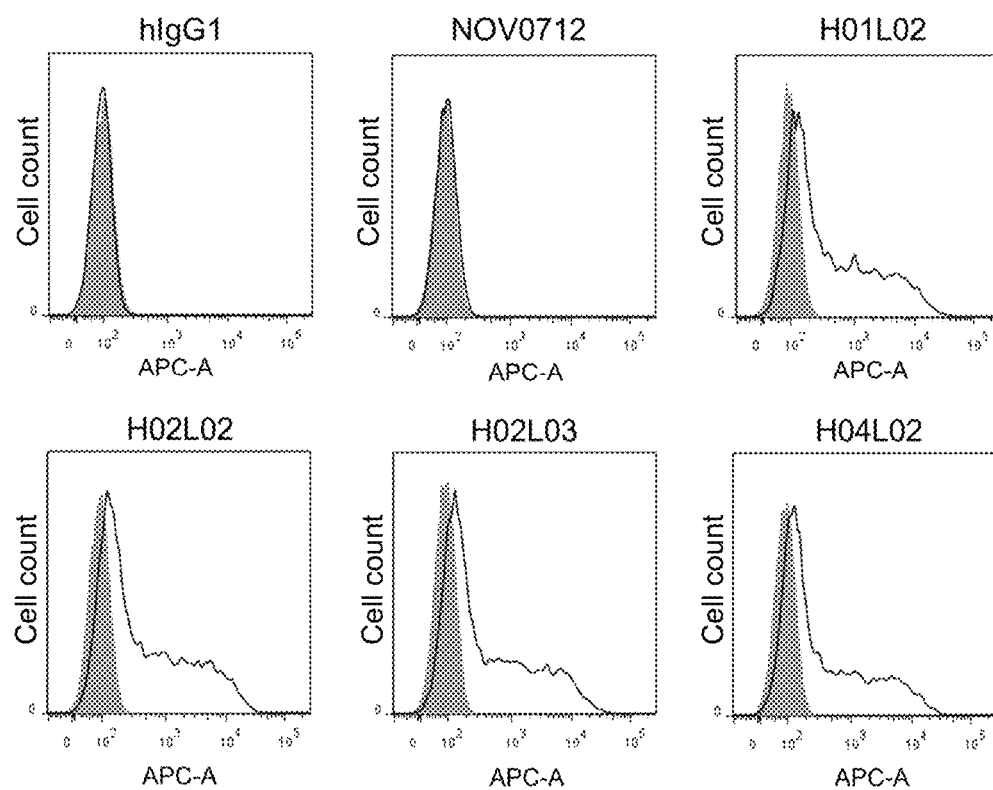

[Figure 8]
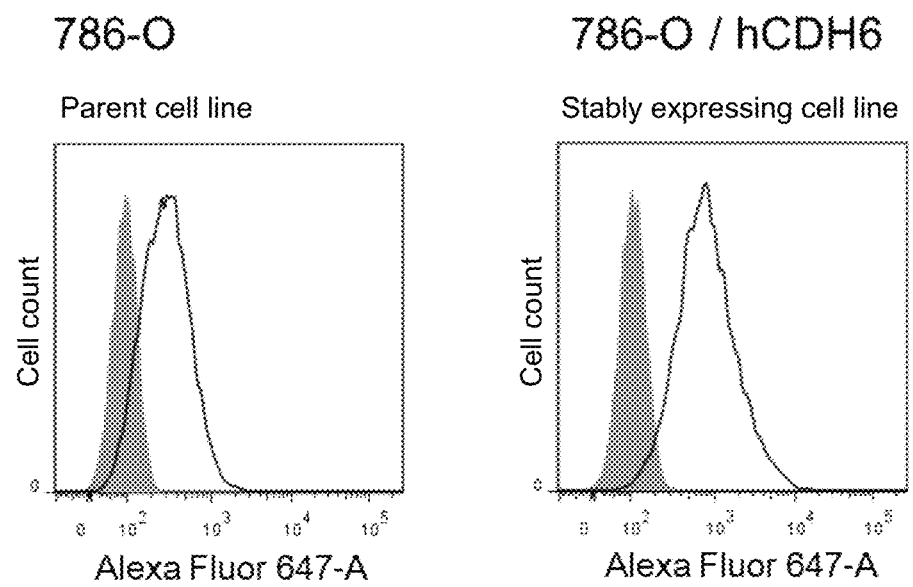

[Figure 9]
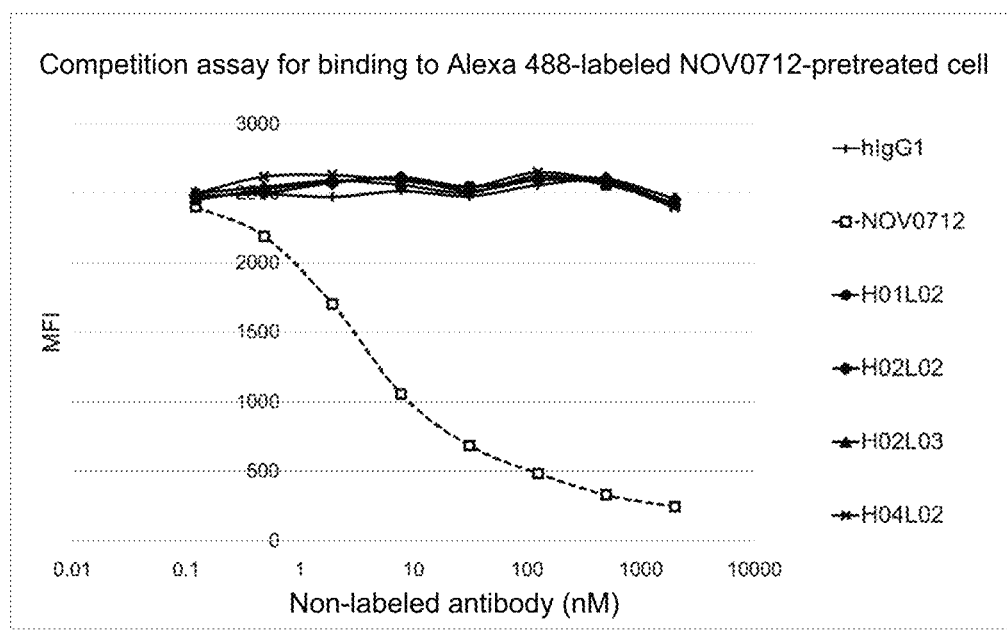
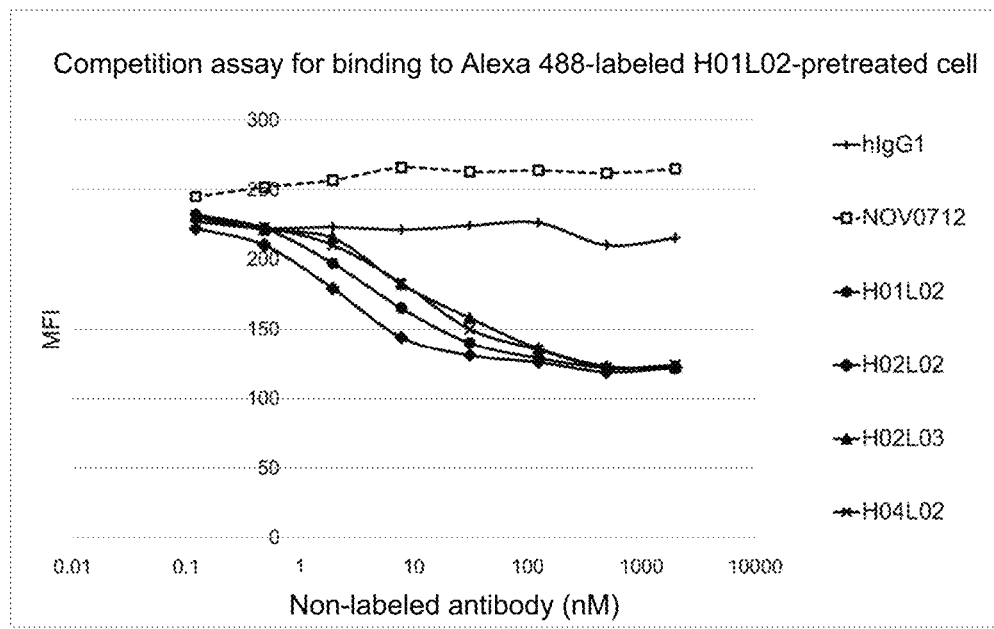

[Figure 10-1]
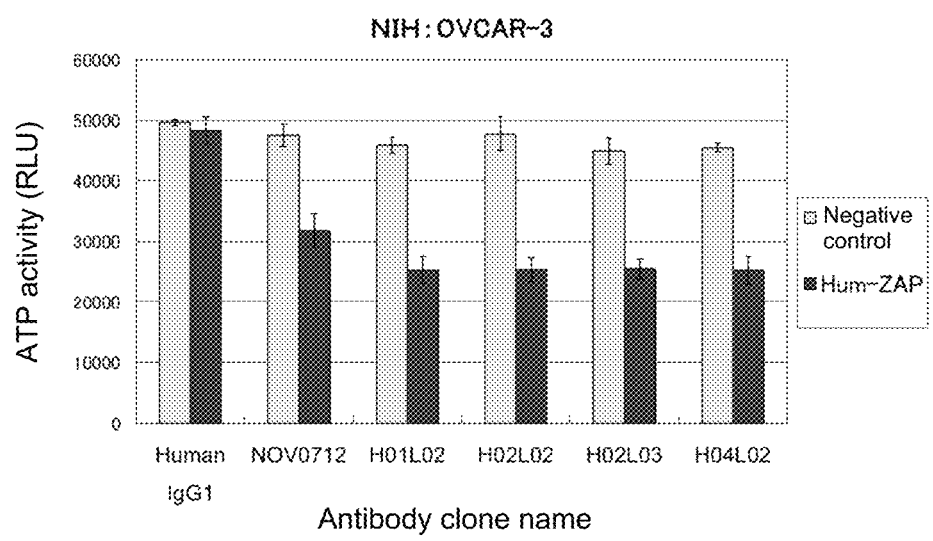

[Figure 10-2]
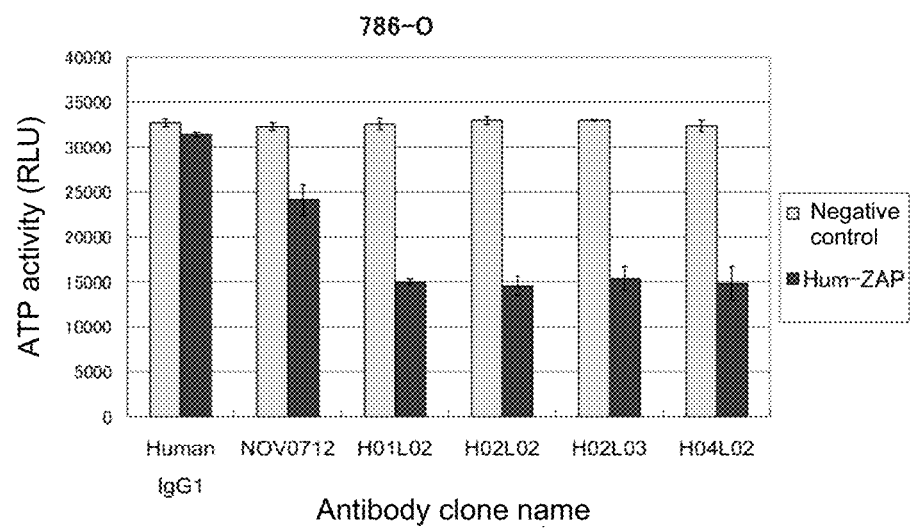

[Figure 10-3]
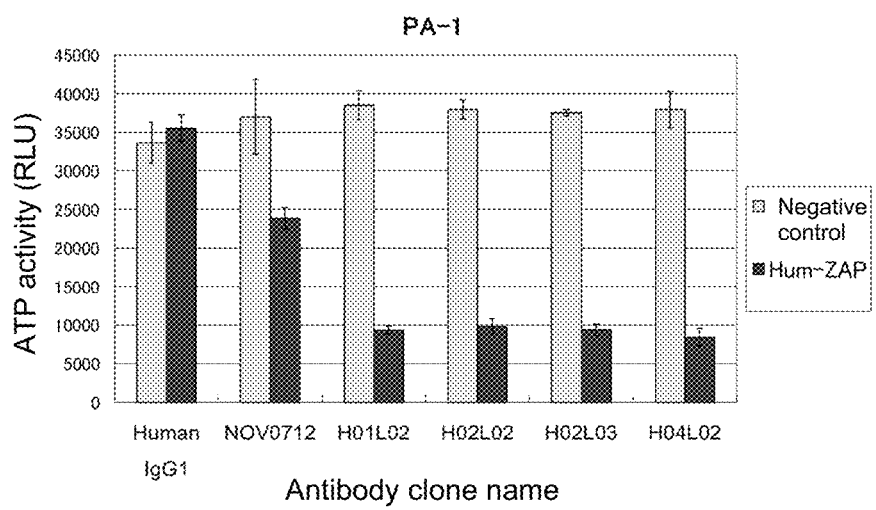

[Figure 11]
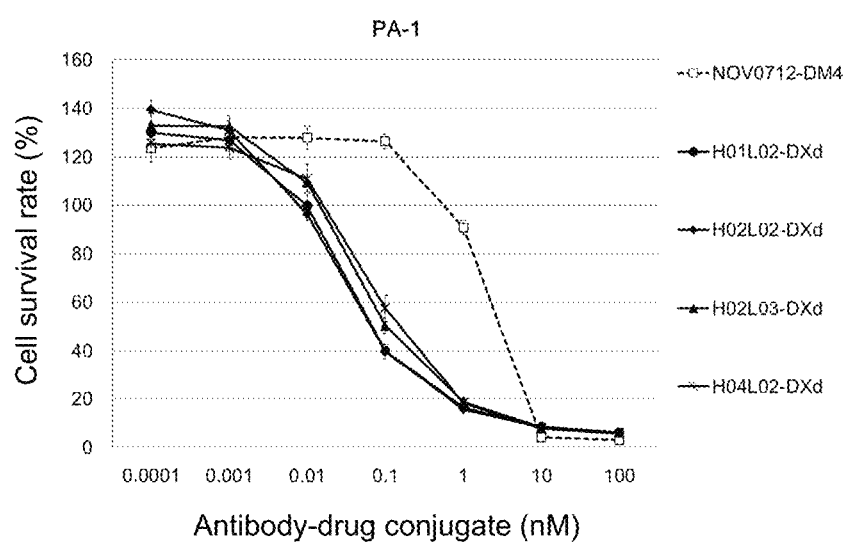

[Figure 12]
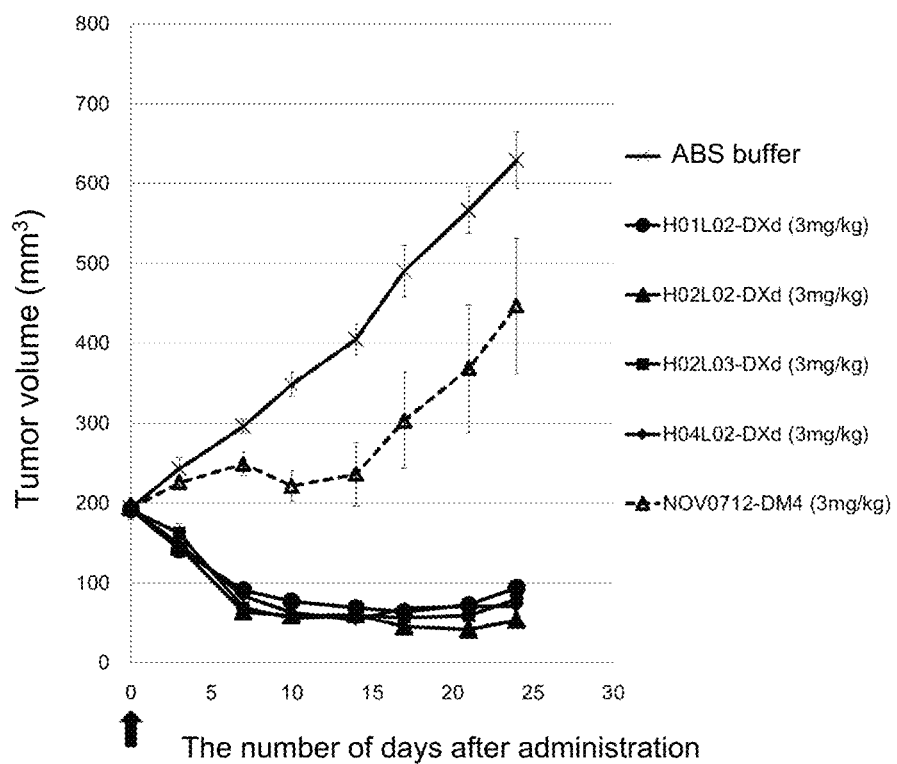

[Figure 13]
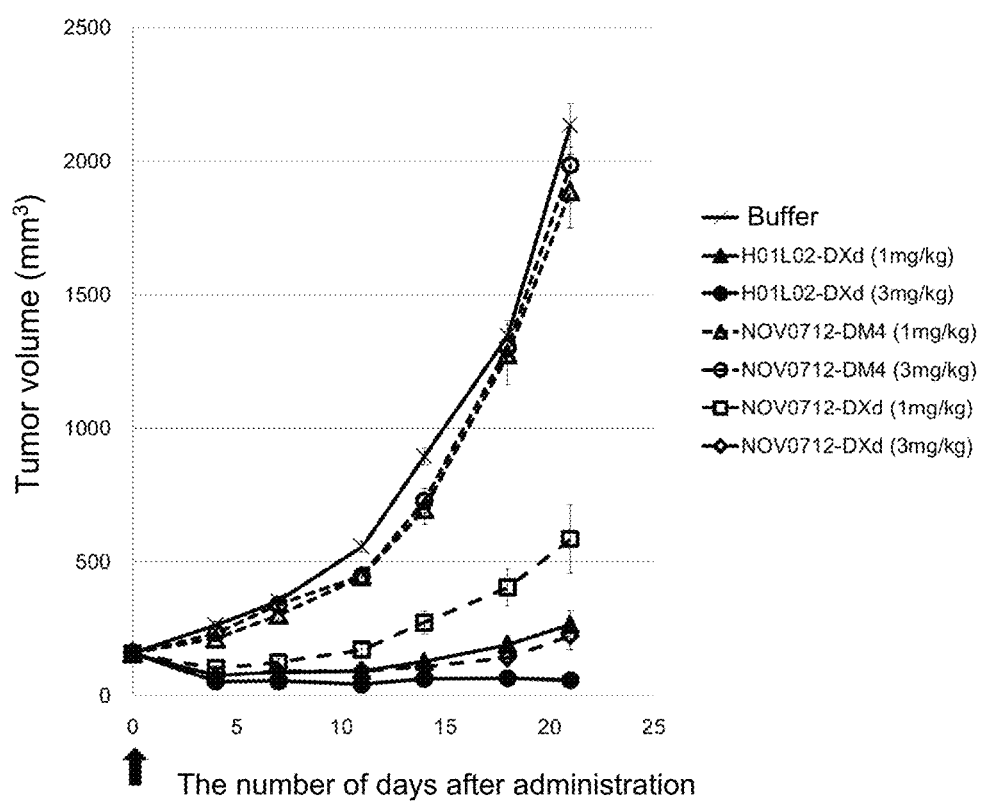

[Figure 14]
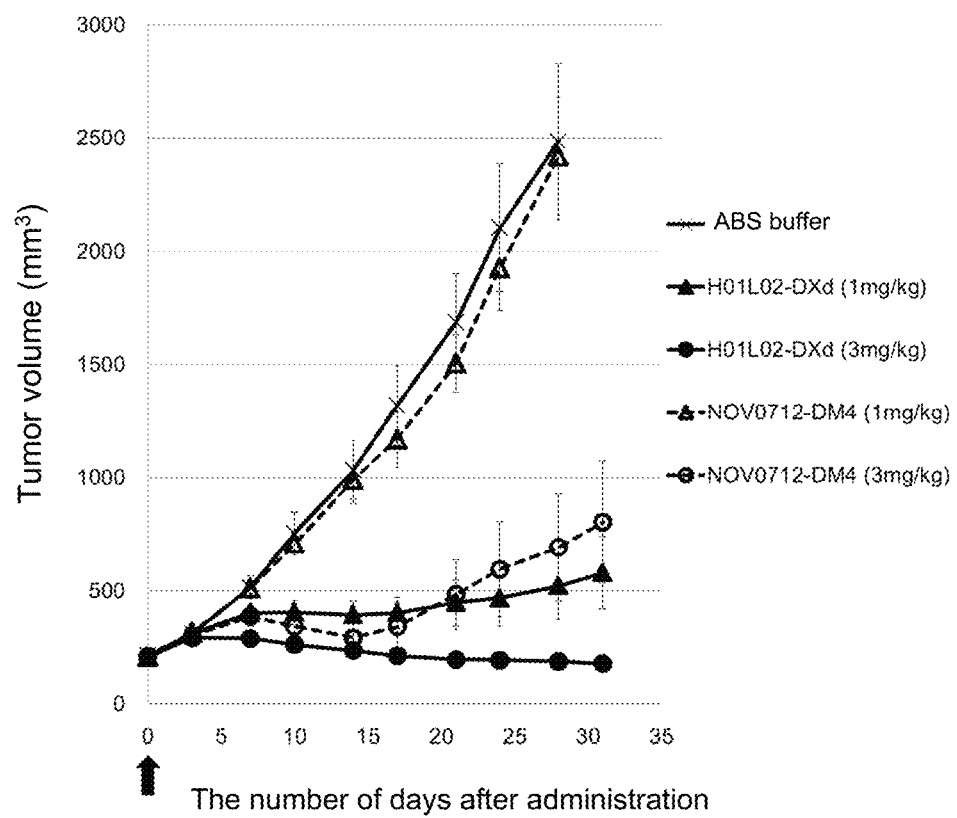

[Figure 15]
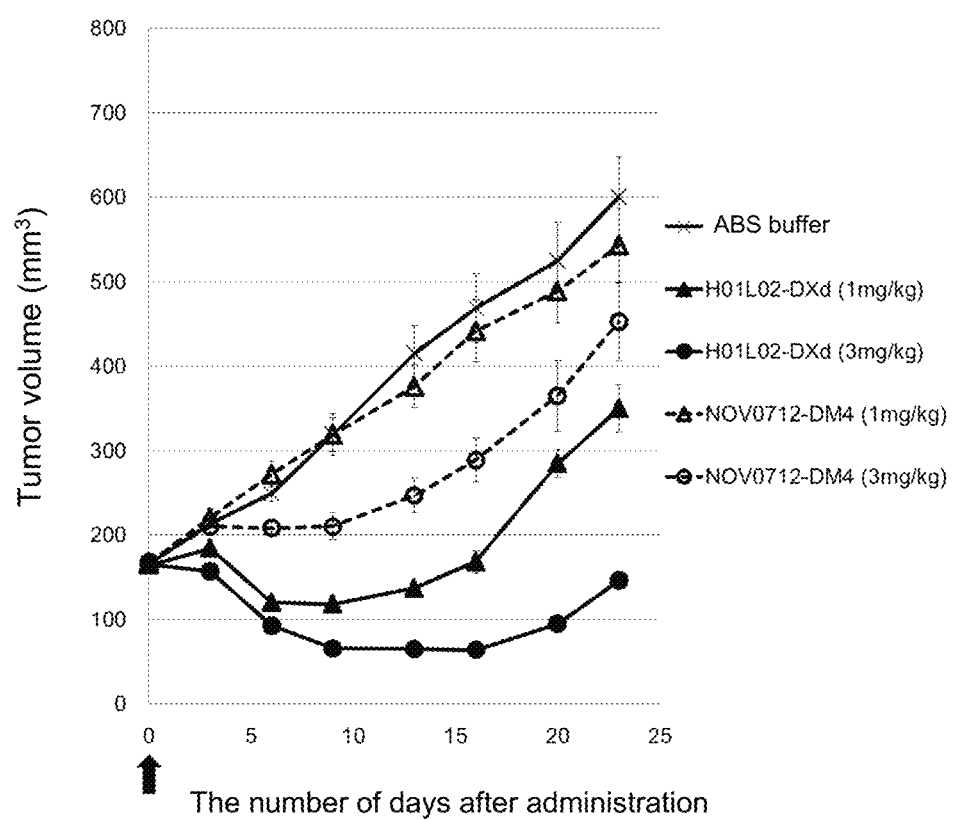

[Figure 16]
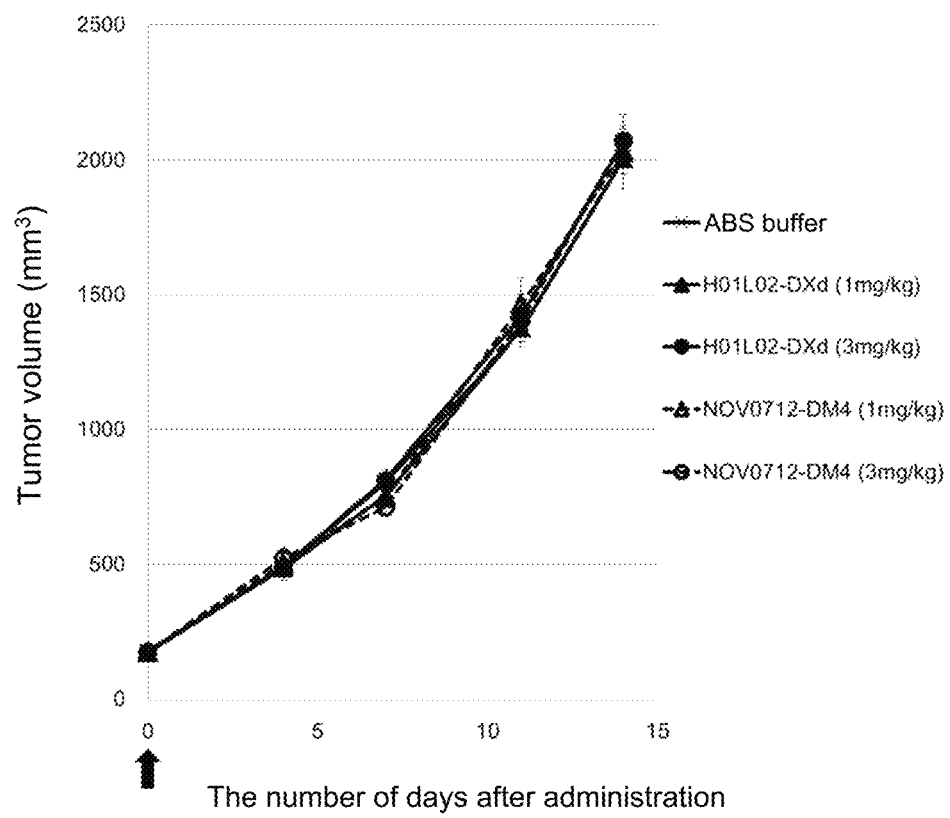

ANTI-CDH6 ANTIBODY AND METHOD OF PRODUCING AN ANTI-CDH6 ANTIBODY-DRUG CONJUGATE

CROSS-REFERENCE TO RELATED APPLICATIONS

The present application claims priority under 37 U.S.C. § 371 to International Patent Application No. PCT/JP2018/018572, filed May 14, 2018, which claims priority to and the benefit of Japanese Patent Application No. 2017-096749, filed on May 15, 2017. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 098065-0249_SL.txt and is 107 kb in size.

TECHNICAL FIELD

The present invention relates to an anti-CDH6 antibody binding to CDH6 and having an internalization effect, a method for producing the anti-CDH6 antibody, an antibody-drug conjugate comprising the antibody, an antitumor agent comprising the antibody-drug conjugate, and the like.

BACKGROUND ART

Cadherins are glycoproteins present on the surface of cell membranes and function as cell-cell adhesion molecules through the calcium ion-dependent binding of their N-terminal extracellular domains, or as signal molecules responsible for cell-cell interaction. Classic cadherins are in the cadherin superfamily and are single-pass transmembrane proteins composed of five extracellular domains (EC domains), one transmembrane region, and an intracellular domain. The classic cadherins are classified into the type I family typified by E-cadherin and N-cadherin, and the type II family according to the homologies of their amino acid sequences.

Cadherin-6 (CDH6) is a single-pass transmembrane protein composed of 790 amino acids, which is classified into the type II cadherin family, and this protein has N-terminal extracellular and C-terminal intracellular domains. The human CDH6 gene was cloned for the first time in 1995 (Non Patent Literature 1), and its sequence can be referred to under, for example, accession Nos. NM_004932 and NP_004923 (NCBI).

CDH6 is specifically expressed in the brain or the kidney at the stage of development and has been reported to play an important role in the circuit formation of the central nervous system (Non Patent Literature 2 and 3) and nephron development in the kidney (Non Patent Literature 4 and 5). The expression of CDH6 in the normal tissues of adult humans is localized to the tubules of the kidney, bile duct epithelial cells, and the like.

Meanwhile, it is known that CDH6 is specifically overexpressed at tumor sites in some types of human adult cancers. The correlation of CDH6 expression with poor prognosis and its applicability as a tumor marker has been reported with respect to human renal cell carcinoma, particularly, renal clear cell carcinoma (Non Patent Literature 6 and 7). The high expression of CDH6 has also been reported with respect to human ovarian cancer (Non Patent Literature 8). It has also been reported that CDH6 is involved in the epithelial-mesenchymal transition of human thyroid cancer (Non Patent Literature 9). Furthermore, it has been reported that CDH6 is also expressed in human bile duct cancer and human small-cell lung cancer (Non Patent Literature 12 and 13).

Cancers rank high in causes of death. Although the number of cancer patients is expected to increase with aging of the population, treatment needs have not yet been sufficiently satisfied. The problems of conventional chemotherapeutics are that: due to their low selectivity, these chemotherapeutics are toxic not only to tumor cells but also to normal cells and thereby have adverse reactions; and the chemotherapeutics cannot be administered in sufficient amounts and thus cannot produce their effects sufficiently. Hence, in recent years, more highly selective molecular target drugs or antibody drugs have been developed, which target molecules that exhibit mutations or a high expression characteristic in cancer cells, or specific molecules involved in malignant transformation of cells.

Antibodies are highly stable in blood, and specifically bind to their target antigens. For these reasons, a reduction in adverse reaction is expected, and a large number of antibody drugs have been developed for molecules highly expressed on the surface of cancer cells. One of the techniques relying on the antigen-specific binding ability of antibodies is to use an antibody-drug conjugate (ADC). ADC is a conjugate in which an antibody that binds to an antigen expressed on the surface of cancer cells and can internalize the antigen into the cell through the binding is conjugated to a drug having cytotoxic activity. ADC can efficiently deliver the drug to cancer cells, and can thereby be expected to kill the cancer cells by accumulating the drug in the cancer cells (Non Patent Literature 10 and Patent Literature 1 and 2). With regard to ADC, for example, Adcetris™ (brentuximab vedotin) comprising an anti-CD30 monoclonal antibody conjugated to monomethyl auristatin E has been approved as a therapeutic drug for Hodgkin's lymphoma and anaplastic large cell lymphoma. Also, Kadcyla™ (trastuzumab emtansine) comprising an anti-HER2 monoclonal antibody conjugated to emtansine is used in the treatment of HER2-positive progressive or recurrent breast cancer.

The features of a target antigen suitable for ADC as an antitumor drug are that: the antigen is specifically highly expressed on the surface of cancer cells but has low expression or is not expressed in normal cells; the antigen can be internalized into cells; the antigen is not secreted from the cell surface; etc. The internalization ability of the antibody depends on the properties of both the target antigen and the antibody. It is difficult to predict an antigen-binding site suitable for internalization from the molecular structure of a target or to predict an antibody having high internalization ability from binding strength, physical properties, and the like of the antibody. Hence, an important challenge in developing ADC having high efficacy is obtaining an antibody having high internalization ability against the target antigen (Non Patent Literature 11).

ADC comprising DM4 conjugated to an anti-CDH6 antibody specifically binding to EC domain 5 (EC5) of CDH6 are known as ADC targeting CDH6 (Patent Literature 3).

CITATION LIST

Patent Literature

Patent Literature 1: WO2014/057687
Patent Literature 2: US2016/0297890
Patent Literature 3: WO2016/024195

Non Patent Literature

Non Patent Literature 1: Shimoyama Y, et al., Cancer Research, 2206-2211, 55, May 15, 1995
Non Patent Literature 2: Inoue T, et al., Developmental Biology, 183-194, 1997
Non Patent Literature 3: Osterhout J A, et al., Neuron, 632-639, 71, Aug. 25, 2011
Non Patent Literature 4: Cho E A, et al., Development, 803-812, 125, 1998
Non Patent Literature 5: Mah S P, et al., Developmental Biology, 38-53, 223, 2000
Non Patent Literature 6: Paul R, et al., Cancer Research, 2741-2748, July 1, 57, 1997
Non Patent Literature 7: Shimazui T, et al., Cancer, 963-968, 101(5), Sep. 1, 2004
Non Patent Literature 8: Koebel M, et al., PLoS Medicine, 1749-1760, 5(12), e232, December. 2008
Non Patent Literature 9: Gugnoni M, et al., Oncogene, 667-677, 36, 2017
Non Patent Literature 10: Polakis P., Pharmacological Reviews, 3-19, 68, 2016
Non Patent Literature 11: Peters C, et al., Bioscience Reports, 1-20, 35, 2015
Non Patent Literature 12: Goeppert B, et al., Epigenetics, 780-790, 11(11), 2016
Non Patent Literature 13: Yokoi S, et al., American Journal of Pathology, 207-216, 161, 1, 2002

SUMMARY OF INVENTION

Technical Problem

It is an object of the present invention to provide an antibody specifically binding to CDH6 and having high internalization activity, an antibody-drug conjugate comprising the antibody and having high antitumor activity, a pharmaceutical product comprising the antibody-drug conjugate and having therapeutic effects on a tumor, a method for treating a tumor using the antibody, the antibody-drug conjugate or the pharmaceutical product, and the like.

Solution to Problem

The present inventors have conducted intensive studies directed towards achieving the above-described object, and found that, surprisingly, an antibody specifically binding to extracellular domain 3 (in the present description, also referred to as EC3) of CDH6 has exceedingly high internalization activity against cells expressing CDH6 and is useful as an antibody for ADC. The inventors have further found that an anti-CDH6 antibody-drug conjugate comprising the aforementioned anti-CDH6 antibody conjugated to a drug exerting toxicity in cells via a linker having a specific structure exhibits stronger antitumor activity than that of conventional CDH6-drug conjugates.

The present invention includes the following aspects of the invention:
[1] an antibody specifically binding to the amino acid sequence shown in SEQ ID NO: 4 and having internalization ability that permits cellular uptake, or a functional fragment of the antibody;
[2] the antibody or the functional fragment of the antibody according to [1], which has competitive inhibitory activity, for binding to the amino acid sequence shown in SEQ ID NO: 4, against at least any one antibody selected from the group consisting of the following antibodies (1) to (5):
(1) an antibody having a light chain consisting of the amino acid sequence at positions 21 to 233 in SEQ ID NO: 53 and a heavy chain consisting of the amino acid sequence at positions 20 to 471 in SEQ ID NO: 56,
(2) an antibody having a light chain consisting of the amino acid sequence at positions 21 to 233 in SEQ ID NO: 61 and a heavy chain consisting of the amino acid sequence at positions 20 to 471 in SEQ ID NO: 69,
(3) an antibody having a light chain consisting of the amino acid sequence at positions 21 to 233 in SEQ ID NO: 61 and a heavy chain consisting of the amino acid sequence at positions 20 to 471 in SEQ ID NO: 73,
(4) an antibody having a light chain consisting of the amino acid sequence at positions 21 to 233 in SEQ ID NO: 65 and a heavy chain consisting of the amino acid sequence at positions 20 to 471 in SEQ ID NO: 73, and
(5) an antibody having a light chain consisting of the amino acid sequence at positions 21 to 233 in SEQ ID NO: 61 and a heavy chain consisting of the amino acid sequence at positions 20 to 471 in SEQ ID NO: 77;
[3] the antibody or the functional fragment of the antibody according to [1] or [2], which comprises CDRL1, CDRL2 and CDRL3 in any one combination selected from the group consisting of the following combinations (1) to (4):
(1) CDRL1 consisting of the amino acid sequence shown in SEQ ID NO: 12, CDRL2 consisting of the amino acid sequence shown in SEQ ID NO: 13, and CDRL3 consisting of the amino acid sequence shown in SEQ ID NO: 14,
(2) CDRL1 consisting of the amino acid sequence shown in SEQ ID NO: 22, CDRL2 consisting of the amino acid sequence shown in SEQ ID NO: 23, and CDRL3 consisting of the amino acid sequence shown in SEQ ID NO: 24,
(3) CDRL1 consisting of the amino acid sequence shown in SEQ ID NO: 32, CDRL2 consisting of the amino acid sequence shown in SEQ ID NO: 33, and CDRL3 consisting of the amino acid sequence shown in SEQ ID NO: 34, and
(4) CDRL1 consisting of the amino acid sequence shown in SEQ ID NO: 42, CDRL2 consisting of the amino acid sequence shown in SEQ ID NO: 43, and CDRL3 consisting of the amino acid sequence shown in SEQ ID NO: 44, and CDRH1, CDRH2 and CDRH3 in any one combination selected from the group consisting of the following combinations (5) to (9):
(5) CDRH1 consisting of the amino acid sequence shown in SEQ ID NO: 17, CDRH2 consisting of the amino acid sequence shown in SEQ ID NO: 18, and CDRH3 consisting of the amino acid sequence shown in SEQ ID NO: 19,
(6) CDRH1 consisting of the amino acid sequence shown in SEQ ID NO: 27, CDRH2 consisting of the amino acid sequence shown in SEQ ID NO: 28, and CDRH3 consisting of the amino acid sequence shown in SEQ ID NO: 29,
(7) CDRH1 consisting of the amino acid sequence shown in SEQ ID NO: 37, CDRH2 consisting of the amino acid sequence shown in SEQ ID NO: 38, and CDRH3 consisting of the amino acid sequence shown in SEQ ID NO: 39,
(8) CDRH1 consisting of the amino acid sequence shown in SEQ ID NO: 47, CDRH2 consisting of the amino acid sequence shown in SEQ ID NO: 48, and CDRH3 consisting of the amino acid sequence shown in SEQ ID NO: 49, and
(9) CDRH1 consisting of the amino acid sequence shown in SEQ ID NO: 17, CDRH2 consisting of the amino acid sequence shown in SEQ ID NO: 60, and CDRH3 consisting of the amino acid sequence shown in SEQ ID NO: 19;
[4] the antibody or the functional fragment of the antibody according to any one of [1] to [3], which comprises CDRL1, CDRL2 and CDRL3, and CDRH1, CDRH2 and CDRH3 in any combination selected from the group consisting of the following combinations (1) to (5):

(1) CDRL1 consisting of the amino acid sequence shown in SEQ ID NO: 12, CDRL2 consisting of the amino acid sequence shown in SEQ ID NO: 13, and CDRL3 consisting of the amino acid sequence shown in SEQ ID NO: 14, and CDRH1 consisting of the amino acid sequence shown in SEQ ID NO: 17, CDRH2 consisting of the amino acid sequence shown in SEQ ID NO: 18, and CDRH3 consisting of the amino acid sequence shown in SEQ ID NO: 19, (2) CDRL1 consisting of the amino acid sequence shown in SEQ ID NO: 22, CDRL2 consisting of the amino acid sequence shown in SEQ ID NO: 23, and CDRL3 consisting of the amino acid sequence shown in SEQ ID NO: 24, and CDRH1 consisting of the amino acid sequence shown in SEQ ID NO: 27, CDRH2 consisting of the amino acid sequence shown in SEQ ID NO: 28, and CDRH3 consisting of the amino acid sequence shown in SEQ ID NO: 29, (3) CDRL1 consisting of the amino acid sequence shown in SEQ ID NO: 32, CDRL2 consisting of the amino acid sequence shown in SEQ ID NO: 33, and CDRL3 consisting of the amino acid sequence shown in SEQ ID NO: 34, and CDRH1 consisting of the amino acid sequence shown in SEQ ID NO: 37, CDRH2 consisting of the amino acid sequence shown in SEQ ID NO: 38, and CDRH3 consisting of the amino acid sequence shown in SEQ ID NO: 39, (4) CDRL1 consisting of the amino acid sequence shown in SEQ ID NO: 42, CDRL2 consisting of the amino acid sequence shown in SEQ ID NO: 43, and CDRL3 consisting of the amino acid sequence shown in SEQ ID NO: 44, and CDRH1 consisting of the amino acid sequence shown in SEQ ID NO: 47, CDRH2 consisting of the amino acid sequence shown in SEQ ID NO: 48, and CDRH3 consisting of the amino acid sequence shown in SEQ ID NO: 49, and (5) CDRL1 consisting of the amino acid sequence shown in SEQ ID NO: 12, CDRL2 consisting of the amino acid sequence shown in SEQ ID NO: 13, and CDRL3 consisting of the amino acid sequence shown in SEQ ID NO: 14, and CDRH1 consisting of the amino acid sequence shown in SEQ ID NO: 17, CDRH2 consisting of the amino acid sequence shown in SEQ ID NO: 60, and CDRH3 consisting of the amino acid sequence shown in SEQ ID NO: 19;

[5] the antibody or the functional fragment of the antibody according to any one of [1] to [4], which is humanized;

[6] the antibody or the functional fragment of the antibody according to any one of [1] to [5], which has any one light chain variable region selected from the group consisting of the following variable regions (1) to (4):

(1) a light chain variable region consisting of the amino acid sequence shown in SEQ ID NO: 63, (2) a light chain variable region consisting of the amino acid sequence shown in SEQ ID NO: 67, (3) an amino acid sequence having a sequence identity of at least 95% or more to the sequence of a framework region other than at each CDR sequence in the amino acid sequences of (1) and (2), and (4) an amino acid sequence comprising a deletion, substitution or addition of one or several amino acids in the sequence of a framework region other than at each CDR sequence in the amino acid sequences of (1) to (3), and any one heavy chain variable region selected from the group consisting of the following variable regions (5) to (9):

(5) a heavy chain variable region consisting of the amino acid sequence shown in SEQ ID NO: 71, (6) a heavy chain variable region consisting of the amino acid sequence shown in SEQ ID NO: 75, (7) a heavy chain variable region consisting of the amino acid sequence shown in SEQ ID NO: 79, (8) an amino acid sequence having a sequence homology of at least 95% or more to the sequence of a framework region other than at each CDR sequence in the amino acid sequences of (5) to (7), and (9) an amino acid sequence comprising a deletion, substitution or addition of one or several amino acids in the sequence of a framework region other than at each CDR sequence in the amino acid sequences of (5) to (8);

[7] the antibody or the functional fragment of the antibody according to any one of [1] to [6], which comprises a light chain variable region and a heavy chain variable region in any of the following combinations (1) to (4):

(1) a light chain variable region consisting of the amino acid sequence shown in SEQ ID NO: 63 and a heavy chain variable region consisting of the amino acid sequence shown in SEQ ID NO: 71, (2) a light chain variable region consisting of the amino acid sequence shown in SEQ ID NO: 63 and a heavy chain variable region consisting of the amino acid sequence shown in SEQ ID NO: 75, (3) a light chain variable region consisting of the amino acid sequence shown in SEQ ID NO: 67 and a heavy chain variable region consisting of the amino acid sequence shown in SEQ ID NO: 75, and (4) a light chain variable region consisting of the amino acid sequence shown in SEQ ID NO: 63 and a heavy chain variable region consisting of the amino acid sequence shown in SEQ ID NO: 79;

[8] the antibody or the functional fragment of the antibody according to any one of [1] to [7], which has any of the following combinations (1) to (4):

(1) a light chain consisting of the amino acid sequence at positions 21 to 233 in SEQ ID NO: 61 and a heavy chain consisting of the amino acid sequence at positions 20 to 471 in SEQ ID NO: 69, (2) a light chain consisting of the amino acid sequence at positions 21 to 233 in SEQ ID NO: 61 and a heavy chain consisting of the amino acid sequence at positions 20 to 471 in SEQ ID NO: 73, (3) a light chain consisting of the amino acid sequence at positions 21 to 233 in SEQ ID NO: 65 and a heavy chain consisting of the amino acid sequence at positions 20 to 471 in SEQ ID NO: 73, and (4) a light chain consisting of the amino acid sequence at positions 21 to 233 in SEQ ID NO: 61 and a heavy chain consisting of the amino acid sequence at positions 20 to 471 in SEQ ID NO: 77;

[9] the antibody or the functional fragment of the antibody according to [8], which has a light chain consisting of the amino acid sequence at positions 21 to 233 in SEQ ID NO: 61 and a heavy chain consisting of the amino acid sequence at positions 20 to 471 in SEQ ID NO: 69;

[10] the antibody or the functional fragment of the antibody according to [8], which has a light chain consisting of the amino acid sequence at positions 21 to 233 in SEQ ID NO: 61 and a heavy chain consisting of the amino acid sequence at positions 20 to 471 in SEQ ID NO: 73;

[11] the antibody or the functional fragment of the antibody according to [8], which has a light chain consisting of the amino acid sequence at positions 21 to 233 in SEQ ID NO: 65 and a heavy chain consisting of the amino acid sequence at positions 20 to 471 in SEQ ID NO: 73;

[12] the antibody or the functional fragment of the antibody according to [8], which has a light chain consisting of the amino acid sequence at positions 21 to 233 in SEQ ID NO:

61 and a heavy chain consisting of the amino acid sequence at positions 20 to 471 in SEQ ID NO: 77;

[13] the functional fragment of the antibody according to any one of [1] to [12], wherein the functional fragment is selected from the group consisting of Fab, F(ab')2, Fab' and Fv;

[14] a polynucleotide encoding the antibody or the functional fragment of the antibody according to any one of [1] to [13];

[15] the polynucleotide according to [14], which comprises polynucleotides in any one combination selected from the group consisting of the following combinations (1) to (5):

(1) a polynucleotide encoding a light chain variable region comprising CDRL1 consisting of the amino acid sequence shown in SEQ ID NO: 12, CDRL2 consisting of the amino acid sequence shown in SEQ ID NO: 13 and CDRL3 consisting of the amino acid sequence shown in SEQ ID NO: 14, and a polynucleotide encoding a heavy chain variable region comprising CDRH1 consisting of the amino acid sequence shown in SEQ ID NO: 17, CDRH2 consisting of the amino acid sequence shown in SEQ ID NO: 18 and CDRH3 consisting of the amino acid sequence shown in SEQ ID NO: 19, (2) a polynucleotide encoding a light chain variable region comprising CDRL1 consisting of the amino acid sequence shown in SEQ ID NO: 22, CDRL2 consisting of the amino acid sequence shown in SEQ ID NO: 23 and CDRL3 consisting of the amino acid sequence shown in SEQ ID NO: 24, and a polynucleotide encoding a heavy chain variable region comprising CDRH1 consisting of the amino acid sequence shown in SEQ ID NO: 27, CDRH2 consisting of the amino acid sequence shown in SEQ ID NO: 28 and CDRH3 consisting of the amino acid sequence shown in SEQ ID NO: 29, (3) a polynucleotide encoding a light chain variable region comprising CDRL1 consisting of the amino acid sequence shown in SEQ ID NO: 32, CDRL2 consisting of the amino acid sequence shown in SEQ ID NO: 33 and CDRL3 consisting of the amino acid sequence shown in SEQ ID NO: 34, and a polynucleotide encoding a heavy chain variable region comprising CDRH1 consisting of the amino acid sequence shown in SEQ ID NO: 37, CDRH2 consisting of the amino acid sequence shown in SEQ ID NO: 38 and CDRH3 consisting of the amino acid sequence shown in SEQ ID NO: 39, (4) a polynucleotide encoding a light chain variable region comprising CDRL1 consisting of the amino acid sequence shown in SEQ ID NO: 42, CDRL2 consisting of the amino acid sequence shown in SEQ ID NO: 43 and CDRL3 consisting of the amino acid sequence shown in SEQ ID NO: 44, and a polynucleotide encoding a heavy chain variable region comprising CDRH1 consisting of the amino acid sequence shown in SEQ ID NO: 47, CDRH2 consisting of the amino acid sequence shown in SEQ ID NO: 48 and CDRH3 consisting of the amino acid sequence shown in SEQ ID NO: 49, and (5) a polynucleotide encoding a light chain variable region comprising CDRL1 consisting of the amino acid sequence shown in SEQ ID NO: 12, CDRL2 consisting of the amino acid sequence shown in SEQ ID NO: 13 and CDRL3 consisting of the amino acid sequence shown in SEQ ID NO: 14, and a polynucleotide encoding a heavy chain variable region comprising CDRH1 consisting of the amino acid sequence shown in SEQ ID NO: 17, CDRH2 consisting of the amino acid sequence shown in SEQ ID NO: 60 and CDRH3 consisting of the amino acid sequence shown in SEQ ID NO: 19;

[16] the polynucleotide according to [14] or [15], which comprises a polynucleotide encoding a light chain consisting of the amino acid sequence at positions 21 to 233 in SEQ ID NO: 61 and a polynucleotide encoding a heavy chain consisting of the amino acid sequence at positions 20 to 471 in SEQ ID NO: 69;

[17] the polynucleotide according to [14] or [15], which comprises a polynucleotide encoding a light chain consisting of the amino acid sequence at positions 21 to 233 in SEQ ID NO: 61 and a polynucleotide encoding a heavy chain consisting of the amino acid sequence at positions 20 to 471 in SEQ ID NO: 73;

[18] the polynucleotide according to [14] or [15], which comprises a polynucleotide encoding a light chain consisting of the amino acid sequence at positions 21 to 233 in SEQ ID NO: 65 and a polynucleotide encoding a heavy chain consisting of the amino acid sequence at positions 20 to 471 in SEQ ID NO: 73;

[19] the polynucleotide according to [14] or [15], which comprises a polynucleotide encoding a light chain consisting of the amino acid sequence at positions 21 to 233 in SEQ ID NO: 61 and a polynucleotide encoding a heavy chain consisting of the amino acid sequence at positions 20 to 471 in SEQ ID NO: 77;

[20] an expression vector comprising the polynucleotide according to any one of [14] to [19];

[21] host cells transformed with the expression vector according to [20];

[22] the host cells according to [21], wherein the host cells are eukaryotic cells;

[23] a method for producing an antibody of interest or a functional fragment of the antibody, which comprises the step of culturing the host cells according to [21] or [22], and the step of collecting an antibody of interest or a functional fragment of the antibody from the culture obtained by the aforementioned step;

[24] the antibody or the functional fragment of the antibody according to any one of [1] to [13], wherein the heavy chain or the light chain has undergone one or two or more modifications selected from the group consisting of N-linked glycosylation, O-linked glycosylation, N-terminal processing, C-terminal processing, deamidation, isomerization of aspartic acid, oxidation of methionine, addition of a methionine residue to the N-terminus, amidation of a proline residue, conversion of N-terminal glutamine or N-terminal glutamic acid to pyroglutamic acid, and a deletion of one or two amino acids from the carboxyl terminus;

[25] the antibody according to [24], wherein one or two amino acids are deleted from the carboxyl terminus of a heavy chain thereof;

[26] the antibody according to [25], wherein one amino acid is deleted from each of the carboxyl termini of both of the heavy chains thereof;

[27] the antibody according to any one of [24] to [26], wherein a proline residue at the carboxyl terminus of a heavy chain thereof is further amidated;

[28] the antibody or the functional fragment of the antibody according to any one of [1] to [13] and [24] to [27], wherein sugar chain modification is regulated in order to enhance antibody-dependent cellular cytotoxic activity;

[29] an antibody-drug conjugate comprising the antibody or the functional fragment of the antibody according to any one of [1] to [13] and [24] to [28] conjugated to a drug;

[30] the antibody-drug conjugate according to [29], wherein the drug is an antitumor compound;

[31] the antibody-drug conjugate according to [30], wherein the antitumor compound is an antitumor compound represented by the following formula:

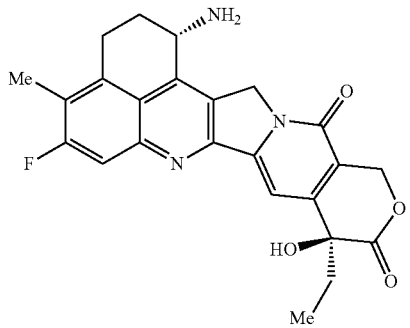

[Formula 1]

[32] the antibody-drug conjugate according to any one of [29] to [31], wherein the antibody is conjugated to the drug via a linker having any structure selected from the group consisting of the following formulas (a) to (f):
(a) -(Succinimid-3-yl-N)—$CH_2CH_2$—C(=O)-GGFG-NH—$CH_2CH_2CH_2$—C(=O)—,
(b) -(Succinimid-3-yl-N)—$CH_2CH_2CH_2CH_2CH_2$—C(=O)-GGFG-NH—$CH_2CH_2CH_2$—C(=O)—,
(c) -(Succinimid-3-yl-N)—$CH_2CH_2CH_2CH_2CH_2$—C(=O)-GGFG-NH—$CH_2$—O—$CH_2$—C(=O)—,
(d) -(Succinimid-3-yl-N)—$CH_2CH_2CH_2CH_2CH_2$—C(=O)-GGFG-NH—$CH_2CH_2$—O—$CH_2$—C(=O)—,
(e) -(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—, and
(f) -(Succinimid-3-yl-N)—$CH_2CH_2$—C(=O)—NH—$CH_2CH_2O$—$CH_2CH_2O$—$CH_2CH_2O$—$CH_2CH_2O$—$CH_2CH_2$—C(=O)-GGFG-NH—$CH_2CH_2CH_2$—C(=O)—, wherein the antibody is connected to the terminus of -(Succinimid-3-yl-N), the antitumor compound is connected to the carbonyl group of the —$CH_2CH_2CH_2$—C(=O)— moiety of (a), (b), (e) or (f), the $CH_2$—O—$CH_2$—C(=O)— moiety of (c) or the $CH_2CH_2$—O—$CH_2$—C(=O)— moiety of (d) with the nitrogen atom of the amino group at position 1 as a connecting position, GGFG represents an amino acid sequence consisting of glycine-glycine-phenylalanine-glycine linked through peptide bonds, and -(Succinimid-3-yl-N)— has a structure represented by the following formula:

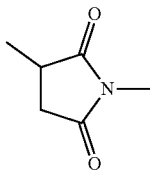

[Formula 2]

which is connected to the antibody at position 3 thereof and is connected to a methylene group in the linker structure containing this structure on the nitrogen atom at position 1;
[33] the antibody-drug conjugate according to any one of [29] to [32], wherein the linker is represented by any formula selected from the group consisting of the following formulas (c), (d) and (e):
(c) -(Succinimid-3-yl-N)—$CH_2CH_2CH_2CH_2CH_2$—C(=O)-GGFG-NH—$CH_2$—O—$CH_2$—C(=O)—,
(d) -(Succinimid-3-yl-N)—$CH_2CH_2CH_2CH_2CH_2$—C(=O)-GGFG-NH—$CH_2CH_2$—O—$CH_2$—C(=O)—, and
(e) -(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—;
[34] the antibody-drug conjugate according to any one of [29] to [33], wherein the linker is represented by the following formula (c) or (e):
(c) -(Succinimid-3-yl-N)—$CH_2CH_2CH_2CH_2CH_2$—C(=O)-GGFG-NH—$CH_2$—O—$CH_2$—C(=O)—, and
(e) -(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—;
[35] the antibody-drug conjugate according to any one of [29] to [34], which has a structure represented by the following formula:

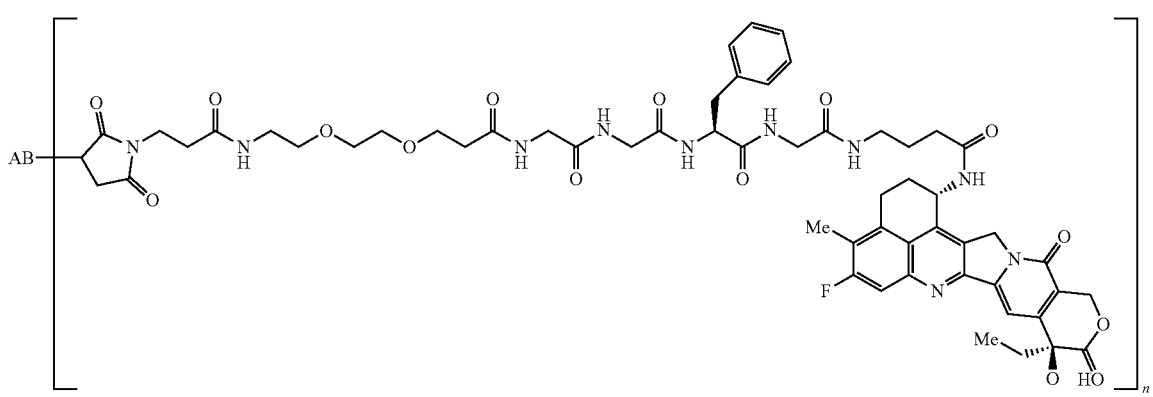

[Formula 3]

wherein AB represents the antibody or the functional fragment of the antibody, n represents the average number of units of the drug-linker structure conjugated to the antibody per antibody, and the antibody is connected to the linker via a sulfhydryl group derived from the antibody;
[36] the antibody-drug conjugate according to any one of [29] to [34], which has a structure represented by the following formula:

[Formula 4]

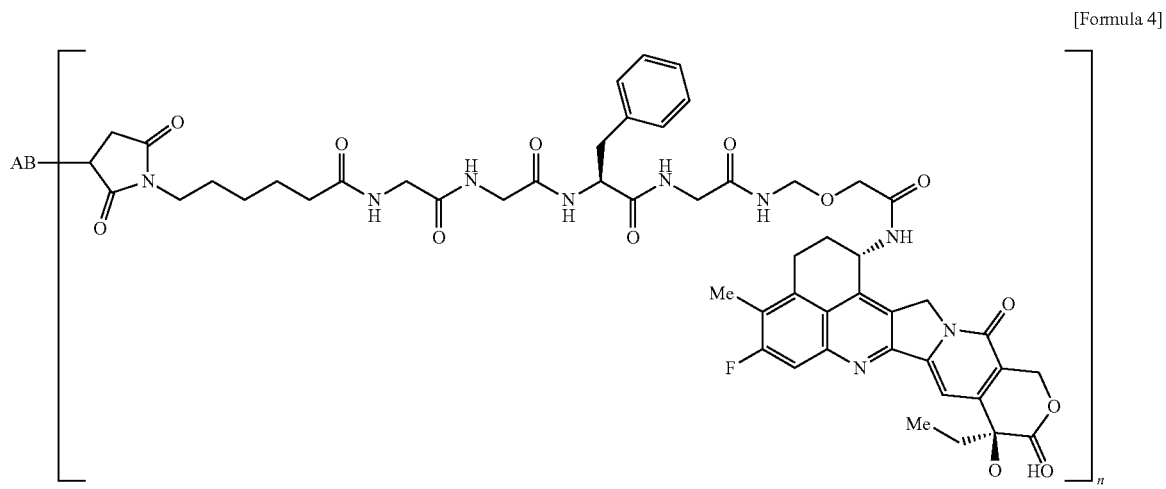

wherein AB represents the antibody or the functional fragment of the antibody, n represents the average number of units of the drug-linker structure conjugated to the antibody per antibody, and the antibody is connected to the linker via a sulfhydryl group derived from the antibody;

[37] the antibody-drug conjugate according to any one of [29] to [36], wherein the antibody is an antibody comprising a light chain and a heavy chain in any one combination selected from the group consisting of the following combinations (1) to (4), or a functional fragment of the antibody:
(1) a light chain consisting of the amino acid sequence at positions 21 to 233 in SEQ ID NO: 61 and a heavy chain consisting of the amino acid sequence at positions 20 to 471 in SEQ ID NO: 69,
(2) a light chain consisting of the amino acid sequence at positions 21 to 233 in SEQ ID NO: 61 and a heavy chain consisting of the amino acid sequence at positions 20 to 471 in SEQ ID NO: 73,
(3) a light chain consisting of the amino acid sequence at positions 21 to 233 in SEQ ID NO: 65 and a heavy chain consisting of the amino acid sequence at positions 20 to 471 in SEQ ID NO: 73, and
(4) a light chain consisting of the amino acid sequence at positions 21 to 233 in SEQ ID NO: 61 and a heavy chain consisting of the amino acid sequence at positions 20 to 471 in SEQ ID NO: 77;

[38] the antibody-drug conjugate according to [37], wherein the antibody is an antibody comprising a light chain consisting of the amino acid sequence at positions 21 to 233 in SEQ ID NO: 61 and a heavy chain consisting of the amino acid sequence at positions 20 to 471 in SEQ ID NO: 69, or a functional fragment of the antibody;

[39] the antibody-drug conjugate according to [37], wherein the antibody is an antibody comprising a light chain consisting of the amino acid sequence at positions 21 to 233 in SEQ ID NO: 61 and a heavy chain consisting of the amino acid sequence at positions 20 to 471 in SEQ ID NO: 77, or a functional fragment of the antibody;

[40] the antibody-drug conjugate according to any one of [29] to [39], wherein the heavy chain or the light chain has undergone one or two or more modifications selected from the group consisting of N-linked glycosylation, O-linked glycosylation, N-terminal processing, C-terminal processing, deamidation, isomerization of aspartic acid, oxidation of methionine, addition of a methionine residue to the N-terminus, amidation of a proline residue, conversion of N-terminal glutamine or N-terminal glutamic acid to pyroglutamic acid, and a deletion of one or two amino acids from the carboxyl terminus;

[41] the antibody-drug conjugate according to any one of [29] to [40], wherein the average number of units of the selected drug-linker structure conjugated per antibody is in the range of from 1 to 10;

[42] the antibody-drug conjugate according to [41], wherein the average number of units of the selected drug-linker structure conjugated per antibody is in the range of from 2 to 8;

[43] the antibody-drug conjugate according to [42], wherein the average number of units of the selected drug-linker structure conjugated per antibody is in the range of from 5 to 8;

[44] the antibody-drug conjugate according to [43], wherein the average number of units of the selected drug-linker structure conjugated per antibody is in the range of from 7 to 8;

[45] a pharmaceutical composition comprising the antibody-drug conjugate according to any one of [29] to [44], a salt thereof, or a hydrate of the conjugate or the salt;

[46] the pharmaceutical composition according to [45], which is an antitumor drug;

[47] the pharmaceutical composition according to [46], wherein the tumor is a tumor expressing CDH6;

[48] the pharmaceutical composition according to [46] or [47], wherein the tumor is renal cell carcinoma, renal clear cell carcinoma, papillary renal cell carcinoma, ovarian cancer, ovarian serous adenocarcinoma, thyroid cancer, bile duct cancer, lung cancer, small-cell lung cancer, glioblastoma, mesothelioma, uterine cancer, pancreatic cancer, Wilms' tumor or neuroblastoma;

[49] a method for treating a tumor, which comprises administering any component selected from the antibody-drug conjugate according to any one of [29] to [44], a salt thereof, and a hydrate of the conjugate or the salt to an individual;

[50] the treatment method according to [49], wherein the tumor is a tumor expressing CDH6;

[51] the treatment method according to [49] or [50], wherein the tumor is renal cell carcinoma, renal clear cell carcinoma, papillary renal cell carcinoma, ovarian cancer, ovarian serous adenocarcinoma, thyroid cancer, bile duct cancer, lung cancer, small-cell lung cancer, glioblastoma, mesothelioma, uterine cancer, pancreatic cancer, Wilms' tumor or neuroblastoma;

[52] a method for treating a tumor, which comprises administering a pharmaceutical composition comprising at least one component selected from the antibody-drug conjugate according to any one of [29] to [44], a salt thereof, and a hydrate of the conjugate or the salt, and at least one antitumor drug to an individual, simultaneously, separately, or continuously;

[53] a method for producing an antibody-drug conjugate, which comprises the step of reacting the antibody or the functional fragment of the antibody according to any one of [1] to [13] and [24] to [28], or an antibody or a functional fragment of the antibody obtained by the production method according to [23] with a drug-linker intermediate compound; and

[54] a method for producing an antibody-drug conjugate, which comprises the step of culturing the host cells according to [21] or [22], the step of collecting an antibody of interest or a functional fragment of the antibody from the culture obtained by the aforementioned step, and the step of reacting the antibody or the functional fragment of the antibody obtained by the aforementioned step with a drug-linker intermediate compound.

Advantageous Effects of Invention

Features of the anti-CDH6 antibody of the present invention are to specifically recognize EC domain 3 (EC3) of CDH6 and to have high internalization activity. An anti-CDH6 antibody-drug conjugate comprising the anti-CDH6 antibody of the present invention conjugated to a drug exerting toxicity in cells via a linker having a specific structure can be expected to achieve an excellent antitumor effect and safety by administration to patients having cancer cells expressing CDH6. Specifically, the anti-CDH6 antibody-drug conjugate of the present invention is useful as an antitumor agent.

BRIEF DESCRIPTION OF DRAWINGS

FIG. 1 shows flow cytometry results of examining the binding of four rat anti-CDH6 monoclonal antibodies (clone Nos. rG019, rG055, rG056 and rG061) or rat IgG control to control cells or hCDH6-transfected 293T cells. The abscissa depicts FITC fluorescence intensity indicating the amount of the antibody bound, and the ordinate depicts cell count.

FIG. 2-1 shows the binding activity of four rat anti-CDH6 monoclonal antibodies (rG019, rG055, rG056 and rG061) or negative control antibody Rat IgG2b against control cells or full-length hCDH6-transfected 293 cells. The abscissa depicts FITC fluorescence intensity indicating the amount of the antibody bound, and the ordinate depicts cell count.

FIG. 2-2 shows the binding activity of four rat anti-CDH6 monoclonal antibodies (rG019, rG055, rG056 and rG061) or rat IgG control against control cells or EC1-deleted hCDH6-transfected 293 cells. The abscissa depicts FITC fluorescence intensity indicating the amount of the antibody bound, and the ordinate depicts cell count.

FIG. 2-3 shows the binding activity of four rat anti-CDH6 monoclonal antibodies (rG019, rG055, rG056 and rG061) or rat IgG control against control cells or EC2-deleted hCDH6-transfected 293 cells. The abscissa depicts FITC fluorescence intensity indicating the amount of the antibody bound, and the ordinate depicts cell count.

FIG. 2-4 shows the binding activity of four rat anti-CDH6 monoclonal antibodies (rG019, rG055, rG056 and rG061) or rat IgG control against control cells or EC3-deleted hCDH6-transfected 293 cells. The abscissa depicts FITC fluorescence intensity indicating the amount of the antibody bound, and the ordinate depicts cell count.

FIG. 2-5 shows the binding activity of four rat anti-CDH6 monoclonal antibodies (rG019, rG055, rG056 and rG061) or rat IgG control against control cells or EC4-deleted hCDH6-transfected 293 cells. The abscissa depicts FITC fluorescence intensity indicating the amount of the antibody bound, and the ordinate depicts cell count.

FIG. 2-6 shows the binding activity of four rat anti-CDH6 monoclonal antibodies (rG019, rG055, rG056 and rG061) or rat IgG control against control cells or EC5-deleted hCDH6-transfected 293 cells. The abscissa depicts FITC fluorescence intensity indicating the amount of the antibody bound, and the ordinate depicts cell count.

FIG. 3 shows flow cytometry results of evaluating the expression of CDH6 on the cell membrane surface of 4 types of human tumor cell lines (human ovarian tumor cell lines NIH:OVCAR-3, PA-1, and ES-2 and human renal cell tumor cell line 786-O). The abscissa depicts FITC fluorescence intensity indicating the amount of the antibody bound, and the ordinate depicts cell count.

FIG. 4 shows a graph on which the internalization activity of 4 types of rat anti-CDH6 antibodies (rG019, rG055, rG056 and rG061) or rat IgG control was evaluated in NIH:OVCAR-3 cells and 786-O cells using anti-rat IgG reagent Rat-ZAP conjugated with a toxin (saporin) inhibiting protein synthesis, or Goat Anti-Rat IgG, Fc (gamma) Fragment Specific unconjugated with the toxin as a negative control. The ordinate of the graph depicts ATP activity (RLU). A cell survival rate (%), calculated as a relative survival rate when the number of live cells in a well supplemented with the negative control instead of Rat-ZAP was defined as 100%, is shown below each graph.

FIG. 5 shows the binding of human chimeric anti-CDH6 antibody chG019 to human CDH6 and monkey CDH6. The abscissa depicts antibody concentration, and the ordinate depicts the amount of antibody bound based on mean fluorescence intensity.

FIGS. 6-1 and 6-2 each show the binding activity of four humanized hG019 antibodies (H01L02, H02L02, H02L03 and H04L02) or a negative control antibody human IgG1 against human CDH6, monkey CDH6, mouse CDH6, and rat CDH6. The abscissa depicts antibody concentration, and the ordinate depicts the amount of the antibody bound based on mean fluorescence intensity.

FIGS. 6-1 and 6-2 each show the binding activity of four humanized hG019 antibodies (H01L02, H02L02, H02L03 and H04L02) or negative control antibody human IgG1 against human CDH6, monkey CDH6, mouse CDH6, and rat CDH6. The abscissa depicts antibody concentration, and the ordinate depicts the amount of the antibody bound based on mean fluorescence intensity.

FIG. 7-1 shows the binding activity of four humanized hG019 antibodies (H01L02, H02L02, H02L03 and H04L02), anti-CDH6 antibody NOV0712 or negative control antibody hIgG1 against control cells or full-length hCDH6-transfected 293α cells. The abscissa depicts APC fluorescence intensity indicating the amount of the antibody bound. The ordinate depicts cell count.

FIG. 7-2 shows the binding activity of four humanized hG019 antibodies (H01L02, H02L02, H02L03 and H04L02), anti-CDH6 antibody NOV0712 or negative control antibody hIgG1 against control cells or EC1-deleted hCDH6-transfected 293α cells. The abscissa depicts APC fluorescence intensity indicating the amount of the antibody bound. The ordinate depicts cell count.

FIG. 7-3 shows the binding activity of four humanized hG019 antibodies (H01L02, H02L02, H02L03 and H04L02), anti-CDH6 antibody NOV0712 or negative control antibody hIgG1 against control cells or EC2-deleted hCDH6-transfected 293α cells. The abscissa depicts APC fluorescence intensity indicating the amount of the antibody bound. The ordinate depicts cell count.

FIG. 7-4 shows the binding activity of four humanized hG019 antibodies (H01L02, H02L02, H02L03 and H04L02), anti-CDH6 antibody NOV0712 or negative control antibody hIgG1 against control cells or EC3-deleted hCDH6-transfected 293α cells. The abscissa depicts APC fluorescence intensity indicating the amount of the antibody bound. The ordinate depicts cell count.

FIG. 7-5 shows the binding activity of four humanized hG019 antibodies (H01L02, H02L02, H02L03 and H04L02), anti-CDH6 antibody NOV0712 or negative control hIgG1 against control cells or EC4-deleted hCDH6-transfected 293α cells. The abscissa depicts APC fluorescence intensity indicating the amount of the antibody bound. The ordinate depicts cell count.

FIG. 7-6 shows the binding activity of four humanized hG019 antibodies (H01L02, H02L02, H02L03 and H04L02), anti-CDH6 antibody NOV0712 or negative control hIgG1 against control cells or EC5-deleted hCDH6-transfected 293α cells. The abscissa depicts APC fluorescence intensity indicating the amount of the antibody bound. The ordinate depicts cell count.

FIG. 8 shows flow cytometry results of examining the expression of human CDH6 in 786-O/hCDH6 stably expressing cell line and its parent cell line 786-O. The abscissa depicts Alexa Fluor 647 fluorescence intensity indicating the amount of the antibody bound, and the ordinate depicts a cell count.

FIG. 9 shows the binding competition assay of four unlabeled humanized hG019 antibodies (H01L02, H02L02, H02L03 and H04L02), anti-CDH6 antibody NOV0712 or negative control hIgG1 using (a) labeled NOV0712 or (b) labeled H01L02. The abscissa depicts the final concentration of the added unlabeled antibody, and the ordinate depicts the amount of the antibody bound based on mean fluorescence intensity.

FIG. 10-1 shows a graph on which the internalization activity of four humanized hG019 antibodies (H01L02, H02L02, H02L03 and H04L02), anti-CDH6 antibody NOV0712 and a negative control antibody was evaluated in NIH:OVCAR-3 cells using anti-human IgG reagent Hum-ZAP conjugated with a toxin (saporin) inhibiting protein synthesis, or F(ab')2 Fragment Goat Anti-human IgG, Fc (gamma) Fragment Specific unconjugated with the toxin as a negative control. The ordinate of the graph depicts ATP activity (RLU). A cell survival rate (%), calculated as a relative survival rate when the number of live cells in a well supplemented with the negative control instead of Hum-ZAP was defined as 100%, is shown below each graph.

FIG. 10-2 shows a graph on which the internalization activity of four humanized hG019 antibodies (H01L02, H02L02, H02L03 and H04L02), anti-CDH6 antibody NOV0712 and a negative control antibody was evaluated in 786-O cells using anti-human IgG reagent Hum-ZAP conjugated with a toxin (saporin) inhibiting protein synthesis, or F(ab')2 Fragment Goat Anti-human IgG, Fc (gamma) Fragment Specific unconjugated with the toxin as a negative control. The ordinate of the graph depicts ATP activity (RLU). A cell survival rate (%), calculated as a relative survival rate when the number of live cells in a well supplemented with the negative control instead of Hum-ZAP was defined as 100%, is shown below each graph.

FIG. 10-3 shows a graph on which the internalization activity of four humanized hG019 antibodies (H01L02, H02L02, H02L03 and H04L02), anti-CDH6 antibody NOV0712 and a negative control antibody was evaluated in PA-1 cells using anti-human IgG reagent Hum-ZAP conjugated with a toxin (saporin) inhibiting protein synthesis, or F(ab')2 Fragment Goat Anti-human IgG, Fc (gamma) Fragment Specific unconjugated with the toxin as a negative control. The ordinate of the graph depicts ATP activity (RLU). A cell survival rate (%), calculated as a relative survival rate when the number of live cells in a well supplemented with the negative control instead of Hum-ZAP was defined as 100%, is shown below each graph.

FIG. 11 shows results of evaluating the in vitro cell growth inhibition activity of four humanized hG019-drug conjugates (H01L02-DXd, H02L02-DXd, H02L03-DXd and H04L02-DXd) or NOV0712-DM4 against PA-1 cells. The abscissa depicts an antibody-drug conjugate concentration, and the ordinate depicts cell survival rate (%).

FIG. 12 shows the in vivo antitumor effects of four humanized hG019-drug conjugates (H01L02-DXd, H02L02-DXd, H02L03-DXd and H04L02-DXd) or NOV0712-DM4. The evaluation was conducted using animal models in which CDH6-positive human renal cell tumor cell line 786-O was inoculated into immunodeficient mice. The abscissa depicts the number of days, and the ordinate depicts tumor volume. The error range depicts a standard error (SE) value.

FIG. 13 shows the in vivo antitumor effects of the humanized hG019-drug conjugate H01L02-DXd or NOV0712-DM4 or NOV0712-DXd. The evaluation was conducted using animal models in which CDH6-positive human ovarian tumor cell line PA-1 was inoculated into immunodeficient mice. The abscissa depicts the number of days, and the ordinate depicts tumor volume. The error range depicts a SE value.

FIG. 14 shows the in vivo antitumor effects of the humanized hG019-drug conjugate H01L02-DXd or NOV0712-DM4. The evaluation was conducted using animal models in which CDH6-positive human ovarian tumor cell line NIH:OVCAR-3 was inoculated into immunodeficient mice. The abscissa depicts the number of days, and the ordinate depicts tumor volume. The error range depicts a SE value.

FIG. 15 shows the in vivo antitumor effects of the humanized hG019-drug conjugate H01L02-DXd or NOV0712-DM4. The evaluation was conducted using animal models in which CDH6-positive human renal cell tumor cell line 786-O was inoculated into immunodeficient mice. The abscissa depicts the number of days, and the ordinate depicts tumor volume. The error range depicts a SE value.

FIG. 16 shows the in vivo antitumor effects of the humanized hG019-drug conjugate H01L02-DXd or NOV0712-DM4. The evaluation was conducted using animal models in which CDH6-negative human ovarian tumor cell line ES-2 was inoculated into immunodeficient mice. The abscissa depicts the number of days, and the ordinate depicts tumor volume. The error range depicts a SE value.

DESCRIPTION OF EMBODIMENTS

Hereinafter, the preferred embodiments for carrying out the present invention will be described with reference to the drawings. It is to be noted that the embodiments described below merely illustrate the representative embodiments of the present invention, and the scope of the present invention shall not be narrowly interpreted due to these examples.

In the present description, the term "cancer" is used to have the same meaning as that of the term "tumor".

In the present description, the term "gene" is used to include not only DNA but also its mRNA and cDNA, and cRNA thereof.

In the present description, the term "polynucleotide" or "nucleotide" is used to have the same meaning as that of a nucleic acid, and also includes DNA, RNA, a probe, an oligonucleotide, and a primer. In the present description, the terms "polynucleotide" and "nucleotide" can be used interchangeably with each other unless otherwise specified.

In the present description, the terms "polypeptide" and "protein" can be used interchangeably with each other.

In the present description, the term "cell" includes cells in an individual animal, and cultured cells.

In the present description, the term "CDH6" can be used to have the same meaning as that of the CDH6 protein. In the present description, human CDH6 is also referred to as "hCDH6".

In the present description, the term "cytotoxic activity" is used to mean that a pathologic change is caused to cells in any given way. The term not only means a direct trauma, but also means all types of structural or functional damage caused to cells, such as DNA cleavage, formation of a base dimer, chromosomal cleavage, damage to cell mitotic apparatus, and a reduction in the activities of various types of enzymes.

In the present description, the phrase "exerting toxicity in cells" is used to mean that toxicity is exhibited in cells in any given way. The term not only means a direct trauma, but also means all types of structural, functional, or metabolic influences caused to cells, such as DNA cleavage, formation of a base dimer, chromosomal cleavage, damage to cell mitotic apparatus, a reduction in the activities of various types of enzymes, and suppression of effects of cell growth factors.

In the present description, the term "functional fragment of an antibody", also called "antigen-binding fragment of an antibody", is used to mean a partial fragment of the antibody having binding activity against an antigen, and includes Fab, F(ab')2, scFv, a diabody, a linear antibody and a multispecific antibody formed from antibody fragments, and the like. Fab', which is a monovalent fragment of antibody variable regions obtained by treating F(ab')2 under reducing conditions, is also included in the antigen-binding fragment of an antibody. However, the antigen-binding fragment of an antibody is not limited to these molecules, as long as the antigen-binding fragment has antigen-binding ability. These antigen-binding fragments include not only those obtained by treating a full-length molecule of an antibody protein with an appropriate enzyme, but proteins produced in appropriate host cells using a genetically engineered antibody gene.

In the present description, the term "epitope" is used to mean the partial peptide or partial three-dimensional structure of CDH6, to which a specific anti-CDH6 antibody binds. Such an epitope, which is the above-described partial peptide of CDH6, can be determined by a method well known to a person skilled in the art, such as an immunoassay. First, various partial structures of an antigen are produced. As regards production of such partial structures, a known oligopeptide synthesis technique can be applied. For example, a series of polypeptides, in which CDH6 has been successively truncated at an appropriate length from the C-terminus or N-terminus thereof, are produced by a genetic recombination technique well known to a person skilled in the art. Thereafter, the reactivity of an antibody to such polypeptides is studied, and recognition sites are roughly determined. Thereafter, further shorter peptides are synthesized, and the reactivity thereof to these peptides can then be studied, so as to determine an epitope. When an antibody binding to a membrane protein having a plurality of extracellular domains is directed to a three-dimensional structure composed of a plurality of domains as an epitope, the domain to which the antibody binds can be determined by modifying the amino acid sequence of a specific extracellular domain, and thereby modifying the three-dimensional structure. The epitope, which is a partial three-dimensional structure of an antigen that binds to a specific antibody, can also be determined by specifying the amino acid residues of an antigen adjacent to the antibody by X-ray structural analysis.

In the present description, the phrase "antibodies binding to the same epitope" is used to mean antibodies that bind to a common epitope. If a second antibody binds to a partial peptide or a partial three-dimensional structure to which a first antibody binds, it can be determined that the first antibody and the second antibody bind to the same epitope. Alternatively, by confirming that a second antibody competes with a first antibody for the binding of the first antibody to an antigen (i.e., a second antibody interferes with the binding of a first antibody to an antigen), it can be determined that the first antibody and the second antibody bind to the same epitope, even if the specific sequence or structure of the epitope has not been determined. In the present description, the phrase "binding to the same epitope" refers to the case where it is determined that the first antibody and the second antibody bind to a common epitope by any one or both of these determination methods. When a first antibody and a second antibody bind to the same epitope and further, the first antibody has special effects such as antitumor activity or internalization activity, the second antibody can be expected to have the same activity as that of the first antibody.

In the present description, the term "CDR" is used to mean a complementarity determining region. It is known that the heavy chain and light chain of an antibody molecule each have three CDRs. Such a CDR is also referred to as a hypervariable region, and is located in the variable regions of the heavy chain and light chain of an antibody. These regions have a particularly highly variable primary structure and are separated into three sites on the primary structure of the polypeptide chain in each of the heavy chain and light chain. In the present description, with regard to the CDR of an antibody, the CDRs of a heavy chain are referred to as CDRH1, CDRH2 and CDRH3, respectively, from the amino-terminal side of the amino acid sequence of the heavy chain, whereas the CDRs of a light chain are referred to as CDRL1, CDRL2 and CDRL3, respectively, from the amino-terminal side of the amino acid sequence of the light chain. These sites are located close to one another on the three-dimensional structure, and determine the specificity of the antibody to an antigen to which the antibody binds.

In the present invention, the phrase "hybridizing under stringent conditions" is used to mean that hybridization is carried out in the commercially available hybridization solution ExpressHyb Hybridization Solution (manufactured by Clontech Laboratories, Inc.) at 68° C., or that hybridization is carried out under conditions in which hybridization is carried out using a DNA-immobilized filter in the presence of 0.7 to 1.0 M NaCl at 68° C., and the resultant is then washed at 68° C. with a 0.1- to 2-fold concentration of SSC solution (wherein 1-fold concentration of SSC consists of 150 mM NaCl and 15 mM sodium citrate) for identification, or conditions equivalent thereto.

In the present description, the term "one to several" is used to mean 1 to 10, 1 to 9, 1 to 8, 1 to 7, 1 to 6, 1 to 5, 1 to 4, 1 to 3, or 1 or 2.

1. CDH6

Cadherins are glycoproteins present on the surface of cell membranes and function as cell-cell adhesion molecules through the calcium ion-dependent binding of their N-terminal extracellular domains, or as signal molecules responsible for cell-cell interaction. Classic cadherins are in the cadherin superfamily and are single-pass transmembrane proteins composed of five extracellular domains (EC domains), one transmembrane region, and an intracellular domain.

CDH6 (cadherin-6) is a single-pass transmembrane protein composed of 790 amino acids, which is classified into the type II cadherin family, and this protein has N-terminal extracellular and C-terminal intracellular domains. The human CDH6 gene was cloned for the first time in 1995 (Non Patent Literature 1), and its sequence can be referred to under, for example, accession Nos. NM_004932 and NP_004923 (NCBI).

The CDH6 protein used in the present invention can be directly purified from the CDH6-expressing cells of a human or a non-human mammal (e.g., a rat, a mouse or a monkey) and can then be used, or a cell membrane fraction of the aforementioned cells can be prepared and can be used as the CDH6 protein. Alternatively, CDH6 can also be obtained by synthesizing it in vitro, or by allowing host cells to produce CDH6 by genetic manipulation. According to such genetic manipulation, the CDH6 protein can be obtained, specifically, by incorporating CDH6 cDNA into a vector capable of expressing the CDH6 cDNA, and then synthesizing CDH6 in a solution containing enzymes, substrate and energetic materials necessary for transcription and translation, or by transforming the host cells of other prokaryotes or eukaryotes, so as to allow them to express CDH6. Also, CDH6-expressing cells based on the above-described genetic manipulation, or a cell line expressing CDH6 may be used to present the CDH6 protein. Alternatively, the expression vector into which CDH6 cDNA has been incorporated can be directly administered to an animal to be immunized, and CDH6 can be expressed in the body of the animal thus immunized.

Moreover, a protein which consists of an amino acid sequence comprising a substitution, deletion and/or addition of one or several amino acids in the above-described amino acid sequence of CDH6, and has a biological activity equivalent to that of the CDH6 protein, is also included within the term "CDH6".

The human CDH6 protein has the amino acid sequence shown in SEQ ID NO: 1. The extracellular region of the human CDH6 protein is composed of extracellular domain 1 (in the present description, also referred to as EC1) having the amino acid sequence at positions 54 to 159 in the amino acid sequence shown in SEQ ID NO: 1, extracellular domain 2 (in the present description, also referred to as EC2) having the amino acid sequence at positions 160 to 268 in the amino acid sequence shown in SEQ ID NO: 1, extracellular domain 3 (in the present description, also referred to as EC3) having the amino acid sequence at positions 269 to 383 in the amino acid sequence shown in SEQ ID NO: 1, extracellular domain 4 (in the present description, also referred to as EC4) having the amino acid sequence at positions 384 to 486 in the amino acid sequence shown in SEQ ID NO: 1, and extracellular domain 5 (in the present description, also referred to as EC5) having the amino acid sequence at positions 487 to 608 in the amino acid sequence shown in SEQ ID NO: 1. The amino acid sequences of EC1 to EC5 are shown in SEQ ID NOs: 2 to 6, respectively (Table 1).

2. Production of Anti-CDH6 Antibody

One example of the anti-CDH6 antibody of the present invention can include an anti-CDH6 antibody which recognizes an amino acid sequence comprising the amino acid sequence shown in SEQ ID NO: 4, and has internalization activity. One example of the anti-CDH6 antibody of the present invention can include an anti-CDH6 antibody which specifically recognizes an amino acid sequence comprising the amino acid sequence shown in SEQ ID NO: 4, and has internalization activity. One example of the anti-CDH6 antibody of the present invention can include an anti-CDH6 antibody which recognizes an amino acid sequence consisting of the amino acid sequence shown in SEQ ID NO: 4, and has internalization activity. One example of the anti-CDH6 antibody of the present invention can include an anti-CDH6 antibody which specifically recognizes an amino acid sequence consisting of the amino acid sequence shown in SEQ ID NO: 4, and has internalization activity. The phrase "specifically recognize an amino acid sequence comprising the amino acid sequence shown in SEQ ID NO: 4" or "specifically recognize an EC3 domain" as applied to an antibody is used to mean that the antibody strongly recognizes or strongly binds to the EC3 domain of CDH6 compared with the other extracellular domains of CDH6.

The anti-CDH6 antibody of the present invention may be derived from any species. Preferred examples of the species can include humans, monkeys, rats, mice and rabbits. When the anti-CDH6 antibody of the present invention is derived from a species other than humans, it is preferred to chimerize or humanize the anti-CDH6 antibody by a well-known technique. The antibody of the present invention may be a polyclonal antibody or may be a monoclonal antibody, and a monoclonal antibody is preferred.

The anti-CDH6 antibody of the present invention is an antibody that can target tumor cells. Specifically, the anti-CDH6 antibody of the present invention possesses the property of being able to recognize tumor cells, the property of being able to bind to tumor cells, and/or the property of being internalized into tumor cells by cellular uptake, and the like. Accordingly, the anti-CDH6 antibody of the present invention can be conjugated to a compound having antitumor activity via a linker to prepare an antibody-drug conjugate.

The binding activity of an antibody against tumor cells can be confirmed by flow cytometry. The uptake of an antibody into tumor cells can be confirmed by (1) an assay of visualizing a cellularly taken-up antibody under a fluorescent microscope using a secondary antibody (fluorescently labeled) binding to the antibody (Cell Death and Differentiation, 2008, 15, 751-761), (2) an assay of measuring the amount of cellularly taken-up fluorescence using a secondary antibody (fluorescently labeled) binding to the antibody (Molecular Biology of the Cell Vol. 15, 5268-5282, December 2004) or (3) a Mab-ZAP assay using an immunotoxin binding to the antibody, wherein the toxin is released upon cellular uptake, so as to suppress cell growth (Bio Techniques 28: 162-165, January 2000). A recombinant conjugated protein of a catalytic region of diphtheria toxin and protein G may be used as the immunotoxin.

In the present description, the term "high internalization ability" is used to mean that the survival rate (which is indicated by a ratio relative to a cell survival rate without antibody addition defined as 100%) of CDH6-expressing cells to which the aforementioned antibody and a saporin-labeled anti-rat IgG antibody have been administered is preferably 70% or less, and more preferably 60% or less.

The antitumor antibody-drug conjugate of the present invention comprises a conjugated compound exerting an antitumor effect. Therefore, it is preferred, but not essential, that the antibody itself should have an antitumor effect. For the purpose of specifically and/or selectively exerting the cytotoxicity of the antitumor compound in tumor cells, it is important and preferred that the antibody should have a property of being internalized and transferred into tumor cells.

The anti-CDH6 antibody can be obtained by immunizing an animal with a polypeptide serving as an antigen by a method usually performed in this field, and then collecting and purifying an antibody produced in a living body thereof. It is preferred to use CDH6 retaining a three-dimensional structure as an antigen. Examples of such a method can include a DNA immunization method.

The origin of the antigen is not limited to a human, and thus, an animal can also be immunized with an antigen derived from a non-human animal such as a mouse or a rat. In this case, an antibody applicable to the disease of a human can be selected by examining the cross-reactivity of the obtained antibody binding to the heterologous antigen with the human antigen.

Furthermore, antibody-producing cells that produce an antibody against the antigen can be fused with myeloma cells according to a known method (e.g., Kohler and Milstein, Nature (1975) 256, 495-497; and Kennet, R. ed., Monoclonal Antibodies, 365-367, Plenum Press, N. Y. (1980)) to establish hybridomas, so as to obtain a monoclonal antibody.

Hereinafter, the method for obtaining an antibody against CDH6 will be specifically described.

(1) Preparation of Antigen

The antigen can be obtained by allowing host cells to produce a gene encoding the antigen protein according to genetic manipulation. Specifically, a vector capable of expressing the antigen gene is produced, and the vector is then introduced into host cells, so that the gene is expressed therein, and thereafter, the expressed antigen may be purified. The antibody can also be obtained by a method of immunizing an animal with the antigen-expressing cells based on the above-described genetic manipulation, or a cell line expressing the antigen.

Alternatively, the antibody can also be obtained, without the use of the antigen protein, by incorporating cDNA of the antigen protein into an expression vector, then administering the expression vector to an animal to be immunized, and expressing the antigen protein in the body of the animal thus immunized, so that an antibody against the antigen protein is produced therein.

(2) Production of Anti-CDH6 Monoclonal Antibody

The anti-CDH6 antibody used in the present invention is not particularly limited. For example, an antibody specified by an amino acid sequence shown in the sequence listing of the present application can be suitably used. The anti-CDH6 antibody used in the present invention is desirably an antibody having the following properties:

(1) an antibody having the following properties:
(a) specifically binding to CDH6, and
(b) having the activity of being internalized into CDH6-expressing cells by binding to CDH6;

(2) the antibody according to the above (1), wherein the CDH6 is human CDH6; or (3) the antibody according to the above (1) or (2, wherein the antibody specifically recognizes EC3 of human CDH6, and has internalization activity.

The method for obtaining the antibody against CDH6 of the present invention is not particularly limited as long as an anti-CDH6 antibody can be obtained. It is preferred to use CDH6 retaining its conformation as an antigen.

One preferred example of the method for obtaining the antibody can include a DNA immunization method. The DNA immunization method is an approach which involves transfecting an animal (e.g., mouse or rat) individual with an antigen expression plasmid, and then expressing the antigen in the individual to induce immunity against the antigen. The transfection approach includes a method of directly injecting the plasmid to the muscle, a method of injecting a transfection reagent such as a liposome or polyethylenimine to the vein, an approach using a viral vector, an approach of injecting gold particles attached with the plasmid using a gene gun, a hydrodynamic method of rapidly injecting a plasmid solution in a large amount to the vein, and the like. With regard to the transfection method of injecting the expression plasmid to the muscle, a technique called in vivo electroporation, which involves applying electroporation to the intramuscular injection site of the plasmid, is known as an approach for improving expression levels (Aihara H, Miyazaki J. Nat Biotechnol. 1998 September; 16 (9): 867-70 or Mir L M, Bureau M F, Gehl J, Rangara R, Rouy D, Caillaud J M, Delaere P, Branellec D, Schwartz B, Scherman D. Proc Natl Acad Sci USA. 1999 Apr. 13; 96 (8): 4262-7). This approach further improves the expression level by treating the muscle with hyaluronidase before the intramuscular injection of the plasmid (McMahon J M1, Signori E, Wells K E, Fazio V M, Wells D J., Gene Ther. 2001 August; (16): 1264-70). Furthermore, the hybridoma production can be performed by a known method, and can also be performed using, for example, a Hybrimune Hybridoma Production System (Cyto Pulse Sciences, Inc.).

Specific examples of obtaining a monoclonal antibody can include the following procedures:

(a) immune response can be induced by incorporating CDH6 cDNA into an expression vector (e.g., pcDNA3.1; Thermo Fisher Scientific Inc.), and directly administering the vector to an animal (e.g., a rat or a mouse) to be immunized by a method such as electroporation or a gene gun, so as to express CDH6 in the body of the animal. The administration of the vector by electroporation or the like may be performed one or more times, preferably a plurality of times, if necessary for enhancing antibody titer;

(b) collection of tissue (e.g., a lymph node) containing antibody-producing cells from the aforementioned animal in which the immune response has been induced;

(c) preparation of myeloma cells (hereinafter, referred to as "myelomas") (e.g., mouse myeloma SP2/0-ag14 cells);

(d) cell fusion between the antibody-producing cells and the myelomas;

(e) selection of a hybridoma group producing an antibody of interest;

(f) division into single cell clones (cloning);

(g) optionally, the culture of hybridomas for the mass production of monoclonal antibodies, or the breeding of animals into which the hybridomas are inoculated; and/or (h) study of the physiological activity (internalization activity) and binding specificity of the monoclonal antibody thus produced, or examination of the properties of the antibody as a labeling reagent.

Examples of the method for measuring the antibody titer used herein can include, but are not limited to, flow cytometry and Cell-ELISA.

Examples of the hybridoma strain thus established can include anti-CDH6 antibody-producing hybridomas rG019, rG055, rG056 and rG061. It is to be noted that, in the present description, an antibody produced by the anti-CDH6 antibody-producing hybridoma rG019 is referred to as a "rG019 antibody" or simply "rG019", an antibody produced by the hybridoma rG055 is referred to as a "rG055 antibody" or simply "rG055", an antibody produced by the hybridoma rG056 is referred to as a "rG056 antibody" or simply "rG056", and an antibody produced by the hybridoma rG061 is referred to as a "rG061 antibody" or simply "rG061".

The light chain variable region of the rG019 antibody consists of the amino acid sequence shown in SEQ ID NO: 10. The amino acid sequence of the light chain variable region of the rG019 antibody is encoded by the nucleotide sequence shown in SEQ ID NO: 11. The light chain variable region of the rG019 antibody has CDRL1 consisting of the amino acid sequence shown in SEQ ID NO: 12, CDRL2 consisting of the amino acid sequence shown in SEQ ID NO: 13, and CDRL3 consisting of the amino acid sequence shown in SEQ ID NO: 14. The heavy chain variable region of the rG019 antibody consists of the amino acid sequence shown in SEQ ID NO: 15. The amino acid sequence of the heavy chain variable region of the rG019 antibody is encoded by the nucleotide sequence shown in SEQ ID NO: 16. The heavy chain variable region of the rG019 antibody has CDRH1 consisting of the amino acid sequence shown in SEQ ID NO: 17, CDRH2 consisting of the amino acid sequence shown in SEQ ID NO: 18, and CDRH3 consisting of the amino acid sequence shown in SEQ ID NO: 19. The sequence of the rG019 antibody is shown in Table 1.

The light chain variable region of the rG055 antibody consists of the amino acid sequence shown in SEQ ID NO: 20. The amino acid sequence of the light chain variable region of the rG055 antibody is encoded by the nucleotide sequence shown in SEQ ID NO: 21. The light chain variable region of the rG055 antibody has CDRL1 consisting of the amino acid sequence shown in SEQ ID NO: 22, CDRL2 consisting of the amino acid sequence shown in SEQ ID NO: 23, and CDRL3 consisting of the amino acid sequence shown in SEQ ID NO: 24. The heavy chain variable region of the rG055 antibody consists of the amino acid sequence shown in SEQ ID NO: 25. The amino acid sequence of the heavy chain variable region of the rG055 antibody is encoded by the nucleotide sequence shown in SEQ ID NO: 26. The heavy chain variable region of the rG055 antibody has CDRH1 consisting of the amino acid sequence shown in SEQ ID NO: 27, CDRH2 consisting of the amino acid sequence shown in SEQ ID NO: 28, and CDRH3 consisting of the amino acid sequence shown in SEQ ID NO: 29. The sequence of the rG055 antibody is shown in Table 1.

The light chain variable region of the rG056 antibody consists of the amino acid sequence shown in SEQ ID NO: 30. The amino acid sequence of the light chain variable region of the rG056 antibody is encoded by the nucleotide sequence shown in SEQ ID NO: 31. The light chain variable region of the rG056 antibody has CDRL1 consisting of the amino acid sequence shown in SEQ ID NO: 32, CDRL2 consisting of the amino acid sequence shown in SEQ ID NO: 33, and CDRL3 consisting of the amino acid sequence shown in SEQ ID NO: 34. The heavy chain variable region of the rG056 antibody consists of the amino acid sequence shown in SEQ ID NO: 35. The amino acid sequence of the heavy chain variable region of the rG056 antibody is encoded by the nucleotide sequence shown in SEQ ID NO: 36. The heavy chain variable region of the rG056 antibody has CDRH1 consisting of the amino acid sequence shown in SEQ ID NO: 37, CDRH2 consisting of the amino acid sequence shown in SEQ ID NO: 38, and CDRH3 consisting of the amino acid sequence shown in SEQ ID NO: 39. The sequence of the rG056 antibody is shown in Table 1.

The light chain variable region of the rG061 antibody consists of the amino acid sequence shown in SEQ ID NO: 40. The amino acid sequence of the light chain variable region of the rG061 antibody is encoded by the nucleotide sequence shown in SEQ ID NO: 41. The light chain variable region of the rG061 antibody has CDRL1 consisting of the amino acid sequence shown in SEQ ID NO: 42, CDRL2 consisting of the amino acid sequence shown in SEQ ID NO: 43, and CDRL3 consisting of the amino acid sequence shown in SEQ ID NO: 44. The heavy chain variable region of the rG061 antibody consists of the amino acid sequence shown in SEQ ID NO: 45. The amino acid sequence of the heavy chain variable region of the rG061 antibody is encoded by the nucleotide sequence shown in SEQ ID NO: 46. The heavy chain variable region of the rG061 antibody has CDRH1 consisting of the amino acid sequence shown in SEQ ID NO: 47, CDRH2 consisting of the amino acid sequence shown in SEQ ID NO: 48, and CDRH3 consisting of the amino acid sequence shown in SEQ ID NO: 49. The sequence of the rG061 antibody is shown in Table 1.

Furthermore, in the case where the steps (a) to (h) in the above "2. Production of anti-CDH6 antibody" are carried out again to obtain independently a monoclonal antibody separately and also in the case where a monoclonal antibody is obtained separately by other methods, an antibody having internalization activity equivalent to that of the rG019 antibody, the rG055 antibody, the rG056 antibody or the rG061 antibody can be obtained. One example of such an antibody can include an antibody binding to the same epitope to which the rG019 antibody, the rG055 antibody, the rG056 antibody or the rG061 antibody binds. If a newly prepared monoclonal antibody binds to a partial peptide or a partial three-dimensional structure to which the rG019 antibody, the rG055 antibody, the rG056 antibody or the rG061 antibody binds, it can be determined that the monoclonal antibody binds to the same epitope to which the rG019 antibody, the rG055 antibody, the rG056 antibody or the rG061 antibody binds. Moreover, by confirming that the monoclonal antibody competes with the rG019 antibody, the rG055 antibody, the rG056 antibody or the rG061 antibody in the binding of the antibody to CDH6 (i.e., the monoclonal antibody interferes with the binding of the rG019 antibody, the rG055 antibody, the rG056 antibody or the rG061 antibody to CDH6), it can be determined that the monoclonal antibody binds to the same epitope to which the anti-CDH6 antibody binds, even if the specific sequence or structure of the epitope has not been determined. When it is confirmed that the monoclonal antibody binds to the same epitope to which the rG019 antibody, the rG055 antibody, the rG056 antibody or the rG061 antibody binds, then it is strongly expected that the monoclonal antibody should have antigen-binding ability, biological activity and/or internalization activity equivalent to that of the rG019 antibody, the rG055 antibody, the rG056 antibody or the rG061 antibody.

(3) Other Antibodies

The antibody of the present invention also includes genetically recombinant antibodies that have been artificially modified for the purpose of reducing heterogenetic antigenicity to humans, such as a chimeric antibody, a humanized antibody and a human antibody, as well as the above-described monoclonal antibody against CDH6. These antibodies can be produced by known methods.

Example of the chimeric antibody can include antibodies in which a variable region and a constant region are heterologous to each other, such as a chimeric antibody formed by conjugating the variable region of a mouse- or rat-derived antibody to a human-derived constant region (see Proc. Natl. Acad. Sci. U.S.A., 81, 6851-6855, (1984)).

Examples of the chimeric antibody derived from the rat anti-human CDH6 antibody include an antibody consisting of a light chain comprising the light chain variable region of each rat anti-human CDH6 antibody described in the present description (e.g., the rG019 antibody, the rG055 antibody, the rG056 antibody or the rG061 antibody) and a human-derived constant region, and a heavy chain comprising the heavy chain variable region thereof and a human-derived constant region.

Other examples of the chimeric antibody derived from the rat anti-human CDH6 antibody include an antibody consisting of a light chain comprising a light chain variable region having a substitution of one to several residues, 1 to 3 residues, 1 or 2 residues, preferably 1 residue, of amino acids in the light chain variable region of each rat anti-human CDH6 antibody described in the present description (e.g., the rG019 antibody, the rG055 antibody, the rG056 antibody or the rG061 antibody) with other amino acid residues, and a heavy chain comprising a heavy chain variable region having a substitution of one to several residues, 1 to 3 residues, 1 or 2 residues, preferably 1 residue, of amino acids in the heavy chain variable region thereof with other amino acid residues. This antibody may have any given human-derived constant region.

Other examples of the chimeric antibody derived from the rat anti-human CDH6 antibody include an antibody consisting of a light chain comprising a light chain variable region having a substitution of 1 or 2 residues, preferably 1 residue, of amino acids in any 1 to 3 CDRs in the light chain variable region of each rat anti-human CDH6 antibody described in the present description (e.g., the rG019 antibody, the rG055 antibody, the rG056 antibody or the rG061 antibody) with other amino acid residues, and a heavy chain comprising a heavy chain variable region having a substitution of 1 or 2 residues, preferably 1 residue, of amino acids in any 1 to 3 CDRs in the heavy chain variable region thereof with other amino acid residues. This antibody may have any given human-derived constant region.

Examples of the chimeric antibody derived from the rG019 antibody include an antibody consisting of a light chain comprising a light chain variable region consisting of the amino acid sequence shown in SEQ ID NO: 10, and a heavy chain comprising a heavy chain variable region consisting of the amino acid sequence shown in SEQ ID NO: 15. This antibody may have any given human-derived constant region.

Other examples of the chimeric antibody derived from the rG019 antibody include an antibody consisting of a light chain comprising a light chain variable region having a substitution of one to several residues, 1 to 3 residues, 1 or 2 residues, preferably 1 residue, of amino acids in the light chain variable region consisting of the amino acid sequence shown in SEQ ID NO: 10 with other amino acid residues, and a heavy chain comprising a heavy chain variable region having a substitution of one to several residues, 1 to 3 residues, 1 or 2 residues, preferably 1 residue, of amino acids in the heavy chain variable region consisting of the amino acid sequence shown in SEQ ID NO: 15 with other amino acid residues. This antibody may have any given human-derived constant region.

Other examples of the chimeric antibody derived from the rG019 antibody include an antibody consisting of a light chain comprising a light chain variable region having a substitution of 1 or 2 residues (preferably 1 residue) of amino acids in any 1 to 3 CDRs in the light chain variable region consisting of the amino acid sequence shown in SEQ ID NO: 10 with other amino acid residues, and a heavy chain comprising a heavy chain variable region having a substitution of 1 or 2 residues (preferably 1 residue) of amino acids in any 1 to 3 CDRs in the heavy chain variable region consisting of the amino acid sequence shown in SEQ ID NO: 15 with other amino acid residues. This antibody may have any given human-derived constant region.

Other examples of the chimeric antibody derived from the rG019 antibody include an antibody consisting of a light chain comprising a light chain variable region consisting of the amino acid sequence shown in SEQ ID NO: 10, and a heavy chain comprising a heavy chain variable region consisting of the amino acid sequence shown in SEQ ID NO: 58. This antibody may have any given human-derived constant region. The amino acid sequence shown in SEQ ID NO: 58 is a sequence with a cysteine residue substituted with a proline residue in CDRH2 in the amino acid sequence shown in SEQ ID NO: 15.

Specific examples of the chimeric antibody derived from the rG019 antibody include an antibody consisting of a light chain consisting of the light chain full-length amino acid sequence shown in SEQ ID NO: 53, and a heavy chain consisting of the heavy chain full-length amino acid sequence shown in SEQ ID NO: 56. In the present description, this chimeric anti-human CDH6 antibody is referred to as a "chimeric G019 antibody", a "chG019 antibody" or "chG019". The light chain full-length amino acid sequence of the chG019 antibody is encoded by the nucleotide sequence shown in SEQ ID NO: 54, and the heavy chain full-length amino acid sequence of the chG019 antibody is encoded by the nucleotide sequence shown in SEQ ID NO: 57.

The amino acid sequence of the light chain variable region of the chG019 antibody is identical to the amino acid sequence of the light chain variable region of the rG019 antibody, and consists of the amino acid sequence shown in SEQ ID NO: 10. The light chain of the chG019 antibody has CDRL1 consisting of the amino acid sequence shown in SEQ ID NO: 12, CDRL2 consisting of the amino acid sequence shown in SEQ ID NO: 13, and CDRL3 consisting of the amino acid sequence shown in SEQ ID NO: 14, which are identical to the light chain CDRL1, CDRL2 and CDRL3, respectively, of rG019. The amino acid sequence of the light chain variable region of the chG019 antibody is encoded by the nucleotide sequence shown in SEQ ID NO: 55.

The amino acid sequence of the heavy chain variable region of the chG019 antibody consists of the amino acid sequence shown in SEQ ID NO: 58. The heavy chain of the chG019 antibody has CDRH1 consisting of the amino acid sequence shown in SEQ ID NO: 17, CDRH2 consisting of the amino acid sequence shown in SEQ ID NO: 60, and CDRH3 consisting of the amino acid sequence shown in SEQ ID NO: 19. The amino acid sequence shown in SEQ ID NO: 58 is a sequence with a cysteine residue substituted with a proline residue in CDRH2 in the amino acid sequence shown in SEQ ID NO: 15. The CDRH2 consisting of the amino acid sequence shown in SEQ ID NO: 60 is a sequence with a cysteine residue substituted with a proline residue in the rG019 CDRH2 shown in SEQ ID NO: 18. The amino acid sequence of the heavy chain variable region of the chG019 antibody is encoded by the nucleotide sequence shown in SEQ ID NO: 59.

The sequence of the chG019 antibody is shown in Table 1.

Examples of the chimeric antibody derived from the rat anti-human CDH6 antibody rG055 antibody include a chimeric antibody consisting of a light chain comprising a light chain variable region consisting of the amino acid sequence shown in SEQ ID NO: 20, and a heavy chain comprising a heavy chain variable region consisting of the amino acid sequence shown in SEQ ID NO: 25. This antibody may have any given human-derived constant region.

Examples of the chimeric antibody derived from the rat anti-human CDH6 antibody rG056 antibody include a chimeric antibody consisting of a light chain comprising a light chain variable region consisting of the amino acid sequence shown in SEQ ID NO: 30, and a heavy chain comprising a heavy chain variable region consisting of the amino acid sequence shown in SEQ ID NO: 35. This antibody may have any given human-derived constant region.

Examples of the chimeric antibody derived from the rat anti-human CDH6 antibody rG061 antibody include a chimeric antibody consisting of a light chain comprising a light chain variable region consisting of the amino acid sequence shown in SEQ ID NO: 40, and a heavy chain comprising a heavy chain variable region consisting of the amino acid sequence shown in SEQ ID NO: 45. This antibody may have any given human-derived constant region.

Examples of the humanized antibody can include an antibody formed by incorporating only complementarity determining regions (CDRs) into a human-derived antibody (see Nature (1986) 321, p. 522-525), an antibody formed by incorporating the amino acid residues from some frameworks, as well as CDR sequences, into a human antibody according to a CDR grafting method (International Publication No. WO90/07861), and an antibody formed by modifying the amino acid sequences of some CDRs while maintaining antigen-binding ability.

In the present description, the humanized antibody derived from the rG019 antibody, the rG055 antibody, the rG056 antibody, the rG061 antibody or the chG019 antibody is not limited to a specific humanized antibody as long as the humanized antibody retains all 6 CDR sequences unique to the rG019 antibody, the rG055 antibody, the rG056 antibody, the rG061 antibody or the chG019 antibody and has internalization activity. The amino acid sequences of some CDRs of this humanized antibody may be further modified as long as it has internalization activity.

Concrete examples of the humanized antibody of the chG019 antibody can include any given combination of: a light chain comprising a light chain variable region consisting of any one amino acid sequence selected from the group consisting of (1) the amino acid sequence shown in SEQ ID NO: 63 or 67, (2) an amino acid sequence having an identity of at least 95% or more (preferably an amino acid sequence having a sequence identity of at least 95% or more to the sequence of a framework region other than at each CDR sequence) to the above-described amino acid sequence (1), and (3) an amino acid sequence comprising a deletion, substitution or addition of one or several amino acids in the above-described amino acid sequence (1); and a heavy chain comprising a heavy chain variable region consisting of any one amino acid sequence selected from the group consisting of (4) the amino acid sequence shown in SEQ ID NO: 71, 75 or 79, (5) an amino acid sequence having an identity of at least 95% or more (preferably an amino acid sequence having a sequence identity of at least 95% or more to the sequence of a framework region other than at each CDR sequence) to the above-described amino acid sequence (4), and (6) an amino acid sequence comprising a deletion, substitution or addition of one or several amino acids in the above-described amino acid sequence (4).

Alternatively, an antibody having a humanized heavy chain or light chain and the other chain derived from a rat antibody or a chimeric antibody can also be used. Examples of such an antibody can include any given combination of: a light chain comprising a light chain variable region consisting of any one amino acid sequence selected from the group consisting of (1) the amino acid sequence shown in SEQ ID NO: 63 or 67, (2) an amino acid sequence having an identity of at least 95% or more (preferably an amino acid sequence having a sequence identity of at least 95% or more to the sequence of a framework region other than at each CDR sequence) to the above-described amino acid sequence (1), and (3) an amino acid sequence comprising a deletion, substitution or addition of one or several amino acids in the above-described amino acid sequence (1); and a heavy chain comprising a heavy chain variable region consisting of any one amino acid sequence selected from the group consisting of (4) the amino acid sequence shown in SEQ ID NO: 15, 25, 35, 45 or 58, (5) an amino acid sequence having an identity of at least 95% or more (preferably an amino acid sequence having a sequence identity of at least 95% or more to the sequence of a framework region other than at each CDR sequence) to the above-described amino acid sequence (4), and (6) an amino acid sequence comprising a deletion, substitution or addition of one or several amino acids in the above-described amino acid sequence (4). Other examples of such an antibody can include any given combination of: a light chain comprising a light chain variable region consisting of any one amino acid sequence selected from the group consisting of (1) the amino acid sequence shown in SEQ ID NO: 10, 20, 30 or 40, (2) an amino acid sequence having an identity of at least 95% or more (preferably an amino acid sequence having a sequence identity of at least 95% or more to the sequence of a framework region other than at each CDR sequence) to the above-described amino acid sequence (1), and (3) an amino acid sequence comprising a deletion, substitution or addition of one or several amino acids in the above-described amino acid sequence (1); and a heavy chain comprising a heavy chain variable region consisting of any one amino acid sequence selected from the group consisting of (4) the amino acid sequence shown in SEQ ID NO: 71, 75 or 79, (5) an amino acid sequence having an identity of at least 95% or more (preferably an amino acid sequence having a sequence identity of at least 95% or more to the sequence of a framework region other than at each CDR sequence) to the above-described amino acid sequence (4), and (6) an amino acid sequence comprising a deletion, substitution or addition of one or several amino acids in the above-described amino acid sequence (4).

The amino acid substitution in the present description is preferably a conservative amino acid substitution. The conservative amino acid substitution is a substitution occurring within an amino acid group associated with certain amino acid side chains. Preferred amino acid groups are the following: acidic group=aspartic acid and glutamic acid; basic group=lysine, arginine, and histidine; non-polar group=alanine, valine, leucine, isoleucine, proline, phenylalanine, methionine, and tryptophan; and uncharged polar family=glycine, asparagine, glutamine, cysteine, serine, threonine, and tyrosine. Other preferred amino acid groups are the following: aliphatic hydroxy group=serine and threonine; amide-containing group=asparagine and glutamine; aliphatic group=alanine, valine, leucine and isoleucine; and aromatic group=phenylalanine, tryptophan and tyrosine. Such amino acid substitution is preferably carried out without impairing the properties of a substance having the original amino acid sequence.

Examples of the antibody having a preferred combination of the above-described light chains and heavy chains include an antibody consisting of a light chain having the light chain variable region amino acid sequence shown in SEQ ID NO: 63 (in the present description, also referred to as a hL02 light chain variable region amino acid sequence) or a light chain having the light chain variable region amino acid sequence shown in SEQ ID NO: 67 (in the present description, also referred to as a hL03 light chain variable region amino acid sequence), and a heavy chain having the heavy chain variable region amino acid sequence shown in SEQ ID NO: 71 (in the present description, also referred to as a hH01 heavy chain variable region amino acid sequence), a heavy chain having the heavy chain variable region amino acid sequence shown in SEQ ID NO: 75 (in the present description, also referred to as a hH02 heavy chain variable region amino acid sequence) or a heavy chain having the heavy chain variable region amino acid sequence shown in SEQ ID NO: 79 (in the present description, also referred to as a hH04 heavy chain variable region amino acid sequence). Preferred examples thereof include: an antibody consisting of a light chain having the light chain variable region amino acid sequence shown in SEQ ID NO: 63 and a heavy chain having the heavy chain variable region amino acid sequence shown in SEQ ID NO: 71; an antibody consisting of a light chain having the light chain variable region amino acid sequence shown in SEQ ID NO: 63 and a heavy chain having the heavy chain variable region amino acid sequence shown in SEQ ID NO: 75; an antibody consisting of a light chain having the light chain variable region amino acid sequence shown in SEQ ID NO: 63 and a heavy chain having the heavy chain variable region amino acid sequence shown in SEQ ID NO: 79; an antibody consisting of a light chain having the light chain variable region amino acid sequence shown in SEQ ID NO: 67 and a heavy chain having the heavy chain variable region amino acid sequence shown in SEQ ID NO: 71; an antibody consisting of a light chain having the light chain variable region amino acid sequence shown in SEQ ID NO: 67 and a heavy chain having the heavy chain variable region amino acid sequence shown in SEQ ID NO: 75; and an antibody consisting of a light chain having the light chain variable region amino acid sequence shown in SEQ ID NO: 67 and a heavy chain having the heavy chain variable region amino acid sequence shown in SEQ ID NO: 79. More preferred examples thereof include: an antibody consisting of a light chain having the light chain variable region amino acid sequence shown in SEQ ID NO: 63 and a heavy chain having the heavy chain variable region amino acid sequence shown in SEQ ID NO: 71; an antibody consisting of a light chain having the light chain variable region amino acid sequence shown in SEQ ID NO: 63 and a heavy chain having the heavy chain variable region amino acid sequence shown in SEQ ID NO: 75; an antibody consisting of a light chain having the light chain variable region amino acid sequence shown in SEQ ID NO: 63 and a heavy chain having the heavy chain variable region amino acid sequence shown in SEQ ID NO: 79; and an antibody consisting of a light chain having the light chain variable region amino acid sequence shown in SEQ ID NO: 67 and a heavy chain having the heavy chain variable region amino acid sequence shown in SEQ ID NO: 75.

Other examples of the antibody having a preferred combination of the above-described light chains and heavy chains include an antibody consisting of a light chain consisting of the amino acid sequence at positions 21 to 233 in the light chain full-length amino acid sequence shown in SEQ ID NO: 61 (in the present description, also referred to as the hL02 light chain full-length amino acid sequence) or a light chain consisting of the amino acid sequence at positions 21 to 233 in the light chain full-length amino acid sequence shown in SEQ ID NO: 65 (in the present description, also referred to as the hL03 light chain full-length amino acid sequence), and a heavy chain consisting of the amino acid sequence at positions 20 to 471 in the heavy chain full-length amino acid sequence shown in SEQ ID NO: 69 (in the present description, also referred to as the hH01 heavy chain full-length amino acid sequence), a heavy chain consisting of the amino acid sequence at positions 20 to 471 in the heavy chain full-length amino acid sequence shown in SEQ ID NO: 73 (in the present description, also referred to as the hH02 heavy chain full-length amino acid sequence) or a heavy chain consisting of the amino acid sequence at positions 20 to 471 in the heavy chain full-length amino acid sequence shown in SEQ ID NO: 77 (in the present description, also referred to as the hH04 heavy chain full-length amino acid sequence). Preferred examples thereof include: an antibody consisting of a light chain consisting of the amino acid sequence at positions 21 to 233 in the light chain full-length amino acid sequence shown in SEQ ID NO: 61 and a heavy chain consisting of the amino acid sequence at positions 20 to 471 in the heavy chain full-length amino acid sequence shown in SEQ ID NO: 69; an antibody consisting of a light chain consisting of the amino acid sequence at positions 21 to 233 in the light chain full-length amino acid sequence shown in SEQ ID NO: 61 and a heavy chain consisting of the amino acid sequence at positions 20 to 471 in the heavy chain full-length amino acid sequence shown in SEQ ID NO: 73; an antibody consisting of a light chain consisting of the amino acid sequence at positions 21 to 233 in the light chain full-length amino acid sequence shown in SEQ ID NO: 61 and a heavy chain consisting of the amino acid sequence at positions 20 to 471 in the heavy chain full-length amino acid sequence shown in SEQ ID NO: 77; an antibody consisting of a light chain consisting of the amino acid sequence at positions 21 to 233 in the light chain full-length amino acid sequence shown in SEQ ID NO: 65 and a heavy chain consisting of the amino acid sequence at positions 20 to 471 in the heavy chain full-length amino acid sequence shown in SEQ ID NO: 69; an antibody consisting of a light chain consisting of the amino acid sequence at positions 21 to 233 in the light chain full-length amino acid sequence shown in SEQ ID NO: 65 and a heavy chain consisting of the amino acid sequence at positions 20 to 471 in the heavy chain full-length amino acid sequence shown in SEQ ID NO: 73; and an antibody consisting of a light chain consisting of the amino acid sequence at positions 21 to 233 in the light chain full-length amino acid sequence shown in SEQ ID NO: 65 and a heavy chain consisting of the amino acid sequence at positions 20 to 471 in the heavy chain full-length amino acid sequence shown in SEQ ID NO: 77. More preferred examples thereof include: an antibody consisting of a light chain consisting of the amino acid sequence at positions 21 to 233 in the light chain full-length amino acid sequence shown in SEQ ID NO: 61 and a heavy chain consisting of the amino acid sequence at positions 20 to 471 in the heavy chain full-length amino acid sequence shown in SEQ ID NO: 69 (in the present description, also referred to as the "H01L02 antibody" or "H01L02"); an antibody consisting of a light chain consisting of the amino acid sequence at positions 21 to 233 in the light chain full-length amino acid sequence shown in SEQ ID NO: 61 and a heavy chain consisting of the amino acid sequence at positions 20 to 471 in the heavy chain full-length amino acid sequence shown in SEQ ID NO: 73 (in the present description, also referred to as the "H02L02 antibody" or "H02L02"); an antibody consisting of a light chain consisting of the amino acid sequence at positions 21 to 233 in the light chain full-length amino acid sequence shown in SEQ ID NO: 61 and a heavy chain consisting of the amino acid sequence at positions 20 to 471 in the heavy chain full-length amino acid sequence shown in SEQ ID NO: 77 (in the present description, also referred to as the "H04L02 antibody" or "H04L02"); and an antibody consisting of a light chain consisting of the amino acid sequence at positions 21 to 233 in the light chain full-length amino acid sequence shown in SEQ ID NO: 65 and a heavy chain consisting of the amino acid sequence at positions 20 to 471 in the heavy chain full-length amino acid sequence shown in SEQ ID NO: 73 (in the present description, also referred to as the "H02L03 antibody" or "H02L03"). The sequences of the H01L02 antibody, the H02L02 antibody, the H02L03 antibody or the H04L02 antibody are shown in Table 1.

By combining together sequences showing a high identity to the above-described heavy chain amino acid sequences and light chain amino acid sequences, it is possible to select an antibody having a biological activity equivalent to that of each of the above-described antibodies. Such an identity is an identity of generally 80% or more, preferably 90% or more, more preferably 95% or more, and most preferably 99% or more. Moreover, also by combining amino acid sequences of a heavy chain and a light chain comprising a substitution, deletion or addition of one or several amino acid residues thereof with respect to the amino acid sequence of a heavy chain or a light chain, it is possible to select an antibody having a biological activity equivalent to that of each of the above-described antibodies.

The identity between two types of amino acid sequences can be determined by aligning the sequences using the default parameters of Clustal W version 2 (Larkin M A, Blackshields G, Brown N P, Chenna R, McGettigan P A, McWilliam H, Valentin F, Wallace I M, Wilm A, Lopez R, Thompson J D, Gibson T J and Higgins D G (2007), "Clustal W and Clustal X version 2.0", Bioinformatics. 23 (21): 2947-2948).

It is to be noted that, in the hL02 light chain full-length amino acid sequence shown in SEQ ID NO: 61, the amino acid sequence consisting of the amino acid residues at positions 1 to 20 is the signal sequence, the amino acid sequence consisting of the amino acid residues at positions 21 to 128 is the variable region, and the amino acid sequence consisting of the amino acid residues at positions 129 to 233 is the constant region. In the hL02 light chain full-length nucleotide sequence shown in SEQ ID NO: 62, the nucleotide sequence consisting of the nucleotides at positions 1 to 60 encodes the signal sequence, the nucleotide sequence consisting of the nucleotides at positions 61 to 384 encodes the variable region, and the nucleotide sequence consisting of the nucleotides at positions 385 to 699 encodes the constant region.

In the hL03 light chain full-length amino acid sequence shown in SEQ ID NO: 65, the amino acid sequence consisting of the amino acid residues at positions 1 to 20 is the signal sequence, the amino acid sequence consisting of the amino acid residues at positions 21 to 128 is the variable region, and the amino acid sequence consisting of the amino acid residues at positions 129 to 233 is the constant region. In the hL03 light chain full-length nucleotide sequence shown in SEQ ID NO: 66, the nucleotide sequence consisting of the nucleotides at positions 1 to 60 encodes the signal sequence, the nucleotide sequence consisting of the nucleotides at positions 61 to 384 encodes the variable region, and the nucleotide sequence consisting of the nucleotides at positions 385 to 699 encodes the constant region.

In the hH01 heavy chain full-length amino acid sequence shown in SEQ ID NO: 69, the amino acid sequence consisting of the amino acid residues at positions 1 to 19 is the signal sequence, the amino acid sequence consisting of the amino acid residues at positions 20 to 141 is the variable region, and the amino acid sequence consisting of the amino acid residues at positions 142 to 471 is the constant region. In the hH01 heavy chain full-length nucleotide sequence shown in SEQ ID NO: 70, the nucleotide sequence consisting of the nucleotides at positions 1 to 57 encodes the signal sequence, the nucleotide sequence consisting of the nucleotides at positions 58 to 423 encodes the variable region, and the nucleotide sequence consisting of the nucleotides at positions 424 to 1413 encodes the constant region.

In the hH02 heavy chain full-length amino acid sequence shown in SEQ ID NO: 73, the amino acid sequence consisting of the amino acid residues at positions 1 to 19 is the signal sequence, the amino acid sequence consisting of the amino acid residues at positions 20 to 141 is the variable region, and the amino acid sequence consisting of the amino acid residues at positions 142 to 471 is the constant region. In the hH02 heavy chain full-length nucleotide sequence shown in SEQ ID NO: 74, the nucleotide sequence consisting of the nucleotides at positions 1 to 57 encodes the signal sequence, the nucleotide sequence consisting of the nucleotides at positions 58 to 423 encodes the variable region, and the nucleotide sequence consisting of the nucleotides at positions 424 to 1413 encodes the constant region.

In the hH04 heavy chain full-length amino acid sequence shown in SEQ ID NO: 77, the amino acid sequence consisting of the amino acid residues at positions 1 to 19 is the signal sequence, the amino acid sequence consisting of the amino acid residues at positions 20 to 141 is the variable region, and the amino acid sequence consisting of the amino acid residues at positions 142 to 471 is the constant region. In the hH04 heavy chain full-length nucleotide sequence shown in SEQ ID NO: 78, the nucleotide sequence consisting of the nucleotides at positions 1 to 57 encodes the signal sequence, the nucleotide sequence consisting of the nucleotides at positions 58 to 423 encodes the variable region, and the nucleotide sequence consisting of the nucleotides at positions 424 to 1413 encodes the constant region.

TABLE 1-1

| SEQ ID NO | | Sequence |
|---|---|---|
| 1 | Amino acid sequence of human CDH6 | MRTYRFLLLFWVGQPYPTLSTPLSKRTSGFPAKKRALELSGNSKNELNRSKRSWMW NQFFLLEEYTGSDYQYVGKLHSDQDRGDGSLKYILSGDGAGDLFIINENTGDIQATK RLDREEKPVYILRAQAINRRTGRPVEPESEFIIKIHDINDNEPIFTKEVYTATVPEM |

TABLE 1-1-continued

| SEQ ID NO | | Sequence |
|---|---|---|
| | ORF | SDVGTFVVQVTATDADDPTYGNSAKVVYSILQGQPYFSVESETGIIKTALLNMDREN REQYQVVIQAKDMGGQMGGLSGTTTVNITLTDVNDNPPRFPQSTYQFKTPESSPPGT PIKRIKASDADVGENAEIEYSITDGEGLDMFDVITDQETQEGIITVKKLLDFEKKKV YTLKVEASNPYVEPRFLYLGPFKDSATVRIVVEDVDEPPVFSKLAYILQIREDAQIN TTIGSVTAQDPDAARNPVKYSVDRHTDMDRIFNIDSGNGSIFTSKLLDRETLLWHNI TVIATEINNPKQSSRVPLYIKVLDVNDNAPEFAEFYETFVCEKAKADQLIQTLHAVD KDDPYSGHQFSSLAPEAASGSNFTIQDNKDNTAGILTRKNGYNRHEMSTYLLPVVI SDNDYPVQSSTGTVTVRVCACDHHGNMQSCHAELIHPTGLSTGALVAILLCIVILL VTVVLFAALRRQRKKEPLIISKEDIRDNIVSYNDEGGGEEDTQAFDIGTLRNPEAIE DNKLRRDIVPEALFLPRRTPTARDNTDVRDFINQRLKENDTDPTAPPYDSLATYAYE GTGSVADSLSSLESVTTDADQDYDLSDWGPRFKKLADMYGGVDSDKDS |
| 2 | Human CDH6 EC1 | SWMWNQFFLLEEYTGSDYQYVGKLHSDQDRGDGSLKYILSGDGAGDLFIINENTGDI QATKRLDREEKPVYILRAQAINRRTGRPVEPESEFIIKIHDINDNEPIF |
| 3 | Human CDH6 EC2 | TKEVYTATVPEMSDVGTFVVQVTATDADDPTYGNSAKVVYSILQGQPYFSVESETGI IKTALLNMDRENDREQYQVVIQAKDMGGQMGGLSGTTTVNITLTDVNDNPPRF |
| 4 | Human CDH6 EC3 | PQSTYQFKTPESSPPGTPIGRIKASDADVGENAEIEYSITDGEGLDMFDVITDQETQ EGIITVKKLLDFEKKKVYTLKVEASNPYVEPRFLYLGPFKDSATVRIVVEDVDEPPV F |
| 5 | Human CDH6 EC4 | SKLAYILQIREDAQINTTIGSVTAQDPDAARNPVKYSVDRHTDMDRIFNIDSGNGSI FTSKLLDRETLLWHNITVIATEINNPKQSSRVPLYIKVLDVNDNAP |
| 6 | Human CDH6 EC5 | EFAEFYETFVCEKAKADQLIQTLHAVDKDDPYSGHQFSGLAPEAASGSNFTIQDNK DNTAGILTRKNGYNRHEMSTYLLPVVISDNDYPVQSSTGTVTVRVCACDHHGNMQSC HAEALIHP |
| 7 | Amino acid sequence of mouse CDH6 ORF | MRTYRFLLLFWVGQPYPTFSNPLSKRTSGFPAKRKALELSANSRNESRSKRSWMW NQFFLLEEYTGSDYQYVGKLHSDQDRGDGSLKYILSGDGAGDLFIINENTGDIQATK RLDREEKPVYILRAQAVNRRTGRPVEPESEFIIKIHDINDNEPIFTKDVYTATVPEM ADVGTFVVQVTATDADDPTYGNSAKVVYSILQGQPYFSVESETGIIKTALLNMDREN REQYQVVIQAKDMGGQMGGLSGTTTVNITLTDVNDNPPRFPQSTYQFKTPESSPPGT PIGRIKASDADVGENAEIEYSITDGEGHEMFDVITDQETQEGIITVKKLLDFEKKKV YTLKVEASNPHVEPRFLYLGPFKDSATVRIVVDDVDEPPVFSKLAYILQIREDARIN TTIGSVAAQDPDAARNPVKYSVDRHTDMDRIFNIDSGNGSIFTSKLLDRETLLWHNI TVIATEINNPKQSSRVPLYIKVLDVNDNAPEFAEFYETFVCEKAKADQLIQTLRAVD KDDPYSGHQFSSLAPEAASGSNFTIQDNKDNTAGILTRKNGYNRHEMSTYLLPVVI SDNDYPVQSSTGTVTVRVCACDHHGNMQSCHAELIHPTGLSTGALVAILLCIVILL VTVVLFAALRRQRKKEPLIISKEDIRDNIVSYNDEGGGEEDTQAFDIGTLRNPEAME DSKSRRDIVPEALFLPRRTPTARDNTDVRDFINQRLKENDTDPTAPPYDSLATYAYE GTGSVADSLSSLESVTTDADQDYDLSDWGPRFKKLADMYGGMDSDKDS |

TABLE 1-2

| 8 | Amino acid sequence of rat CDH6 ORF | MRTYRYFLLLFWVGQPYPTFSNPLSKRTSGFPAKRRALELSANSRNELSRSKRSWMW NQFFLLEEYTGSDYQYVGKLHSDQDRGDGSLKYILSGDGAGDLFIINENTGDIQATK RLDREEKPVYILRAQAINRRTGRPVEPESEFIIKIHDINDNEPIFTKDVYTATVPEM ADVGTFVVQVTATQADPTYGNSAKVVYSILQGQPYFSVESETGIIKTALLNMDREN REQYQVVIQAKDMGGQMGGLSGTTTVNITLTDVNQNPPRFPQSTYFKTPESSPPGT PIGRIKASDADVGENAEIEYSITDGEGHDMFDVITDQETQEGIITVKKLLDFEKKRV YTLKVEASNPHIEPRFLYLGPFK0SATVRIVVQQVQEPPVFSKPAYILQIREDAQIN TTIGSVAAQDPDAARNPVKYSVDRHTDMDRIFNIDSGNGSIFTSKLLDRETLLWHNI TVIATEINNPKGSSRVPLYIKVLDVNDNAPEFAEFYETFVCEKAKADQLIQTLHAVD KDDPYSGHQFSFSLAPEAASGSNFTIGDNKQNTAGILTRKNGYNRHEMSTYLLPVVI S0NDYPVQSSTGTVTVRVCACDHHGNMQSCHAEALIHPTGLSTGALVAILLCIVILL VTVVLFAALRRQRKKEPLIISKEDIRDNIVSYNDEGGGEEDTQAFDIGTLRNPKPWR QQSRRDMVPEALFLPRRTPTARDNTDVRDFISGRLRKMNTDPTAPPY0SLATYAYEG TGSVADSLSSLESVTTDGDQDYGLSDWGPRFKKLAQMYGGMDSDKDS |
|---|---|---|
| 9 | Amino acid sequence of cynomolgus monkey CDH6 ORF | MRTYRYFLLLFWVGQPYPTLSTPLSKRTSGFPAKKRALELSGNSKNELNRSKRSWMW NQFFLLEEYTGSDYQYVGKLHSDQDRGDGSLKYILSGDGAGDLFIINENTGDIQATK RLDREEKPVYILRAQAINRRTGRPVEPESEFIIKIHDINDNEPIFTKEVYTATVPEM SDVGTFVVQVTATDADDPTYGNSAKVVYSILQGQPYFSVESETGIIKTALLNMDREN REQYQVVIQAKDMGGQMGGLSGTTTVNITLTDVNDNPPRFPQSTYQFKTPESSPPGT PIGRIKASDADVGENAEIEYSITDGEGLDMFDVITDQETQEGIITVKKLLDFEKKKV YTLKVEASNPHVEPRFLYLGPFKDSATVRIVVEDVDEPPVFSKLAYILQIREDAQIN TTIGSVTAQDPDAARNPVKYSVDRHTDMDRIFNIDSGNGSIFTSKLLDRETLLWHNI TVIATEINNPKQSSRVPLYIKVLDVNDNAPEFAEFYETFVCEKAKADQLIQTLRAVD KDDPYSGHQFSFSLAPEAASGSNFTIQDNKDNTAGILTRKNGYNRHEMSTYLLPVVI SDNDYPVQSSTGTVTVRVCACDHHGNMQSCHAEALIHPTGLSTGALVAILLCIVILL VTVVLFAALRRQRKKEPLIISKEDIRDNIVSYNDEGGGEEDTQAFDIGTLRNPEAIE |

TABLE 1-2-continued

| | | |
|---|---|---|
| | | DNKLRRDIVPEALFLPRRTPTARDNTDVRDFINQRLKENDTDPTAPPYDSLATYAYE GTGSVADSLSSLESVTTDGDQDYDYLSDWGPRFKKLADWYGGVDSDKDS |
| 10 | rG019 light chain variable region amino acid sequence | DIQMTQSPSLLSASVGDRVTLNCKASQNIYKNLAWYQQKLGEGPKLLIYDANTLQTG IPSRFSGSGSGSDFTLTISSLQPEDVATYFCQQYYSGWAFGGVTNLELKRA |
| 11 | rG019 light chain variable region nucleotide sequence | GACATCCAGATGACCCAGTCTCCTTCACTCCTGTCTGCATCTGTGGGAGACAGAGTC ACTCTCAACTGCAAAGCAAGTCAGAATATTTATAAGAACTTAGCCTGGTATCAGCAA AAGCTTGGAGAAGGTCCCAAACTCCTGATTTATGATGCAAACACTTTGCAAACGGGC ATCCCATCAAGGTTCAGTGGCAGTGGATCTGGTTCAGATTTCACACTCACCATCAGC AGCCTGCAGCCTGAAGATGTTGCCACATATTTCTGCCAGCAGTACTATAGCGGGTGG GCGTTCGGTGGAGTCACCAACCTGGAATTGAAACGGGCT |
| 12 | rG019 CDRL1 | KASQNIYKNLA |
| 13 | rG019 CDRL2 | DANTLQT |
| 14 | rG019 CDRL3 | QQYYSGWA |

TABLE 1-3

| | | |
|---|---|---|
| 15 | rG019 heavy chain variable region amino acid sequence | QVQLQQSGAELVKPGSSVKISCKASGYTFTRNFMHWIKQQPGNGLEWIGWIYCGDGE TEYNQKFNGKATLTADRSSSTAYMELSRLTSEDSAVYFCARGVYGGFAGGYFDF GVMVTVSS |
| 16 | rG019 heavy chain variable region nucleotide sequence | CAGGTACAGCTGCAGCAATCTGGGGCTGAACTGGTGAAGCCTGGGTCCTCAGTGAAA ATTTGCTGCAAGGGTTCTGGCTACACCTTCACCAGGAACTTTATGCACTGGATAAAA CAGCAGCGTGGAAATGGCCTTGAGTGGATTGGGTGGATTTATTGTGGAGATGGTGAG ACAGAGTAGAATCAAAAGTTCAATGGGAAGGCAACACTCACTGCGGACAGATCCTCC AGCACAGCCTATATGGAGCTCAGCAGACTGACATCTGAGGACTCTGCAGTCTATTTC TGTGCAAGAGGGGTTTACGGAGGGTTTGCCGGGGGCTACTTTGATTTCTGGGGCCAA GGAGTCATGGTCACAGTCTCCTCA |
| 17 | rG019 CDRH1 | GYTFTRNFMH |
| 18 | rG019 CDRH2 | WIYCGDGETE |
| 19 | rG019 CDRH3 | GVYGGFAGGYFDF |
| 20 | rG055 light chain variable region amino acid sequence | DVQMTHSPSYLAASPGESVSISCKTSKNISNYLVWYQQKPGEAYKLLIYSGSTLQSG TPSRFSGSGSGTDFTLTIRSLEPEDFGLYFCQQYYEKPFTFGSGTKLEIKRA |
| 21 | rG055 light chain variable region nucleotide sequence | GATGTCCAGATGACCCACTCTCCGTCTTATCTTGCTGCGTCTCCTGGAGAAAGTGTT TCCATCAGTTGCAAGACAAGTAAGAAGATTAGTAATTATTTAGTCTGGTATCAACAG AAACCTGGGGAAGCATATAAGCTTCTTATCTATTCTGGGTCAACTTTGCAATCTGGA ACTCCATCAAGGTTCAGTGGCAGTGGATCTGGTACAGATTTCACTGTCACTATCAGA AGCCTGGAGCCTGAAGATTTTGGACTCTATTTCTGTCAACAGTATTATGAAAAACCA TTCACGTTCGGCTCAGGGACGAAGTTGGAAATAAAACGGGCT |
| 22 | rG055 CDRL1 | KTSKNISNYLV |
| 23 | rG055 CDRL2 | SGSTLQS |
| 24 | rG055 CDRL3 | QQYYEKPFT |
| 25 | rG055 heavy chain variable region amino acid sequence | EVQLQESGPGLVRPSQSLSLSCSVTDYSITSNYWGWIRRFPGNKMEWMGYITYSGYT SYNPSLQSRISITRDTSKNQFFLQLNSVTAEDTATYYCARSINHGGYSYVVDAWGPG ASVTVSS |
| 26 | rG055 heavy chain variable region nucleotide sequence | GAGGTGCAACTTCAGGAGTCAGGACCTGGCGTTGTGAGACCCTCACAGTCACTCTCC CTCTCCTGTTCTGTCACTGATTACTCCATCACTAGTAATTACTGGGGCTGGATCCGG AGGTTCCCAGGAAATAAAATGGAGTGGATGGGATACATAACCTATAGTGGTTACACT AGCTACAACCCATCTCTCCAAAGTCGAATCTCCATTACTAGAGACACATCGAAGAAT CAGTTCTTCCTGCAGTTGAACTCTGTAACTGCTGAGGACACAGCCACATATTACTGT GCAAGATCGATTAACCACGGAGGATATAGTTATGTTGTGGATGCCTGGGGTCCGGGA GCTTCAGTCACTGTCTCCTCA |
| 27 | rG055 CDRH1 | DYSITSNYVSG |
| 28 | rG055 CDRH2 | YITYSGYTS |
| 29 | rG055 CDRH3 | SINHGGYSYWDA |

TABLE 1-4

| | | |
|---|---|---|
| 30 | rG056 light chain variable region amino acid sequence | DVGMTQSPSSLAASPGESVSISCRATKSIGIYLAWYQQKPGKTFKLLIYSGSTLQSGTPSRFSGSGSGTDFTLTIRSLEPEDFGLYFCQQFYENPFTFGSGTKLEIRRA |
| 31 | rG056 light chain variable region nucleotide sequence | GATGTCCAGATGACCCAGTCTCCGTCTTCTCTTGCTGCGTCTCCTGGAGAAAGTGTTTCCATCAGTTGCAGGGCAACTAAGAGCATTGGTATTTATTTAGCCTGGTATCAACAGAAACCTGGGAAAAGATTTAAGCTTCTTATCTACTCTGGGTCAACTTTGCAATCTGGAACTCCATCAAGGTTCAGTGGCAGTGGGTCTGGTACAGATTTCACTCTCACCATCAGAAGCCTGGAGCCTGAAGATTTTGGACTCTATTTCTGTCAACAGTTTTATGAAAACCCATTCACGTTCGGCTCAGGGACGAAGTTGGAAATAAGACGGGCT |
| 32 | rG056 CDRL1 | RATKSIGIYLA |
| 33 | rG056 CDRL2 | SGSTLQS |
| 34 | rQ056 CDRL3 | QQFYENPFT |
| 35 | rG056 heavy chain variable region amino acid sequence | EVQLQESGPGLVKPSQSLSLTCSVTDYSITTYFWGWIRKFPGNKMEWMGYMSYRGGTSYNPSLKSRISITRDTSKNQFFLQLNSVTTEDTATYYCARCPNYGGHSLVFDYWGQGVMVTVSS |
| 36 | rG056 heavy chain variable region nucleotide sequence | GAGGTGCAGCTTCAGGAGTGAGGACGTGGCCTTGTGAAACCCTCACAGTCACTCTCCCTCACCTGTTCTGTCAGTGATTACTCCATCACTACTTATTTCTGGGGCTGGATCCGGAAGTTCCCAGGAAATAAATGGAGTGGATGGGATACATGAGCTACCGTGGTGGCACTTCCTACAACCCATCTCTCAAGAGTCGAATCTCCATTACTAGAGACACATCGAAGAATCAGTTCTTCCTGCAGTTGAACTCTGTAACTACTGAGGACACAGCCACATATTACTGTGCAAGATGCCCTAACTACGGAGGGCATTCCCTTGTTTTTGATTACTGGGGCCAAGGAGTCATGGTCAGAGTGTCCTCA |
| 37 | rG056 CDRH1 | DYSITTYFWG |
| 38 | rG056 CDRH2 | YMSYRGGTS |
| 39 | rG056 CDRH3 | CPNYGGHSLVFOY |
| 40 | rG061 light chain variable region amino acid sequence | DVQMTQSPSYLAASPGESVSISCKATKSISNYLAWYQQKPGEAYKVLIYSGSTLQSGTPSRFSGSGSGTDFTLTIRSLEPEDFGLYSCQQYYEKPLTFGSGTKLEIKRA |
| 41 | rG061 light chain variable region nucleotide sequence | GATGTCCAGATGACCCAGTCTCCGTCTTATCTTGCTGCGTCTCCTGGAGAAAGTGTTTCCATCAGTTGCAAGGGAACTAAGAGGATTAGTAATTATTTAGCCTGGTATCAACAGAAACCTGGGGAAGCATATAAGGTTCTTATCTATTGTGGGTCAACTTTGCAATCTGGAACTCCATCAAGGTTCAGTGGCAGTGGATCTGGTACAGATTTCACTCTCACCATCAGAAGCCTGGAGCCTGAAGATTTTGGACTCTATTCCTGTCAACAGTATTATGAAAAACCGCTCAGGTTCGGTTCTGGGACCAAGCTGGAGATCAAACGGGCT |
| 42 | rG061 CDRL1 | KATKSISNYLA |
| 43 | rG061 CDRL2 | SGSTLQS |
| 44 | rG061 CDRL3 | QQYYEKPLT |

TABLE 1-5

| | | |
|---|---|---|
| 45 | rG061 heavy chain variable region amino acid sequence | EVQLQESGPGLVKPSQSLSLTCSVTGYSITTYYWGWIRKFPGNKMEWMGYISYSGRTSYNPSLKSRMSITRDASKNQFFLQLNSVTTDDTATYYCARSPINHGGYWYFDFWGPGTMVTVSS |
| 46 | rG061 heavy chain variable region nucleotide sequence | GAGGTGCAGCTTCAGGAGTCAGGACCTGGCCTTGTGAAACCCTCACAGTCACTCTCCCTCACCTGTTCTGTCACTGGTTACTCCATCACTACTTATTACTGGGGCTGGATCCGGAAGTTCCCAGGAAATAAATGGAGTGGATGGGGTACATAAGCTACAGTGGTCGCACTAGTTATAACCCATCTCTCAAAAGTCGAATGTCCATTACTAGAGACGCATCGAAGAATCAGTTCTTCCTACAGTTGAACTCTGTAACTACTGACGACACAGCCACATATTACTGTGCAAGATCCCCAATTAACCACGGAGGGTACTGGTACTTTGACTTCTGGGGCCCAGGAACCATGGTCACCGTGTCCTCA |
| 47 | rG061 CDRH1 | GYSITTYYWG |
| 48 | rG061 CDRH2 | YISYSGRTS |
| 49 | rG061 CDRH3 | SPINHGGYWYFDF |
| 50 | DNA fragment comprising DNA sequence | gcctccggactctagagccaccATGGTGCTGCAGACCCAGGTGTTCATCTCCCTGCTGCTGTGGATCTCCGGCGCGTACGGCGATATCGTGATGATTAAACGTACGGTGGCCGCCCGCTCCGTGTTCATCTTCCCCCCCTCCGACGAGCAGCTGAAGTCCGGCACCGCCTC |

TABLE 1-5-continued

| | encoding human light chain signal sequence and human κ chain constant region | CGTGGTGTGCCTGCTGAATAACTTCTACCCCAGAGAGGCCAAGGTGCAGTGGAAGGT GGACAACGCCCTGCAGTCGGGGAACTCCCAGGAGAGCGTGACCGAGCAGGACAGCAA GGACAGCACCTACAGCCTGAGCAGCACCCTGACCCTGAGCAAAGCCGACTACGAGAA GCACAAGGTGTACGCCTGCGAGGTGACCCACCAGGGCCTGAGCTCCCCGTCACCAA GAGCTTCAACAGGGGGGAGTGTtaggggcccattaaacgggggaggcta |
|---|---|---|

TABLE 1-6

| 51 | DNA fragment comprising DNA sequence encoding human heavy chain signal sequence and human IgG1 constant region | gcctccggactctagagccaccATGAAACACCTGTGGTTCTTCCTCCTGCTGGTGGC AGCTCCCAGATGGGTGCTGAGCCAGGTGCAATTGTGCAGGCGGTTAGCTCAGCCTCC ACCAAGGGCCCAAGCGTGTTCCCGCTGGCACCCTCCTCCAAGAGCACCTCTGGCGGC ACAGCCGCCCTGGGCTGCCTGGTCAAGGACTACTTCCCCGAACCCGTGACCGTGAGC TGGAACTCAGGCGCCCTGACCAGCGGCGTGCACACCTTCCCGGCTGTCCTGCAGTCA TCAGGACTGTACTCCCTGAGCAGCGTGGTGACCGTGCCCTCCAGCAGGTTGGGCACC CAGACCTACATCTGCAACGTGAATCACAAGCCCAGGAACACCAAGGTGGACAAGAGA GTTGAGCCCAAATCTTGTGACAAAACTCACACATGCCCACCCTGCCCAGCACCTGAA CTCCTGGGGGGACCCTCAGTCTTCCTCTTCCCCCCAAAACCCAAGGACACCCTCATG ATCTCCGGGACCCCTGAGGTCACATGCGTGGTGGTGGACGTGAGCCACGAAGACCCT GAGGTCAAGTTCAACTGGTACGTGGACGGCGTGGAGGTGCATAATGCCAAGACAAAG CCCCGGGAGGAGCAGTACAACAGCACGTACCGGGTGGTCAGCGTCCTCACCGTGCTG CACCAGGACTGGCTGAATGGCAAGGAGTACAAGTGCAAGGTCTCCAACAAAGCCCTC CCAGCCCCCATCGAGAAAACCATCTCCAAAGCCAAAGGCCAGCCCCGGGAACCACAG GTGTACACCCTGCCCCCATCCCGGGAGGAGATGACCAAGAACCAGGTCAGCCTGACC TGCCTGGTCAAAGGCTTCTATCCCAGCGACATCGCCGTGGAGTGGGAGAGCAATGGC CAGCCGGAGAACAACTACAAGACCACCCCTCCCGTGCTGGACTCCGACGGCTCCTTC TTCCTCTACAGCAAGCTCACCGTGGACAAGAGCAGGTGGCAGCAGGGCAACGTCTTC TCATGCTCCGTGATGCATGAGGCTCTGCACAACCACTACACCCAGAAGAGCCTCTCC CTGTCTCCGGGCAAAtgagatatcgggcccgtttaaacggggga ggcta |
|---|---|---|
| 52 | DNA fragment comprising DNA sequence encoding chG019 light chain | ccagcctccggactctagagccaccATGGTGCTGCAGACCCAGGTGTTCATCAGCCT GCTGCTGTGGATCAGCGGCGCCTACGGCGACATCCAGATGACCCAGAGCCCTAGCCT GCTGAGCGCCAGCGTGGGCGATAGAGTGACCCTGAACTGCAAGGCCAGCCAGAACAT CTACAAGAACCTGGCCTGGTATCAGCAGAAGCTGGGCGAGGGCCCCAAGCTGCTGAT CTACGACGCCAACACCCTGCAGACCGGCATCCCCAGCAGATTTTCTGGCAGGGGCAG CGGCTCCGACTTCACCCTGACAATCAGCAGCCTGCAGCCCGAGGACGTGGCCACCTA CTTTTGCCAGCAGTACTACAGCGGCTGGGCCTTCGGCGGCGTGACCAACCTGGAACT GAAGAGAGCCGTGGCCGCTCCCTCCGTGTTCATCTTCCCACCTAGCGACGAGCAGCT GAAGTCCGGCACAGCCTCTGTCGTGTGCCTGCTGAACAACTTCTACCCCCGCGAGGC CAAGGTGCAGTGGAAGGTGGACAATGCCCTGCAGTCTGGCAACAGCCAGGAAAGCGT GACCGAGCAGGACAGCAAGGACTCCACCTACAGCCTGAGCAGCACCCTGACCCTGAG CAAGGCCGACTACGAGAAGCACAAGGTGTACGCCTGCGAAGTGACCCACCAGGGCCT GTCTAGCCCCGTGACCAAGAGCTTCAACCGGGGCGAGTGTgagtttaaacggggga ggctaact |
| 53 | chG019 light chain full-length amino acid sequence | MVLQTQVFISLLLWISGAYGDIQMTQSPSLLSASVGDRVTLNCKASQNIYKNLAWYQ QKLGEGPKLLIYDANTLQTGIPSRFSGSGSGSDFTLTISSLQPEDVATYFCQQYYSG WAFGGVTNLELKRAVAAPSVFIFPPSDEQLKSGTASVVCLLNNFYPREAKVQWKVDN ALQSGNSQESVTEQDSKDSTYSLSSTTLTLSKADYEKHKVYACEVTHQGLSSPVTKSF NRGEC |

TABLE 1-7

| 54 | chG019 light chain full-length nucleotide sequence | ATGGTGCTGCAGACCCAGGTGTTCATCAGCCTGCTGCTGTGGATCAGCGGCGCCTAC GGCGACATCCAGATGACCCAGAGCCCTAGCCTGCTGAGCGCCAGCGTGGGCGATAGA GTGACCCTGAACTGCAAGGCCAGCCAGAACATCTACAAGAACCTGGCCTGGTATCAG CAGAAGCTGGGCGAGGGCCCCAAGCTGCTGATCTACGACGCCAACACCCTGCAGACC GGCATCCCCAGCAGATTTTCTGGCAGGGGCAGGGGCTCCGACTTCACCCTGACAATC AGCAGCCTGCAGCCCGAGGACGTGGCCACCTACTTTTGCCAGCAGTACTACAGCGGC TGGGCCTTCGGCGGCGTGACCAACCTGGAACTGAAGAGAGCCGTGGCCGCTCCCTCC GTGTTCATCTTCCCACCTAGCGACGAGCAGCTGAAGTCCGGCACAGCCTCTGTCGTG TGCCTGCTGAACAACTTCTACCCGCGCGAGGCCAAGGTGCAGTGGAAGGTGGACAAT GCCCTGCAGTCTGGCAACAGCCAGGAAAGCGTGACCGAGCAGGACAGCAAGGACTCC ACCTACAGCCTGAGCAGCACCCTGACCCTGAGCAAGGCCGACTACGAGAAGCACAAG GTGTACGCCTGCGAAGTGACCCACCAGGGCCTGTCTAGCCCCGTGACCAAGAGCTTC AACCGGGGCGAGTGT |
|---|---|---|
| 10 | chG019 light chain variable region amino acid sequence | DIQMTQSPSLLSASVGDRVTLNCKASQNIYKNLAWYQQKLGEGPKLLIYDANTLQTG IPSRFSGSGSGSDFTLTISSLQPEDVATYFCQQYYSGWAFGGVTNLELKRA |

TABLE 1-7-continued

| 55 | chG019 light chain variable region nucleotide sequence | GACATCCAGATGACCCAGAGCCCTAGCCTGCTGAGCGCCAGCGTGGGCGATAGAGTG<br>ACCCTGAACTGCAAGGCCAGCCAGAACATCTACAAGAACCTGGCCTGGTATCAGCAG<br>AAGCTGGGCGAGGGCCCCAAGCTGCTGATCTACGACGCCAACACCCTGCAGACCGGC<br>ATCCCCAGCAGATTTTCTGGCAGCGGCAGCGGCTCCGACTTCACCCTGACAATCAGC<br>AGCCTGCAGCCCGAGGACGTGGCCACCTACTTTTGCCAGCAGTACTACAGCGGCTGG<br>GCCTTCGGCGGCGTGACCAACCTGGAACTGAAGAGAGCC |
| --- | --- | --- |
| 12 | chG019 CDRL1 | KASQNIYKNLA |
| 13 | chG019 CORL2 | DANTLQT |
| 14 | chG019 CDRL3 | QQYYSGWA |
| 56 | chG019 heavy chain full-length amino acid sequence | MKHLWFFLLLVAAPRWVLSQVQLQQSGAELVKPGSSVKISCKASGYTFTRNFMHWIK<br>QQPGNGLEWIGWIYPGDGETEYNQKNGKATLTADRSSSTAYMELSRLTSEDSAVYF<br>CARGVYGGFAGGYFDFWGQGVMVTVSSASTKGPSVFPLAPSSKSTSGGTAALGCLVK<br>DYFPEPVTVSWNSGALTSGVHTFPAVLQSSGLYSLSSVVTVPSSSLGTQTYICNVNH<br>KPSNTKVDKRVEPKSCDKTHTCPPCPAPELLGGPSVFLFPPKPKDTLMISRTPEVTC<br>VVVDVSHEDPEVKFNWYVDGVEVHNAKTKPREEQYNSTYRVVVSLTVLHQDWLNGKE<br>YKCKVSNKALPAPIEKTISKAKGQPREPQVYTLPPSREEMTKNQVSLTCLVKGFYPS<br>DIAVEWESNGQPENNYKTTPPVLDSDGSFFLYSKLTVDKSRWQQGNVFSCSVMHEAL<br>HNHYTQKSLKSPGK |

TABLE 1-8

| 57 | chG019 heavy chain full-length nucleotide sequence | ATGAAACACCTGTGGTTCTTCCTCCTGCTGGTGGCAGCTCCCAGATGGGTGCTGAGC<br>CAGGTGCAGCTGCAGCAGTCTGGCGCCGAGCTCGTGAAGCCTGGCAGCAGCGTGAAG<br>ATCAGCTGCAAGGCCAGCGGCTACACCTTCACCCGGAACTTCATGCACTGGATCAAG<br>CAGCAGCCCGGCAACGGCCTGGAATGGATCGGCTGGATCTATCCCGGCGACGGCGAG<br>ACAGAGTACAACCAGAAGTTCAACGGCAAGGCCACCCTGACCGCCGACAGAAGCAGC<br>TCCACCGCCTACATGGAACTGAGCCGGCTGACCAGCGAGGACAGCGCCGTGTACTTT<br>TGCGCCAGAGGCGTATACGGCGGCTTCGCTGGCGGCTACTTCGATTTTTGGGGCCAG<br>GGCGTGATGGTCACCGTCAGCTCAGCCTCCACCAAGGGCCCAAGCGTCTTCCCCCTG<br>GCACCCTCCTCCAAGAGCACCTCTGGCGGCACAGCCGCCCTGGGCTGCCTGGTCAAG<br>GACTACTTCCCCGAACCCGTGACCGTGAGCTGGAACTCAGGCGCCCTGACCAGCGGC<br>GTGCACACCTTCCCGGCTGTCCTGCAGTCCTCAGGACTCTACTCCCTCAGCAGCGTG<br>GTGACCGTGCCCTCCAGCAGCTTGGGCACCCAGACCTACATCTGCAACGTGAATCAC<br>AAGCCCAGCAACACCAAGGTGGACAAGAGAGTTGAGCCCAAATCTTGTGACAAAACT<br>CACACATGCCCACCGTGCCCAGCACCTGAACTCCTGGGGGGACCCTCAGTCTTCCTC<br>TTCCGCCCAAAACCCAAGGACACCCTCATGATCTCCCGGACCCCTGAGGTCACATGC<br>GTGGTGGTGGACGTGAGCCACGAAGACCCTGAGGTCAAGTTCAACTGGTACGTGGAC<br>GGCGTGGAGGTGCATAATGCCAAGACAAAGCCCCGGGAGGAGCAGTACAACAGCACG<br>TACCGGGTGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAACCATCTCC<br>AAAGCCAAAGGCCAGCCCCGGGAACCACAGGTGTACACCCTGCCCCCATCCCGGGAG<br>GAGATGACCAAGAACCAGGTCAGCCTGACCTGCCTGGTCAAAGGCTTCTATCCCAGC<br>GACATCGCCGTGGAGTGGGAGAGCAATGGCCAGCCCGAGAACAACTACAAGACCACC<br>CCTGCCGTGCTGGACTCCGACGGCTCCTTCTTCCTCTACAGCAAGCTCACCGTGGAC<br>AAGAGCAGGTGGCAGCAGGGCAACGTCTTCTCATGCTCCGTGATGCATGAGGCTCTG<br>CACAACCACTACACCCAGAAGAGCCTCTCCCTGTCTCCCGGCAAA |
| --- | --- | --- |
| 58 | chG019 heavy chain variable region amino acid sequence | QVQLQQSGAELVKPGSSVKISCKASGYTFTRNFMHWIKQQPGNGLEWIGWIYPGDGE<br>TEYNQKFNGKATLTADRSSSTAYMELSRLTSEDSAVYFCARGVYGGFAGGYFDFWGQ<br>GVMVTVSS |
| 59 | chG019 heavy chain variable region nucleotide sequence | CAGGTGCAGCTGCAGCAGTCTGGCGCCGAGCTCGTGAAGCCTGGCAGCAGCGTGAAG<br>ATCAGCTGCAAGGCCAGCGGCTACACCTTCACCCGGAACTTCATGCACTGGATCAAG<br>CAGCAGCCCGGCAACGGCCTGGAATGGATCGGCTGGATCTATCCCGGCGACGGCGAG<br>ACAGAGTACAACCAGAAGTTCAACGGCAAGGCCACCCTGACCGCCGACAGAAGCAGC<br>TCCACCGCCTACATGGAACTGAGCCGGCTGACCAGCGAGGACAGCGCCGTGTACTTT<br>TGCGCCAGAGGCGTATACGGCGGCTTCGCTGGCGGCTACTTCGATTTTTGGGGCCAG<br>GGCGTGATGGTCACCGTCAGCTCA |
| 17 | chG019 CDRH1 | GYTFTRNFMH |
| 60 | chG019 CDRH2 | WIYPGDGETE |
| 19 | ch3019 CDRH3 | GVYGGFAGGYFDF |

TABLE 1-9

| 61 | hL02 light chain full-length amino acid sequence | MVLQTQVFISLLLWISGAYGDIQMTQSPSSLSASVGDRVTITCKASQNIYKNLAWYQ QKPGKAPKLLIYDANTLQTGVPSRFSGSGSGSDFTLTISSLQPEDFATYFCQQYYSG WAFGQGTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSPVTKSF NRGEC |
|---|---|---|
| 62 | hL02 light chain full-length nucleotide sequence | ATGGTGCTGCAGACCCAGGTGTTCATCTCCCTGCTGCTGTGGATCTCCGGCGCGTAC GGCGACATCCAGATGACCCAGAGCCCTAGCAGCCTGAGCGCCAGCGTGGGCGACAGA GTGACCATCACATGCAAGGCCAGCCAGAACATCTACAAGAACCTGGCCTGGTATCAG CAGAAGCCCGGCAAGGCCCCCAAGCTGCTGATCTACGACGCCAACACCCTGCAGACC GGCGTGCCCAGCAGATTTTCTGGCAGCGGCAGCGGCTCCGACTTCACCCTGACAATC AGCAGCCTGCAGCCCGAGGACTTCGCCACCTACTTTTGCCAGCAGTACTACAGCGGC TGGGCCTTCGGCCAGGGCACCAAGGTGGAAATCAAGCGTACGGTGGCCGCCCCCTCC GTGTTCATCTTCCCCCCCTCCGACGAGCAGCTGAAGTCCGGCACCGCCTCCGTGGTG TGCCTGCTGAATAACTTCTACCCCAGAGAGGCCAAGGTGCAGTGGAAGGTGGACAAC GCCCTGCAGTCCGGGAACTCCCAGGAGAGCGTGACCGAGCAGGACAGCAAGGACAGC ACCTACAGCCTGAGCAGCACCCTGACCCTGAGCAAAGCCGACTACGAGAAGCACAAG GTGTACGCCTGCGAGGTGACCCACCAGGGCCTGAGCTCCCCCGTCACCAAGAGCTTC AACAGGGGGGAGTGT |
| 63 | hL02 light chain variable region amino acid sequence | DIQMTQSPSSLSASVGDRVTITCKASQNIYKNLAWYQQKPGKAPKLLIYDANTLQTG VPSRFSGSGSGSDFTLTISSLQPEDFATYFCQQYYSGWAFGQGTKVEIKRT |
| 64 | hL02 light chain variable region nucleotide sequence | GACATCCAGATGACCCAGAGCCCTAGCAGCCTGAGCGCCAGCGTGGGCGACAGAGTG ACCATCACATGCAAGGCCAGCCAGAACATCTACAAGAACCTGGCCTGGTATCAGCAG AAGCCCGGCAAGGCCCCCAAGCTGCTGATCTACGACGCCAACACCCTGCAGACCGGC GTGCCCAGCAGATTTTCTGGCAGCGGCAGCGGCTCCGACTTCACCCTGACAATCAGC AGCCTGCAGCCCGAGGACTTCGCCACCTACTTTTGCCAGCAGTACTACAGCGGCTGG GCCTTCGGCCAGGGCACCAAGGTGGAAATCAAGCGTACG |
| 65 | hL03 light chain full-length amino acid sequence | MVLQTQVFISLLLWISGAYGDIQMTQSPSSLSASVGDRVTITCKASQNIYKNLAWYQ QKLGEGPKLLIYDANTLQTGVPSRFSGSGSGTDFTLTISSLQPEDFATYYCQQYYSG WAFGQGTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSPVTKSF NRGEC |

TABLE 1-10

| 66 | hL03 light chain full-length nucleotide sequence | ATGGTGCTGCAGACCCAGGTGTTCATCTCCCTGCTGCTGTGGATCTCCGGCGCGTAC GGCGACATCCAGATGACCCAGAGCCCTAGCAGCCTGAGCGCCAGCGTGGGCGACAGA GTGACCATCACATGCAAGGCCAGCCAGAACATCTACAAGAACCTGGCCTGGTATCAG CAGAAGCTGGGCGAGGGCCCCAAGCTGCTGATCTACGACGCCAACACCCTGCAGACC GGCGTGCCCAGCAGATTTTCTGGCAGCGGCTCCGGCACCGACTTCACCCTGACAATC AGCAGCCTGCAGCCCGAGGACTTCGCCACCTACTACTGCCAGCAGTACTACAGCGGC TGGGCCTTTGGCCAGGGCACCAAGGTGGAAATCAAGCGTACGGTGGCCGCCCCCTCC GTGTTCATCTTCCCCCCCTCCGACGAGCAGCTGAAGTCCGGCACCGCCTCCGTGGTG TGCCTGCTGAATAACTTCTACCCCAGAGAGGCCAAGGTGCAGTGGAAGGTGGACAAC GCCCTGCAGTCCGGGAACTCCCAGGAGAGCGTGACCGAGCAGGACAGCAAGGACAGC ACCTACAGCCTGAGCAGCACCCTGACCCTGAGCAAAGCCGACTACGAGAAGCACAAG GTGTACGCCTGCGAGGTGACCCACCAGGGCCTGAGCTCCCCCGTCACCAAGAGCTTC AACAGGGGGGAGTGT |
|---|---|---|
| 67 | hL03 light chain variable region amino acid sequence | DIQMTQSPSSLSASVGDRVTITCKASQNIYKNLAWYQQKLGEGPKLLIYDANTLQTG VPSRFSGSGSGTDFTLTISSLQPEDFATYYCQQYYSGWAFGQGTVEIKRT |
| 68 | hL03 light chain variable region nucleotide sequence | GACATCCAGATGACCCAGAGCCCTAGCAGCCTGAGCGCCAGCGTGGGCGACAGAGTG ACCATCACATGCAAGGCCAGCCAGAACATCTACAAGAACCTGGCCTGGTATCAGCAG AAGCTGGGCGAGGGCCCCAAGCTGCTGATCTACGACGCCAACACCCTGCAGACCGGC GTGCCCAGCAGATTTTCTGGCAGCGGCTCCGGCACCGACTTCACCCTGACAATCAGC AGCCTGCAGCCCGAGGACTTCGCCACCTACTACTGCCAGCAGTACTACAGCGGCTGG GCCTTTGGCCAGGGCACCAAGGTGGAAATCAAGCGTACG |
| 69 | hH01 heavy chain full-length amino acid sequence | MKWLWFFLLLVAAPRWVLSEVQLVQSGAEVKKPGASVKVSCKASGYTFTRNFMHWVR QAPGQGLEWMGWIYPGDGETEYAQKFQGRVTITADTSTSTAYMELSSLRSEDTAVYY CARGVYGGFAGGYFDFWGQGTLVTVSSASTKGPSVFPLAPSSKSTSGGTAALGCLVK DYFPEPVTVSWNSGALTSGVHTFPAVLQSSGLYSLSSVVTVPSSSLGTQTYICNVNH KPSNTKVDKRVEPKSCDKTHTCPPCPAPELLGGPSVFLFPPKPKDTLMISRTPEVTC VVVDVSHEDPEVKFNWYVDGVEVHNAKTKPREEQYNSTYRVVSVLTVLHQDWLNGKE YKCKVSNKALPAPIEKTISKAKGQPREPQVYTLPPSREEMTKNQVSLTCLVKGFYPS DIAVEWESNGQPENNYKTTPPVLDSDGSFFLYSKLTVDKSRWQQGNVFSCSVMHEAL HNHYTQKSLSLSPGK |

TABLE 1-11

| 70 | hH01 heavy chain full-length nucleotide sequence | ATGAAACACCTGTGGTTCTTCCTCCTGCTGGTGGCAGCTCCCAGATGGGTGCTGAGC
GAAGTGCAGCTGGTGCAGTCTGGCGCCGAAGTGAAGAAACCAGGCGCCAGCGTGAAG
GTGTCCTGCAAGGCCAGCGGCTACACCTTTACCCGGAACTTCATGCACTGGGTGCGC
CAGGCTCCAGGCCAGGGACTGGAATGGATGGGCTGGATCTATCCCGGCGACGGCGAG
ACAGAGTACGCCCAGAAATTCCAGGGCAGAGTGACCATCACCGCCGACACCAGCACC
TCCACCGCCTACATGGAACTGAGCAGCCTGCGGAGCGAGGACACCGCCGTGTACTAT
TGTGCCAGAGGCGTGTACGGCGGCTTCGCTGGCGGCTACTTCGATTTTGGGGCCAG
GGCACCCTCGTGACCGTCAGCTCAGCCTCCACCAAGGGCCCAAGCGTCTTCCCCCTG
GCACCCTCCTCCAAGAGCACCTCTGGCGGCACAGCCGCCCTGGGCTGCCTGGTCAAG
GACTACTTCCCCGAACCCGTGACCGTGAGCTGGAACTCAGGCGCCCTGACCAGCGGC
GTGCACACCTTGCCCGCTGTCCTGCAGTCCTCAGGACTCTACTCCCTCAGCAGCGTG
GTGACCGTGCCGTCCAGCAGCTTGGGCACCCAGACCTACATCTGCAACGTGAATCAC
AAGCCCAGCAACACCAAGGTGGACAAGAGAGTTGAGCCCAAATCTTGTGACAAAACT
CACACATGCCCACCCTGCCCAGCACCTGAACTCCTGGGGGGACCCTCAGTCTTCCTC
TTCCCCCCAAAACCCAAGGACACCCTCATGATCTCCGGGACCGCTGAGGTCACATGC
GTGGTGGTGGACGTGAGCCACGAAGACCCTGAGGTCAAGTTCAACTGGTACGTGGAC
GGCGTGGAGGTGCATAATGCCAAGACAAAGCCCGGGAGGAGCAGTACAACAGCACG
TACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTCC
AAAGCCAAAGGCCAGCCCCGGGAACCACAGGTGTACACCCTGCCCCCATCCCGGGAG
GAGATGACCAAGAACCAGGTCAGCCTGACCTGCCTGGTCAAAGGCTTCTATCCCAGC
GACATCGCCGTGGAGTGGGAGAGCAATGGCCAGCCCGAGAACAACTACAAGACCACC
CCTCCCGTGCTGGACTCCGACGGCTCCTTCTTCCTCTACAGCAAGCTCACCGTGGAC
AAGAGCAGGTGGCAGCAGGGCAACGTCTTCTCATGCTCCGTGATGCATGAGGCTCTG
CACAACCACTACACCCAGAAGAGCCTCTCCCTGTCTCCGGCAAA |
| 71 | hH01 heavy chain variable region amino acid sequence | EVQLVQSGAEVKKPGASVKVSCKASGYTFTRNFMHWVRQAPGQGLEWMGWIYPGDGE
TEYAQKFQGRVTITADTSTSTAYMELSSLRSEDTAVYYCARGVYGGFAGGYFDFWGQ
GTLVTVSS |
| 72 | hH01 heavy chain variable region nucleotide sequence | GAAGTGCAGCTGGTGCAGTCTGGCGCCGAAGTGAAGAAACCAGGCGCCAGCGTGAAG
GTGTCCTGCAAGGCCAGCGGCTACACCTTTACCCGGAACTTCATGCACTGGGTGCGC
CAGGCTCCAGGCCAGGGACTGGAATGGATGGGCTGGATCTATCCCGGCGACGGCGAG
ACAGAGTACGCCCAGAAATTCCAGGGCAGAGTGACCATCACCGCCGACACCAGCACC
TCCACCGCCTACATGGAACTGAGCAGCCTGCGGAGCGAGGACACCGCCGTGTACTAT
TGTGCCAGAGGCGTGTACGGCGGCTTCGCTGGCGGCTACTTCGATTTTGGGGCCAG
GGCACCCTCGTGACCGTCAGCTCA |

TABLE 1-12

| 73 | hH02 heavy chain full-length amino acid sequence | MKHLWFFLLLVAAPRWVLSEVQLVQSGAEVKKPGASVKVSCKASGYTFTRNFMHWVR
QAPGQGLEWMGWIYPGDGETEYNQKFQGRVTITADRSTSTAYMELSSLRSEDTAVYF
CARGVYGGFAGGYFDFWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNH
KPSNTKVDKRVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEAL
HNHYTQKSLSLSPGK |
| 74 | hH02 heavy chain full-length nucleotide sequence | ATGAAACACCTGTGGTTCTTCCTCCTGCTGGTGGCAGCTCCCAGATGGGTGCTGAGC
GAAGTGCAGCTGGTGCAGTCTGGCGCCGAAGTGAAGAAACCAGGCGCCAGCGTGAAG
GTGTCCTGCAAGGCCAGGGGCTACACCTTTACCCGGAACTTCATGCACTGGGTGCGC
CAGGCTCCAGGCCAGGGACTGGAATGGATGGGCTGGATCTATCCCGGCGACGGCGAG
ACAGAGTACAACCAGAAATTCCAGGGCAGAGTGACCATCACCGCCGACAGAAGCACC
AGCACCGCCTACATGGAACTGAGCAGCCTGCGGAGCGAGGATACCGCCGTGTACTTC
TGTGCCAGAGGCGTGTACGGCGGCTTCGCTGGCGGCTACTTCGATTTTGGGGCCAG
GGCACCCTCGTGACCGTCAGCTCAGCCTCCACCAAGGGCCCAAGCGTCTTCCCCCTG
GCACCGTCCTCCAAGAGCACCTCTGGCGGCACAGCCGCCCTGGGCTGCCTGGTCAAG
GACTACTTCCCCGAACCCGTGACCGTGAGCTGGAACTCAGGCGCCCTGACCAGCGGC
GTGCACACCTTCCCCGCTGTCCTGCAGTCCTCAGGACTCTACTCCCTCAGCAGCGTG
GTGACCGTGCCCTCCAGCAGCTTGGGCACCCAGACCTACATCTGCAACGTGAATCAC
AAGCCCAGCAACACCAAGGTGGACAAGAGAGTTGAGCCCAAATCTTGTGACAAAACT
CACACATGCCCACCCTGCCCAGCACCTGAACTCCTGGGGGGACCCTCAGTCTTCCTC
TTCCCCGCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGAC
GGCGTGGAGGTGCATAATGCCAAGACAAAGCCCCGGGAGGAGCAGTACAACAGCACG
TACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTCC
AAAGCCAAAGGCCAGCCCCGGGAACCACAGGTGTACACCCTGCCCCCATCCCGGGAG
GAGATGACCAAGAACCAGGTCAGCCTGACCTGCCTGGTCAAAGGCTTCTATCCCAGC
GACATCGCCGTGGAGTGGGAGAGCAATGGCCAGCCCGAGAACAACTACAAGACCACC
CCTCCCGTGCTGGACTCCGACGGCTCCTTCTTCCTCTACAGCAAGCTCACCGTGGAC
AAGAGCAGGTGGCAGCAGGGCAACGTCTTCTCATGCTCCGTGATGCATGAGGCTCTG
CACAACCACTACACCCAGAAGAGCCTCTCCCTGTCTCCGGGCAAA |

TABLE 1-12-continued

| 75 | hH02 heavy chain variable region amino acid sequence | EVQLVQSGAEVKKPGASVKVSCKASGYTFTRNFMHWVRQAPGQGLEWMGWIYPGDGE TEYNQKFQGRVTITADRSTSTAYMELSSLRSEDTAVYFCARGVYGGFAGGYFDFWGQ GTLVTVSS |

TABLE 1-13

| 76 | hH02 heavy chain variable region nucleotide sequence | GAAGTGCAGCTGGTGCAGTCTGGCGCCGAAGTGAAGAAACCAGGCGCCAGCGTGAAG GTGTGCTGCAAGGCCAGCGGCTACACCTTTACCCGGAACTTCATGCACTGGGTGCGC CAGGCTCCAGGCCAGGGACTGGAATGGATGGGCTGGATCTATCCCGGCGACGGCGAG ACAGAGTACAACCAGAAATTCCAGGGCAGAGTGACCATCACCGCCGACAGAAGCACC AGCACCGCCTACATGGAACTGAGCAGCCTGCGGAGCGAGGATACCGCCGTGTACTTC TGTGCCAGAGGCGTGTACGGCGGCTTCGCTGGCGGCTACTTCGATTTTTGGGGCCAG GGCACCCTCGTGACCGTCAGCTCA |
| 77 | hH04 heavy chain full-length amino acid sequence | MKHLWFFLLLVAAPRWVLSQVQLVQSGAEVKKPGASVKVSCKASGYTFTRNFMHWIR QAPGQGLEWMGWIYPGDGETEYAQKFQGRVTLTADRSTSTAYMELSSLRSEDTAVYY CARGVYGGFAGGYFDFWGQGTLVTVSSASTKGPSVFPLAPSSKSTSGGTAALGCLVK DYFPEPVTVSWNSGALTSGVHTFPAVLQSSGLYSLSSVVTVPSSSLGTQTYICNVNH KPSNTKVDKRVEPKSCDKTHTCPPCPAPELLGGPSVFLFPPKPKDTLMISRTPEVTC VVVDVSHEDPEVKFNWYVDGVEVHNAKTKPREEQYNSTYRVVSVLTVLHQDWLNGKE YKCKVSNKALPAPIEKTISKAKGQPREPQVYTLPPSREEMTKNQVSLTCLVKGFYPS DIAVEWESNGQPENNYKTTPPVLDSDGSFFLYSKLTVDKSRWQQGNVFSCSVMHEAL HNHYTQKSLSLSPGK |
| 78 | hH04 heavy chain full-length nucleotide sequence | ATGAAACACCTGTGGTTCTTCCTCCTGCTGGTGGCAGCTCCCAGATGGGTGCTGAGC CAGGTGCAGCTGGTGCAGTCTGGCGCCGAAGTGAAGAAACCAGGCGCCAGCGTGAAG GTGTCCTGCAAGGCCAGCGGCTACACCTTTACCCGGAACTTCATGCACTGGATCCGG CAGGCCCCTGGACAGGGCCTGGAATGGATGGGCTGGATCTATCCCGGCGACGGCGAG ACAGAGTACGCCCAGAAATTCCAGGGCAGAGTGACCCTGACCGCCGACAGAAGCACC AGCACCGCCTACATGGAACTGAGCAGCCTGCGGAGCGAGGACACCGCCGTGTACTAT TGTGCCAGAGGCGTGTACGGCGGCTTCGCTGGCGGCTACTTCGATTTTTGGGGCCAG GGCACCCTCGTGACCGTCAGCTCAGCCTCCACCAAGGGCCCAAGCGTCTTCCCCCTG GCACCCTCCTCCAAGAGCACCTCTGGCGGCACAGCCGCCCTGGGCTGCCTGGTCAAG GACTACTTGCCCGAACCCGTGACCGTGAGCTGGAACTCAGGCGCCCTGACCAGCGGC GTGCACACCTTCCCCGCTGTCCTGCAGTCCTCAGGACTCTACTCCCTCAGCAGCGTG GTGACCGTGCCCTCCAGCAGCTTGGGCACCCAGACCTACATCTGCAACGTGAATCAC AAGCCCAGCAACACCAAGGTGGACAAGAGAGTTGAGCCCAAATCTTGTGACAAAACT CACACATGCCCACCCTGCCCAGCACCTGAACTCCTGGGGGGACCCTCAGTCTTCCTC TTCCCCCCAAAACCCAAGGACACCCTCATGATCTCCCGGACCCCTGAGGTCACATGC GTGGTGGTGGACGTGAGCCACGAAGACCCTGAGGTCAAGTTCAACTGGTACGTGGAC GGCGTGGAGGTGCATAATGCCAAGACAAAGCCCCGGGAGGAGCAGTACAACAGCACG TACCGGGTGGTCAGCGTCCTCACCGTCCTGCACCAGGACTGGCTGAATGGCAAGGAG TACAAGTGCAAGGTCTCCAACAAAGCCCTCCCAGCCGCCATCGAGAAAACCATCTCC AAAGCCAAAGGCCAGCCCCGGGAACCACAGGTGTACACCCTGCCCCCATCCCGGGAG GAGATGACCAAGAACCAGGTCAGCCTGACCTGCCTGGTCAAAGGCTTCTATCCCAGC GACATCGCCGTGGAGTGGGAGAGCAATGGCCAGGCCGAGAACAACTACAAGACCACC CCTCCCGTGCTGGACTCCGACGGCTCCTTCTTCCTCTACAGCAAGCTCACCGTGGAC AAGAGCAGGTGGCAGCAGGGCAACGTCTTCTCATGCTCCGTGATGCATGAGGCTCTG CACAACCACTACACCCAGAAGAGCCTCTCCCTGTCTGCCGGCAAA |

TABLE 1-14

| 79 | hH04 heavy chain variable region amino acid sequence | QVQLVQSGAEVKKPGASVKVSCKASGYTFTRNFMHWIRQAPGQGLEWMGWIYPGDGE TEYAQKFQGRVILTADRSTSTAYMELSSLRSEDTAVYYCARGVYGGFAGGYFDFWGQ GTLVTVSS |
| 80 | hH04 heavy chain variable region nucleotide sequence | CAGGTGCAGCTGGTGCAGTCTGGCGCCGAAGTGAAGAAACCAGGCGCCAGCGTGAAG GTGTCCTGCAAGGCCAGCGGCTACACCTTTACCCGGAACTTCATGCACTGGATCCGG CAGGCCCCTGGACAGGGCCTGGAATGGATGGGCTGGATCTATCCGGGCGACGGCGAG ACAGAGTACGCCCAGAAATTCCAGGGCAGAGTGACCCTGACCGCCGACAGAAGCACC AGCACCGCCTACATGGAACTGAGCAGCCTGCGGAGCGAGGACACCGCCGTGTACTAT TGTGCCAGAGGCGTGTACGGCGGCTTCGCTGGCGGCTACTTCGATTTTTGGGGCCAG GGCACCCTCGTGACCGTCAGCTCA |

TABLE 1-14-continued

| 81 | NOV0712 light chain full-length amino acid sequence | MVLQTQVFISLLLWISGAYGDIQMTQSPSSLSASVGDRVTITCRASQSISSYLNWYQ<br>QKPGKAPKLLIYAVSTLQSGVPSRFSGSGSGTDFTLTISSLQPEDFATYYCQQSGTF<br>PPTTFGQGTKVEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQGLSSPVTK<br>SFNRGEC |
| --- | --- | --- |
| 82 | NOV0712 light chain full-length nucleotide sequence | ATGGTGCTGCAGACCCAGGTGTTCATCTCCCTGCTGCTGTGGATCTCCGGCGCGTAC<br>GGCGACATCCAGATGACCCAGAGCCCTAGCAGGCTGAGCGCCAGGGTGGGCGACAGA<br>GTGACCATCACCTGTAGAGCCAGCCAGAGGATCAGGAGCTACCTGAACTGGTATGAG<br>CAGAAGGCCGGCAAGGCCGCCAAACTGCTGATCTAGGCCGTGTCCACACTGCAGAGC<br>GGCGTGCCCAGGAGATTTTCTGGGAGCGGCTCCGGCACCGACTTCACCCTGAGAATC<br>AGGAGCCTGCAGCCCGAGGACTTCGCCACCTACTACTGTCAGCAGTCCGGCACCTTC<br>CCCCCCACCACATTTGGCCAGGGCACCAAGGTGGAAATCAAGCGTACGGTGGCCGCC<br>CCCTCCGTGTTCATCTTCCCGCCCTCCGACGAGCAGCTGAAGTCCGGCACCGCCTCC<br>GTGGTGTGCCTGCTGAATAACTTCTACCCGAGAGAGGCCAAGGTGCAGTGGAAGGTG<br>GAGAACGCGCTGCAGTCCGGGAACTCCCAGGAGAGCGTGACCGAGCAGGACAGCAAG<br>GAGAGCACCTACAGGCTGAGGAGCACCCTGACCCTGAGGAAAGCCGACTACGAGAAG<br>CACAAGGTGTACGCCTGCGAGGTGACCCACCAGGGCCTGAGGTCGCCGGTCACCAAG<br>AGCTTGAACAGGGGGGAGTGT |
| 83 | NOV0712 heavy chain full-length amino acid sequence | MKHLWFFLLLVAAPRWVLSQVQLLESGGGLVQPGGSLRLSCAASGFTFSSHGMHWVR<br>QAPGKGLEWVSVISGSGSNTGYADSVKGRFTISRDNSKNTLYLQMNSLRAEDTAVYY<br>CARQWGSYAFDSWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNVNHKPSN<br>TKVDKRVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCSVMHEALHNHY<br>TQKSLSLSPGK |

TABLE 1-15

| 84 | NOV0712 heavy chain full-length nucleotide sequence | ATGAAACACCTGTGGTTCTTCCTCCTGCTGGTGGCAGCTCCCAGATGGGTGCTGAGC<br>CAGGTGCAGCTGCTGGAATCTGGCGGAGGACTGGTGCAGCCTGGCGGCTCTCTGAGA<br>CTGTCTTGTGCCGCCAGGGGCTTGACCTTCAGCAGCCACGGAATGCACTGGGTGCGC<br>CAGGCCCCTGGAAAGGGACTGGAATGGGTGTCCGTGATCAGCGGCAGCGGCTCCAAT<br>ACCGGCTACGCCGATAGCGTGAAGGGCCGGTTCACCATCAGCCGGGACAACAGCAAG<br>AAGACCCTGTACCTGCAGATGAACAGCCTGCGGGCCGAGGACACCGCCGTGTACTAT<br>TGTGCCAGACAGTGGGGCAGCTACGCCTTCGATTCTTGGGGCCAGGGCACCCTCGTG<br>ACCGTCAGCTCAGCCTCCACCAAGGGCCCAAGCGTCTTCCCCCTGGCACCCTCCTCC<br>AAGAGGACCTCTGGCGGGACAGCGGCCCTGGGCTGCCTGGTCAAGGACTACTTCCCC<br>GAACCCGTGACCGTGAGCTGGAACTCAGGCGCCCTGACCAGCGGCGTGCACACCTTC<br>CCCGCTGTCCTGCAGTGCTCAGGACTCTACTCCCTCAGCAGCGTGGTGACCGTGCCC<br>TCGAGCAGGTTGGGCACCCAGACCTACATCTGCAACGTGAATCACAAGCCCAGCAAC<br>ACCAAGGTGGACAAGAGAGTTGAGCCCAAATCTTGTGACAAAACTCACACATGCCCA<br>CCCTGCCCAGCACCTGAACTCCTGGGGGGACCCTCAGTCTTCCTCTTCCCCCCAAAA<br>CCCAAGGACACGCTCATGATCTCGCGGACCCCTGAGGTCACATGCGTGGTGGTGGAC<br>GTGAGCCACGAAGACCCTGAGGTCAAGTTCAACTGGTACGTGGACGGCGTGGAGGTG<br>CATAATGCCAAGACAAAGCCCCGGGAGGAGCAGTACAACAGCACGTACCGGGTGGTC<br>AGGGTCCTGACCGTGCTGCACCAGGACTGGCTGAATGGCAAGGAGTACAAGTGCAAG<br>GTCTCCAACAAAGCCCTCCCAGCCCCCATCGAGAAAACCATCTCCAAAGCCAAAGGC<br>CAGCCCCGGGAACCACAGGTGTACACCCTGCCCCCATCCCGGGAGGAGATGACCAAG<br>AACCAGGTCAGGCTGACCTGCCTGGTCAAAGGCTTCTATCCCAGCGACATCGCCGTG<br>GAGTGGGAGAGCAATGGCCAGCCCGAGAACAACTACAAGACCACCCCTCCCGTGCTG<br>GACTCCGACGGCTCCTTCTTCCTCTACAGCAAGCTCACCGTGGACAAGAGCAGGTGG<br>CAGCAGGGCAACGTCTTCTCATGCTCCGTGATGCATGAGGCTCTGCACAACCACTAC<br>ACCCAGAAGAGCCTCTCCCTGTCTCCGGCAAA |

In the present description, Tables 1-1 to 1-15 are also collectively referred to as Table 1.

Further examples of the antibody of the present invention can include a human antibody binding to CDH6. The anti-CDH6 human antibody means a human antibody having only the gene sequence of an antibody derived from human chromosomes. The anti-CDH6 human antibody can be obtained by a method using a human antibody-producing mouse having a human chromosomal fragment comprising the heavy chain and light chain genes of a human antibody (see Tomizuka, K. et al., Nature Genetics (1997) 16, p. 133-143; Kuroiwa, Y. et al., Nucl. Acids Res. (1998) 26, p. 3447-3448; Yoshida, H. et al., Animal Cell Technology: Basic and Applied Aspects vol. 10, p. 69-73 (Kitagawa, Y., Matsuda, T. and Iijima, S. eds.), Kluwer Academic Publishers, 1999; Tomizuka, K. et al., Proc. Natl. Acad. Sci. USA (2000) 97, p. 722-727; etc.).

Such a human antibody-producing mouse can be specifically produced by using a genetically modified animal, the gene loci of endogenous immunoglobulin heavy chain and light chain of which have been disrupted and instead the gene loci of human immunoglobulin heavy chain and light chain have been then introduced using a yeast artificial chromosome (YAC) vector or the like, then producing a knock-out animal and a transgenic animal from such a genetically modified animal, and then breeding such animals with one another.

Otherwise, the anti-CDH6 human antibody can also be obtained by transforming eukaryotic cells with cDNA encoding each of the heavy chain and light chain of such a human antibody, or preferably with a vector comprising the cDNA, according to genetic recombination techniques, and then culturing the transformed cells producing a genetically modified human monoclonal antibody, so that the antibody can be obtained from the culture supernatant.

In this context, eukaryotic cells, and preferably, mammalian cells such as CHO cells, lymphocytes or myelomas can, for example, be used as a host.

Furthermore, a method of obtaining a phage display-derived human antibody that has been selected from a human antibody library (see Wormstone, I. M. et al., Investigative Ophthalmology & Visual Science. (2002) 43 (7), p. 2301-2308; Carmen, S. et al., Briefings in Functional Genomics and Proteomics (2002), 1 (2), p. 189-203; Siriwardena, D. et al., Ophthalmology (2002) 109 (3), p. 427-431; etc.) is also known.

For example, a phage display method, which comprises allowing the variable regions of a human antibody to express as a single chain antibody (scFv) on the surface of phages, and then selecting a phage binding to an antigen, can be applied (Nature Biotechnology (2005), 23, (9), p. 1105-1116).

By analyzing the phage gene that has been selected because of its binding ability to the antigen, DNA sequences encoding the variable regions of a human antibody binding to the antigen can be determined.

Once the DNA sequence of scFv binding to the antigen is determined, an expression vector having the aforementioned sequence is produced, and the produced expression vector is then introduced into an appropriate host and can be allowed to express therein, thereby obtaining a human antibody (International Publication Nos. WO92/01047, WO92/20791, WO93/06213, WO93/11236, WO93/19172, WO95/01438, and WO95/15388, Annu. Rev. Immunol (1994) 12, p. 433-455, Nature Biotechnology (2005) 23 (9), p. 1105-1116).

If a newly produced human antibody binds to a partial peptide or a partial three-dimensional structure to which any one rat anti-human CDH6 antibody, chimeric anti-human CDH6 antibody or humanized anti-human CDH6 antibody described in the present description (e.g., the rG019 antibody, the rG055 antibody, the rG056 antibody, the rG061 antibody, the chG019 antibody, the H01L02 antibody, the H02L02 antibody, the H02L03 antibody or the H04L02 antibody) binds, it can be determined that the human antibody binds to the same epitope to which the rat anti-human CDH6 antibody, the chimeric anti-human CDH6 antibody or the humanized anti-human CDH6 antibody binds. Alternatively, by confirming that the human antibody competes with the rat anti-human CDH6 antibody, the chimeric anti-human CDH6 antibody or the humanized anti-human CDH6 antibody described in the present description (e.g., the rG019 antibody, the rG055 antibody, the rG056 antibody, the rG061 antibody, the chG019 antibody, the H01L02 antibody, the H02L02 antibody, the H02L03 antibody or the H04L02 antibody) in the binding of the antibody to CDH6 (e.g., the human antibody interferes with the binding of the rG019 antibody, the rG055 antibody, the rG056 antibody, the rG061 antibody, the chG019 antibody, the H01L02 antibody, the H02L02 antibody, the H02L03 antibody or the H04L02 antibody to CDH6, preferably EC3 of CDH6), it can be determined that the human antibody binds to the same epitope to which the rat anti-human CDH6 antibody, the chimeric anti-human CDH6 antibody or the humanized anti-human CDH6 antibody described in the present description binds, even if the specific sequence or structure of the epitope has not been determined. In the present description, when it is determined by at least one of these determination methods that the human antibody "binds to the same epitope", it is concluded that the newly prepared human antibody "binds to the same epitope" as that for the rat anti-human CDH6 antibody, the chimeric anti-human CDH6 antibody or the humanized anti-human CDH6 antibody described in the present description. When it is confirmed that the human antibody binds to the same epitope, then it is expected that the human antibody should have a biological activity equivalent to that of the rat anti-human CDH6 antibody, the chimeric anti-human CDH6 antibody or the humanized anti-human CDH6 antibody (e.g., the rG019 antibody, the rG055 antibody, the rG056 antibody, the rG061 antibody, the chG019 antibody, the H01L02 antibody, the H02L02 antibody, the H02L03 antibody or the H04L02 antibody).

The chimeric antibodies, the humanized antibodies, or the human antibodies obtained by the above-described methods are evaluated for their binding activity against the antigen according to a known method, etc., so that a preferred antibody can be selected.

One example of another indicator for comparison of the properties of antibodies can include the stability of an antibody. A differential scanning calorimeter (DSC) is an apparatus capable of promptly and exactly measuring a thermal denaturation midpoint (Tm) serving as a good indicator for the relative structural stability of a protein. By using DSC to measure Tm values and making a comparison regarding the obtained values, differences in thermal stability can be compared. It is known that the preservation stability of an antibody has a certain correlation with the thermal stability of the antibody (Lori Burton, et al., Pharmaceutical Development and Technology (2007) 12, p. 265-273), and thus, a preferred antibody can be selected using thermal stability as an indicator. Other examples of the indicator for selection of an antibody can include high yield in suitable host cells and low agglutination in an aqueous solution. For example, since an antibody with the highest yield does not always exhibit the highest thermal stability, it is necessary to select an antibody most suitable for administration to a human by comprehensively determining it based on the aforementioned indicators.

The antibody of the present invention also includes a modification of an antibody. The modification is used to mean the antibody of the present invention, which is chemically or biologically modified. Examples of such a chemical modification include the binding of a chemical moiety to an amino acid skeleton, and the chemical modification of an N-linked or O-linked carbohydrate chain. Examples of such a biological modification include antibodies which have undergone a posttranslational modification (e.g., N-linked or O-linked glycosylation, N-terminal or C-terminal processing, deamidation, isomerization of aspartic acid, oxidation of methionine, and conversion of N-terminal glutamine or N-terminal glutamic acid to pyroglutamic acid), and antibodies, to the N-terminus of which a methionine residue is added as a result of having been allowed to be expressed using prokaryote host cells. In addition, such a modification is also meant to include labeled antibodies for enabling detection or isolation of the antibody of the present invention or an antigen, for example, an enzymatically labeled antibody, a fluorescently labeled antibody, and an affinity-labeled antibody. Such a modification of the antibody of the present invention is useful for the improvement of the stability and retention in blood of an antibody; a reduction in antigenicity; detection or isolation of an antibody or an antigen; etc.

Moreover, by regulating a sugar chain modification (glycosylation, de-fucosylation, etc.) that binds to the antibody of the present invention, antibody-dependent cellular cytotoxic activity can be enhanced. As techniques of regulating the sugar chain modification of an antibody, those described in International Publication Nos. WO1999/54342, WO2000/61739, and WO2002/31140, etc. are known, though the techniques are not limited thereto. The antibody of the present invention also includes antibodies in respect of which the aforementioned sugar chain modification has been regulated.

Once an antibody gene is isolated, the gene can be introduced into an appropriate host to produce an antibody, using an appropriate combination of a host and an expression vector. A specific example of the antibody gene can be a combination of a gene encoding the heavy chain sequence of the antibody described in the present description and a gene encoding the light chain sequence of the antibody described therein. Upon transformation of host cells, such a heavy chain sequence gene and a light chain sequence gene may be inserted into a single expression vector, or these genes may instead each be inserted into different expression vectors.

When eukaryotic cells are used as hosts, animal cells, plant cells or eukaryotic microorganisms can be used. In particular, examples of the animal cells can include mammalian cells such as COS cells which are monkey cells (Gluzman, Y., Cell (1981) 23, p. 175-182, ATCC CRL-1650), mouse fibroblasts NIH3T3 (ATCC No. CRL-1658), a dihydrofolate reductase-deficient cell line of Chinese hamster ovary cells (CHO cells, ATCC CCL-61) (Urlaub, G. and Chasin, L. A. Proc. Natl. Acad. Sci. U.S.A. (1980) 77, p. 4126-4220), and FreeStyle 293F cells (Invitrogen Corp.).

When prokaryotic cells are used as hosts, *Escherichia coli* or *Bacillus subtilis* can be used, for example.

An antibody gene of interest is introduced into these cells for transformation, and the transformed cells are then cultured in vitro to obtain an antibody. In the aforementioned culture, there are cases where yield is different depending on the sequence of the antibody, and thus, it is possible to select an antibody, which is easily produced as a medicament, from antibodies having equivalent binding activity, using the yield as an indicator. Accordingly, the antibody of the present invention also includes an antibody obtained by the above-described method for producing an antibody, which comprises a step of culturing the transformed host cells and a step of collecting an antibody of interest or a functional fragment of the antibody from the culture obtained in the aforementioned step.

It is known that the lysine residue at the carboxyl terminus of the heavy chain of an antibody produced in cultured mammalian cells is deleted (Journal of Chromatography A, 705: 129-134 (1995)), and also, it is known that the two amino acid residues at the heavy chain carboxyl terminus, glycine and lysine, are deleted, and that the proline residue newly positioned at the carboxyl terminus is amidated (Analytical Biochemistry, 360: 75-83 (2007)). However, such deletion and modification of these heavy chain sequences does not have an influence on the antigen-binding activity and effector function (activation of complement, antibody-dependent cellular cytotoxicity, etc.) of an antibody. Accordingly, the antibody according to the present invention also includes an antibody that has undergone the aforementioned modification, and a functional fragment of the antibody, and specific examples of such an antibody include a deletion mutant comprising a deletion of 1 or 2 amino acids at the heavy chain carboxyl terminus, and a deletion mutant formed by amidating the aforementioned deletion mutant (e.g., a heavy chain in which the proline residue at the carboxyl-terminal site is amidated). However, deletion mutants involving a deletion at the carboxyl terminus of the heavy chain of the antibody according to the present invention are not limited to the above-described deletion mutants, as long as they retain antigen-binding activity and effector function. Two heavy chains constituting the antibody according to the present invention may be any one type of heavy chain selected from the group consisting of a full-length antibody and the above-described deletion mutants, or may be a combination of any two types selected from the aforementioned group. The ratio of individual deletion mutants can be influenced by the types of cultured mammalian cells that produce the antibody according to the present invention, and the culture conditions. Examples of the main ingredient of the antibody according to the present invention can include antibodies where one amino acid residue is deleted at each of the carboxyl termini of the two heavy chains.

Examples of the isotype of the antibody of the present invention can include IgG (IgG1, IgG2, IgG3, and IgG4). Among others, IgG1 and IgG4 are preferable.

Examples of the biological activity of an antibody can generally include antigen-binding activity, activity of being internalized into cells expressing an antigen by binding to the antigen, activity of neutralizing the activity of an antigen, activity of enhancing the activity of an antigen, antibody-dependent cellular cytotoxic (ADCC) activity, complement-dependent cytotoxic (CDC) activity, and antibody-dependent cellular phagocytosis (ADCP). The function of the antibody according to the present invention is binding activity against CDH6 and is preferably the activity of being internalized into CDH6-expressing cells by binding to CDH6. Moreover, the antibody of the present invention may have ADCC activity, CDC activity and/or ADCP activity, as well as cellular internalization activity.

The obtained antibody can be purified to a homogenous state. For separation and purification of the antibody, separation and purification methods used for ordinary proteins may be used. For example, column chromatography, filtration, ultrafiltration, salting-out, dialysis, preparative polyacrylamide gel electrophoresis, and isoelectric focusing are appropriately selected and combined with one another, so that the antibody can be separated and purified (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)), though examples of the separation and purification methods are not limited thereto.

Examples of the chromatography can include affinity chromatography, ion exchange chromatography, hydrophobic chromatography, gel filtration chromatography, reverse phase chromatography, and absorption chromatography.

These chromatographic techniques can be carried out using liquid chromatography such as HPLC or FPLC.

Examples of the column used in the affinity chromatography can include a Protein A column and a Protein G column. Examples of the column involving the use of Protein A can include Hyper D, POROS, and Sepharose F. F. (Pharmacia).

Also, using an antigen-immobilized carrier, the antibody can be purified by utilizing the binding activity of the antibody to the antigen.

3. Anti-CDH6 Antibody-Drug Conjugate (1) Drug

The anti-CDH6 antibody obtained in the above "2. Production of anti-CDH6 antibody" can be conjugated to a drug via a linker structure moiety to prepare an anti-CDH6 antibody-drug conjugate. The drug is not particularly limited as long as it has a substituent or a partial structure that can be connected to a linker structure. The anti-CDH6 antibody-drug conjugate can be used for various purposes according to the conjugated drug. Examples of such a drug can include substances having antitumor activity, substances effective for blood diseases, substances effective for autoimmune diseases, anti-inflammatory substances, antimicrobial substances, antifungal substances, antiparasitic substances, antiviral substances, and anti-anesthetic substances.

(1)-1 Antitumor Compound

An example using an antitumor compound as a compound to be conjugated in the anti-CDH6 antibody-drug conjugate of the present invention will be described below. The antitumor compound is not particularly limited as long as the compound has an antitumor effect and has a substituent or a partial structure that can be connected to a linker structure. Upon cleavage of a part or the whole of the linker in tumor cells, the antitumor compound moiety is released so that the antitumor compound exhibits an antitumor effect. As the linker is cleaved at a connecting position with the drug, the antitumor compound is released in its original structure to exert its original antitumor effect.

The anti-CDH6 antibody obtained in the above "2. Production of anti-CDH6 antibody" can be conjugated to the antitumor compound via a linker structure moiety to prepare an anti-CDH6 antibody-drug conjugate.

As one example of the antitumor compound used in the present invention, exatecan, a camptothecin derivative ((1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione represented by the following formula) can preferably be used.

[Formula 5]

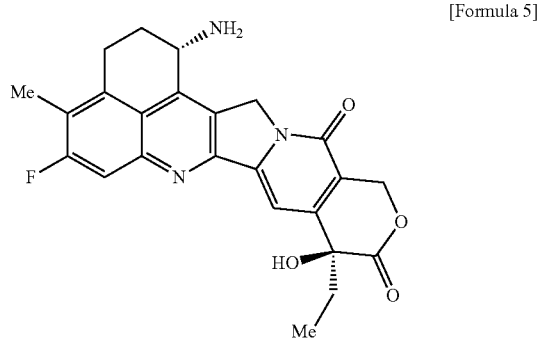 [SMILES: CC[C@@]1(O)C(=O)OCc2c1cc1n(c2=O)Cc2c-1nc1cc(F)c(C)c3c1c2[C@@H](N)CC3]

The compound can be easily obtained by, for example, a method described in U.S. Patent Publication No. US2016/0297890 or other known methods, and the amino group at position 1 can be preferably used as a connecting position to the linker structure. Further, exatecan may be released in tumor cells while a part of the linker is still attached thereto. However, the compound exerts an excellent antitumor effect even in such a state.

Since exatecan has a camptothecin structure, it is known that the equilibrium shifts to a structure with a formed lactone ring (closed ring) in an acidic aqueous medium (e.g., of the order of pH 3) whereas the equilibrium shifts to a structure with an opened lactone ring (open ring) in a basic aqueous medium (e.g., of the order of pH 10). A drug conjugate into which exatecan residues corresponding to such a closed ring structure and an open ring structure have been introduced is also expected to have an equivalent antitumor effect, and it is needless to say that any of such drug conjugate is included within the scope of the present invention.

Other examples of the antitumor compound can include antitumor compounds described in the literature (Pharmacological Reviews, 68, p. 3-19, 2016). Specific examples thereof can include doxorubicin, calicheamicin, dolastatin 10, auristatins such as monomethyl auristatin E (MMAE) and monomethyl auristatin F (MMAF), maytansinoids such as DM1 and DM4, a pyrrolobenzodiazepine dimer SG2000 (SJG-136), a camptothecin derivative SN-38, duocarmycins such as CC-1065, amanitin, daunorubicin, mitomycin C, bleomycin, cyclocytidine, vincristine, vinblastine, methotrexate, platinum-based antitumor agents (cisplatin and derivatives thereof), and Taxol and derivatives thereof.

In the antibody-drug conjugate, the number of conjugated drug molecules per antibody molecule is a key factor having an influence on the efficacy and safety thereof. The production of the antibody-drug conjugate is carried out by specifying reaction conditions such as the amounts of starting materials and reagents used for reaction, so as to attain a constant number of conjugated drug molecules. Unlike the chemical reaction of a low-molecular-weight compound, a mixture containing different numbers of conjugated drug molecules is usually obtained. The number of conjugated drug molecules per antibody molecule is defined and indicated as an average value, i.e., the average number of conjugated drug molecules. Unless otherwise specified, i.e., except in the case of representing an antibody-drug conjugate having a specific number of conjugated drug molecules that is included in an antibody-drug conjugate mixture having different numbers of conjugated drug molecules, the number of conjugated drug molecules according to the present invention also means an average value as a rule. The number of exatecan molecules conjugated to an antibody molecule is controllable, and as an average number of conjugated drug molecules per antibody, approximately 1 to 10 exatecan molecules can be conjugated. The number of exatecan molecules is preferably 2 to 8, 3 to 8, 4 to 8, 5 to 8, 6 to 8, or 7 to 8, more preferably 5 to 8, further preferably 7 to 8, still further preferably 8. It is to be noted that a person skilled in the art can design a reaction for conjugating a required number of drug molecules to an antibody molecule based on the description of Examples of the present application, and can obtain an antibody-drug conjugate with a controlled number of conjugated exatecan molecules.

(2) Linker Structure

The linker structure which conjugates the drug to the anti-CDH6 antibody in the anti-CDH6 antibody-drug conjugate of the present invention will be described.

In the antibody-drug conjugate of the present application, the linker structure which conjugates the anti-CDH6 antibody to the drug is not particularly limited as long as the resulting antibody-drug conjugate can be used. The linker structure may be appropriately selected and used according to the purpose of use. One example of the linker structure can include a linker described in known literature (Pharmacol Rev 68: 3-19, January 2016, Protein Cell DOI 10.1007/s13238-016-0323-0, etc.). Further specific examples thereof can include VC (valine-citrulline), MC (maleimidocaproyl), SMCC (succinimidyl 4-(N-maleimidomethyl) cyclohexane-1-carboxylate), SPP (N-succinimidyl 4-(2-pyridyldithio) pentanoate, SS (disulfide), SPDB (N-succinimidyl 4-(2-pyridyldithio)butyrate, SS/hydrazone, hydrazone and carbonate.

Another example can include a linker structure described in U.S. Patent Publication No. US2016/0297890 (as one example, those described in paragraphs [0260] to [0289] thereof). Any linker structure given below can preferably be used. It is to be noted that the left terminus of the structure is a connecting position to the antibody, and the right terminus thereof is a connecting position to the drug. Furthermore, GGFG in the linker structures given below represents an amino acid sequence consisting of glycine-glycine-phenylalanine-glycine (GGFG) linked through peptide bonds.

-(Succinimid-3-yl-N)—CH$_2$CH$_2$—C(=O)-GGFG-NH—CH$_2$CH$_2$CH$_2$—C(=O)—,
-(Succinimid-3-yl-N)—CH$_2$CH$_2$CH$_2$CH$_2$CH$_2$—C(=O)-GGFG-NH—CH$_2$CH$_2$CH$_2$—C(=O)—,
-(Succinimid-3-yl-N)—CH$_2$CH$_2$CH$_2$CH$_2$CH$_2$—C(=O)-GGFG-NH—CH$_2$—O—CH$_2$—C(=O)—,
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—,
-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—, and
-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—.

More preferred are the following:
-(Succinimid-3-yl-N)—CH$_2$CH$_2$CH$_2$CH$_2$CH$_2$—C(=O)-GGFG-NH—CH$_2$—O—CH$_2$—C(=O)—,
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—, and
-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—.

Still more preferred are the following:
-(Succinimid-3-yl-N)—CH$_2$CH$_2$CH$_2$CH$_2$CH$_2$—C(=O)-GGFG-NH—CH$_2$—O—CH$_2$—C(=O)—, and
-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—.

The antibody is connected to the terminus of -(Succinimid-3-yl-N) (e.g., a terminus opposite (left terminus) to the terminus to which —CH$_2$CH$_2$CH$_2$CH$_2$CH$_2$— is connected in "-(Succinimid-3-yl-N)—CH$_2$CH$_2$CH$_2$CH$_2$CH$_2$—C(=O)-GGFG-NH—CH$_2$—O—CH$_2$—C(=O)—"), and the antitumor compound is connected to a terminus (the carbonyl group of CH$_2$—O—CH$_2$—C(=O)— at the right terminus in the above-described example) opposite to the terminus to which the antibody is connected to -(Succinimid-3-yl-N). "-(Succinimid-3-yl-N)—" has a structure represented by the following formula:

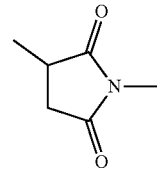

[Formula 6]

Position 3 of this partial structure is the connecting position to the anti-CDH6 antibody. This connection to the antibody at position 3 is characterized by forming a thioether bond. The nitrogen atom at position 1 of this structure moiety is connected to the carbon atom of methylene which is present within the linker including the structure.

In the antibody-drug conjugate of the present invention having exatecan as the drug, a drug-linker structure moiety having any structure given below is preferred for conjugation to the antibody. For these drug-linker structure moieties, the average number conjugated per antibody may be 1 to 10 and is preferably 2 to 8, more preferably 5 to 8, further preferably 7 to 8, and still further preferably 8.

-(Succinimid-3-yl-N)—CH$_2$CH$_2$—C(=O)-GGFG-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX),
-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX), and
-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX).

More preferred are the following:
-(Succinimid-3-yl-N)—CH$_2$CH$_2$CH$_2$CH$_2$CH$_2$—C(=O)-GGFG-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX), and
-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX).

Still more preferred are the following:
-(Succinimid-3-yl-N)—CH$_2$CH$_2$CH$_2$CH$_2$CH$_2$—C(=O)-GGFG-NH—CH$_2$—O—CH$_2$—C(=O)—(NH-DX), and
-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX).

—(NH-DX) has a structure represented by the following formula:

[Formula 7]

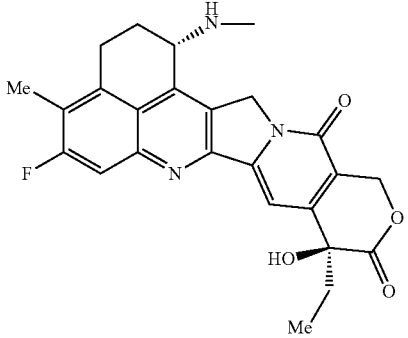

and it represents a group that is derived by removing one hydrogen atom from the amino group at position 1 of exatecan.

(3) Method for Producing Antibody-Drug Conjugate

The antibody that can be used in the antibody-drug conjugate of the present invention is not particularly limited as long as it is an anti-CDH6 antibody having internalization activity or a functional fragment of the antibody, as described in the above section "2. Production of anti-CDH6 antibody" and the Examples.

Next, a typical method for producing the antibody-drug conjugate of the present invention will be described. It is to be noted that, in the description below, "compound No." shown in each reaction scheme is used to represent a compound. Specifically, each compound is referred to as a "compound of formula (1)", "compound (1)", or the like. The same holds true for the other compound Nos.

(3)-1 Production Method 1

The antibody-drug conjugate represented by formula (1) given below in which the anti-CDH6 antibody is connected to the linker structure via a thioether can be produced by reacting an antibody having a sulfhydryl group converted from a disulfide bond by the reduction of the anti-CDH6 antibody, with the compound (2), the compound (2) being obtainable by a known method (e.g., obtainable by a method described in the patent publication literature US2016/297890 (e.g., a method described in the paragraphs [0336] to [0374])). This antibody-drug conjugate can be produced by the following method, for example.

[Expression 1]

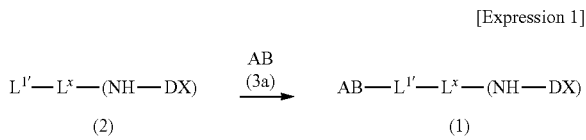

wherein AB represents an antibody with a sulfhydryl group, wherein $L^1$ has a structure represented by -(Succinimid-3-yl-N)—, and $L^{1'}$ represents a maleimidyl group represented by the following formula.

[Formula 8]

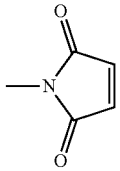

-$L^1$-$L^x$ has a structure represented by any of the following formulas:
-(Succinimid-3-yl-N)—$CH_2CH_2$—C(=O)-GGFG-NH—$CH_2CH_2CH_2$—C(=O)—,
-(Succinimid-3-yl-N)—$CH_2CH_2CH_2CH_2CH_2$—C(=O)-GGFG-NH—$CH_2CH_2CH_2$—C(=O)—,
-(Succinimid-3-yl-N)—$CH_2CH_2CH_2CH_2CH_2$—C(=O)-GGFG-NH—$CH_2$—O—$CH_2$—C(=O)—,
-(Succinimid-3-yl-N)—$CH_2CH_2CH_2CH_2CH_2$—C(=O)-GGFG-NH—$CH_2CH_2$—O—$CH_2$—C(=O)—,
-(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—, and
-(Succinimid-3-yl-N)—$CH_2CH_2$—C(=O)—NH—$CH_2CH_2O$—$CH_2CH_2O$—$CH_2CH_2O$—$CH_2CH_2O$—$CH_2CH_2$—C(=O)-GGFG-NH—$CH_2CH_2CH_2$—C(=O)—.

Among them, more preferred are the following:
-(Succinimid-3-yl-N)—$CH_2CH_2CH_2CH_2CH_2$—C(=O)-GGFG-NH—$CH_2$—O—$CH_2$—C(=O)—,
-(Succinimid-3-yl-N)—$CH_2CH_2CH_2CH_2CH_2$—C(=O)-GGFG-NH—$CH_2CH_2$—O—$CH_2$—C(=O)—, and
-(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—.

Further preferred are the following:
-(Succinimid-3-yl-N)—$CH_2CH_2CH_2CH_2CH_2$—C(=O)-GGFG-NH—$CH_2$—O—$CH_2$—C(=O)—, and
-(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—.

In the above-described reaction scheme, the antibody-drug conjugate (1) can be understood as having a structure in which one structure moiety from the drug to the linker terminus is connected to one antibody. However, this description is given for the sake of convenience, and there are actually many cases in which a plurality of the aforementioned structure moieties is connected to one antibody molecule. The same holds true for the explanation of the production method described below.

Specifically, the antibody-drug conjugate (1) can be produced by reacting the compound (2) obtainable by a known method (e.g., obtainable by a method described in the patent publication literature US2016/297890 (e.g., obtainable by a method described in the paragraphs [0336] to [0374])), with the antibody (3a) having a sulfhydryl group.

The antibody (3a) having a sulfhydryl group can be obtained by a method well known to a person skilled in the art (Hermanson, G. T, Bioconjugate Techniques, pp. 56-136, pp. 456-493, Academic Press (1996)). Examples of the method can include, but are not limited to: Traut's reagent being reacted with the amino group of the antibody; N-succinimidyl S-acetylthioalkanoates being reacted with the amino group of the antibody followed by reaction with hydroxylamine; N-succinimidyl 3-(pyridyldithio)propionate being reacted with the antibody, followed by reaction with a reducing agent; the antibody being reacted with a reducing agent such as dithiothreitol, 2-mercaptoethanol, or tris(2-carboxyethyl)phosphine hydrochloride (TCEP) to reduce the interchain disulfide bond in the antibody, so as to form a sulfhydryl group.

Specifically, an antibody with interchain disulfide bonds partially or completely reduced can be obtained by using 0.3 to 3 molar equivalents of TCEP as a reducing agent per interchain disulfide bond in the antibody, and reacting the reducing agent with the antibody in a buffer solution containing a chelating agent. Examples of the chelating agent can include ethylenediaminetetraacetic acid (EDTA) and diethylenetriaminepentaacetic acid (DTPA). The chelating agent can be used at a concentration of 1 mM to 20 mM. A solution of sodium phosphate, sodium borate, sodium acetate, or the like can be used as the buffer solution. As a specific example, the antibody (3a) having partially or completely reduced sulfhydryl groups can be obtained by reacting the antibody with TCEP at 4° C. to 37° C. for 1 to 4 hours.

It is to be noted that by carrying out an addition reaction of a sulfhydryl group to a drug-linker moiety, the drug-linker moiety can be conjugated by a thioether bond.

Then, using 2 to 20 molar equivalents of the compound (2) per antibody (3a) having a sulfhydryl group, the antibody-drug conjugate (1) in which 2 to 8 drug molecules are conjugated per antibody can be produced. Specifically, a solution containing the compound (2) dissolved therein may be added to a buffer solution containing the antibody (3a) having a sulfhydryl group for the reaction. In this context, a sodium acetate solution, sodium phosphate, sodium borate, or the like can be used as the buffer solution. pH for the reaction is 5 to 9, and more preferably, the reaction may be performed near pH 7. An organic solvent such as dimethyl sulfoxide (DMSO), dimethylformamide (DMF), dimethylacetamide (DMA), or N-methyl-2-pyrrolidone (NMP) can be used as a solvent for dissolving the compound (2). The reaction may be performed by adding the solution containing the compound (2) dissolved in the organic solvent at 1 to 20% v/v to a buffer solution containing the antibody (3a) having a sulfhydryl group. The reaction temperature is 0 to 37° C., more preferably 10 to 25° C., and the reaction time is 0.5 to 2 hours. The reaction can be terminated by deactivating the reactivity of unreacted compound (2) with a thiol-containing reagent. The thiol-containing reagent is, for example, cysteine or N-acetyl-L-cysteine (NAC). More specifically, the reaction can be terminated by adding 1 to 2 molar equivalents of NAC to the compound (2) used, and incubating the obtained mixture at room temperature for 10 to 30 minutes.

(4) Identification of Antibody-Drug Conjugate

The produced antibody-drug conjugate (1) can be subjected to concentration, buffer exchange, purification, and measurement of antibody concentration and the average number of conjugated drug molecules per antibody molecule according to common procedures described below, to identify the antibody-drug conjugate (1).

(4)-1 Common Procedure A: Concentration of Aqueous Solution of Antibody or Antibody-Drug Conjugate To an Amicon Ultra (50,000 MWCO, Millipore Corporation) container, a solution of an antibody or an antibody-drug conjugate was added, and the solution of the antibody or the antibody-drug conjugate was concentrated by centrifugation (centrifugation at 2000 G to 3800 G for 5 to 20 minutes) using a centrifuge (Allegra X-15R, Beckman Coulter, Inc.)

(4)-2 Common Procedure B: Measurement of Antibody Concentration

Using a UV detector (Nanodrop 1000, Thermo Fisher Scientific Inc.), measurement of the antibody concentration was carried out according to the method defined by the manufacturer. In this respect, 280 nm absorption coefficient differing among antibodies (1.3 mLmg$^{-1}$cm$^{-1}$ to 1.8 mLmg$^{-1}$cm$^{-1}$) was used.

(4)-3 Common Procedure C: Buffer Exchange for Antibody

A NAP-25 column (Cat. No. 17-0852-02, GE Healthcare Japan Corporation) using Sephadex G-25 carrier was equilibrated with a phosphate buffer (50 mM, pH 6.0) (referred to as PBS6.0/EDTA in the present description) containing sodium chloride (50 mM) and EDTA (2 mM) according to the method defined by the manufacturer. An aqueous solution of the antibody was applied in an amount of 2.5 mL per NAP-25 column, and thereafter, a fraction (3.5 mL) eluted with 3.5 mL of PBS6.0/EDTA was collected. This fraction was concentrated by common procedure A. After measurement of the concentration of the antibody using common procedure B, the antibody concentration was adjusted to 20 mg/mL using PBS6.0/EDTA.

(4)-4 Common Procedure D: Purification of Antibody-Drug Conjugate

A NAP-25 column was equilibrated with any commercially available buffer solution such as an acetate buffer containing sorbitol (5%) (10 mM, pH 5.5; referred to as ABS in the present description). An aqueous reaction solution of the antibody-drug conjugate (approximately 2.5 mL) was applied to the NAP-25 column, and thereafter, elution was carried out with the buffer solution in an amount defined by the manufacturer, so as to collect an antibody fraction. A gel filtration purification process, in which the collected fraction was applied again to the NAP-25 column, and elution was carried out with the buffer solution, was repeated a total of 2 or 3 times to obtain the antibody-drug conjugate excluding non-conjugated drug linker and low-molecular-weight compounds (tris(2-carboxyethyl)phosphine hydrochloride (TCEP), N-acetyl-L-cysteine (NAC), and dimethyl sulfoxide).

(4)-5 Common Procedure E: Measurement of Antibody Concentration in Antibody-Drug Conjugate and Average Number of Conjugated Drug Molecules Per Antibody Molecule The conjugated drug concentration in the antibody-drug conjugate can be calculated by measuring UV absorbance of an aqueous solution of the antibody-drug conjugate at two wavelengths of 280 nm and 370 nm, and thereafter performing the calculation shown below.

The total absorbance at any given wavelength is equal to the sum of the absorbance of all light-absorbing chemical species that are present in a system [additivity of absorbance]. Therefore, based on the hypothesis that the molar absorption coefficients of the antibody and the drug do not vary between before and after conjugation between the antibody and the drug, the antibody concentration and the drug concentration in the antibody-drug conjugate are represented by the following equations.

$$A_{280} = A_{D,280} + A_{A,280} = \varepsilon_{D,280} C_D + \varepsilon_{A,280} C_A \qquad \text{Equation (1)}$$

$$A_{370} = A_{D,370} + A_{A,370} = \varepsilon_{D,370} C_D + \varepsilon_{A,370} C_A \qquad \text{Equation (2)}$$

In this context, $A_{280}$ represents the absorbance of an aqueous solution of the antibody-drug conjugate at 280 nm, $A_{370}$ represents the absorbance of an aqueous solution of the antibody-drug conjugate at 370 nm, $A_{A,280}$ represents the absorbance of the antibody at 280 nm, $A_{A,370}$ represents the absorbance of the antibody at 370 nm, $A_{D,280}$ represents the absorbance of a conjugate precursor at 280 nm, $A_{D,370}$ represents the absorbance of a conjugate precursor at 370 nm, $\varepsilon_{A,280}$ represents the molar absorption coefficient of the antibody at 280 nm, $\varepsilon_{A,370}$ represents the molar absorption coefficient of the antibody at 370 nm, $\varepsilon_{D,280}$ represents the molar absorption coefficient of a conjugate precursor at 280 nm, $\varepsilon_{D,370}$ represents the molar absorption coefficient of a conjugate precursor at 370 nm, $C_A$ represents the antibody concentration in the antibody-drug conjugate, and $C_D$ represent the drug concentration in the antibody-drug conjugate.

In this context, with regard to $\varepsilon_{A,280}$, $\varepsilon_{A,370}$, $\varepsilon_{D,280}$, and $\varepsilon_{D,370}$, preliminarily prepared values (estimated values based on calculation or measurement values obtained by UV measurement of the compound) are used. For example, $\varepsilon_{A,280}$ can be estimated from the amino acid sequence of the antibody by a known calculation method (Protein Science, 1995, vol. 4, 2411-2423). $\varepsilon_{A,370}$ is generally zero. $\varepsilon_{D,280}$ and $\varepsilon_{D,370}$ can be obtained according to Lambert-Beer's law (Absorbance=Molar concentration×Molar absorption coefficient×Cell path length) by measuring the absorbance of a solution in which the conjugate precursor used is dissolved at a certain molar concentration. $C_A$ and $C_D$ can be determined by measuring $A_{280}$ and $A_{370}$ of an aqueous solution of the antibody-drug conjugate, and then solving the simultaneous equations (1) and (2) by substitution of these values. Further, by dividing $C_D$ by $C_A$, the average number of conjugated drug molecules per antibody can be determined.

(4)-6 Common Procedure F: Measurement of Average Number of Conjugated Drug Molecules Per Antibody Molecule in Antibody-Drug Conjugate—(2)

The average number of conjugated drug molecules per antibody molecule in the antibody-drug conjugate can also be determined by high-performance liquid chromatography (HPLC) analysis using the following method, in addition to the aforementioned "(4)-5 Common procedure E". Hereinafter, the method for measuring the average number of conjugated drug molecules by HPLC when the antibody is conjugated to the drug linker by a disulfide bond will be described. A person skilled in the art is capable of appropriately measuring the average number of conjugated drug molecules by HPLC, depending on the connecting manner between the antibody and the drug linker, with reference to this method.

F-1. Preparation of Sample for HPLC Analysis (Reduction of Antibody-Drug Conjugate)

An antibody-drug conjugate solution (approximately 1 mg/mL, 60 µL) is mixed with an aqueous solution of dithiothreitol (DTT) (100 mM, 15 µL). By incubating the mixture at 37° C. for 30 minutes, the disulfide bond between the light chain and heavy chain of the antibody-drug conjugate is cleaved. The resulting sample is used in HPLC analysis.

F-2. HPLC Analysis

The HPLC analysis is carried out under the following measurement conditions.

HPLC system: Agilent 1290 HPLC system (Agilent Technologies, Inc.)

Detector: Ultraviolet absorption spectrometer (measurement wavelength: 280 nm)

Column: ACQUITY UPLC BEH Phenyl (2.1×50 mm, 1.7 µm, 130 angstroms; Waters Corp., P/N 186002884)

Column temperature: 80° C.

Mobile phase A: Aqueous solution containing 0.10% trifluoroacetic acid (TFA) and 15% 2-propanol Mobile phase B: Acetonitrile solution containing 0.075% TFA and 15% 2-propanol Gradient program: 14%-36% (0 min-15 min), 36%-80% (15 min-17 min), 80%-14% (17 min-17.01 min.), and 14% (17.01 min-25 min)

Sample injection: 10 µL

F-3. Data Analysis

F-3-1. Compared with non-conjugated antibody light (L0) and heavy (H0) chains, a light chain bound to drug molecule(s) (light chain bound to i drug molecule(s): $L_i$) and a heavy chain bound to drug molecule(s) (heavy chain bound to i drug molecule(s): $H_i$) exhibit higher hydrophobicity in proportion to the number of conjugated drug molecules and thus have a larger retention time. These chains are therefore eluted in the order of, for example, L0 and L1 or H0, H1, H2, and H3. Detection peaks can be assigned to any of L0, L1, H0, H1, H2, and H3 by the comparison of retention times with L0 and H0. The number of conjugated drug molecules can be defined by a person skilled in the art, but is preferably L0, L1, H0, H1, H2, and H3.

F-3-2. Since the drug linker has UV absorption, peak area values are corrected in response to the number of conjugated drug linker molecules according to the following expression using the molar absorption coefficients of the light chain or heavy chain and the drug linker.

$$\text{Corrected value of peak area of light chain bound to } i \text{ drug molecule(s)}(A_{Li}) = \text{Peak area} \times \frac{\text{Molor absorption coeffiicient of light chain}}{\text{Molar absorption coefficient of light chain} + \text{The number of conjugated drug molecules }(i) \times \text{Molar absorption coefficient of drug linker}}$$ [Expression 2]

$$\text{Corrected value of peak area of heavy chain bound to } i \text{ drug molecule(s)}(A_{Hi}) = \text{Peak area} \times \frac{\text{Molor absorption coeffiicient of light chain}}{\text{Molar absorption coefficient of heavy chain} + \text{The number of conjugated drug molecules }(i) \times \text{Molar absorption coefficient of drug linker}}$$ [Expression 3]

In this context, a value estimated from the amino acid sequence of the light chain or heavy chain of each antibody by a known calculation method (Protein Science, 1995, vol. 4, 2411-2423) can be used as the molar absorption coefficient (280 nm) of the light chain or heavy chain of the antibody. In the case of H01L02, a molar absorption coefficient of 31710 and a molar absorption coefficient of 79990 were used as estimated values for the light chain and heavy chain, respectively, according to the amino acid sequence of the antibody. The actually measured molar absorption coefficient (280 nm) of a compound in which the maleimide group has been converted to succinimide thioether by the reaction of each drug linker with mercaptoethanol or N-acetylcysteine was used as the molar absorption coefficient (280 nm) of the drug linker. The wavelength for absorbance measurement can be appropriately set by a person skilled in the art, but is preferably a wavelength at which the peak of the antibody can be measured, and more preferably 280 nm.

F-3-3. The peak area ratio (%) of each chain is calculated for the total of the corrected values of peak areas according to the following expression.

Peak area ratio of light chain to i drug [Expression 4]

$$\text{molecule(s)} = \frac{A_{Li}}{A_{L0} + A_{L1}} \times 100$$

Peak area ratio of heavy chain bound to $i$ drug $$\text{molecule(s)} = \frac{A_{Hi}}{A_{H0} + A_{H1} + A_{H2} + A_{H3}} \times 100$$

$A_{Li}$ and $A_{Hi}$:

Corrected values of peak areas of $L_i$ and $H_i$, respectively

F-3-4. The average number of conjugated drug molecules per antibody molecule in the antibody-drug conjugate is calculated according to the following expression.

Average number of conjugated drug molecules=($L_0$ peak area ratio×0+$L_1$ peak area ratio×1+$H_0$ peak area ratio×0+$H_1$ peak area ratio×1+$H_2$ peak area ratio×2+$H_3$ peak area ratio×3)/100×2

It is to be noted that, in order to secure the amount of the antibody-drug conjugate, a plurality of antibody-drug conjugates having almost the same average number of conjugated drug molecules (e.g., on the order of ±1), which have been produced under similar conditions, can be mixed to prepare a new lot. In this case, the average number of drug molecules of the new lot falls between the average numbers of drug molecules before the mixing.

One specific example of the antibody-drug conjugate of the present invention can include an antibody-drug conjugate having a structure represented by the following formula:

[Formula 9]

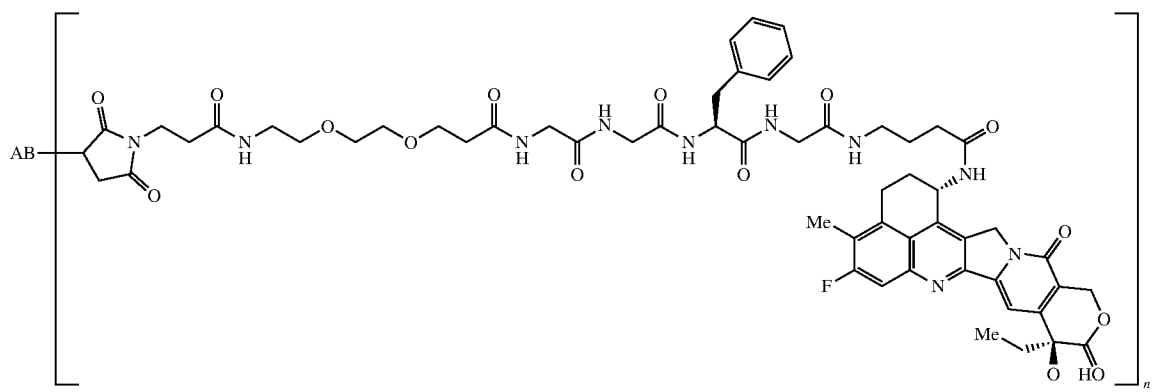

or the following formula:

[Formula 10]

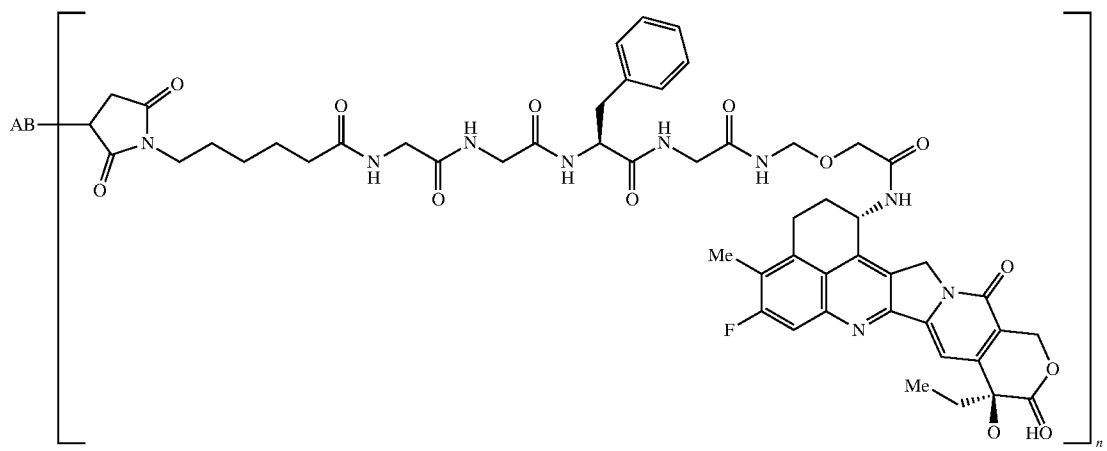

In this context, AB represents the anti-CDH6 antibody disclosed in the present description, and the antibody is conjugated to the drug linker via a sulfhydryl group stemming from the antibody. In this context, n has the same meaning as that of the so-called DAR (drug-to-antibody Ratio), and represents a drug-to-antibody ratio per antibody. Specifically, n represents the number of conjugated drug molecules per antibody molecule, which is a numeric value defined and indicated as an average value, i.e., the average number of conjugated drug molecules. In the case of the antibody-drug conjugate represented by [Formula 9] or [Formula 10] of the present invention, n can be 2 to 8 and is preferably 5 to 8, more preferably 7 to 8, and still more preferably 8, in measurement by common procedure F.

One example of the antibody-drug conjugate of the present invention can include an antibody-drug conjugate having a structure represented by the above-described formula [Formula 9] or [Formula 10] wherein the antibody represented by AB comprises any one antibody selected from the group consisting of the following antibodies (a) to (g), or a functional fragment of the antibody, or a pharmacologically acceptable salt of the antibody-drug conjugate:

(a) an antibody consisting of a light chain consisting of the amino acid sequence at positions 21 to 233 in the light chain full-length amino acid sequence shown in SEQ ID NO: 61 and a heavy chain consisting of the amino acid sequence at positions 20 to 471 in the heavy chain full-length amino acid sequence shown in SEQ ID NO: 69;

(b) an antibody consisting of a light chain consisting of the amino acid sequence at positions 21 to 233 in the light chain full-length amino acid sequence shown in SEQ ID NO: 61 and a heavy chain consisting of the amino acid sequence at positions 20 to 471 in the heavy chain full-length amino acid sequence shown in SEQ ID NO: 73;

(c) an antibody consisting of a light chain consisting of the amino acid sequence at positions 21 to 233 in the light chain full-length amino acid sequence shown in SEQ ID NO: 61 and a heavy chain consisting of the amino acid sequence at positions 20 to 471 in the heavy chain full-length amino acid sequence shown in SEQ ID NO: 77;

(d) an antibody consisting of a light chain consisting of the amino acid sequence at positions 21 to 233 in the light chain full-length amino acid sequence shown in SEQ ID NO: 65 and a heavy chain consisting of the amino acid sequence at positions 20 to 471 in the heavy chain full-length amino acid sequence shown in SEQ ID NO: 69;

(e) an antibody consisting of a light chain consisting of the amino acid sequence at positions 21 to 233 in the light chain full-length amino acid sequence shown in SEQ ID NO: 65 and a heavy chain consisting of the amino acid sequence at positions 20 to 471 in the heavy chain full-length amino acid sequence shown in SEQ ID NO: 73;

(f) an antibody consisting of a light chain consisting of the amino acid sequence at positions 21 to 233 in the light chain full-length amino acid sequence shown in SEQ ID NO: 65 and a heavy chain consisting of the amino acid sequence at positions 20 to 471 in the heavy chain full-length amino acid sequence shown in SEQ ID NO: 77; and (g) any one antibody selected from the group consisting of the antibodies (a) to (f), wherein the heavy chain or the light chain comprises one or two or more modifications selected from the group consisting of posttranslational modifications typified by N-linked glycosylation, O-linked glycosylation, N-terminal processing, C-terminal processing, deamidation, isomerization of aspartic acid, oxidation of methionine, addition of a methionine residue to the N-terminus, amidation of a proline residue, and conversion of N-terminal glutamine or N-terminal glutamic acid to pyroglutamic acid, and a deletion of one or two amino acids at the carboxyl terminus 4. Medicament Since the anti-CDH6 antibody of the present invention or the functional fragment of the antibody described in the above section "2. Production of anti-CDH6 antibody" and the Examples binds to CDH6 on the surface of tumor cells and has internalization activity, it can be used as a medicament, and in particular, as a therapeutic agent for cancer such as renal cell tumor or ovarian tumor, for example, renal cell carcinoma, renal clear cell carcinoma, papillary renal cell carcinoma, ovarian cancer, ovarian serous adenocarcinoma, thyroid cancer, bile duct cancer, lung cancer (e.g., small-cell lung cancer or non-small cell lung cancer), glioblastoma, mesothelioma, uterine cancer, pancreatic cancer, Wilms' tumor or neuroblastoma, either alone or in combination with an additional drug.

Furthermore, the anti-CDH6 antibody of the present invention or the functional fragment of the antibody can be used in the detection of cells expressing CDH6.

Moreover, since the anti-CDH6 antibody of the present invention or the functional fragment of the antibody has internalization activity, it can be applied as the antibody in an antibody-drug conjugate.

When a drug having antitumor activity such as cytotoxic activity is used as the drug, the anti-CDH6 antibody-drug conjugate of the present invention described in the above section "3. Anti-CDH6 antibody-drug conjugate" and the Examples is a conjugate of the anti-CDH6 antibody and/or the functional fragment of the antibody having internalization activity, and the drug having antitumor activity such as cytotoxic activity. Since this anti-CDH6 antibody-drug conjugate exhibits antitumor activity against cancer cells expressing CDH6, it can be used as a medicament, and in particular, as a therapeutic agent and/or a prophylactic agent for cancer.

The anti-CDH6 antibody-drug conjugate of the present invention may absorb moisture or have adsorption water, for example, to turn into a hydrate when it is left in air or subjected to recrystallization or purification procedures. Such a compound or a pharmacologically acceptable salt containing water is also included in the present invention.

When the anti-CDH6 antibody-drug conjugate of the present invention has a basic group such as an amino group, it can form a pharmacologically acceptable acid-addition salt, if desired. Examples of such an acid-addition salt can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as formate, acetate, trifluoroacetate, malate, fumarate, succinate, citrate, tartrate, oxalate, and maleate; and amino acid salts such as ornithine salt, glutamate, and aspartate.

When the anti-CDH6 antibody-drug conjugate of the present invention has an acidic group such as a carboxy group, it can form a pharmacologically acceptable base-addition salt, if desired. Examples of such a base-addition salt can include: alkali metal salts such as a sodium salt, a potassium salt, and lithium salt; alkaline earth metal salts such as a calcium salt and a magnesium salt; inorganic salts such as an ammonium salt; and organic amine salts such as a dibenzylamine salt, a morpholine salt, a phenylglycine alkyl ester salt, an ethylenediamine salt, an N-methylglucamine salt, a diethylamine salt, a triethylamine salt, a cyclohexylamine salt, a dicyclohexylamine salt, an N,N'-dibenzylethylenediamine salt, a diethanolamine salt, an N-benzyl-N-(2-phenylethoxy)amine salt, a piperazine salt, tetramethylammonium salt, and a tris(hydroxymethyl)aminomethane salt.

The present invention can also include an anti-CDH6 antibody-drug conjugate in which one or more atoms constituting the antibody-drug conjugate are replaced with isotopes of the atoms. There exist two types of isotopes: radioisotopes and stable isotopes. Examples of the isotope can include isotypes of hydrogen ($2H$ and $3H$), isotopes of carbon ($11C$, $13C$ and $14C$), isotopes of nitrogen ($13N$ and $15N$), isotopes of oxygen ($15O$, $17O$ and $18O$), and isotopes of fluorine ($18F$). A composition comprising the antibody-drug conjugate labeled with such an isotope is useful as, for example, a therapeutic agent, a prophylactic agent, a research reagent, an assay reagent, a diagnostic agent, and an in vivo diagnostic imaging agent. Each and every antibody-drug conjugate labeled with an isotope, and mixtures of antibody-drug conjugates labeled with an isotope at any given ratio are included in the present invention. The antibody-drug conjugate labeled with an isotope can be produced, for example, by using a starting material labeled with an isotope, instead of a starting material for the production method of the present invention mentioned later, according to a method known in the art.

In vitro cytotoxicity can be measured based on the activity of suppressing the proliferative responses of cells, for example. For example, a cancer cell line overexpressing CDH6 is cultured, and the anti-CDH6 antibody-drug conjugate is added at different concentrations to the culture system. Thereafter, its suppressive activity against focus formation, colony formation and spheroid growth can be measured. In this context, for example, by using a renal cell tumor- or ovarian tumor-derived cancer cell line, cell growth inhibition activity against renal cell tumor or ovarian tumor can be examined.

In vivo therapeutic effects on cancer in an experimental animal can be measured, for example, by administering the anti-CDH6 antibody-drug conjugate to a nude mouse into which a tumor cell line highly expressing CDH6 has been inoculated, and then measuring a change in the cancer cells. In this context, for example, by using an animal model derived from an immunodeficient mouse by the inoculation of renal cell carcinoma-, renal clear cell carcinoma-, papillary renal cell carcinoma-, ovarian cancer-, ovarian serous adenocarcinoma- or thyroid cancer-derived cells, therapeutic effects on renal cell carcinoma, renal clear cell carcinoma, papillary renal cell carcinoma, ovarian cancer, ovarian serous adenocarcinoma or thyroid cancer can be measured.

The type of cancer to which the anti-CDH6 antibody-drug conjugate of the present invention is applied is not particularly limited as long as the cancer expresses CDH6 in cancer cells to be treated. Examples thereof can include renal cell carcinoma (e.g., renal clear cell carcinoma or papillary renal cell carcinoma), ovarian cancer, ovarian serous adenocarcinoma, thyroid cancer, bile duct cancer, lung cancer (e.g., small-cell lung cancer or non-small cell lung cancer), glioblastoma, mesothelioma, uterine cancer, pancreatic cancer, Wilms' tumor and neuroblastoma, though the cancer is not limited thereto as long as the cancer expresses CDH6. More preferred examples of the cancer can include renal cell carcinoma (e.g., renal clear cell carcinoma and papillary renal cell carcinoma) and ovarian cancer.

The anti-CDH6 antibody-drug conjugate of the present invention can preferably be administered to a mammal, and more preferably to a human.

A substance used in a pharmaceutical composition comprising the anti-CDH6 antibody-drug conjugate of the present invention can be appropriately selected from pharmaceutical additives and others usually used in this field, in terms of the applied dose or the applied concentration, and then used.

The anti-CDH6 antibody-drug conjugate of the present invention can be administered as a pharmaceutical composition comprising one or more pharmaceutically compatible components. For example, the pharmaceutical composition typically comprises one or more pharmaceutical carriers (e.g., sterilized liquids (e.g., water and oil (including petroleum oil and oil of animal origin, plant origin, or synthetic origin (e.g., peanut oil, soybean oil, mineral oil, and sesame oil))). Water is a more typical carrier when the pharmaceutical composition is intravenously administered. An aqueous saline solution, an aqueous dextrose solution, and an aqueous glycerol solution can also be used as a liquid carrier, in particular, for an injection solution. Suitable pharmaceutical vehicles are known in the art. If desired, the composition may also comprise a trace amount of a moisturizing agent, an emulsifying agent, or a pH buffering agent. Examples of suitable pharmaceutical carriers are disclosed in "Remington's Pharmaceutical Sciences" by E. W. Martin. The prescription corresponds to an administration mode.

Various delivery systems are known, and they can be used for administering the anti-CDH6 antibody-drug conjugate of the present invention. Examples of the administration route can include, but are not limited to, intradermal, intramuscular, intraperitoneal, intravenous, and subcutaneous routes. The administration can be made by injection or bolus injection, for example. According to a specific preferred embodiment, the administration of the above-described antibody-drug conjugate is performed by injection. Parenteral administration is a preferred administration route.

According to a representative embodiment, the pharmaceutical composition is prescribed, as a pharmaceutical composition suitable for intravenous administration to a human, according to conventional procedures. The composition for intravenous administration is typically a solution in a sterile and isotonic aqueous buffer solution. If necessary, the medicament may also contain a solubilizing agent and a local anesthetic to alleviate pain at an injection area (e.g., lignocaine). In general, the above-described ingredients are provided, either separately or together in a mixture in unit dosage form, as a freeze-dried powder or an anhydrous concentrate contained in a container which is obtained by sealing in, for example, an ampoule or a sachet indicating the amount of the active agent. When the medicament is to be administered by injection, it may be administered using, for example, an injection bottle containing water or saline of sterile pharmaceutical grade. When the medicament is to be administered by injection, an ampoule of sterile water or saline for injection may be provided such that the above-described ingredients are admixed with one another before administration.

The pharmaceutical composition of the present invention may be a pharmaceutical composition comprising only the anti-CDH6 antibody-drug conjugate of the present application, or may be a pharmaceutical composition comprising the anti-CDH6 antibody-drug conjugate and at least one other therapeutic agent for cancer. The anti-CDH6 antibody-drug conjugate of the present invention can also be administered together with an additional therapeutic agent for cancer, and can thereby enhance an anticancer effect. The additional anticancer agent used for such a purpose may be administered to an individual, simultaneously, separately, or continuously, together with the antibody-drug conjugate. Otherwise, the additional anticancer agent and the anti-CDH6 antibody-drug conjugate may each be administered to the subject at different administration intervals. Examples of such a therapeutic agent for cancer can include tyrosine kinase inhibitors including imatinib, sunitinib, and regorafenib, CDK4/6 inhibitors including palbociclib, HSP90 inhibitors including TAS-116, MEK inhibitors including MEK162, and immune checkpoint inhibitors including nivolumab, pembrolizumab, and ipilimumab, though the therapeutic agent for cancer is not limited thereto as long as the drug has antitumor activity.

Such a pharmaceutical composition can be prepared as a formulation having a selected composition and a necessary purity in the form of a freeze-dried formulation or a liquid formulation. The pharmaceutical composition prepared as a freeze-dried formulation may be a formulation containing an appropriate pharmaceutical additive used in this field. Likewise, the liquid formulation can be prepared such that the liquid formulation contains various pharmaceutical additives used in this field.

The composition and concentration of the pharmaceutical composition also vary depending on the administration method. With regard to the affinity of the anti-CDH6 antibody-drug conjugate comprised in the pharmaceutical composition of the present invention for the antigen, i.e., the dissociation constant (Kd value) of the anti-CDH6 antibody-drug conjugate to the antigen, as the affinity increases (i.e., the Kd value is low), the pharmaceutical composition can exert medicinal effects, even if the applied dose thereof is decreased. Accordingly, the applied dose of the antibody-drug conjugate can also be determined by setting the applied dose based on the status of the affinity of the antibody-drug conjugate for the antigen. When the antibody-drug conjugate of the present invention is administered to a human, it may be administered at a dose of, for example, from approximately 0.001 to 100 mg/kg once or a plurality of times at intervals of 1 to 180 days. It can be administered preferably at a dose of from 0.1 to 50 mg/kg and more preferably 1 to 50 mg/kg, 1 to 30 mg/kg, 1 to 20 mg/kg, 1 to 15 mg/kg, 2 to 50 mg/kg, 2 to 30 mg/kg, 2 to 20 mg/kg or 2 to 15 mg/kg a plurality of times at intervals of 1 to 4 weeks, preferably 2 to 3 weeks.

EXAMPLES

Hereinafter, the present invention will be specifically described in the following examples. However, these examples are not intended to limit the scope of the present invention. Furthermore, these examples should not be construed in a limited manner by any means. It is to be noted that, in the following examples, unless otherwise specified, individual operations regarding genetic manipulation have been carried out according to the method described in "Molecular Cloning" (Sambrook, J., Fritsch, E. F. and Maniatis, T., published by Cold Spring Harbor Laboratory Press in 1989) or other methods described in experimental manuals used by persons skilled in the art, or when commercially available reagents or kits have been used, the examples have been carried out in accordance with the instructions included in the commercially available products. In the present description, reagents, solvents and starting materials are readily available from commercially available sources, unless otherwise specified.

Example 1: Obtaining Rat Anti-Human CDH6 Antibody Having Internalization Activity 1)-1 Construction of Human, Mouse, Rat and Cynomolgus Monkey CDH6 Expression Vectors Using a human CDH6 protein (NP_004923)-encoding cDNA expression vector (OriGene Technologies Inc., RC217889), the cDNA was incorporated into a vector for mammalian expression according to a method known to a person skilled in the art to produce human CDH6 expression vector pcDNA3.1-hCDH6. The amino acid sequence of the human CDH6 ORF (open reading frame) is shown in SEQ ID NO: 1.

Using a mouse CDH6 protein (NP_031692)-encoding cDNA expression vector (OriGene Technologies Inc., MC221619), the cDNA was incorporated into a vector for mammalian expression according to a method known to a person skilled in the art to produce mouse CDH6 expression vectors pcDNA3.1-mCDH6 and p3×FLAG-CMV-9-mCDH6. The amino acid sequence of the mouse CDH6 ORF is shown in SEQ ID NO: 7.

Using each cDNA moiety of the rat CDH6 protein (NP_037059)-encoding cDNA expression vector (OriGene Technologies Inc., RN211850), the cDNA was incorporated into a vector for mammalian expression according to a method known to a person skilled in the art to produce rat CDH6 expression vectors pcDNA3.1-rCDH6 and p3×FLAG-CMV-9-rCDH6. The amino acid sequence of the rat CDH6 ORF is shown in SEQ ID NO: 8.

cDNA encoding cynomolgus monkey CDH6 protein was cloned with cDNA synthesized from total RNA of the cynomolgus monkey kidney as a template using primer 1 (5'-CACCATGAGAACTTACCGC-TACTTCTTGCTGCTC-3') (SEQ ID NO: 85) and primer 2 (5'-TTAGGAGTCTTTGTCACTGTCCACTCCTCC-3') (SEQ ID NO: 86). It was confirmed that the obtained sequence corresponded to the extracellular region of cynomolgus monkey CDH6 (NCBI, XP_005556691.1). It was also confirmed that the sequence corresponded to the full-length sequence of cynomolgus monkey CDH6 (EHH54180.1) registered in EMBL. The cDNA was incorporated into a vector for mammalian expression according to a method known to a person skilled in the art to produce cynomolgus monkey CDH6 expression vector pcDNA3.1-cynoCDH6. The amino acid sequence of the cynomolgus monkey CDH6 ORF is shown in SEQ ID NO: 9.

EndoFree Plasmid Giga Kit (Qiagen N.V.) was used for mass production of the produced plasmid DNA.

1)-2 Immunization

For immunization, WKY/Izm female rats (Japan SLC, Inc.) were used. First, the lower limbs of each rat were pre-treated with Hyaluronidase (Sigma-Aldrich Co. LLC), and thereafter, the human CDH6 expression vector pcDNA3.1-hCDH6 produced in Example 1)-1 was intramuscularly injected into the same sites. Subsequently, employing ECM830 (BTX), in vivo electroporation was carried out on the same sites using a two-needle electrode. Approximately once every two weeks, the same in vivo electroporation was repeated, and thereafter, lymph nodes or the spleen were collected from the rat, and then used in production of hybridomas.

1)-3 Production of Hybridomas

The lymph node cells or the spleen cells were fused with mouse myeloma SP2/0-ag14 cells (ATCC, No. CRL-1 581)

according to electrical cell fusion, using a LF301 Cell Fusion Unit (BEX Co., Ltd.), and the cells were then suspended and diluted with ClonaCell-HY Selection Medium D (StemCell Technologies Inc.), and then cultured under conditions of 37° C. and 5% $CO_2$. Individual hybridoma colonies that appeared in the culture medium were collected as monoclonal hybridomas, then suspended in ClonaCell-HY Selection Medium E (StemCell Technologies Inc.), and then cultured under conditions of 37° C. and 5% $CO_2$. After moderate proliferation of cells, frozen stocks of individual hybridoma cells were produced, while the obtained hybridoma culture supernatant was used to screen for anti-human CDH6 antibody-producing hybridomas.

1)-4 Antibody-Producing Hybridoma Screening According to Cell-ELISA Method

1)-4-1 Preparation of Antigen Gene-Expressing Cells for Use in Cell-ELISA

293α cells (a stable expression cell line derived from HEK293 cells expressing integrin αv and integrin β3) were prepared at $5\times10^5$ cells/mL in DMEM medium supplemented with 10% FBS. In accordance with transduction procedures for using LIPOFECTAMINE™ 2000 (Thermo Fisher Scientific Inc.), DNA of pcDNA3.1-hCDH6 or pcDNA3.1-cynoCDH6, or pcDNA3.1 as a negative control was introduced into the 293α cells, and the cells were dispensed in an amount of 100 µL/well onto a 96-well plate (Coming Inc.). Thereafter, the cells were cultured under conditions of 37° C. and 5% $CO_2$ in DMEM medium supplemented with 10% FBS for 24 to 27 hours. The obtained transfected cells were used for Cell-ELISA in an adhesive state.

The culture supernatant of the 293α cells transfected with the expression vector prepared in Example 1)-4-1 was removed, and the culture supernatant from each hybridoma was then added to the 293α cells transfected with pcDNA3.1-hCDH6 or pcDNA3.1-cynoCDH6, or pcDNA3.1. The cells were left standing at 4° C. for 1 hour. The cells in the wells were washed once with PBS (+) supplemented with 5% FBS, and thereafter, Anti-Rat IgG-Peroxidase antibody produced in rabbit (Sigma-Aldrich Co. LLC) that had been 500-fold diluted with PBS (+) supplemented with 5% FBS was added to the wells. The cells were left standing at 4° C. for 1 hour. The cells in the wells were washed three times with PBS (+) supplemented with 5% FBS, and thereafter, OPD coloring solution (which had been prepared by dissolving o-phenylenediamine dihydrochloride (Wako Pure Chemical Industries, Ltd.) and $H_2O_2$ in an OPD solution (0.05 M trisodium citrate, 0.1 M disodium hydrogen phosphate 12-water; pH 4.5), so that the substances became 0.4 mg/ml and 0.6% (v/v), respectively, was added in an amount of 100 µL/well to the wells. A coloring reaction was carried out with occasional stirring. Thereafter, 1 M HCl was added to the plate (100 µL/well) to terminate the coloring reaction, followed by measurement of the absorbance at 490 nm using a plate reader (ENVISION™: PerkinElmer, Inc.). Hybridomas that produced a culture supernatant exhibiting higher absorbance in the 293α cells transfected with the pcDNA3.1-hCDH6 or pcDNA3.1-cynoCDH6 expression vector than that in the 293α cells transfected with the control pcDNA3.1 were selected as hybridomas producing antibodies binding to human CDH6 and cynomolgus monkey CDH6.

1)-5 Selective Screening for Antibody Binding to Cynomolgus Monkey CDH6 According to Flow Cytometry 1)-5-1 Preparation of Antigen Gene-Expressing Cells for Use in Flow Cytometry Analysis 293T cells were seeded in a 225-$cm^2$ flask (Sumitomo Bakelite Co., Ltd.) at $5\times10^4$ cells/$cm^2$, and the cells were then cultured overnight under conditions of 37° C. and 5% $CO_2$ in DMEM medium supplemented with 10% FBS. pcDNA3.1-cynoCDH6 or pcDNA3.1 as a negative control was introduced into the 293T cells using LIPOFECTAMINE™ 2000, and the cells were further cultured overnight under conditions of 37° C. and 5% $CO_2$. The 293T cells transfected with each vector were treated with TRYPLE™ Express (Thermo Fisher Scientific Corp.), and the cells were washed with DMEM supplemented with 10% FBS, and then suspended in PBS supplemented with 5% FBS. The obtained cell suspension was used in flow cytometry analysis.

1)-5-2 Flow Cytometry Analysis

The binding specificity to cynomolgus monkey CDH6 of an antibody produced from the human CDH6- and cynomolgus monkey CDH6-binding antibody-producing hybridomas that had been selected by Cell-ELISA in Example 1)-4 was further confirmed by flow cytometry. The suspension of the transiently expressing 293T cells prepared in Example 1)-5-1 was centrifuged, and the supernatant was then removed. Thereafter, the cells were suspended by the addition of the culture supernatant from each hybridoma. The cells were left standing at 4° C. for 1 hour. The cells were washed twice with PBS supplemented with 5% FBS, and thereafter, the cells were suspended by the addition of Anti-Rat IgG FITC conjugate (Sigma-Aldrich Co. LLC) that had been 500-fold diluted with PBS supplemented with 5% FBS. The cells were left standing at 4° C. for 1 hour. The cells were washed twice with PBS supplemented with 5% FBS, and then re-suspended in PBS supplemented with 5% FBS and 2 µg/ml 7-aminoactinomycin D (Molecular Probes, Inc.), followed by detection using a flow cytometer (FC500; Beckman Coulter, Inc.). The data was analyzed using FlowJo (Tree Star, Inc.). After dead cells were removed from analysis by gating out 7-aminoactinomycin D-positive cells, a histogram of the FITC fluorescence intensity of live cells was generated. Hybridomas producing antibodies specifically binding to cynomolgus monkey CDH6 expressed on the cell membrane surface were selected based on results where the histogram for the antibody shifted to the strong fluorescence intensity side in the 293T cells transfected with pcDNA3.1-cynoCDH6 compared with the 293T cells transfected with the control pcDNA3.1.

1)-6 Determination of Isotype of Rat Monoclonal Antibody

Clones rG019, rG055, rG056, and rG061 suggested to bind specifically and strongly to human CDH6 and monkey CDH6 were selected from among the rat anti-CDH6 antibody-producing hybridomas selected in Example 1)-5, and the isotype of each antibody was identified. The heavy chain subclass and the light chain type of the antibody were determined using a RAT MONOCLONAL ANTIBODY ISOTYPING TEST KIT (DS Pharma Biomedical Co., Ltd.). As a result, it was confirmed that all of these 4 clones rG019, rG055, rG056, and rG061 had a heavy chain of IgG2b subclass and a light chain of κ chain type.

1)-7 Preparation of Rat Anti-Human CDH6 Antibody

1)-7-1 Production of Culture Supernatant

The rat anti-human CDH6 monoclonal antibodies were purified from the hybridoma culture supernatants. First, the volume of each rat anti-CDH6 monoclonal antibody-producing hybridoma was sufficiently increased with ClonaCell-HY Selection Medium E (StemCell Technologies Inc.), and thereafter, the medium was exchanged with Hybridoma SFM (Thermo Fisher Scientific Corp.) to which 20% of Ultra Low IgG FBS (Thermo Fisher Scientific Corp.) had been added. Thereafter, the hybridoma was cultured for 4 to 5 days. The resulting culture supernatant was harvested, and insoluble matter was removed therefrom by passing through a 0.8-μm filter, and through a 0.2-μm filter.

1)-7-2 Purification of Rat Anti-CDH6 Antibody

An antibody (rat anti-CDH6 antibody (rG019, rG055, rG056 or rG061)) was purified from the culture supernatant of hybridomas prepared in Example 1)-7-1 according to Protein G affinity chromatography. The antibody was adsorbed on a Protein G column (GE Healthcare Biosciences Corp.), the column was then washed with PBS, and the antibody was then eluted with a 0.1 M glycine/HCl aqueous solution (pH 2.7). 1 M Tris-HCl (pH 9.0) was added to the eluate, so that the pH was adjusted to pH 7.0 to 7.5. Thereafter, using Centrifugal UF Filter Device VIVASPIN®20 (molecular weight cutoff: UF30K, Sartorius Inc.), the buffer was replaced with HBSor (25 mM histidine/5% sorbitol, pH 6.0), while the antibody was concentrated, so that the concentration of the antibody was adjusted to 1 mg/mL. Finally, the antibody was filtrated through a Minisart-Plus filter (Sartorius Inc.) to obtain a purified sample.

Example 2: In Vitro Evaluation of Rat Anti-CDH6 Antibody

2)-1 Evaluation of Binding Ability of Rat Anti-CDH6 Antibody by Flow Cytometry

The human CDH6-binding activity of the rat anti-CDH6 antibody produced in Example 1)-7 was evaluated by flow cytometry. Using LIPOFECTAMINE™ 2000 (Thermo Fisher Scientific Inc.), pcDNA3.1-hCDH6 produced in Example 1)-1 was transiently introduced into 293T cells (ATCC). The cells were cultured overnight under conditions of 37° C. and 5% $CO_2$, and thereafter, a cell suspension was prepared. The suspension of the transfected 293T cells was centrifuged, and the supernatant was then removed. Thereafter, the cells were suspended by the addition of each of the 4 rat anti-CDH6 monoclonal antibodies (clone Nos: rG019, rG055, rG056 and rG061), which had been prepared in Example 1)-7, or rat IgG control (R&D Systems, Inc.) (final concentration: 10 ng/mL). The cells were left standing at 4° C. for 1 hour. The cells were washed twice with PBS supplemented with 5% FBS, and then suspended by the addition of Anti-Rat IgG (whole molecule)-FITC antibody produced in rabbit (Sigma-Aldrich Co. LLC) that had been 50-fold diluted with PBS supplemented with 5% FBS. The cells were left standing at 4° C. for 1 hour. The cells were washed twice with PBS supplemented with 5% FBS, followed by detection using a flow cytometer (FC500; Beckman Coulter, Inc.). The data was analyzed using FlowJo (Tree Star, Inc.). The results are shown in FIG. 1. In the histogram of FIG. 1, the abscissa depicts FITC fluorescence intensity indicating the amount of the antibody bound, and the ordinate depicts a cell count. The shaded histogram shows that negative control 293T cells untransfected with hCDH6 were used, and the open solid line histogram shows that hCDH6-transfected 293T cells were used. As seen, fluorescence intensity was enhanced by the binding of the antibody to hCDH6 on the cell surface. The rat IgG control binds to neither of the cells. As a result, it was confirmed that the 4 produced rat anti-CDH6 monoclonal antibodies bind to 293T cells transfected with pcDNA3.1-hCDH6.

2)-2 Analysis of CDH6-Binding Site of Rat Anti-CDH6 Antibody by Flow Cytometry

2)-2-1 Construction of Expression Vector for Each Domain Deletion Mutant of Human CDH6

The full-length extracellular region of human CDH6 has five extracellular domains, EC1 (SEQ ID NO: 2), EC2 (SEQ ID NO: 3), EC3 (SEQ ID NO: 4), EC4 (SEQ ID NO: 5), and EC5 (SEQ ID NO: 6). A gene to be expressed such that each one of the five EC domains could be deleted from full-length human CDH6 was synthesized by GeneArt, and incorporated into p3×FLAG-CMV-9 vectors for mammalian expression (Sigma-Aldrich Co. LLC) according to a method known to a person skilled in the art in order to produce an expression vector for each domain deletion mutant lacking any one of EC1 to EC5.

2)-2-2 Epitope Analysis of Rat Anti-CDH6 Antibody by Flow Cytometry Using Domain Deletion Mutant The epitopes to which the rat anti-human CDH6 antibodies bound were identified by flow cytometry analysis using a 293α cell line transfected with each EC domain deletion vector. Using LIPOFECTAMINE™ 2000 (Thermo Fisher Scientific Inc.), each domain deletion mutant expression vector produced in Example 2)-2-1, or pcDNA3.1-hCDH6 for the expression of full-length human CDH6 was transiently introduced into a 293α cell line, which was a cell line derived from HEK293 cells by stable transfection with integrin αv and integrin β3 expression vectors. The cells were cultured overnight under conditions of 37° C. and 5% $CO_2$, and thereafter, a cell suspension was prepared. The suspension of the transfected 293α cells was centrifuged, and a supernatant was then removed. Thereafter, the cells were suspended by the addition of each of the 4 rat anti-CDH6 monoclonal antibodies (clone Nos: rG019, rG055, rG056 and rG061), which had been prepared in Example 1)-7, or rat IgG control (R&D Systems, Inc.) (final concentration: 20 nM). The cells were left standing at 4° C. for 1 hour. The cells were washed twice with PBS supplemented with 5% FBS, and then suspended by the addition of Anti-Rat IgG (whole molecule)-FITC antibody produced in rabbit (Sigma-Aldrich Co. LLC) that had been 50-fold diluted with PBS supplemented with 5% FBS. The cells were left standing at 4° C. for 1 hour. The cells were washed twice with PBS supplemented with 5% FBS, followed by detection using a flow cytometer (Canto II; BD Biosciences). The data was analyzed using FlowJo (Tree Star, Inc.). The results are shown in FIGS. 2-1 to 2-6. In the histograms of FIGS. 2-1 to 2-6, the abscissa depicts FITC fluorescence intensity indicating the amount of the antibody bound, and the ordinate depicts cell count. The shaded histogram shows that negative control untransfected 293α cells were used, and the open solid line histogram shows that 293 cells expressing full-length hCDH6 or each EC domain deletion mutant were used. Fluorescence intensity is enhanced when the antibody binds to full-length hCDH6 or each EC domain deletion mutant on the surface of cells. The rat IgG control binds to none of the transfected cells. The 4 produced rat anti-CDH6 monoclonal antibodies bind to the full-length hCDH6, the EC1 deletion mutant, the EC2 deletion mutant, the EC4 deletion mutant, and the EC5 deletion mutant, but do not bind to the EC3 deletion mutant. From this result, it was demonstrated that the 4 rat anti-CDH6 monoclonal antibodies specifically bind to hCDH6 with EC3 as an epitope.

2)-3 Internalization Activity of Rat Anti-CDH6 Antibody

2)-3-1 Confirmation of CDH6 Expression in Human Tumor Cell Line

In order to select a CDH6-positive human tumor cell line for use in the evaluation of the obtained antibodies, CDH6 expression information was retrieved from a known database, and the expression of CDH6 on the cell membrane surface was evaluated by flow cytometry. Human ovarian tumor cell lines NIH:OVCAR-3, PA-1 and ES-2 and human renal cell tumor cell line 786-O (all obtained from ATCC) were each cultured under conditions of 37° C. and 5% $CO_2$, and thereafter, a cell suspension was prepared. The cells were centrifuged, and the supernatant was then removed. Thereafter, the cells were suspended by the addition of a commercially available anti-human CDH6 antibody (MABU2715, R&D Systems, Inc.) or mouse IgG1 (BD Pharmingen) as a negative control (final concentration: 50 µg/mL). The cells were left standing at 4° C. for 1 hour. The cells were washed twice with PBS supplemented with 5% FBS, and then suspended by the addition of F(ab')2 Fragment of FITC-conjugated Goat Anti-mouse immunoglobulins (Dako) that had been 50-fold diluted with PBS supplemented with 5% FBS. The cells were left standing at 4° C. for 1 hour. The cells were washed twice with PBS supplemented with 5% FBS, followed by detection using a flow cytometer (Canto II; BD Biosciences). The data was analyzed using FlowJo (Tree Star, Inc.). The results are shown in FIG. 3. In the histogram of FIG. 3, the abscissa depicts FITC fluorescence intensity indicating the amount of the antibody bound, and the ordinate depicts cell count. The shaded histogram shows that the negative control mIgG1 was used in staining, and the open solid line histogram shows that the anti-human CDH6 antibody was used in staining. As seen, fluorescence intensity was enhanced by the binding of the antibody to hCDH6 on the surface of cells. The mIgG1 control binds to none of the cells. As a result, it was confirmed that the NIH:OVCAR-3, PA-1 and 786-O cell lines endogenously express CDH6 on the cell surface. On the other hand, it was demonstrated that the ES-2 cell line expresses no CDH6.

2)-3-2 Evaluation of Internalization Activity of Rat Anti-CDH6 Antibody

The internalization activity of the rat anti-CDH6 antibodies was evaluated using an anti-rat IgG reagent Rat-ZAP (Advanced Targeting Systems) conjugated with a toxin (saporin) inhibiting protein synthesis. Specifically, human CDH6-positive ovarian tumor cell line NIH:OVCAR-3 (ATCC) was seeded at $4 \times 10^3$ cells/well on a 96-well plate, and then cultured overnight under conditions of 37° C. and 5% $CO_2$. Human CDH6-positive renal cell tumor cell line 786-O (ATCC) was seeded at $1 \times 10^3$ cells/well on a 96-well plate, and then cultured overnight. On the next day, each rat anti-CDH6 antibody (final concentration: 1 nM) or rat IgG2b antibody (R&D Systems, Inc.) as a negative control antibody was added to the plate. Rat-ZAP (final concentration: 0.5 nM) or Goat Anti-Rat IgG, Fc (gamma) Fragment Specific (Jackson ImmunoResearch Laboratories, Inc.) unconjugated with the toxin (final concentration: 0.5 nM) as a negative control was further added to the plate, and the cells were cultured under conditions of 37° C. and 5% $CO_2$ for 3 days. The number of live cells was measured by the quantification of ATP activity (RLU) using a CellTiter-Glo™ Luminescent Cell Viability Assay (Promega Corp.). In this evaluation, Rat-ZAP is taken up into cells in a manner dependent on the internalization activity of the rat anti-CDH6 antibody, so that saporin inhibiting protein synthesis is released into the cells, so as to suppress cell growth. A cell growth inhibition effect brought about by the addition of the anti-CDH6 antibody was indicated by a relative survival rate when the number of live cells in a well supplemented with the negative control instead of Rat-ZAP was defined as 100%. FIG. 4 shows a graph and a table of the cell survival rate. As a result, it was demonstrated that the rat anti-CDH6 antibodies bind to CDH6 and cause internalization.

Example 3: Determination of Nucleotide Sequence of cDNA Encoding Variable Region of Rat Anti-CDH6 Antibody 3)-1 Amplification and Sequencing of rG019 Heavy Chain Variable Region and Light Chain Variable Region Gene Fragments 3)-1-1 Preparation of Total RNA from G019

In order to amplify cDNA encoding each variable region of rG019, total RNA was prepared from G019 using TRIzol Reagent (Ambion, Inc.).

3)-1-2 Amplification of cDNA Encoding rG019 Heavy Chain Variable Region by 5'-RACE PCR and Determination of Nucleotide Sequence cDNA encoding the heavy chain variable region was amplified using approximately 1 µg of the total RNA prepared in Example 3)-1-1 and a SMARTer RACE cDNA Amplification Kit (Clontech Laboratories, Inc.). As primers used to amplify the cDNA of the variable region of the rG019 heavy chain gene according to PCR, UPM (Universal Primer A Mix: included with SMARTer RACE cDNA Amplification Kit) and primers designed from the sequences of the constant regions of known rat heavy chains were used.

The heavy chain variable region-encoding cDNA amplified by 5'-RACE PCR was cloned into a plasmid, and thereafter, the nucleotide sequence of the cDNA of the heavy chain variable region was subjected to sequence analysis.

The determined nucleotide sequence of the cDNA encoding the heavy chain variable region of rG019 is shown in SEQ ID NO: 16, and the amino acid sequence thereof is shown in SEQ ID NO: 15.

3)-1-3 Amplification of cDNA Encoding rG019 Light Chain Variable Region by 5'-RACE PCR and Determination of Nucleotide Sequence Amplification and sequencing were carried out by the same method as that applied in Example 3)-1-2. However, as primers used to amplify the cDNA of the variable region of the rG019 light chain gene according to PCR, UPM (Universal Primer A Mix: included with SMARTer RACE cDNA Amplification Kit) and primers designed from the sequences of the constant regions of known rat light chains were used.

The determined nucleotide sequence of the cDNA encoding the light chain variable region of rG019 is shown in SEQ ID NO: 11, and the amino acid sequence thereof is shown in SEQ ID NO: 10.

3)-2 Amplification and Sequencing of rG055 Heavy Chain Variable Region and Light Chain Variable Region Gene Fragments The sequences were determined by the same method as that applied in Example 3)-1.

The determined nucleotide sequence of the cDNA encoding the heavy chain variable region of rG055 is shown in SEQ ID NO: 26, and the amino acid sequence thereof is shown in SEQ ID NO: 25. The nucleotide sequence of the cDNA encoding the light chain variable region of rG055 is shown in SEQ ID NO: 21, and the amino acid sequence thereof is shown in SEQ ID NO: 20.

3)-3 Amplification and Sequencing of rG056 Heavy Chain Variable Region and Light Chain Variable Region Gene Fragments The sequences were determined by the same method as that applied in Example 3)-1.

The determined nucleotide sequence of the cDNA encoding the heavy chain variable region of rG056 is shown in SEQ ID NO: 36, and the amino acid sequence thereof is shown in SEQ ID NO: 35. The nucleotide sequence of the cDNA encoding the light chain variable region of rG056 is shown in SEQ ID NO: 31, and the amino acid sequence thereof is shown in SEQ ID NO: 30.

3)-4 Amplification and Sequencing of rG061 Heavy Chain Variable Region and Light Chain Variable Region Gene Fragments The sequences were determined by the same method as that applied in Example 3)-1.

The determined nucleotide sequence of the cDNA encoding the heavy chain variable region of rG061 is shown in SEQ ID NO: 46, and the amino acid sequence thereof is shown in SEQ ID NO: 45. The nucleotide sequence of the cDNA encoding the light chain variable region of rG061 is shown in SEQ ID NO: 41, and the amino acid sequence thereof is shown in SEQ ID NO: 40.

Example 4: Production of Human Chimeric Anti-CDH6 Antibody chG019

4)-1 Construction of Human Chimeric Anti-CDH6 Antibody chG019 Expression Vector

4)-1-1 Construction of Chimeric and Humanized Light Chain Expression Vector pCMA-LK An approx. 5.4-kb fragment, which had been obtained by digesting plasmid pcDNA3.3-TOPO/LacZ (Invitrogen Corp.) with the restriction enzymes XbaI and PmeI, was bound to a DNA fragment comprising a DNA sequence (SEQ ID NO: 50) encoding a human light chain signal sequence and a human κ chain constant region, using an In-Fusion Advantage PCR cloning kit (Clontech Laboratories, Inc.), to produce pcDNA3.3/LK.

A neomycin expression unit was removed from pcDNA3.3/LK to construct pCMA-LK.

4)-1-2 Construction of Chimeric and Humanized IgG1 Type Heavy Chain Expression Vector pCMA-G1

A DNA fragment, which had been obtained by digesting pCMA-LK with XbaI and PmeI to remove the DNA sequence encoding the light chain signal sequence and the human κ chain constant region therefrom, was bound to a DNA fragment comprising a DNA sequence (SEQ ID NO: 51) encoding a human heavy chain signal sequence and a human IgG1 constant region, using an In-Fusion Advantage PCR cloning kit (Clontech Laboratories, Inc.), to construct pCMA-G1.

4)-1-3 Construction of chG019 Heavy Chain Expression Vector

A DNA fragment from nucleotide positions 36 to 440 in the nucleotide sequence of the chG019 heavy chain shown in SEQ ID NO: 57 was synthesized (GENEART). Using an In-Fusion HD PCR cloning kit (Clontech Laboratories, Inc.), the synthesized DNA fragment was inserted into a site of pCMA-G1 that had been cleaved with the restriction enzyme BlpI, so as to construct a chG019 heavy chain expression vector. It is to be noted that, for the chG019 heavy chain, a CDR sequence with cysteine substituted with proline was used in order to prevent unpredictable disulfide bonds.

4)-1-4 Construction of chG019 Light Chain Expression Vector

A DNA fragment comprising a DNA sequence (SEQ ID NO: 52) encoding the chG019 light chain was synthesized (GENEART). Using an In-Fusion HD PCR cloning kit (Clontech Laboratories, Inc.), the synthesized DNA fragment was bound to a DNA fragment, which had been obtained by digesting pCMA-LK with XbaI and PmeI to remove the DNA sequence encoding the light chain signal sequence and the human κ chain constant region therefrom, so as to construct a chG019 light chain expression vector.

4)-2 Production and Purification of Human Chimeric Anti-CDH6 Antibody chG019

4)-2-1 Production of chG019

In accordance with the manual, FreeStyle 293F cells (Invitrogen Corp.) were cultured and passaged. $1.2 \times 10^9$ FreeStyle 293F cells (Invitrogen Corp.) in the logarithmic growth phase were seeded on a 3-L Fernbach Erlenmeyer Flask (Corning Inc.), then diluted with FreeStyle 293 expression medium (Invitrogen Corp.) at $2.0 \times 10^6$ cells/mL. To 40 ml of Opti-Pro SFM medium (Invitrogen Corp.), 0.24 mg of the heavy chain expression vector, 0.36 mg of the light chain expression vector and 1.8 mg of Polyethyleneimine (Polyscience #24765) were added, and the obtained mixture was gently stirred. After incubation for 5 minutes, the mixture was added to the FreeStyle 293F cells. The cells were shake-cultured at 90 rpm in an 8% $CO_2$ incubator at 37° C. for 4 hours, and thereafter, 600 mL of EX-CELL VPRO medium (SAFC Biosciences Inc.), 18 mL of GlutaMAX I (GIBCO), and 30 mL of Yeastolate Ultrafiltrate (GIBCO) were added to the culture. The cells were further shake-cultured at 90 rpm in an 8% $CO_2$ incubator at 37° C. for 7 days. The obtained culture supernatant was filtrated through a Disposable Capsule Filter (Advantec # CCS-045-E1H).

4)-2-2 Purification of chG019

An antibody was purified from the culture supernatant obtained in Example 4)-2-1 by a one-step process according to rProtein A affinity chromatography. The culture supernatant was applied to a column that had been packed with MabSelectSuRe (GE Healthcare Biosciences Corp.) equilibrated with PBS, and thereafter, the column was washed with PBS in an amount of two or more times the volume of the column. Subsequently, the antibody was eluted with a 2 M arginine hydrochloride solution (pH 4.0), so that a fraction containing an antibody was collected. The fraction was dialyzed (Thermo Fisher Scientific Inc., Slide-A-Lyzer Dialysis Cassette), so that the buffer was replaced with HBSor (25 mM histidine/5% sorbitol, pH 6.0). Using a Centrifugal UF Filter Device VIVASPIN®V20 (molecular weight cutoff: UF1OK, Sartorius Inc.), the antibody was concentrated, so that the concentration of IgG was adjusted to 5 mg/ml or more. Finally, the antibody was filtrated through a Minisart-Plus filter (Sartorius Inc.) to obtain a purified sample.

4)-3 Evaluation of Binding Activity of Human Chimeric Anti-CDH6 Antibody chG019

The CDH6-binding activity of the human chimeric anti-CDH6 antibody chG019 purified in 4)-2 was confirmed by flow cytometry. Using LIPOFECTAMINE™ 2000, pcDNA3.1-hCDH6 or pcDNA3.1-cynoCDH6 produced in Example 1)-1, or pcDNA3.1 was transiently introduced into 293α cells. The cells were cultured overnight under conditions of 37° C. and 5% $CO_2$, and thereafter, a cell suspension was prepared. chG019 was added to the suspension of each of these cells. The cells were left standing at 4° C. for 1 hour. Thereafter, the cells were washed twice with PBS supplemented with 5% FBS, and then suspended by the addition of PE-labeled F(ab')2 Fragment anti-human IgG, Fcγ antibody (Jackson ImmunoResearch Laboratories, Inc.) that had been 500-fold diluted with PBS supplemented with 5% FBS. The cells were left standing at 4° C. for 1 hour. The cells were washed twice with PBS supplemented with 5% FBS, and then re-suspended in PBS supplemented with 5% FBS, followed by detection using a flow cytometer (Canto II; BD Biosciences). The data was analyzed using FlowJo (Tree Star, Inc.). As shown in FIG. 5, chG019 did not bind to the 293T cells transfected with pcDNA3.1 as a negative control, but did bind to the 293T cells transfected with pcDNA3.1-hCDH6 or pcDNA3.1-cynoCDH6 in an antibody concentration-dependent manner. In FIG. 5, the abscissa depicts antibody concentration, and the ordinate depicts the amount of the antibody bound, based on mean fluorescence intensity. It is evident from this result that chG019 specifically binds to human CDH6 and cynomolgus monkey CDH6 with almost equivalent binding activity.

Example 5: Production of Humanized Anti-CDH6 Antibody

5)-1 Design of Humanized Form of Anti-CDH6 Antibody
5)-1-1 Molecular Modeling of chG019 Variable Region
The molecular modeling of the variable regions of chG019 exploited a method known as homology modeling (Methods in Enzymology, 203, 121-153, (1991)). The commercially available protein three-dimensional structure analysis program BioLuminate (manufactured by Schrodinger, LLC) was employed using, as a template, a structure (PDB ID: 2I9L) registered in Protein Data Bank (Nuc. Acid Res. 35, D301-D303 (2007)) with a high sequence identity to the heavy chain and light chain variable regions of chG019.

5)-1-2 Design of Amino Acid Sequence of Humanized hG019
chG019 was humanized by CDR grafting (Proc. Natl. Acad. Sci. USA 86, 10029-10033 (1989)). The consensus sequences of human gamma chain subgroup 1 and kappa chain subgroup 1 determined by KABAT et al. (Sequences of Proteins of Immunological Interest, 5th Ed. Public Health Service National Institutes of Health, Bethesda, Md. (1991)) had high identity to the framework regions of chG019, and based on this, they were selected as acceptors for the heavy chain and the light chain, respectively. Donor residues to be grafted onto the acceptors were selected by analyzing three-dimensional models with reference to, for example, the criteria given by Queen et al. (Proc. Natl. Acad. Sci. USA 86, 10029-10033 (1989)).

5)-2 Humanization of chG019 Heavy Chain
Three heavy chains thus designed were named hH01, hH02 and hH04. The full-length amino acid sequence of the hH01 heavy chain is shown in SEQ ID NO: 69. The nucleotide sequence encoding the amino acid sequence of SEQ ID NO: 69 is shown in SEQ ID NO: 70. The full-length amino acid sequence of the heavy chain hH02 is shown in SEQ ID NO: 73. The nucleotide sequence encoding the amino acid sequence of SEQ ID NO: 73 is shown in SEQ ID NO: 74. The full-length amino acid sequence of the heavy chain hH04 is shown in SEQ ID NO: 77. The nucleotide sequence encoding the amino acid sequence of SEQ ID NO: 77 is shown in SEQ ID NO: 78.

5)-3 Humanization of chG019 Light Chain
Two light chains thus designed were named hL02 and hL03. The full-length amino acid sequence of the hL02 light chain is shown in SEQ ID NO: 61. The nucleotide sequence encoding the amino acid sequence of SEQ ID NO: 61 is shown in SEQ ID NO: 62. The full-length amino acid sequence of the light chain hL03 is shown in SEQ ID NO: 65. The nucleotide sequence encoding the amino acid sequence of SEQ ID NO: 65 is shown in SEQ ID NO: 66.

5)-4 Design of Humanized hG019 by Combination of Heavy Chain and Light Chain
An antibody consisting of hH01 and hL02 was named "H01L02 antibody" or "H01L02". An antibody consisting of hH02 and hL02 was named "H02L02 antibody" or "H02L02". An antibody consisting of hH02 and hL03 was named "H02L03 antibody" or "H02L03". An antibody consisting of hH04 and hL02 was named "H04L02 antibody" or "H04L02".

5)-5 Expression of Humanized Anti-CDH6 Antibody
5)-5-1 Construction of Humanized hG019 Heavy Chain expression vector
5)-5-1-1 Construction of Humanized hG019-H01 Type Heavy Chain Expression Vector
A DNA fragment from nucleotide positions 36 to 440 in the nucleotide sequence of the humanized hG019-H01 type heavy chain shown in SEQ ID NO: 70 was synthesized (GENEART). A humanized hG019-H01 type heavy chain expression vector was constructed by the same method as that applied in Example 4)-1-3.

5)-5-1-2 Construction of Humanized hG019-H02 Type Heavy Chain Expression Vector
A DNA fragment from nucleotide positions 36 to 440 in the nucleotide sequence of the humanized hG019-H02 type heavy chain shown in SEQ ID NO: 74 was synthesized (GENEART). A humanized hG019-H02 type heavy chain expression vector was constructed by the same method as that applied in Example 4)-1-3.

5)-5-1-3 Construction of Humanized hG019-H04 Type Heavy Chain Expression Vector
A DNA fragment from nucleotide positions 36 to 440 in the nucleotide sequence of the humanized hG019-H04 type heavy chain shown in SEQ ID NO: 78 was synthesized (GENEART). A humanized hG019-H04 type heavy chain expression vector was constructed by the same method as that applied in Example 4)-1-3.

5)-5-2 Construction of Humanized hG019 Light Chain Expression Vector
5)-5-2-1 Construction of Humanized hG019-L02 Type Light Chain Expression Vector
A DNA fragment comprising a humanized hG019-L02 type light chain variable region-encoding DNA sequence from nucleotide positions 37 to 399 in the nucleotide sequence of the humanized hG019-L02 type light chain shown in SEQ ID NO: 62 was synthesized (GENEART). Using an In-Fusion HD PCR cloning kit (Clontech Laboratories, Inc.), the synthesized DNA fragment was inserted into a site of pCMA-LK that had been cleaved with the restriction enzyme BsiWI, so as to construct a humanized hG019-L02 type light chain expression vector.

5)-5-2-2 Construction of Humanized hG019-L03 Type Light Chain Expression Vector
A DNA fragment comprising a humanized hG019-L03 type light chain variable region-encoding DNA sequence from nucleotide positions 37 to 399 in the nucleotide sequence of the humanized hG019-L03 type light chain shown in SEQ ID NO: 66 was synthesized (GENEART). A humanized hG019-L03 type light chain expression vector was constructed by the same method as that applied in Example 5)-5-2-1.

5)-5-3 Preparation of Humanized hG019

5)-5-3-1 Production of H01L02, H02L02, H02L03 and H04L02

The antibodies were produced by the same method as that applied in Example 4)-2-1. H01L02, H02L02, H02L03 and H04L02 were produced by the combination of the heavy chain and the light chain shown in Example 5)-4.

5)-5-3-2 Two-Step Purification of H01L02, H02L02, H02L03 and H04L02

The antibody was purified from the culture supernatant obtained in Example 5)-5-3-1, by a two-step process, namely, by rProtein A affinity chromatography and ceramic hydroxyapatite. The culture supernatant was applied to a column that had been packed with MabSelectSuRe (manufactured by GE Healthcare Biosciences Corp.) equilibrated with PBS, and thereafter, the column was washed with PBS in an amount of two or more times the volume of the column. Subsequently, the antibody was eluted using a 2 M arginine hydrochloride solution (pH 4.0). A fraction containing the antibody was dialyzed (Thermo Fisher Scientific Inc., Slide-A-Lyzer Dialysis Cassette), so that the buffer was replaced with PBS. The antibody solution was 5-fold diluted with a buffer of 5 mM sodium phosphate/50 mM MES/pH 7.0, and then applied to a ceramic hydroxyapatite column (Bio-Rad Laboratories, Inc., Bio-Scale CHT Type-1 Hydroxyapatite Column) that had been equilibrated with a buffer of 5 mM NaPi/50 mM MES/30 mM NaCl/pH 7.0. Elution was carried out on a linear concentration gradient of sodium chloride, so that a fraction containing an antibody was collected. This fraction was dialyzed (Thermo Fisher Scientific Inc., Slide-A-Lyzer Dialysis Cassette), so that the buffer was replaced with HBSor (25 mM histidine/5% sorbitol, pH 6.0). The antibody was concentrated with Centrifugal UF Filter Device VIVASPIN®20 (molecular weight cutoff: UF10K, Sartorius Inc.), thereby adjusting the IgG concentration to 20 mg/ml. Finally, the antibody was filtrated through a Minisart-Plus filter (Sartorius Inc.) to obtain a purified sample.

Reference Example 1: Production of Anti-CDH6 Antibody NOV0712

The anti-CDH6 antibody NOV0712 used in the Examples was produced with reference to the light chain full-length and heavy chain full-length amino acid sequences (SEQ ID NO: 235 and SEQ ID NO: 234, respectively, in International Publication No. WO 2016/024195) of NOV0712 described in International Publication No. WO 2016/024195.

Reference Example 1)-1 Anti-CDH6 Antibody NOV0712

Reference Example 1)-1-1 Construction of Anti-CDH6 Antibody NOV0712 Heavy Chain Expression Vector A NOV0712 heavy chain variable region-encoding DNA fragment from nucleotide positions 36 to 428 in the nucleotide sequence of the NOV0712 heavy chain shown in SEQ ID NO: 84 was synthesized (GENEART). A NOV0712 heavy chain expression vector was constructed by the same method as that applied in Example 4)-1-3. The amino acid sequence of the NOV0712 heavy chain expressed by the NOV0712 heavy chain expression vector is shown in SEQ ID NO: 83. In the amino acid sequence shown in SEQ ID NO: 83, the amino acid sequence consisting of the amino acid residues at positions 1 to 19 is a signal sequence.

Reference Example 1)-1-2 Construction of Anti-CDH6 Antibody NOV0712 Light Chain Expression Vector A DNA fragment comprising a NOV0712 light chain variable region-encoding DNA sequence from nucleotide positions 37 to 405 in the nucleotide sequence of the NOV0712 light chain shown in SEQ ID NO: 82 was synthesized (GENEART). A NOV0712 light chain expression vector was constructed by the same method as that applied in Example 5)-5-2-1. The amino acid sequence of the NOV0712 light chain expressed by the NOV0712 light chain expression vector is shown in SEQ ID NO: 81. In the amino acid sequence shown in SEQ ID NO: 81, the amino acid sequence consisting of the amino acid residues at positions 1 to 20 is a signal sequence.

Reference Example 1)-2 Preparation of Anti-CDH6 Antibody NOV0712

Reference Example 1)-2-1 Production of Anti-CDH6 Antibody NOV0712

NOV0712 was produced by the same method as that applied in Example 4)-2-1.

Reference Example 1)-2-2 One-Step Purification of Anti-CDH6 Antibody NOV0712

The anti-CDH6 antibody NOV0712 was purified from the culture supernatant obtained in Reference Example 1)-2-1 by the same method as that applied in Example 4)-2-2 (antibody concentration: 5 mg/l HBSor).

Example 6: In Vitro Evaluation of Humanized hG019 and NOV0712

6)-1 Evaluation of Binding Activity of Humanized hG019

6)-1-1 Human CDH6 Antigen-Binding Ability of Humanized hG019

The dissociation constant between the antibody and the antigen (Recombinant Human CDH6 Fc His chimera, R&D Systems, Inc.) was measured by using Biacore T200 (GE Healthcare Biosciences Corp.), according to a capture method, which comprises capturing the antigen as a ligand with the immobilized anti-His antibody and then measuring the dissociation constant using an antibody as an analyte. Approximately 1000 RU of the anti-histidine antibody (His capture kit, GE Healthcare Biosciences Corp.) was covalently bound to sensor chip CM5 (GE Healthcare Biosciences Corp.) by the amine coupling method. The antibody was also immobilized onto reference cells in the same manner as above. HBS-P+ (10 mM HEPES pH 7.4, 0.15 M NaCl, 0.05% Surfactant P20) supplemented with 1 mM $CaCl_2$ was used as a running buffer. The antigen was added onto the anti-histidine antibody-immobilized chip for 60 seconds, and a dilution series solution (0.391 to 100 nM) of the antibody was then added at a flow rate of 30 µl/min for 300 seconds. Subsequently, the dissociation phase was monitored for 600 seconds. As a regeneration solution, a glycine solution (pH 1.5) supplemented with 5 M MgCl2 was added twice at a flow rate of 10 µl/min for 30 seconds. A Steady State Affinity model in analysis software (BIAevaluation software, version 4.1) was used in data analysis, and the dissociation constant (KD) was calculated. The results are shown in Table 2.

TABLE 2

| | Antibody | KD (M) |
|---|---|---|
| 1 | H01L02 | 1.5E−09 |
| 2 | H02L02 | 1.1E−09 |
| 3 | H02L03 | 1.4E−09 |
| 4 | H04L02 | 1.1E−09 |

6)-1-2 Binding Activity Against Human, Monkey, Mouse or Rat CDH6

Using LIPOFECTAMINE™ 2000 (Thermo Fisher Scientific Inc.), pcDNA3.1-hCDH6, pcDNA3.1-cynoCDH6, p3×FLAG-CMV-9-mCDH6, or p3×FLAG-CMV-9-rCDH6 produced in Example 1)-1 was transiently introduced into 293α cells. The cells were cultured overnight under conditions of 37° C. and 5% $CO_2$, and thereafter, a cell suspension was prepared. Untransfected 293α cells were used as a negative control. The suspension of the 293α cells produced as described above was centrifuged, and the supernatant was then removed. Thereafter, the cells were suspended by the addition of each of the 4 humanized hG019 antibodies (clone Nos: H01L02, H02L02, H02L03 and H04L02), which had been prepared in Example 5)-5-3, or human IgG1 control (Calbiochem). The cells were left standing at 4° C. for 1 hour. The cells were washed twice with PBS supplemented with 5% FBS, and then suspended by the addition of anti-human IgG, Fc(gamma) PE goat F(ab') (Jackson ImmunoResearch Laboratories, Inc.) that had been 500-fold diluted with PBS supplemented with 5% FBS. The cells were left standing at 4° C. for 1 hour. The cells were washed twice with PBS supplemented with 5% FBS, followed by detection using a flow cytometer (Canto II; BD Biosciences). The data was analyzed using FlowJo (Tree Star, Inc.). In FIGS. 6-1 and 6-2, the abscissa depicts antibody concentration, and the ordinate depicts the amount of the antibody bound based on mean fluorescence intensity. As shown in FIGS. 6-1 and 6-2, the human IgG1 control as a negative control binds to none of the CDH6-transfected cells. The 4 humanized hG019 antibodies (clone Nos: H01L02, H02L02, H02L03 and H04L02) bind to human CDH6 and cynomolgus monkey CDH6, but bind to neither mouse nor rat CDH6. None of the antibodies bind to the cells transfected with the empty vector pcDNA3.1 as a negative control. On the other hand, International Publication No. WO 2016/024195 discloses that the NOV0712 antibody exhibits binding activity against all of human CDH6, cynomolgus monkey CDH6, mouse CDH6, and rat CDH6. As a result, it was demonstrated that the 4 humanized hG019 antibodies obtained in the present description are anti-CDH6 antibodies that exhibit binding properties different from those of the NOV0712 antibody.

6)-2 Analysis of CDH6-Binding Sites of Humanized hG019 and NOV0712

6)-2-1 Epitope Analysis Using Domain Deletion Mutant

Using Lipofectamine 2000 (Thermo Fisher Scientific Inc.), each domain deletion mutant expression vector produced in Example 2)-2-1, or pcDNA3.1-hCDH6 for the expression of full-length human CDH6 was transiently introduced into cells. The cells were cultured overnight under conditions of 37° C. and 5% $CO_2$, and thereafter, a cell suspension was prepared. The suspension of the transfected 293α cells was centrifuged, and the supernatant was then removed. Thereafter, the cells were suspended by the addition of each of the 4 humanized hG019 antibodies (clone Nos: H01L02, H02L02, H02L03 and H04L02), which had been prepared in Example 5)-5-3, or the anti-CDH6 antibody NOV0712, which had been prepared in Reference Example 1, or human IgG1 (Calbiochem) as a negative control. The cells were left standing at 4° C. for 1 hour. The cells were washed twice with PBS supplemented with 5% FBS, and then suspended by the addition of APC-anti-human IgG goat F(ab')2 (Jackson ImmunoResearch Laboratories, Inc.) that had been 500-fold diluted with PBS supplemented with 5% FBS. The cells were left standing at 4° C. for 1 hour. The cells were washed twice with PBS supplemented with 5% FBS, followed by detection using a flow cytometer (Canto II; BD Biosciences). The data was analyzed using FlowJo (Tree Star, Inc.). The results are shown in FIGS. 7-1 to 7-6. In the histograms of FIGS. 7-1 to 7-6, the abscissa depicts APC fluorescence intensity indicating the amount of the antibody bound, and the ordinate depicts cell count. The shaded histogram shows that negative control untransfected 293α cells were used, and the open solid line histogram shows that 293α cells expressing full-length hCDH6 or each EC domain deletion mutant were used. Fluorescence intensity is enhanced when the antibody binds to full-length hCDH6 or each EC domain deletion mutant on cell surface. The human IgG1 control binds to none of the transfected cells. The 4 humanized hG019 antibodies (clone Nos: H01L02, H02L02, H02L03 and H04L02) bind to the full-length hCDH6, the EC1 deletion mutant, the EC2 deletion mutant, the EC4 deletion mutant, and the EC5 deletion mutant, but do not bind to the EC3 deletion mutant. Specifically, it was demonstrated that the 4 humanized hG019 antibodies specifically bind to hCDH6 with EC3 as an epitope. On the other hand, the anti-CDH6 antibody NOV0712 binds to the full-length hCDH6, the EC1 deletion mutant, the EC2 deletion mutant, the EC3 deletion mutant, and the EC4 deletion mutant, but does not bind to the EC5 deletion mutant. Specifically, it was demonstrated that the anti-CDH6 antibody NOV0712 specifically binds to hCDH6 with EC5 as an epitope. This is consistent with epitope information on NOV0712 described in International Publication No. WO 2016/024195. From this result, it was demonstrated that the 4 humanized hG019 antibodies obtained in the present description are anti-CDH6 antibodies that exhibit properties different from those of NOV0712.

6)-2-2 Binding Competition Assay of Antibodies

6)-2-2-1 Production of 786-O/hCDH6 Stably Expressing Cell Line

The 786-O/hCDH6 stably expressing cell line was produced by infecting 786-O cells (ATCC) with a recombinant retrovirus for full-length human CDH6 expression. A human CDH6 expression retrovirus vector (pQCXIN-hCDH6) was produced by using a human CDH6 protein (NP_004923)-encoding cDNA expression vector (OriGene Technologies Inc., RC217889), and incorporating the cDNA into retrovirus vector pQCXIN (Clontech Laboratories, Inc.) according to a method known to a person skilled in the art. Using FuGene HD (Promega Corp.), pQCXIN-hCDH6 was transiently introduced into retrovirus packaging cells RetroPack PT67 (Clontech Laboratories, Inc.). After 48 hours, a culture supernatant containing recombinant retrovirus was recovered, and then added to the 786-O cell culture system, so that the cells were infected. From 3 days after the infection, the infected cells were cultured under conditions of 37° C. and 5% $CO_2$ in a medium supplemented with G418 (Gibco) (final concentration: 50 mg/mL) and screened with the drug, so as to establish cell line 786-O/hCDH6 stably expressing human CDH6. The high expression of human CDH6 in the stably expressing line was confirmed by flow cytometry in the same manner as that applied in Example 2)-3-1 (FIG. 8). Goat anti-Mouse IgG1 Secondary Antibody Alexa Fluor 647 (Thermo Fisher Scientific Inc.) that had been 500-fold diluted with PBS supplemented with 5% FBS was used as an antibody for detection. The results are shown in FIG. 8. In the histogram of FIG. 8, the abscissa depicts Alexa Fluor 647 fluorescence intensity indicating the amount of the antibody bound, and the ordinate depicts cell count. The shaded histogram shows that the negative control mIgG1 was used in staining, and the open solid line histogram shows that the anti-human CDH6 antibody was used in staining. As seen, fluorescence intensity was enhanced by the binding of the antibody to hCDH6 on cell surface. The mIgG1 control binds to none of the cells. As a result, it was demonstrated that the 786-O/hCDH6 stably expressing cell line more highly expresses human CDH6 than the parent line 786-O cells.

6)-2-2-2 Binding Competition Assay Using Labeled H01L02 and Labeled NOV0712

Labeled H01L02 and labeled NOV0712 were produced using an Alexa Fluor 488 Monoclonal Antibody Labeling Kit (Thermo Fisher Scientific Inc.). The cell suspension of the 786-O/hCDH6 stably expressing cell line produced in 6)-2-2-1 was centrifuged, and the supernatant was then removed. Thereafter, the cells were suspended by the addition of labeled NOV0712 or labeled H01L02 (final concentration: 5 nM) and, further, the addition of each of the 4 humanized hG019 antibodies (clone Nos: H01L02, H02L02, H02L03 and H04L02), which had been prepared in Example 5)-5-3, or the anti-CDH6 antibody NOV0712, which had been prepared in Reference Example 1, or human IgG1 (Calbiochem) as a negative control (final concentration: as shown in the abscissa of FIG. 9). The cells were left standing at 4° C. for 1 hour. Thereafter, the cells were washed twice with PBS supplemented with 5% FBS, followed by detection using a flow cytometer (Canto II; BD Biosciences). The data was analyzed using FlowJo (Tree Star, Inc.). The results are shown in FIG. 9. The abscissa depicts the final concentration of the added unlabeled antibody, and the ordinate depicts the amount of the antibody bound based on mean fluorescence intensity. When unlabeled NOV0712 is added to cells supplemented with labeled NOV0712, the amount of the labeled antibody bound is decreased by replacement with the unlabeled antibody in an addition concentration-dependent manner because they compete with each other for binding to the same epitope. On the other hand, even if each of the 4 humanized hG019 antibodies or human IgG1 as a negative control is added to cells supplemented with labeled NOV0712, there is no change in the amount of the labeled antibody bound, indicating that these antibodies differ in epitope and thus do not compete with each other for binding. Likewise, when each of the 4 unlabeled humanized hG019 antibodies is added to cells supplemented with labeled H01L02, the amount of the labeled antibody bound is decreased by replacement with the unlabeled antibody in an addition concentration-dependent manner because they compete with each other for binding to the same epitope. On the other hand, even if NOV0712 or human IgG1 as a negative control is added to cells supplemented with labeled H01L02, there is no change in the amount of the labeled antibody bound, indicating that these antibodies differ in epitope and thus do not compete with each other for binding.

6)-3 Evaluation of Internalization Activity of Humanized hG019 and NOV0712

The internalization activity of humanized hG019 and NOV0712 was evaluated using an anti-human IgG reagent Hum-ZAP (Advanced Targeting Systems) conjugated with a toxin (saporin) inhibiting protein synthesis. Specifically, human CDH6-positive ovarian tumor cell line NIH: OVCAR-3 (ATCC) was seeded at $4 \times 10^3$ cells/well on a 96-well plate, and then cultured overnight under conditions of 37° C. and 5% $CO_2$. Human CDH6-positive renal cell tumor cell line 786-O (ATCC) was seeded at $1 \times 10^3$ cells/well on a 96-well plate, and then cultured overnight. Human CDH6-positive ovarian tumor cell line PA-1 (ATCC) was seeded at $1 \times 10^3$ cells/well on a 96-well plate, and then cultured overnight under conditions of 37° C. and 5% $CO_2$. On the next day, each anti-CDH6 antibody (final concentration: 1 nM) or human IgG1 antibody (Calbiochem) as a negative control antibody was added to the plate. Hum-ZAP (final concentration: 0.5 nM) or F(ab')2 Fragment Goat Anti-human IgG, Fc (gamma) Fragment Specific (Jackson ImmunoResearch Laboratories, Inc.) unconjugated with the toxin (final concentration: 0.5 nM) as a negative control was further added to the plate, and the cells were cultured under conditions of 37° C. and 5% $CO_2$ for 3 days. The number of live cells was measured by the quantification of ATP activity (RLU) using CellTiter-Glo™ Luminescent Cell Viability Assay. In this evaluation, Hum-ZAP is taken up into cells in a manner dependent on the internalization activity of the humanized anti-CDH6 antibody, so that saporin, which inhibits protein synthesis, is released into the cells, so as to suppress cell growth. A cell growth inhibition effect brought about by the addition of the anti-CDH6 antibody was indicated by a relative survival rate when the number of live cells in a well supplemented with the negative control instead of Hum-ZAP was defined as 100%. FIGS. 10-1 to 10-3 each show a graph and a table of the cell survival rate. In this experiment, an antibody having strong internalization activity is considered to offer a low cell survival rate. As a result, the 4 humanized hG019 antibodies have an internalization rate of approximately 50 to 75% predicted from the cell survival rates for all of the 3 cell lines. Thus, the 4 humanized hG019 antibodies exhibit very high internalization activity and exhibit much higher internalization activity than that of NOV0712. From the mechanism of the medicinal effects of ADC, an antibody having higher internaliza-

Example 7: Production of Humanized hG019-Drug Conjugate

7)-1 Production of Antibody-Drug Conjugate H01L02-DXd

Step 1: Antibody-Drug Conjugate (1)

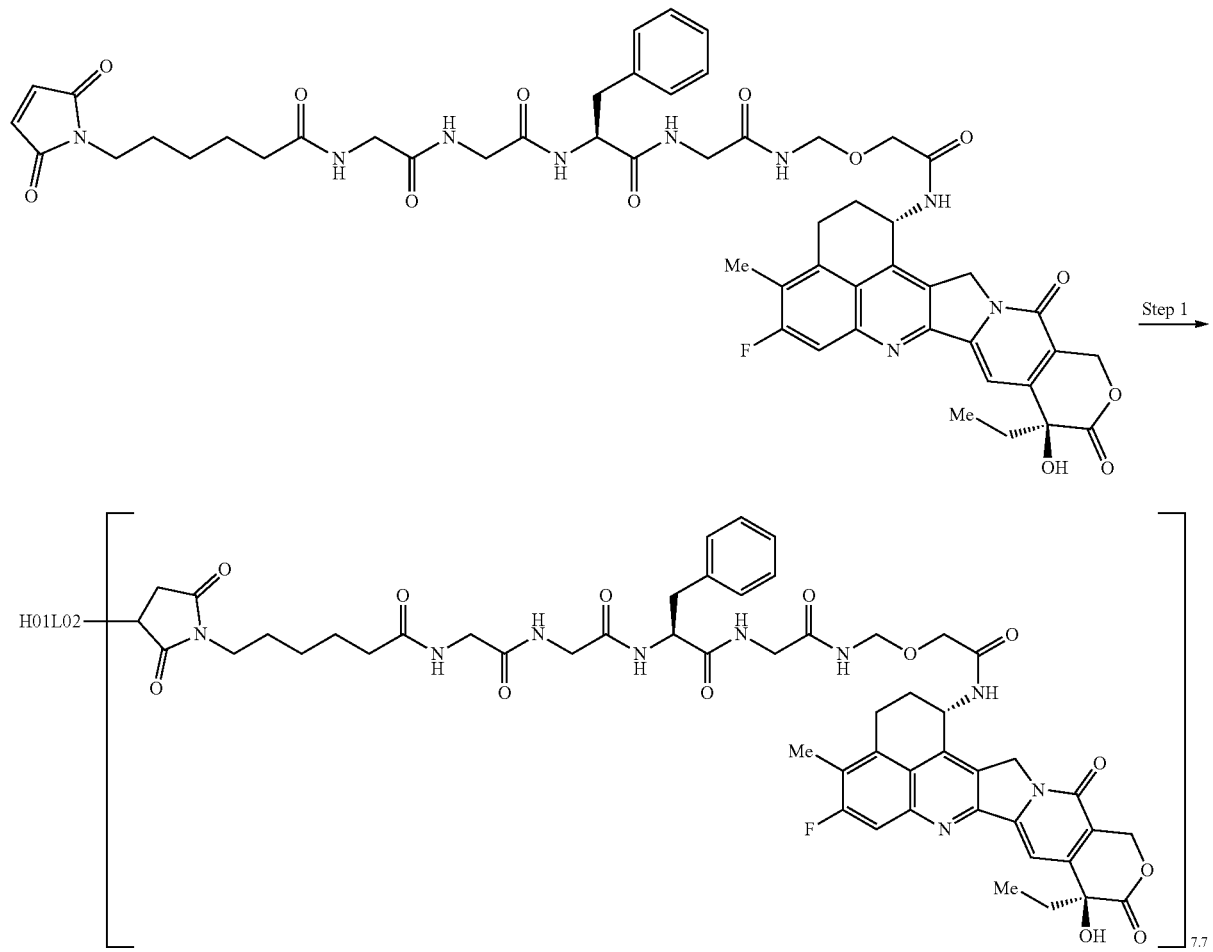

[Formula 11]

Reduction of antibody: H01L02 produced in Example 5 was adjusted to 9.85 mg/mL with PBS6.0/EDTA by using common procedures B (using 1.53 mLmg$^{-1}$cm$^{-1}$ as 280 nm absorption coefficient) and C described in production method 1. To this solution (5.7 mL), an aqueous solution of 10 mM TCEP (Tokyo Chemical Industry Co., Ltd.) (0.231 mL; 6.0 equivalents per antibody molecule) and a 1 M aqueous dipotassium hydrogen phosphate solution (Nacalai Tesque, Inc.; 0.0855 mL) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.386 mL; 10 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0347 mL; 9 equivalents per antibody molecule) was added thereto, and the obtained mixture was further stirred at room temperature for 20 minutes to terminate the reaction of the drug linker.

Purification: The above-described solution was purified by common procedure D described in production method 1 to obtain 19 mL of a solution containing the title antibody-drug conjugate "H01L02-ADC".

Characterization: Using common procedure E (using $\varepsilon_{D,280}$=5440 and $\varepsilon_{D,370}$=21240) described in production method 1, the following characteristic values were obtained.

Antibody concentration: 2.26 mg/mL, antibody yield: 42.9 mg (76%), average number of conjugated drug molecules (n) per antibody molecule measured by common procedure E: 5.9, and average number of conjugated drug molecules (n) per antibody molecule measured by common procedure F: 7.7.

7)-2 Production of antibody-drug conjugate H02L02-DXd

Step 1: Antibody-Drug Conjugate (2)

[Formula 12]

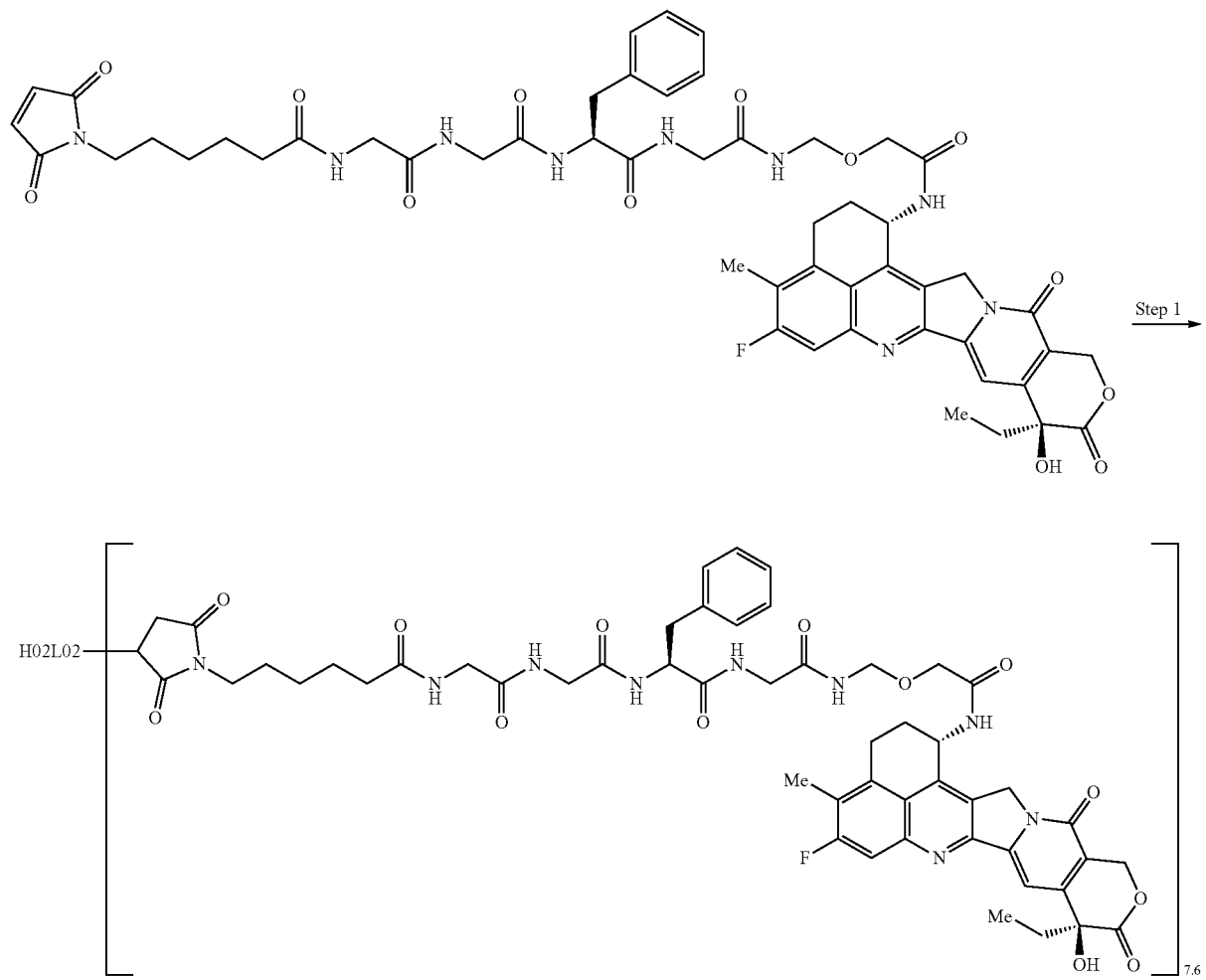

Reduction of antibody: H02L02 produced in Example 5 was adjusted to 9.95 mg/mL with PBS6.0/EDTA by using common procedures B (using 1.51 mLmg$^{-1}$cm$^{-1}$ as 280 nm absorption coefficient) and C described in production method 1. To this solution (5.7 mL), an aqueous solution of 10 mM TCEP (Tokyo Chemical Industry Co., Ltd.) (0.234 mL; 6.0 equivalents per antibody molecule) and a 1 M aqueous dipotassium hydrogen phosphate solution (Nacalai Tesque, Inc.; 0.0855 mL) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.389 mL; 10 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0350 mL; 9 equivalents per antibody molecule) was added thereto, and the obtained mixture was further stirred at room temperature for 20 minutes to terminate the reaction of the drug linker.

Purification: The above-described solution was purified by common procedure D described in production method 1 to obtain 19 mL of a solution containing the title antibody-drug conjugate "H02L02-ADC".

Characterization: Using common procedure E (using $\varepsilon_{D,280}$=5440 and $\varepsilon_{D,370}$=21240) described in production method 1, the following characteristic values were obtained.

Antibody concentration: 2.61 mg/mL, antibody yield: 49.6 mg (87%), average number of conjugated drug molecules (n) per antibody molecule measured by common procedure E: 5.9, and average number of conjugated drug molecules (n) per antibody molecule measured by common procedure F: 7.6.

7)-3 Production of Antibody-Drug Conjugate H02L03-DXd

Step 1: Antibody-Drug Conjugate (3)

[Formula 13]

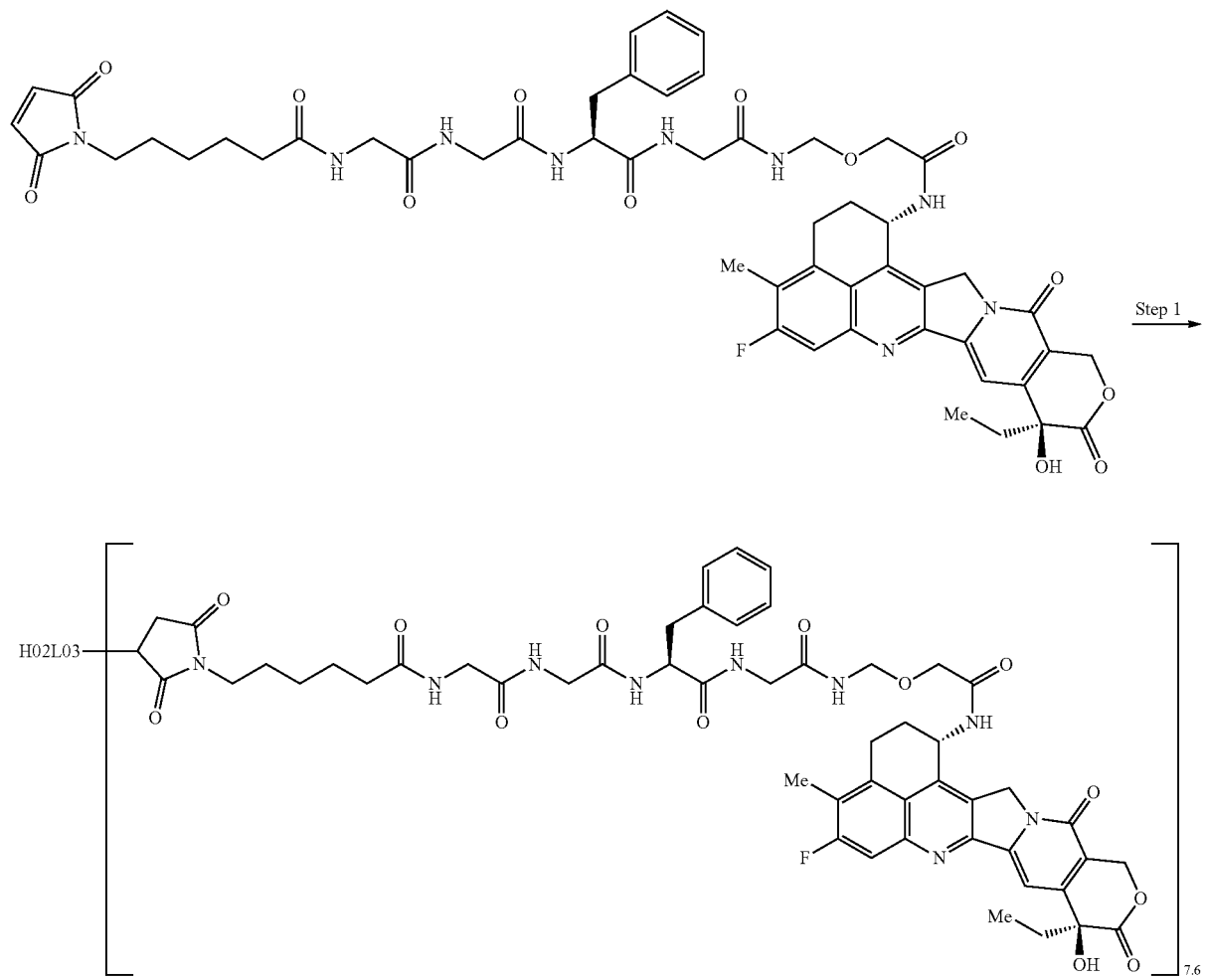

Reduction of antibody: H02L03 produced in Example 5 was adjusted to 9.86 mg/mL with PBS6.0/EDTA by using common procedures B (using 1.53 mLmg$^{-1}$cm$^{-1}$ as 280 nm absorption coefficient) and C described in production method 1. To this solution (5.7 mL), an aqueous solution of 10 mM TCEP (Tokyo Chemical Industry Co., Ltd.) (0.270 mL; 7.0 equivalents per antibody molecule) and a 1 M aqueous dipotassium hydrogen phosphate solution (Nacalai Tesque, Inc.; 0.0855 mL) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.386 mL; 10 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0347 mL; 9 equivalents per antibody molecule) was added thereto, and the obtained mixture was further stirred at room temperature for 20 minutes to terminate the reaction of the drug linker.

Purification: The above-described solution was purified by common procedure D described in production method 1 to obtain 19 mL of a solution containing the title antibody-drug conjugate "H01L02-ADC".

Characterization: Using common procedure E ((using $\varepsilon_{D,280}$=5440 and $\varepsilon_{D,370}$=21240) described in production method 1, the following characteristic values were obtained.

Antibody concentration: 2.71 mg/mL, antibody yield: 51.4 mg (91%), average number of conjugated drug molecules (n) per antibody molecule measured by common procedure E: 5.7, and average number of conjugated drug molecules (n) per antibody molecule measured by common procedure F: 7.6.

7)-4 Production of Antibody-Drug Conjugate H04L02-DXd

Step 1: Antibody-Drug Conjugate (4)

[Formula 14]

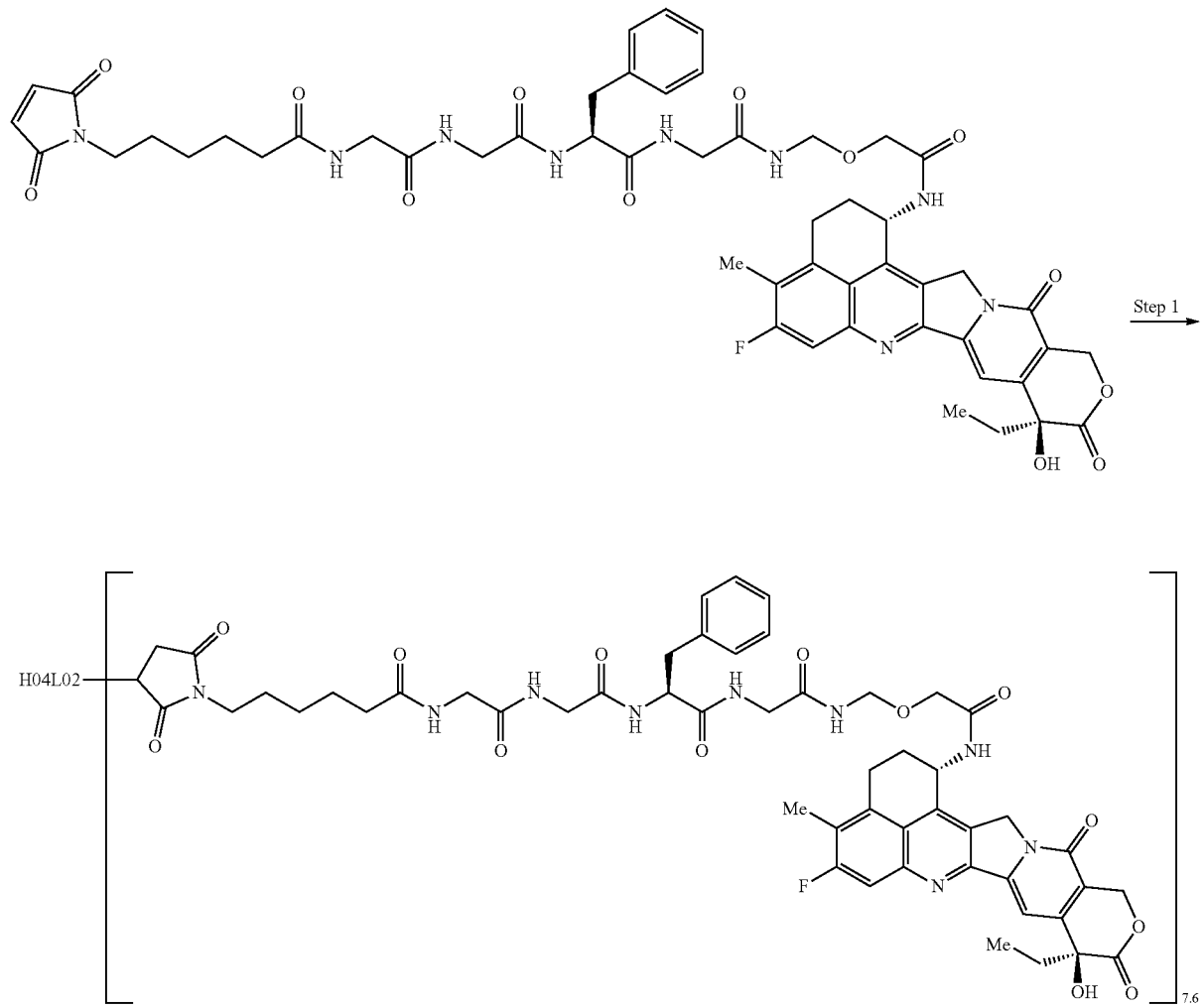

Reduction of antibody: H04L02 produced in Example 5 was adjusted to 9.86 mg/mL with PBS6.0/EDTA by using common procedures B (using 1.53 mLmg$^{-1}$cm$^{-1}$ as 280 nm absorption coefficient) and C described in production method 1. To this solution (5.7 mL), an aqueous solution of 10 mM TCEP (Tokyo Chemical Industry Co., Ltd.) (0.232 mL; 6.0 equivalents per antibody molecule) and a 1 M aqueous dipotassium hydrogen phosphate solution (Nacalai Tesque, Inc.; 0.0855 mL) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.386 mL; 10 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0347 mL; 9 equivalents per antibody molecule) was added thereto, and the obtained mixture was further stirred at room temperature for 20 minutes to terminate the reaction of the drug linker.

Purification: The above-described solution was purified by common procedure D described in production method 1 to obtain 19 mL of a solution containing the title antibody-drug conjugate "H04L02-ADC".

Characterization: Using common procedure E (using $\varepsilon_{D,280}$=5440 and $\varepsilon_{D,370}$=21240) described in production method 1, the following characteristic values were obtained.

Antibody concentration: 2.56 mg/mL, antibody yield: 48.7 mg (87%), average number of conjugated drug molecules (n) per antibody molecule measured by common procedure E: 5.8, and average number of conjugated drug molecules (n) per antibody molecule measured by common procedure F: 7.6.

Reference Example 2: Production of NOV0712-Drug Conjugate

Reference Example 2)-1 Production of Antibody-Drug Conjugate NOV0712-DM4

Antibody-Drug Conjugate (5)

Conjugation between antibody and drug linker: NOV0712 produced in Reference Example 1 was adjusted to 9.7 mg/mL with 20 mM HEPES8.1 (HEPES, 1 M Buffer Solution (20 mL) manufactured by Life Technologies Corp. was pH-adjusted to 8.1 with 1 M sodium hydroxide, and then brought to 1 L with distilled water) by using common procedures B (using 1.51 mLmg$^{-1}$cm$^{-1}$ as 280 nm absorption coefficient) and C described in production method 1. The solution was incubated at 20° C. for 10 minutes. Subsequently, a 10 mM solution of 1-(2,5-dioxopyrrolidin-1-yloxy)-1-oxo-4-(pyridin-2-yldisulfanyl)butane-2-sulfonic acid described in WO2016/024195 in DMA (0.366 mL; 5.2 equivalents per antibody molecule), a 10 mM solution of N2-deacetyl-deacetyl-N2-(4-methyl-4-mercapto-1-oxopentyl)-maytansine (DM4) in DMA (0.366 mL; 6.8 equivalents per antibody molecule), and 0.243 mL of DMA were added thereto, and the obtained mixture was incubated at 20° C. for 16 hours to conjugate the drug linker to the antibody. Subsequently, an aqueous solution of 1 M acetic acid was added thereto to adjust the pH to 5.0, and the obtained mixture was further stirred at room temperature for 20 minutes to terminate the reaction of the drug linker.

Purification: The above-described solution was purified by common procedure D described in production method 1 to obtain 28 mL of a solution containing the title antibody-drug conjugate "NOV0712-DM4".

Characterization: Using common procedure E (using $\varepsilon_{A,280}=200500$, $\varepsilon_{A,252}=76295$, $\varepsilon_{D,280}=43170$, and $\varepsilon_{D,252}=23224$) described in production method 1, the following characteristic values were obtained.

Antibody concentration: 2.58 mg/mL, antibody yield: 72.2 mg (93%), and average number of conjugated drug molecules (n) per antibody molecule measured by common procedure E: 3.0.

Reference Example 2)-2 Production of Antibody-Drug Conjugate NOV0712-DXd

Step 1: Antibody-Drug Conjugate (6)

[Formula 15]

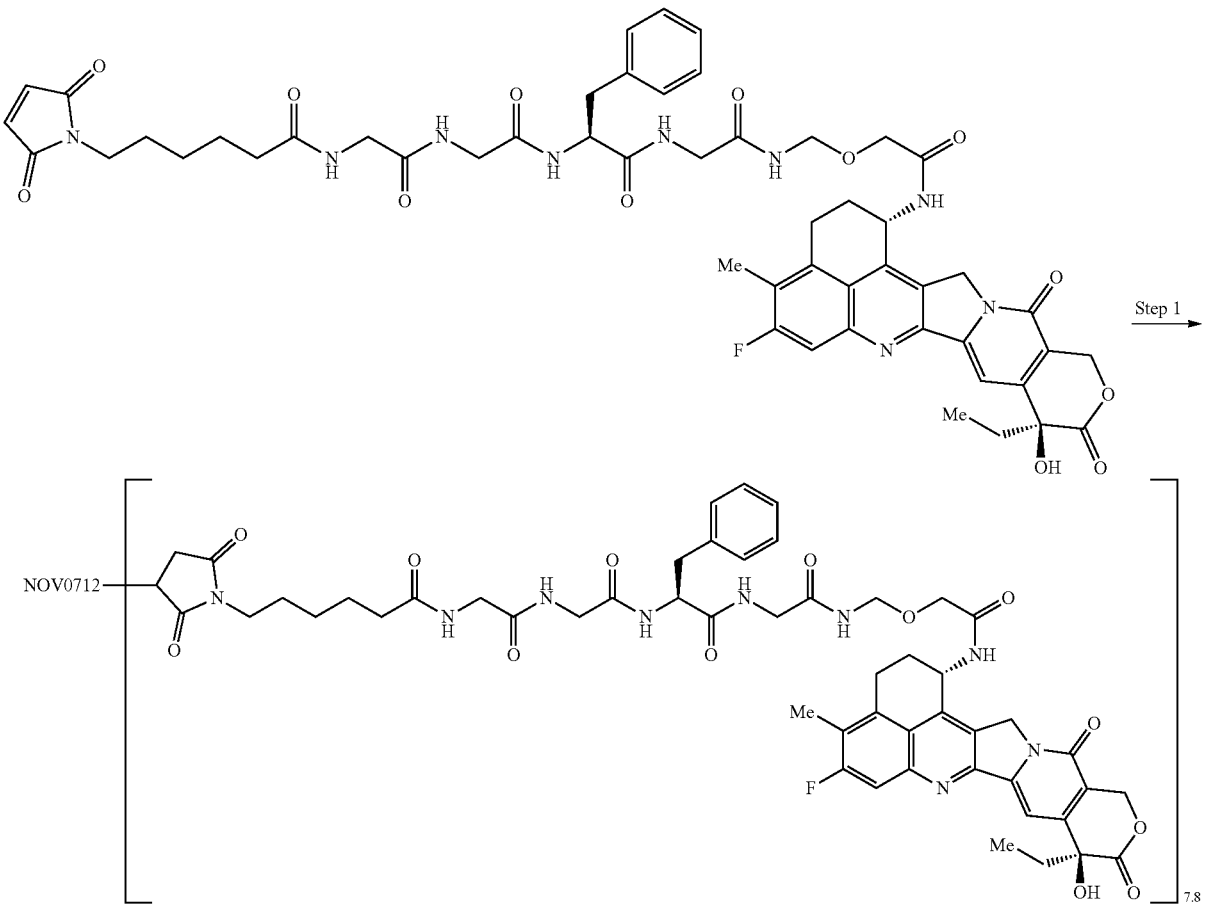

Reduction of antibody: NOV0712 produced in Reference Example 1 was adjusted to 9.26 mg/mL with PBS6.0/EDTA by using common procedures B (using 1.5 mLmg$^{-1}$cm$^{-1}$ as 280 nm absorption coefficient) and C described in production method 1. To this solution (6.6 mL), an aqueous solution of 10 mM TCEP (Tokyo Chemical Industry Co., Ltd.) (0.254 mL; 6.0 equivalents per antibody molecule) and a 1 M aqueous dipotassium hydrogen phosphate solution (Nacalai Tesque, Inc.; 0.0990 mL) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.381 mL; 9 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0381 mL; 9 equivalents per antibody molecule) was added thereto, and the obtained mixture was further stirred at room temperature for 20 minutes to terminate the reaction of the drug linker.

Purification: The above-described solution was purified by common procedure D described in production method 1 to obtain 23.5 mL of a solution containing the title antibody-drug conjugate "NOV0712-ADC".

Characterization: Using common procedure E (using $\varepsilon_{D,280}=5440$ and $\varepsilon_{D,370}=21240$) described in production method 1, the following characteristic values were obtained.

Antibody concentration: 2.26 mg/mL, antibody yield: 56.4 mg (92%), average number of conjugated drug molecules (n) per antibody molecule measured by common procedure E: 6.4, and average number of conjugated drug molecules (n) per antibody molecule measured by common procedure F: 7.8.

Reference Example 3: Production of H01L02-DM4

Reference Example 3)-1 Production of Antibody-Drug Conjugate H01L02-DM4

Antibody-Drug Conjugate (7)

Conjugation between antibody and drug linker: H01L02 produced in Example 5 was adjusted to 9.8 mg/mL with 20 mM HEPES8.1 (HEPES, 1 M Buffer Solution (20 mL) manufactured by Life Technologies Corp. was pH-adjusted to 8.1 with 1 M sodium hydroxide, and then brought to 1 L with distilled water) by using common procedures B (using 1.53 mLmg$^{-1}$cm$^{-1}$ as 280 nm absorption coefficient) and C described in production method 1. The solution was incubated at 20° C. for 10 minutes. Subsequently, a 10 mM solution of 1-(2,5-dioxopyrrolidin-1-yloxy)-1-oxo-4-(pyridin-2-yldisulfanyl)butane-2-sulfonic acid described in WO2016/024195 in DMA (0.062 mL; 11.5 equivalents per antibody molecule) and a 10 mM solution of N2-deacetyl-N2-(4-methyl-4-mercapto-1-oxopentyl)-maytansine (DM4) in DMA (0.082 mL; 15.1 equivalents per antibody molecule) were added thereto, and the obtained mixture was incubated at 20° C. for 18 hours to conjugate the drug linker to the antibody. Subsequently, an aqueous solution of 1 M acetic acid was added thereto to adjust the pH to 5.0, and the obtained mixture was further stirred at room temperature for 20 minutes to terminate the reaction of the drug linker.

Purification: The above-described solution was purified by common procedure D described in production method 1 to obtain 3.5 mL of a solution containing the title antibody-drug conjugate "H01L02-DM4".

Characterization: Using common procedure E (using $\varepsilon A,280=223400$, $\varepsilon A,252=85646$, $\varepsilon D,280=4317$, and $\varepsilon D,252=23224$) described in production method 1, the following characteristic values were obtained.

Antibody concentration: 1.97 mg/mL, antibody yield: 6.90 mg (88%), and average number of conjugated drug molecules (n) per antibody molecule measured by common procedure E: 3.6.

Example 8: Evaluation of In Vitro Activity of Antibody-Drug Conjugate

8)-1 Evaluation of In Vitro Cell Growth Inhibition Activity of Antibody-Drug Conjugate Against CDH6-Positive Human Tumor Cell Line CDH6-positive human ovarian tumor cell line PA-1 was seeded over a 96-well plate at $2\times10^3$ cells/100 µL/well in MEM medium supplemented with 10% FBS, and the cells were then cultured overnight under conditions of 37° C. and 5% $CO_2$. On the next day, each of the 4 humanized hG019-drug conjugates (clone names: H01L02-DXd, H02L02-DXd, H02L03-DXd and H04L02-DXd) produced in Example 7, or the NOV0712-drug conjugate (NOV0712-DM4) produced in Reference Example 2 was added to the cells such that the final concentrations were from 0.0001 (nM) to 100 (nM). After culture for 4 days, the number of live cells was measured by the quantification of ATP using CellTiter-Glo™ Luminescent Cell Viability Assay (Promega Corp.). FIG. 11 shows concentration-dependent cell growth inhibition activity when each antibody-drug conjugate was added to the cells. From this result, it was demonstrated that the 4 humanized hG019-drug conjugates exhibit growth inhibition activity against tumor cells from a lower addition concentration than that of the NOV0712-drug conjugate, and have high antitumor activity.

Example 9: In Vivo Antitumor Effect of Antibody-Drug Conjugate

The antitumor effects of the antibody-drug conjugates were evaluated using animal models derived from immunodeficient mice by the inoculation of CDH6-positive human tumor cell line cells. Four- to 5-week-old BALB/c nude mice (CAnN.Cg-Foxnl[nu]/CrlCrlj[Foxnlnu/Foxnlnu], Charles River Laboratories Japan Inc.) and SCID mice (CB17/Icr-Prkdc[scid]/CrlCrlj, Charles River Laboratories Japan Inc.) were acclimatized for 3 days or longer under SPF conditions before use in the experiment. The mice were fed with a sterilized solid diet (FR-2, Funabashi Farms Co., Ltd) and given sterilized tap water (which had been prepared by adding a 5 to 15 ppm sodium hypochlorite solution to tap water). The long diameter and short diameter of the inoculated tumor were measured twice a week using electronic digital calipers (CD-15CX, Mitutoyo Corp.), and the volume of the tumor was then calculated according to the following expression.

Tumor volume (mm$^3$)=½×Long diameter (mm)× [Short diameter (mm)]$^2$

Each antibody-drug conjugate was diluted with ABS buffer (10 mM acetate buffer, 5% sorbitol, pH 5.5) (Nacalai Tesque, Inc.), and the dilution was intravenously administered at a dose shown in each Example to the tail of each mouse. ABS buffer was administered in the same manner as above to a control group (vehicle group). Six mice per group were used in the experiment.

9)-1 Antitumor Effect—(1)

The CDH6-positive human renal cell tumor cell line 786-O (ATCC), the CDH6 expression of which had been confirmed in Example 2)-3-1, was suspended in Matrigel (Corning Inc.), and the cell suspension was subcutaneously inoculated at a dose of $5\times10^6$ cells to the right flank region of each male SCID mouse (Day 0). On Day 18, the mice were randomly grouped. On the day of grouping, each of the 4 antibody-drug conjugates (clone names: H01L02-DXd, H02L02-DXd, H02L03-DXd and H04L02-DXd) produced in Example 7, or NOV0712-DM4 produced in Reference Example 2 was intravenously administered at a dose of 3 mg/kg to the tail of each mouse. The results are shown in FIG. 12. The abscissa depicts the number of days, and the ordinate depicts tumor volume. The error range depicts a SE value.

NOV0712-DM4 exhibited no significant antitumor effect in this tumor model. All the 4 antibody-drug conjugates produced in Example 7 decreased tumor volume after administration, exerted significant tumor regression, and sustained the tumor regression effect for 24 days after administration (FIG. 12).

9)-2 Antitumor Effect—(2)

The CDH6-positive human ovarian tumor cell line PA-1 (ATCC), the CDH6 expression of which had been confirmed in Example 2)-3-1, was suspended in Matrigel (Corning Inc.), and the cell suspension was subcutaneously inoculated at a dose of $8.5\times10^6$ cells to the right flank region of each female nude mouse (Day 0). On Day 11, the mice were randomly grouped. On the day of grouping, the antibody-drug conjugate H01L02-DXd produced in Example 7, or NOV0712-DM4 or NOV0712-DXd produced in Reference Example 2 was intravenously administered at doses of 1 or 3 mg/kg to the tail of each mouse. The results are shown in FIG. 13. The abscissa depicts the number of days, and the ordinate depicts tumor volume. The error range depicts a SE value.

NOV0712-DM4 exhibited no antitumor effect at any of the doses of 1 and 3 mg/kg in this tumor model. On the other hand, H01L02-DXd significantly decreased tumor volume after administration at both the doses of 1 and 3 mg/kg and exerted a tumor regression effect (FIG. 13). The H01L02 antibody obtained in the present description and the NOV0712 antibody were conjugated to the same drug DXd, and the medicinal effects of the resulting samples were compared. As a result, H01L02-DXd exerted a stronger antitumor effect than that of NOV0712-DXd at both the doses of 1 and 3 mg/kg. Specifically, it was demonstrated that the H01L02 antibody of the present invention is a superior antibody for antibody-drug conjugates as antitumor agents to the NOV0712 antibody (FIG. 13).

9)-3 Antitumor Effect—(3)

The CDH6-positive human ovarian tumor cell line NIH: OVCAR-3 (ATCC), the CDH6 expression of which had been confirmed in Example 2)-3-1, was suspended in Matrigel (Corning Inc.), and the cell suspension was subcutaneously inoculated at a dose of $1\times10^7$ cells to the right flank region of each female nude mouse (Day 0). On Day 22, the mice were randomly grouped. On the day of grouping, the antibody-drug conjugate H01L02-DXd produced in Example 7, or NOV0712-DM4 produced in Reference Example 2 was intravenously administered at doses of 1 or 3 mg/kg to the tail of each mouse. The results are shown in FIG. 14. The abscissa depicts the number of days, and the ordinate depicts tumor volume. The error range depicts a SE value.

NOV0712-DM4 exhibited no antitumor effect at the dose of 1 mg/kg, and exhibited an antitumor effect at the dose of 3 mg/kg, though tumor regrowth was observed from 2 weeks after administration. On the other hand, H01L02-DXd significantly suppressed increase in tumor volume after administration at both the doses of 1 and 3 mg/kg, and sustained, particularly, at the dose of 3 mg/kg, the tumor growth inhibition effect over a long period of 31 days after administration (FIG. 14).

The tumor growth inhibition effect of NOV0712-DM4 produced in Reference Example 2 or H01L02-DM4 produced in Reference Example 3 was evaluated in the same manner as above using PA-1 cells. H01L02-DM4 further decreased tumor volume than NOV0712-DM4. Thus, the H01L02 antibody of the present invention is superior as an antibody for antibody-drug conjugates acting as antitumor agents as compared with the NOV0712 antibody.

9)-4 Antitumor Effect—(4)

The CDH6-positive human renal cell tumor cell line 786-O (ATCC), the CDH6 expression of which had been confirmed in Example 2)-3-1, was suspended in Matrigel (Corning Inc.), and the cell suspension was subcutaneously inoculated at a dose of $5\times10^6$ cells to the right flank region of each male SCID mouse (Day 0). On Day 20, the mice were randomly grouped. On the day of grouping, the antibody-drug conjugate H01L02-DXd produced in Example 7, or NOV0712-DM4 produced in Reference Example 2 was intravenously administered at doses of 1 or 3 mg/kg to the tail of each mouse. The results are shown in FIG. 15. The abscissa depicts the number of days, and the ordinate depicts tumor volume. The error range depicts a SE value.

NOV0712-DM4 exhibited no significant antitumor effect at any of the doses of 1 and 3 mg/kg in this tumor model. On the other hand, H01L02-DXd decreased tumor volume after administration at both the doses of 1 and 3 mg/kg, and exerted, particularly, at the dose of 3 mg/kg, significant tumor regression, and sustained the tumor regression effect for 20 days after administration (FIG. 15).

9)-5 Antitumor Effect—(5)

The CDH6-negative human ovarian tumor cell line ES-2 (ATCC), the absence of the CDH6 expression of which had been confirmed in Example 2)-3-1, was suspended in physiological saline, and the cell suspension was subcutaneously inoculated at a dose of $1\times10^6$ cells to the right flank region of each female nude mouse (Day 0). On Day 7, the mice were randomly grouped. On the day of grouping, the antibody-drug conjugate H01L02-DXd produced in Example 7, or NOV0712-DM4 produced in Reference Example 2 was intravenously administered at doses of 1 or 3 mg/kg to the tail of each mouse. The results are shown in FIG. 16. The abscissa depicts the number of days, and the ordinate depicts tumor volume. The error range depicts a SE value.

In this tumor model expressing no CDH6, H01L02-DXd and NOV0712-DM4 exhibited no antitumor effect at any of the doses. From this result, the antitumor effect of the antibody-drug conjugate in the CDH6-positive tumor model demonstrated in Examples 9)-1, 9)-2, 9)-3, and 9)-4 is an effect dependent on CDH6 expression in the tumor cells. Thus, the antibody-drug conjugate of the present invention is considered as a selective and safe antitumor drug that specifically exhibits an antitumor effect on CDH6-positive tumor without causing cytotoxicity to CDH6-negative normal tissues (FIG. 16).

INDUSTRIAL APPLICABILITY

The present invention provides an anti-CDH6 antibody having internalization activity and an antibody-drug conjugate comprising the antibody. The antibody-drug conjugate can be used as a therapeutic drug for cancer, and the like.

The invention claimed is:

1. A human or humanized monoclonal antibody that specifically binds to the amino acid sequence shown of SEQ ID NO: 4 and possesses an ability to internalize that permits cellular uptake, or a functional fragment of the antibody that binds to the amino acid sequence of SEQ ID NO: 4 and possesses an ability to internalize that permits cellular uptake.

2. The antibody or the functional fragment of the antibody according to claim 1, which has competitive inhibitory activity, for binding to the amino acid sequence shown in SEQ ID NO: 4, against at least any one antibody selected from the group consisting of the following antibodies (1) to (5):

(1) an antibody having a light chain consisting of the amino acid sequence at positions 21 to 233 in SEQ ID NO: 53 and a heavy chain consisting of the amino acid sequence at positions 20 to 471 in SEQ ID NO: 56, (2) an antibody having a light chain consisting of the amino acid sequence at positions 21 to 233 in SEQ ID NO: 61 and a heavy chain consisting of the amino acid sequence at positions 20 to 471 in SEQ ID NO: 69,
(3) an antibody having a light chain consisting of the amino acid sequence at positions 21 to 233 in SEQ ID NO: 61 and a heavy chain consisting of the amino acid sequence at positions 20 to 471 in SEQ ID NO: 73,
(4) an antibody having a light chain consisting of the amino acid sequence at positions 21 to 233 in SEQ ID NO: 65 and a heavy chain consisting of the amino acid sequence at positions 20 to 471 in SEQ ID NO: 73, and
(5) an antibody having a light chain consisting of the amino acid sequence at positions 21 to 233 in SEQ ID NO: 61 and a heavy chain consisting of the amino acid sequence at positions 20 to 471 in SEQ ID NO: 77.

3. The antibody or the functional fragment of the antibody according to claim 1, which comprises CDRL1, CDRL2 and CDRL3 in any one combination selected from the group consisting of the following combinations (1) to (4):
(1) CDRL1 consisting of the amino acid sequence shown in SEQ ID NO: 12, CDRL2 consisting of the amino acid sequence shown in SEQ ID NO: 13, and CDRL3 consisting of the amino acid sequence shown in SEQ ID NO: 14,
(2) CDRL1 consisting of the amino acid sequence shown in SEQ ID NO: 22, CDRL2 consisting of the amino acid sequence shown in SEQ ID NO: 23, and CDRL3 consisting of the amino acid sequence shown in SEQ ID NO: 24,
(3) CDRL1 consisting of the amino acid sequence shown in SEQ ID NO: 32, CDRL2 consisting of the amino acid sequence shown in SEQ ID NO: 33, and CDRL3 consisting of the amino acid sequence shown in SEQ ID NO: 34, and
(4) CDRL1 consisting of the amino acid sequence shown in SEQ ID NO: 42, CDRL2 consisting of the amino acid sequence shown in SEQ ID NO: 43, and CDRL3 consisting of the amino acid sequence shown in SEQ ID NO: 44, and
CDRH1, CDRH2 and CDRH3 in any one combination selected from the group consisting of the following combinations (5) to (9):
(5) CDRH1 consisting of the amino acid sequence shown in SEQ ID NO: 17, CDRH2 consisting of the amino acid sequence shown in SEQ ID NO: 18, and CDRH3 consisting of the amino acid sequence shown in SEQ ID NO: 19,
(6) CDRH1 consisting of the amino acid sequence shown in SEQ ID NO: 27, CDRH2 consisting of the amino acid sequence shown in SEQ ID NO: 28, and CDRH3 consisting of the amino acid sequence shown in SEQ ID NO: 29,
(7) CDRH1 consisting of the amino acid sequence shown in SEQ ID NO: 37, CDRH2 consisting of the amino acid sequence shown in SEQ ID NO: 38, and CDRH3 consisting of the amino acid sequence shown in SEQ ID NO: 39,
(8) CDRH1 consisting of the amino acid sequence shown in SEQ ID NO: 47, CDRH2 consisting of the amino acid sequence shown in SEQ ID NO: 48, and CDRH3 consisting of the amino acid sequence shown in SEQ ID NO: 49, and
(9) CDRH1 consisting of the amino acid sequence shown in SEQ ID NO: 17, CDRH2 consisting of the amino acid sequence shown in SEQ ID NO: 60, and CDRH3 consisting of the amino acid sequence shown in SEQ ID NO: 19.

4. The antibody or the functional fragment of the antibody according to claim 1, which comprises CDRL1, CDRL2 and CDRL3, and CDRH1, CDRH2 and CDRH3 in any combination selected from the group consisting of the following combinations (1) to (5):
(1) CDRL1 consisting of the amino acid sequence shown in SEQ ID NO: 12, CDRL2 consisting of the amino acid sequence shown in SEQ ID NO: 13, and CDRL3 consisting of the amino acid sequence shown in SEQ ID NO: 14, and CDRH1 consisting of the amino acid sequence shown in SEQ ID NO: 17, CDRH2 consisting of the amino acid sequence shown in SEQ ID NO: 18, and CDRH3 consisting of the amino acid sequence shown in SEQ ID NO: 19,
(2) CDRL1 consisting of the amino acid sequence shown in SEQ ID NO: 22, CDRL2 consisting of the amino acid sequence shown in SEQ ID NO: 23, and CDRL3 consisting of the amino acid sequence shown in SEQ ID NO: 24, and CDRH1 consisting of the amino acid sequence shown in SEQ ID NO: 27, CDRH2 consisting of the amino acid sequence shown in SEQ ID NO: 28, and CDRH3 consisting of the amino acid sequence shown in SEQ ID NO: 29,
(3) CDRL1 consisting of the amino acid sequence shown in SEQ ID NO: 32, CDRL2 consisting of the amino acid sequence shown in SEQ ID NO: 33, and CDRL3 consisting of the amino acid sequence shown in SEQ ID NO: 34, and CDRH1 consisting of the amino acid sequence shown in SEQ ID NO: 37, CDRH2 consisting of the amino acid sequence shown in SEQ ID NO: 38, and CDRH3 consisting of the amino acid sequence shown in SEQ ID NO: 39,
(4) CDRL1 consisting of the amino acid sequence shown in SEQ ID NO: 42, CDRL2 consisting of the amino acid sequence shown in SEQ ID NO: 43, and CDRL3 consisting of the amino acid sequence shown in SEQ ID NO: 44, and CDRH1 consisting of the amino acid sequence shown in SEQ ID NO: 47, CDRH2 consisting of the amino acid sequence shown in SEQ ID NO: 48, and CDRH3 consisting of the amino acid sequence shown in SEQ ID NO: 49, and
(5) CDRL1 consisting of the amino acid sequence shown in SEQ ID NO: 12, CDRL2 consisting of the amino acid sequence shown in SEQ ID NO: 13, and CDRL3 consisting of the amino acid sequence shown in SEQ ID NO: 14, and CDRH1 consisting of the amino acid sequence shown in SEQ ID NO: 17, CDRH2 consisting of the amino acid sequence shown in SEQ ID NO: 60, and CDRH3 consisting of the amino acid sequence shown in SEQ ID NO: 19.

5. The antibody or the functional fragment of the antibody according to claim 1, which is humanized.

6. The antibody or the functional fragment of the antibody according to claim 1, which has any one light chain variable region selected from the group consisting of the following variable regions (1) to (4):
(1) a light chain variable region consisting of the amino acid sequence shown in SEQ ID NO: 63,
(2) a light chain variable region consisting of the amino acid sequence shown in SEQ ID NO: 67,
(3) an amino acid sequence having a sequence identity of at least 95% or more to the sequence of a framework region other than at each CDR sequence in the amino acid sequences of (1) and (2), and
(4) an amino acid sequence comprising a deletion, substitution or addition of one or several amino acids in the sequence of a framework region other than at each CDR sequence in the amino acid sequences of (1) to (3), and any one heavy chain variable region selected from the group consisting of the following variable regions (5) to (9):

(5) a heavy chain variable region consisting of the amino acid sequence shown in SEQ ID NO: 71, (6) a heavy chain variable region consisting of the amino acid sequence shown in SEQ ID NO: 75, (7) a heavy chain variable region consisting of the amino acid sequence shown in SEQ ID NO: 79, (8) an amino acid sequence having a sequence homology of at least 95% or more to the sequence of a framework region other than at each CDR sequence in the amino acid sequences of (5) to (7), and (9) an amino acid sequence comprising a deletion, substitution or addition of one or several amino acids in the sequence of a framework region other than at each CDR sequence in the amino acid sequences of (5) to (8).

7. The antibody or the functional fragment of the antibody according to claim 1, which comprises a light chain variable region and a heavy chain variable region in any of the following combinations (1) to (4):

(1) a light chain variable region consisting of the amino acid sequence shown in SEQ ID NO: 63 and a heavy chain variable region consisting of the amino acid sequence shown in SEQ ID NO: 71, (2) a light chain variable region consisting of the amino acid sequence shown in SEQ ID NO: 63 and a heavy chain variable region consisting of the amino acid sequence shown in SEQ ID NO: 75, (3) a light chain variable region consisting of the amino acid sequence shown in SEQ ID NO: 67 and a heavy chain variable region consisting of the amino acid sequence shown in SEQ ID NO: 75, and (4) a light chain variable region consisting of the amino acid sequence shown in SEQ ID NO: 63 and a heavy chain variable region consisting of the amino acid sequence shown in SEQ ID NO: 79.

8. The antibody or the functional fragment of the antibody according to claim 1, which has any of the following combinations (1) to (4):

(1) a light chain consisting of the amino acid sequence at positions 21 to 233 in SEQ ID NO: 61 and a heavy chain consisting of the amino acid sequence at positions 20 to 471 in SEQ ID NO: 69, (2) a light chain consisting of the amino acid sequence at positions 21 to 233 in SEQ ID NO: 61 and a heavy chain consisting of the amino acid sequence at positions 20 to 471 in SEQ ID NO: 73, (3) a light chain consisting of the amino acid sequence at positions 21 to 233 in SEQ ID NO: 65 and a heavy chain consisting of the amino acid sequence at positions 20 to 471 in SEQ ID NO: 73, and (4) a light chain consisting of the amino acid sequence at positions 21 to 233 in SEQ ID NO: 61 and a heavy chain consisting of the amino acid sequence at positions 20 to 471 in SEQ ID NO: 77.

9. The antibody or the functional fragment of the antibody according to claim 8, which has a light chain consisting of the amino acid sequence at positions 21 to 233 in SEQ ID NO: 61 and a heavy chain consisting of the amino acid sequence at positions 20 to 471 in SEQ ID NO: 69.

10. The antibody or the functional fragment of the antibody according to claim 8, which has a light chain consisting of the amino acid sequence at positions 21 to 233 in SEQ ID NO: 61 and a heavy chain consisting of the amino acid sequence at positions 20 to 471 in SEQ ID NO: 73.

11. The antibody or the functional fragment of the antibody according to claim 8, which has a light chain consisting of the amino acid sequence at positions 21 to 233 in SEQ ID NO: 65 and a heavy chain consisting of the amino acid sequence at positions 20 to 471 in SEQ ID NO: 73.

12. The antibody or the functional fragment of the antibody according to claim 8, which has a light chain consisting of the amino acid sequence at positions 21 to 233 in SEQ ID NO: 61 and a heavy chain consisting of the amino acid sequence at positions 20 to 471 in SEQ ID NO: 77.

13. The functional fragment of the antibody according to claim 1, wherein the functional fragment is selected from the group consisting of Fab, F(ab')2, Fab' and Fv.

14. The antibody or the functional fragment of the antibody according to claim 1, wherein the heavy chain or the light chain has undergone one or two or more modifications selected from the group consisting of N-linked glycosylation, O-linked glycosylation, N-terminal processing, C-terminal processing, deamidation, isomerization of aspartic acid, oxidation of methionine, addition of a methionine residue to the N-terminus, amidation of a proline residue, conversion of N-terminal glutamine or N-terminal glutamic acid to pyroglutamic acid, and a deletion of one or two amino acids from the carboxyl terminus.

15. The antibody according to claim 14, wherein one or two amino acids are deleted from the carboxyl terminus of a heavy chain thereof.

16. The antibody according to claim 15, wherein one amino acid is deleted from each of the carboxyl termini of both of the heavy chains thereof.

17. The antibody according to claim 14, wherein a proline residue at the carboxyl terminus of a heavy chain thereof is further amidated.

18. The antibody or the functional fragment of the antibody according to claim 1, wherein sugar chain modification is regulated in order to enhance antibody-dependent cellular cytotoxic activity.

* * * * *

SEQUENCE LISTING

<160> NUMBER OF SEQ ID NOS: 86

<210> SEQ ID NO 1
<211> LENGTH: 790
<212> TYPE: PRT
<213> ORGANISM: Homo sapiens

<400> SEQUENCE: 1

Met Arg Thr Tyr Arg Tyr Phe Leu Leu Phe Trp Val Gly Gln Pro
1               5                   10                  15

Tyr Pro Thr Leu Ser Thr Pro Leu Ser Lys Arg Thr Ser Gly Phe Pro
            20                  25                  30

Ala Lys Lys Arg Ala Leu Glu Leu Ser Gly Asn Ser Lys Asn Glu Leu
            35                  40                  45

Asn Arg Ser Lys Arg Ser Trp Met Trp Asn Gln Phe Phe Leu Leu Glu
            50                  55                  60

Glu Tyr Thr Gly Ser Asp Tyr Gln Tyr Val Gly Lys Leu His Ser Asp
65                  70                  75                  80

Gln Asp Arg Gly Asp Gly Ser Leu Lys Tyr Ile Leu Ser Gly Asp Gly
                85                  90                  95

Ala Gly Asp Leu Phe Ile Ile Asn Glu Asn Thr Gly Asp Ile Gln Ala
                100                 105                 110

Thr Lys Arg Leu Asp Arg Glu Glu Lys Pro Val Tyr Ile Leu Arg Ala
                115                 120                 125

Gln Ala Ile Asn Arg Arg Thr Gly Arg Pro Val Glu Pro Glu Ser Glu
130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175

Phe Val Val Gln Val Thr Ala Thr Asp Ala Asp Asp Pro Thr Tyr Gly
                180                 185                 190

Asn Ser Ala Lys Val Val Tyr Ser Ile Leu Gln Gly Gln Pro Tyr Phe
                195                 200                 205

Ser Val Glu Ser Glu Thr Gly Ile Ile Lys Thr Ala Leu Leu Asn Met
210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Thr Val Asn Ile
                245                 250                 255

Thr Leu Thr Asp Val Asn Asp Asn Pro Pro Arg Phe Pro Gln Ser Thr
                260                 265                 270

Tyr Gln Phe Lys Thr Pro Glu Ser Ser Pro Pro Gly Thr Pro Ile Gly
            275                 280                 285

Arg Ile Lys Ala Ser Asp Ala Asp Val Gly Glu Asn Ala Glu Ile Glu
            290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Lys Val Tyr Thr Leu Lys Val Glu Ala Ser Asn Pro
                340                 345                 350

Tyr Val Glu Pro Arg Phe Leu Tyr Leu Gly Pro Phe Lys Asp Ser Ala
                355                 360                 365

```
Thr Val Arg Ile Val Val Glu Asp Val Asp Glu Pro Pro Val Phe Ser
    370                 375                 380
Lys Leu Ala Tyr Ile Leu Gln Ile Arg Glu Asp Ala Gln Ile Asn Thr
385                 390                 395                 400
Thr Ile Gly Ser Val Thr Ala Gln Asp Pro Asp Ala Ala Arg Asn Pro
                405                 410                 415
Val Lys Tyr Ser Val Asp Arg His Thr Asp Met Asp Arg Ile Phe Asn
                420                 425                 430
Ile Asp Ser Gly Asn Gly Ser Ile Phe Thr Ser Lys Leu Leu Asp Arg
            435                 440                 445
Glu Thr Leu Leu Trp His Asn Ile Thr Val Ile Ala Thr Glu Ile Asn
450                 455                 460
Asn Pro Lys Gln Ser Ser Arg Val Pro Leu Tyr Ile Lys Val Leu Asp
465                 470                 475                 480
Val Asn Asp Asn Ala Pro Glu Phe Ala Glu Phe Tyr Glu Thr Phe Val
                485                 490                 495
Cys Glu Lys Ala Lys Ala Asp Gln Leu Ile Gln Thr Leu His Ala Val
                500                 505                 510
Asp Lys Asp Asp Pro Tyr Ser Gly His Gln Phe Ser Phe Ser Leu Ala
                515                 520                 525
Pro Glu Ala Ala Ser Gly Ser Asn Phe Thr Ile Gln Asp Asn Lys Asp
530                 535                 540
Asn Thr Ala Gly Ile Leu Thr Arg Lys Asn Gly Tyr Asn Arg His Glu
545                 550                 555                 560
Met Ser Thr Tyr Leu Leu Pro Val Val Ile Ser Asp Asn Asp Tyr Pro
                565                 570                 575
Val Gln Ser Ser Thr Gly Thr Val Thr Val Arg Val Cys Ala Cys Asp
                580                 585                 590
His His Gly Asn Met Gln Ser Cys His Ala Glu Ala Leu Ile His Pro
            595                 600                 605
Thr Gly Leu Ser Thr Gly Ala Leu Val Ala Ile Leu Leu Cys Ile Val
            610                 615                 620
Ile Leu Leu Val Thr Val Val Leu Phe Ala Ala Leu Arg Arg Gln Arg
625                 630                 635                 640
Lys Lys Glu Pro Leu Ile Ile Ser Lys Glu Asp Ile Arg Asp Asn Ile
                645                 650                 655
Val Ser Tyr Asn Asp Glu Gly Gly Gly Glu Glu Asp Thr Gln Ala Phe
                660                 665                 670
Asp Ile Gly Thr Leu Arg Asn Pro Glu Ala Ile Glu Asp Asn Lys Leu
            675                 680                 685
Arg Arg Asp Ile Val Pro Glu Ala Leu Phe Leu Pro Arg Arg Thr Pro
690                 695                 700
Thr Ala Arg Asp Asn Thr Asp Val Arg Asp Phe Ile Asn Gln Arg Leu
705                 710                 715                 720
Lys Glu Asn Asp Thr Asp Pro Thr Ala Pro Pro Tyr Asp Ser Leu Ala
                725                 730                 735
Thr Tyr Ala Tyr Glu Gly Thr Gly Ser Val Ala Asp Ser Leu Ser Ser
                740                 745                 750
Leu Glu Ser Val Thr Thr Asp Ala Asp Gln Asp Tyr Asp Tyr Leu Ser
            755                 760                 765
Asp Trp Gly Pro Arg Phe Lys Lys Leu Ala Asp Met Tyr Gly Gly Val
770                 775                 780

Asp Ser Asp Lys Asp Ser
```

<210> SEQ ID NO 2
<211> LENGTH: 106
<212> TYPE: PRT
<213> ORGANISM: Homo sapiens

<400> SEQUENCE: 2

Ser Trp Met Trp Asn Gln Phe Phe Leu Leu Glu Glu Tyr Thr Gly Ser
1               5                   10                  15

Asp Tyr Gln Tyr Val Gly Lys Leu His Ser Asp Gln Asp Arg Gly Asp
            20                  25                  30

Gly Ser Leu Lys Tyr Ile Leu Ser Gly Asp Gly Ala Gly Asp Leu Phe
        35                  40                  45

Ile Ile Asn Glu Asn Thr Gly Asp Ile Gln Ala Thr Lys Arg Leu Asp
    50                  55                  60

Arg Glu Glu Lys Pro Val Tyr Ile Leu Arg Ala Gln Ala Ile Asn Arg
65                  70                  75                  80

Arg Thr Gly Arg Pro Val Glu Pro Glu Ser Glu Phe Ile Ile Lys Ile
                85                  90                  95

His Asp Ile Asn Asp Asn Glu Pro Ile Phe
            100                 105

<210> SEQ ID NO 3
<211> LENGTH: 109
<212> TYPE: PRT
<213> ORGANISM: Homo sapiens

<400> SEQUENCE: 3

Thr Lys Glu Val Tyr Thr Ala Thr Val Pro Glu Met Ser Asp Val Gly
1               5                   10                  15

Thr Phe Val Val Gln Val Thr Ala Thr Asp Ala Asp Asp Pro Thr Tyr
            20                  25                  30

Gly Asn Ser Ala Lys Val Val Tyr Ser Ile Leu Gln Gly Gln Pro Tyr
        35                  40                  45

Phe Ser Val Glu Ser Glu Thr Gly Ile Ile Lys Thr Ala Leu Leu Asn
    50                  55                  60

Met Asp Arg Glu Asn Arg Glu Gln Tyr Gln Val Val Ile Gln Ala Lys
65                  70                  75                  80

Asp Met Gly Gly Gln Met Gly Gly Leu Ser Gly Thr Thr Thr Val Asn
                85                  90                  95

Ile Thr Leu Thr Asp Val Asn Asp Asn Pro Pro Arg Phe
            100                 105

<210> SEQ ID NO 4
<211> LENGTH: 115
<212> TYPE: PRT
<213> ORGANISM: Homo sapiens

<400> SEQUENCE: 4

Pro Gln Ser Thr Tyr Gln Phe Lys Thr Pro Glu Ser Ser Pro Pro Gly
1               5                   10                  15

Thr Pro Ile Gly Arg Ile Lys Ala Ser Asp Ala Asp Val Gly Glu Asn
            20                  25                  30

Ala Glu Ile Glu Tyr Ser Ile Thr Asp Gly Glu Gly Leu Asp Met Phe
        35                  40                  45

Asp Val Ile Thr Asp Gln Glu Thr Gln Glu Gly Ile Ile Thr Val Lys
    50                  55                  60

```
Lys Leu Leu Asp Phe Glu Lys Lys Val Tyr Thr Leu Lys Val Glu
 65                  70                  75                  80

Ala Ser Asn Pro Tyr Val Glu Pro Arg Phe Leu Tyr Leu Gly Pro Phe
                 85                  90                  95

Lys Asp Ser Ala Thr Val Arg Ile Val Val Glu Asp Val Asp Glu Pro
            100                 105                 110

Pro Val Phe
        115

<210> SEQ ID NO 5
<211> LENGTH: 103
<212> TYPE: PRT
<213> ORGANISM: Homo sapiens

<400> SEQUENCE: 5

Ser Lys Leu Ala Tyr Ile Leu Gln Ile Arg Glu Asp Ala Gln Ile Asn
  1               5                  10                  15

Thr Thr Ile Gly Ser Val Thr Ala Gln Asp Pro Asp Ala Ala Arg Asn
             20                  25                  30

Pro Val Lys Tyr Ser Val Asp Arg His Thr Asp Met Asp Arg Ile Phe
         35                  40                  45

Asn Ile Asp Ser Gly Asn Gly Ser Ile Phe Thr Ser Lys Leu Leu Asp
 50                  55                  60

Arg Glu Thr Leu Leu Trp His Asn Ile Thr Val Ile Ala Thr Glu Ile
 65                  70                  75                  80

Asn Asn Pro Lys Gln Ser Ser Arg Val Pro Leu Tyr Ile Lys Val Leu
                 85                  90                  95

Asp Val Asn Asp Asn Ala Pro
            100

<210> SEQ ID NO 6
<211> LENGTH: 122
<212> TYPE: PRT
<213> ORGANISM: Homo sapiens

<400> SEQUENCE: 6

Glu Phe Ala Glu Phe Tyr Glu Thr Phe Val Cys Glu Lys Ala Lys Ala
  1               5                  10                  15

Asp Gln Leu Ile Gln Thr Leu His Ala Val Asp Lys Asp Pro Tyr
             20                  25                  30

Ser Gly His Gln Phe Ser Phe Ser Leu Ala Pro Glu Ala Ala Ser Gly
         35                  40                  45

Ser Asn Phe Thr Ile Gln Asp Asn Lys Asp Asn Thr Ala Gly Ile Leu
 50                  55                  60

Thr Arg Lys Asn Gly Tyr Asn Arg His Glu Met Ser Thr Tyr Leu Leu
 65                  70                  75                  80

Pro Val Val Ile Ser Asp Asn Asp Tyr Pro Val Gln Ser Ser Thr Gly
                 85                  90                  95

Thr Val Thr Val Arg Val Cys Ala Cys Asp His His Gly Asn Met Gln
            100                 105                 110

Ser Cys His Ala Glu Ala Leu Ile His Pro
            115                 120

<210> SEQ ID NO 7
<211> LENGTH: 790
<212> TYPE: PRT
<213> ORGANISM: Mus musculus
```

<400> SEQUENCE: 7

```
Met Arg Thr Tyr Arg Tyr Phe Leu Leu Phe Trp Val Gly Gln Pro
1               5                   10                  15

Tyr Pro Thr Phe Ser Asn Pro Leu Ser Lys Arg Thr Ser Gly Phe Pro
            20                  25                  30

Ala Lys Arg Lys Ala Leu Glu Leu Ser Ala Asn Ser Arg Asn Glu Leu
        35                  40                  45

Ser Arg Ser Lys Arg Ser Trp Met Trp Asn Gln Phe Phe Leu Leu Glu
    50                  55                  60

Glu Tyr Thr Gly Ser Asp Tyr Gln Tyr Val Gly Lys Leu His Ser Asp
65                  70                  75                  80

Gln Asp Arg Gly Asp Gly Ser Leu Lys Tyr Ile Leu Ser Gly Asp Gly
            85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
            115                 120                 125

Gln Ala Val Asn Arg Arg Thr Gly Arg Pro Val Glu Pro Glu Ser Glu
130                 135                 140

Phe Ile Ile Lys Ile His Asp Ile Asn Asp Asn Glu Pro Ile Phe Thr
145                 150                 155                 160

Lys Asp Val Tyr Thr Ala Thr Val Pro Glu Met Ala Asp Val Gly Thr
                165                 170                 175

Phe Val Val Gln Val Thr Ala Thr Asp Ala Asp Asp Pro Thr Tyr Gly
            180                 185                 190

Asn Ser Ala Lys Val Val Tyr Ser Ile Leu Gln Gly Gln Pro Tyr Phe
            195                 200                 205

Ser Val Glu Ser Glu Thr Gly Ile Ile Lys Thr Ala Leu Leu Asn Met
210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Thr Val Asn Ile
                245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Gly Thr Pro Ile Gly
            275                 280                 285

Arg Ile Lys Ala Ser Asp Ala Asp Val Gly Glu Asn Ala Glu Ile Glu
290                 295                 300

Tyr Ser Ile Thr Asp Gly Glu Gly His Glu Met Phe Asp Val Ile Thr
305                 310                 315                 320

Asp Gln Glu Thr Gln Glu Gly Ile Ile Thr Val Lys Lys Leu Leu Asp
            325                 330                 335

Phe Glu Lys Lys Lys Val Tyr Thr Leu Lys Val Glu Ala Ser Asn Pro
            340                 345                 350

His Val Glu Pro Arg Phe Leu Tyr Leu Gly Pro Phe Lys Asp Ser Ala
            355                 360                 365

Thr Val Arg Ile Val Val Asp Val Asp Glu Pro Pro Val Phe Ser
            370                 375                 380

Lys Leu Ala Tyr Ile Leu Gln Ile Arg Glu Asp Ala Arg Ile Asn Thr
385                 390                 395                 400

Thr Ile Gly Ser Val Ala Ala Gln Asp Pro Asp Ala Ala Arg Asn Pro
```

```
                405                 410                 415
Val Lys Tyr Ser Val Asp Arg His Thr Asp Met Asp Arg Ile Phe Asn
            420                 425                 430
Ile Asp Ser Gly Asn Gly Ser Ile Phe Thr Ser Lys Leu Leu Asp Arg
            435                 440                 445
Glu Thr Leu Leu Trp His Asn Ile Thr Val Ile Ala Thr Glu Ile Asn
            450                 455                 460
Asn Pro Lys Gln Ser Ser Arg Val Pro Leu Tyr Ile Lys Val Leu Asp
465                 470                 475                 480
Val Asn Asp Asn Ala Pro Glu Phe Ala Glu Phe Tyr Glu Thr Phe Val
                485                 490                 495
Cys Glu Lys Ala Lys Ala Asp Gln Leu Ile Gln Thr Leu Arg Ala Val
            500                 505                 510
Asp Lys Asp Asp Pro Tyr Ser Gly His Gln Phe Ser Phe Ser Leu Ala
            515                 520                 525
Pro Glu Ala Ala Ser Ser Ser Asn Phe Thr Ile Gln Asp Asn Lys Asp
            530                 535                 540
Asn Thr Ala Gly Ile Leu Thr Arg Lys Asn Gly Tyr Asn Arg His Glu
545                 550                 555                 560
Met Ser Thr Tyr Leu Leu Pro Val Val Ile Ser Asp Asn Asp Tyr Pro
                565                 570                 575
Val Gln Ser Ser Thr Gly Thr Val Thr Val Arg Val Cys Ala Cys Asp
            580                 585                 590
His His Gly Asn Met Gln Ser Cys His Ala Glu Ala Leu Ile His Pro
            595                 600                 605
Thr Gly Leu Ser Thr Gly Ala Leu Val Ala Ile Leu Leu Cys Ile Val
            610                 615                 620
Ile Leu Leu Val Thr Val Leu Phe Ala Ala Leu Arg Arg Gln Arg
625                 630                 635                 640
Lys Lys Glu Pro Leu Ile Ile Ser Lys Glu Asp Ile Arg Asp Asn Ile
                645                 650                 655
Val Ser Tyr Asn Asp Glu Gly Gly Glu Glu Asp Thr Gln Ala Phe
            660                 665                 670
Asp Ile Gly Thr Leu Arg Asn Pro Glu Ala Met Glu Asp Ser Lys Ser
            675                 680                 685
Arg Arg Asp Ile Val Pro Glu Ala Leu Phe Leu Pro Arg Arg Thr Pro
            690                 695                 700
Thr Ala Arg Asp Asn Thr Asp Val Arg Asp Phe Ile Asn Gln Arg Leu
705                 710                 715                 720
Lys Glu Asn Asp Thr Asp Pro Thr Ala Pro Pro Tyr Asp Ser Leu Ala
                725                 730                 735
Thr Tyr Ala Tyr Glu Gly Thr Gly Ser Val Ala Asp Ser Leu Ser Ser
            740                 745                 750
Leu Glu Ser Val Thr Thr Asp Gly Asp Gln Asp Tyr Asp Tyr Leu Ser
            755                 760                 765
Asp Trp Gly Pro Arg Phe Lys Lys Leu Ala Asp Met Tyr Gly Gly Met
            770                 775                 780
Asp Ser Asp Lys Asp Ser
785                 790

<210> SEQ ID NO 8
<211> LENGTH: 789
<212> TYPE: PRT
<213> ORGANISM: Rattus norvegicus
```

<400> SEQUENCE: 8

Met Arg Thr Tyr Arg Tyr Phe Leu Leu Leu Phe Trp Val Gly Gln Pro
1               5                   10                  15

Tyr Pro Thr Phe Ser Asn Pro Leu Ser Lys Arg Thr Ser Gly Phe Pro
            20                  25                  30

Ala Lys Arg Arg Ala Leu Glu Leu Ser Ala Asn Ser Arg Asn Glu Leu
        35                  40                  45

Ser Arg Ser Lys Arg Ser Trp Met Trp Asn Gln Phe Phe Leu Leu Glu
    50                  55                  60

Glu Tyr Thr Gly Ser Asp Tyr Gln Tyr Val Gly Lys Leu His Ser Asp
65                  70                  75                  80

Gln Asp Arg Gly Asp Gly Ser Leu Lys Tyr Ile Leu Ser Gly Asp Gly
                85                  90                  95

Ala Gly Asp Leu Phe Ile Ile Asn Glu Asn Thr Gly Asp Ile Gln Ala
            100                 105                 110

Thr Lys Arg Leu Asp Arg Glu Glu Lys Pro Val Tyr Ile Leu Arg Ala
        115                 120                 125

Gln Ala Ile Asn Arg Arg Thr Gly Arg Pro Val Glu Pro Glu Ser Glu
130                 135                 140

Phe Ile Ile Lys Ile His Asp Ile Asn Asp Asn Glu Pro Ile Phe Thr
145                 150                 155                 160

Lys Asp Val Tyr Thr Ala Thr Val Pro Glu Met Ala Asp Val Gly Thr
                165                 170                 175

Phe Val Val Gln Val Thr Ala Thr Asp Ala Asp Asp Pro Thr Tyr Gly
            180                 185                 190

Asn Ser Ala Lys Val Val Tyr Ser Ile Leu Gln Gly Gln Pro Tyr Phe
        195                 200                 205

Ser Val Glu Ser Glu Thr Gly Ile Ile Lys Thr Ala Leu Leu Asn Met
    210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Thr Val Asn Ile
                245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Gly Thr Pro Ile Gly
        275                 280                 285

Arg Ile Lys Ala Ser Asp Ala Asp Val Gly Glu Asn Ala Glu Ile Glu
290                 295                 300

Tyr Ser Ile Thr Asp Gly Glu Gly His Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Arg Val Tyr Thr Leu Lys Val Glu Ala Ser Asn Pro
            340                 345                 350

His Ile Glu Pro Arg Phe Leu Tyr Leu Gly Pro Phe Lys Asp Ser Ala
        355                 360                 365

Thr Val Arg Ile Val Val Asp Val Asp Glu Pro Pro Val Phe Ser
    370                 375                 380

Lys Pro Ala Tyr Ile Leu Gln Ile Arg Glu Asp Ala Gln Ile Asn Thr
385                 390                 395                 400

Thr Ile Gly Ser Val Ala Ala Gln Asp Pro Asp Ala Ala Arg Asn Pro

```
                405                 410                 415
Val Lys Tyr Ser Val Asp Arg His Thr Asp Met Asp Arg Ile Phe Asn
            420                 425                 430

Ile Asp Ser Gly Asn Gly Ser Ile Phe Thr Ser Lys Leu Leu Asp Arg
            435                 440                 445

Glu Thr Leu Leu Trp His Asn Ile Thr Val Ile Ala Thr Glu Ile Asn
        450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
            485                 490                 495

Cys Glu Lys Ala Lys Ala Asp Gln Leu Ile Gln Thr Leu His Ala Val
            500                 505                 510

Asp Lys Asp Asp Pro Tyr Ser Gly His Gln Phe Ser Phe Ser Leu Ala
            515                 520                 525

Pro Glu Ala Ala Ser Gly Ser Asn Phe Thr Ile Gln Asp Asn Lys Asp
            530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
            565                 570                 575

Val Gln Ser Ser Thr Gly Thr Val Thr Val Arg Val Cys Ala Cys Asp
            580                 585                 590

His His Gly Asn Met Gln Ser Cys His Ala Glu Ala Leu Ile His Pro
            595                 600                 605

Thr Gly Leu Ser Thr Gly Ala Leu Val Ala Ile Leu Leu Cys Ile Val
        610                 615                 620

Ile Leu Leu Val Thr Val Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
            645                 650                 655

Val Ser Tyr Asn Asp Glu Gly Gly Glu Glu Asp Thr Gln Ala Phe
            660                 665                 670

Asp Ile Gly Thr Leu Arg Asn Pro Lys Pro Trp Arg Gln Gln Ser Arg
            675                 680                 685

Arg Asp Met Val Pro Glu Ala Leu Phe Leu Pro Arg Arg Thr Pro Thr
            690                 695                 700

Ala Arg Asp Asn Thr Asp Val Arg Asp Phe Ile Ser Gln Arg Leu Arg
705                 710                 715                 720

Lys Met Asn Thr Asp Pro Thr Ala Pro Pro Tyr Asp Ser Leu Ala Thr
            725                 730                 735

Tyr Ala Tyr Glu Gly Thr Gly Ser Val Ala Asp Ser Leu Ser Ser Leu
            740                 745                 750

Glu Ser Val Thr Thr Asp Gly Asp Gln Asp Tyr Gly Tyr Leu Ser Asp
            755                 760                 765

Trp Gly Pro Arg Phe Lys Lys Leu Ala Asp Met Tyr Gly Gly Met Asp
        770                 775                 780

Ser Asp Lys Asp Ser
785

<210> SEQ ID NO 9
<211> LENGTH: 790
<212> TYPE: PRT
<213> ORGANISM: Macaca fascicularis
```

<400> SEQUENCE: 9

```
Met Arg Thr Tyr Arg Tyr Phe Leu Leu Phe Trp Val Gly Gln Pro
 1               5                  10                  15

Tyr Pro Thr Leu Ser Thr Pro Leu Ser Lys Arg Thr Ser Gly Phe Pro
             20                  25                  30

Ala Lys Lys Arg Ala Leu Glu Leu Ser Gly Asn Ser Lys Asn Glu Leu
             35                  40                  45

Asn Arg Ser Lys Arg Ser Trp Met Trp Asn Gln Phe Phe Leu Leu Glu
         50                  55                  60

Glu Tyr Thr Gly Ser Asp Tyr Gln Tyr Val Gly Lys Leu His Ser Asp
 65                  70                  75                  80

Gln Asp Arg Gly Asp Gly Ser Leu Lys Tyr Ile Leu Ser Gly Asp Gly
                 85                  90                  95

Ala Gly Asp Leu Phe Ile Ile Asn Glu Asn Thr Gly Asp Ile Gln Ala
                100                 105                 110

Thr Lys Arg Leu Asp Arg Glu Glu Lys Pro Val Tyr Ile Leu Arg Ala
            115                 120                 125

Gln Ala Ile Asn Arg Arg Thr Gly Arg Pro Val Glu Pro Glu Ser Glu
        130                 135                 140

Phe Ile Ile Lys Ile His Asp Ile Asn Asp Asn Glu Pro Ile Phe Thr
145                 150                 155                 160

Lys Glu Val Tyr Thr Ala Thr Val Pro Glu Met Ser Asp Val Gly Thr
                165                 170                 175

Phe Val Val Gln Val Thr Ala Thr Asp Ala Asp Asp Pro Thr Tyr Gly
            180                 185                 190

Asn Ser Ala Lys Val Val Tyr Ser Ile Leu Gln Gly Gln Pro Tyr Phe
        195                 200                 205

Ser Val Glu Ser Glu Thr Gly Ile Ile Lys Thr Ala Leu Leu Asn Met
    210                 215                 220

Asp Arg Glu Asn Arg Glu Gln Tyr Gln Val Val Ile Gln Ala Lys Asp
225                 230                 235                 240

Met Gly Gly Gln Met Gly Gly Leu Ser Gly Thr Thr Val Asn Ile
                245                 250                 255

Thr Leu Thr Asp Val Asn Asp Asn Pro Pro Arg Phe Pro Gln Ser Thr
            260                 265                 270

Tyr Gln Phe Lys Thr Pro Glu Ser Ser Pro Gly Thr Pro Ile Gly
        275                 280                 285

Arg Ile Lys Ala Ser Asp Ala Asp Val Gly Glu Asn Ala Glu Ile Glu
290                 295                 300

Tyr Ser Ile Thr Asp Gly Glu Gly Leu Asp Met Phe Asp Val Ile Thr
305                 310                 315                 320

Asp Gln Glu Thr Gln Glu Gly Ile Ile Thr Val Lys Lys Leu Leu Asp
                325                 330                 335

Phe Glu Lys Lys Lys Val Tyr Thr Leu Lys Val Glu Ala Ser Asn Pro
            340                 345                 350

His Val Glu Pro Arg Phe Leu Tyr Leu Gly Pro Phe Lys Asp Ser Ala
        355                 360                 365

Thr Val Arg Ile Val Val Glu Asp Val Asp Glu Pro Pro Val Phe Ser
    370                 375                 380

Lys Leu Ala Tyr Ile Leu Gln Ile Arg Glu Asp Ala Gln Ile Asn Thr
385                 390                 395                 400

Thr Ile Gly Ser Val Thr Ala Gln Asp Pro Asp Ala Ala Arg Asn Pro
```

-continued

```
                    405                 410                 415
Val Lys Tyr Ser Val Asp Arg His Thr Asp Met Asp Arg Ile Phe Asn
                420                 425                 430

Ile Asp Ser Gly Asn Gly Ser Ile Phe Thr Ser Lys Leu Leu Asp Arg
            435                 440                 445

Glu Thr Leu Leu Trp His Asn Ile Thr Val Ile Ala Thr Glu Ile Asn
        450                 455                 460

Asn Pro Lys Gln Ser Ser Arg Val Pro Leu Tyr Ile Lys Val Leu Asp
465                 470                 475                 480

Val Asn Asp Asn Ala Pro Glu Phe Ala Glu Phe Tyr Glu Thr Phe Val
                485                 490                 495

Cys Glu Lys Ala Lys Ala Asp Gln Leu Ile Gln Thr Leu Arg Ala Val
            500                 505                 510

Asp Lys Asp Asp Pro Tyr Ser Gly His Gln Phe Ser Phe Ser Leu Ala
        515                 520                 525

Pro Glu Ala Ala Ser Gly Ser Asn Phe Thr Ile Gln Asp Asn Lys Asp
    530                 535                 540

Asn Thr Ala Gly Ile Leu Thr Arg Lys Asn Gly Tyr Asn Arg His Glu
545                 550                 555                 560

Met Ser Thr Tyr Leu Leu Pro Val Val Ile Ser Asp Asn Asp Tyr Pro
                565                 570                 575

Val Gln Ser Ser Thr Gly Thr Val Thr Val Arg Val Cys Ala Cys Asp
            580                 585                 590

His His Gly Asn Met Gln Ser Cys His Ala Glu Ala Leu Ile His Pro
        595                 600                 605

Thr Gly Leu Ser Thr Gly Ala Leu Val Ala Ile Leu Leu Cys Ile Val
    610                 615                 620

Ile Leu Leu Val Thr Val Leu Phe Ala Ala Leu Arg Arg Gln Arg
625                 630                 635                 640

Lys Lys Glu Pro Leu Ile Ile Ser Lys Glu Asp Ile Arg Asp Asn Ile
                645                 650                 655

Val Ser Tyr Asn Asp Glu Gly Gly Glu Glu Asp Thr Gln Ala Phe
            660                 665                 670

Asp Ile Gly Thr Leu Arg Asn Pro Glu Ala Ile Glu Asp Asn Lys Leu
        675                 680                 685

Arg Arg Asp Ile Val Pro Glu Ala Leu Phe Leu Pro Arg Arg Thr Pro
    690                 695                 700

Thr Ala Arg Asp Asn Thr Asp Val Arg Asp Phe Ile Asn Gln Arg Leu
705                 710                 715                 720

Lys Glu Asn Asp Thr Asp Pro Thr Ala Pro Pro Tyr Asp Ser Leu Ala
                725                 730                 735

Thr Tyr Ala Tyr Glu Gly Thr Gly Ser Val Ala Asp Ser Leu Ser Ser
            740                 745                 750

Leu Glu Ser Val Thr Thr Asp Gly Asp Gln Asp Tyr Asp Tyr Leu Ser
        755                 760                 765

Asp Trp Gly Pro Arg Phe Lys Lys Leu Ala Asp Met Tyr Gly Gly Val
    770                 775                 780

Asp Ser Asp Lys Asp Ser
785                 790

<210> SEQ ID NO 10
<211> LENGTH: 108
<212> TYPE: PRT
<213> ORGANISM: Rattus norvegicus
```

<400> SEQUENCE: 10

Asp Ile Gln Met Thr Gln Ser Pro Ser Leu Leu Ser Ala Ser Val Gly
1               5                   10                  15

Asp Arg Val Thr Leu Asn Cys Lys Ala Ser Gln Asn Ile Tyr Lys Asn
            20                  25                  30

Leu Ala Trp Tyr Gln Gln Lys Leu Gly Glu Gly Pro Lys Leu Leu Ile
        35                  40                  45

Tyr Asp Ala Asn Thr Leu Gln Thr Gly Ile Pro Ser Arg Phe Ser Gly
    50                  55                  60

Ser Gly Ser Gly Ser Asp Phe Thr Leu Thr Ile Ser Ser Leu Gln Pro
65                  70                  75                  80

Glu Asp Val Ala Thr Tyr Phe Cys Gln Gln Tyr Tyr Ser Gly Trp Ala
                85                  90                  95

Phe Gly Gly Val Thr Asn Leu Glu Leu Lys Arg Ala
            100                 105

<210> SEQ ID NO 11
<211> LENGTH: 324
<212> TYPE: DNA
<213> ORGANISM: Rattus norvegicus

<400> SEQUENCE: 11
gacatccaga tgacccagtc tccttcactc ctgtctgcat ctgtgggaga cagagtcact     60
ctcaactgca aagcaagtca gaatatttat aagaacttag cctggtatca gcaaaagctt    120
ggagaaggtc ccaaactcct gatttatgat gcaaacactt tgcaaacggg catcccatca    180
aggttcagtg gcagtggatc tggttcagat ttcacactca ccatcagcag cctgcagcct    240
gaagatgttg ccacatattt ctgccagcag tactatagcg ggtgggcgtt cggtggagtc    300
accaacctgg aattgaaacg ggct                                          324

<210> SEQ ID NO 12
<211> LENGTH: 11
<212> TYPE: PRT
<213> ORGANISM: Rattus norvegicus

<400> SEQUENCE: 12

Lys Ala Ser Gln Asn Ile Tyr Lys Asn Leu Ala
1               5                   10

<210> SEQ ID NO 13
<211> LENGTH: 7
<212> TYPE: PRT
<213> ORGANISM: Rattus norvegicus

<400> SEQUENCE: 13

Asp Ala Asn Thr Leu Gln Thr
1               5

<210> SEQ ID NO 14
<211> LENGTH: 8
<212> TYPE: PRT
<213> ORGANISM: Rattus norvegicus

<400> SEQUENCE: 14

Gln Gln Tyr Tyr Ser Gly Trp Ala
1               5

<210> SEQ ID NO 15

<211> LENGTH: 122
<212> TYPE: PRT
<213> ORGANISM: Rattus norvegicus

<400> SEQUENCE: 15

```
Gln Val Gln Leu Gln Gln Ser Gly Ala Glu Leu Val Lys Pro Gly Ser
1               5                   10                  15
Ser Val Lys Ile Ser Cys Lys Ala Ser Gly Tyr Thr Phe Thr Arg Asn
            20                  25                  30
Phe Met His Trp Ile Lys Gln Gln Pro Gly Asn Gly Leu Glu Trp Ile
        35                  40                  45
Gly Trp Ile Tyr Cys Gly Asp Gly Glu Thr Glu Tyr Asn Gln Lys Phe
    50                  55                  60
Asn Gly Lys Ala Thr Leu Thr Ala Asp Arg Ser Ser Thr Ala Tyr
65                  70                  75                  80
Met Glu Leu Ser Arg Leu Thr Ser Glu Asp Ser Ala Val Tyr Phe Cys
                85                  90                  95
Ala Arg Gly Val Tyr Gly Gly Phe Ala Gly Tyr Phe Asp Phe Trp
            100                 105                 110
Gly Gln Gly Val Met Val Thr Val Ser Ser
        115                 120
```

<210> SEQ ID NO 16
<211> LENGTH: 366
<212> TYPE: DNA
<213> ORGANISM: Rattus norvegicus

<400> SEQUENCE: 16

```
caggtacagc tgcagcaatc tggggctgaa ctggtgaagc ctgggtcctc agtgaaaatt      60
tcctgcaagg cttctggcta caccttcacc aggaactta tgcactggat aaaacagcag     120
cctggaaatg gccttgagtg gattgggtgg atttattgtg gagatggtga cagagtac      180
aatcaaaagt tcaatgggaa ggcaacactc actgcggaca tcctccag cacagcctat      240
atggagctca gcagactgac atctgaggac tctgcagtct atttctgtgc aagaggggtt    300
tacggagggt ttgccggggg ctactttgat tctggggcc aaggagtcat ggtcacagtc     360
tcctca                                                                366
```

<210> SEQ ID NO 17
<211> LENGTH: 10
<212> TYPE: PRT
<213> ORGANISM: Rattus norvegicus

<400> SEQUENCE: 17

```
Gly Tyr Thr Phe Thr Arg Asn Phe Met His
1               5                   10
```

<210> SEQ ID NO 18
<211> LENGTH: 10
<212> TYPE: PRT
<213> ORGANISM: Rattus norvegicus

<400> SEQUENCE: 18

```
Trp Ile Tyr Cys Gly Asp Gly Glu Thr Glu
1               5                   10
```

<210> SEQ ID NO 19
<211> LENGTH: 13
<212> TYPE: PRT
<213> ORGANISM: Rattus norvegicus

<400> SEQUENCE: 19

Gly Val Tyr Gly Gly Phe Ala Gly Gly Tyr Phe Asp Phe
1               5                   10

<210> SEQ ID NO 20
<211> LENGTH: 109
<212> TYPE: PRT
<213> ORGANISM: Rattus norvegicus

<400> SEQUENCE: 20

Asp Val Gln Met Thr His Ser Pro Ser Tyr Leu Ala Ala Ser Pro Gly
1               5                   10                  15

Glu Ser Val Ser Ile Ser Cys Lys Thr Ser Lys Asn Ile Ser Asn Tyr
            20                  25                  30

Leu Val Trp Tyr Gln Gln Lys Pro Gly Glu Ala Tyr Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Ser Leu Glu Pro
65                  70                  75                  80

Glu Asp Phe Gly Leu Tyr Phe Cys Gln Gln Tyr Tyr Glu Lys Pro Phe
                85                  90                  95

Thr Phe Gly Ser Gly Thr Lys Leu Glu Ile Lys Arg Ala
            100                 105

<210> SEQ ID NO 21
<211> LENGTH: 327
<212> TYPE: DNA
<213> ORGANISM: Rattus norvegicus

<400> SEQUENCE: 21
gatgtccaga tgacccactc tccgtcttat cttgctgcgt ctcctggaga aagtgtttcc      60
atcagttgca agacaagtaa gaacattagt aattatttag tctggtatca acagaaacct    120
ggggaagcat ataagcttct tatctattct gggtcaactt tgcaatctgg aactccatca    180
aggttcagtg gcagtggatc tggtacagat ttcactctca ctatcagaag cctggagcct    240
gaagattttg gactctattt ctgtcaacag tattatgaaa aaccattcac gttcggctca    300
gggacgaagt tggaaataaa acgggct                                        327

<210> SEQ ID NO 22
<211> LENGTH: 11
<212> TYPE: PRT
<213> ORGANISM: Rattus norvegicus

<400> SEQUENCE: 22

Lys Thr Ser Lys Asn Ile Ser Asn Tyr Leu Val
1               5                   10

<210> SEQ ID NO 23
<211> LENGTH: 7
<212> TYPE: PRT
<213> ORGANISM: Rattus norvegicus

<400> SEQUENCE: 23

Ser Gly Ser Thr Leu Gln Ser
1               5

<210> SEQ ID NO 24

```
<211> LENGTH: 9
<212> TYPE: PRT
<213> ORGANISM: Rattus norvegicus

<400> SEQUENCE: 24

Gln Gln Tyr Tyr Glu Lys Pro Phe Thr
1               5

<210> SEQ ID NO 25
<211> LENGTH: 121
<212> TYPE: PRT
<213> ORGANISM: Rattus norvegicus

<400> SEQUENCE: 25

Glu Val Gln Leu Gln Glu Ser Gly Pro Gly Leu Val Arg Pro Ser Gln
1               5                   10                  15

Ser Leu Ser Leu Ser Cys Ser Val Thr Asp Tyr Ser Ile Thr Ser Asn
            20                  25                  30

Tyr Trp Gly Trp Ile Arg Arg Phe Pro Gly Asn Lys Met Glu Trp Met
        35                  40                  45

Gly Tyr Ile Thr Tyr Ser Gly Tyr Thr Ser Tyr Asn Pro Ser Leu Gln
    50                  55                  60

Ser Arg Ile Ser Ile Thr Arg Asp Thr Ser Lys Asn Gln Phe Phe Leu
65                  70                  75                  80

Gln Leu Asn Ser Val Thr Ala Glu Asp Thr Ala Thr Tyr Tyr Cys Ala
                85                  90                  95

Arg Ser Ile Asn His Gly Gly Tyr Ser Tyr Val Val Asp Ala Trp Gly
            100                 105                 110

Pro Gly Ala Ser Val Thr Val Ser Ser
        115                 120

<210> SEQ ID NO 26
<211> LENGTH: 363
<212> TYPE: DNA
<213> ORGANISM: Rattus norvegicus

<400> SEQUENCE: 26
gaggtgcaac ttcaggagtc aggacctggc cttgtgagac cctcacagtc actctccctc      60
tcctgttctg tcactgatta ctccatcact agtaattact ggggctggat ccggaggttc     120
ccaggaaata aaatggagtg gatgggatac ataacctata gtggttacac tagctacaac     180
ccatctctcc aaagtcgaat ctccattact agagacacat cgaagaatca gttcttcctg     240
cagttgaact ctgtaactgc tgaggacaca gccacatatt actgtgcaag atcgattaac     300
cacggaggat atagttatgt tgtggatgcc tggggtccgg gagcttcagt cactgtctcc     360
tca                                                                   363

<210> SEQ ID NO 27
<211> LENGTH: 10
<212> TYPE: PRT
<213> ORGANISM: Rattus norvegicus

<400> SEQUENCE: 27

Asp Tyr Ser Ile Thr Ser Asn Tyr Trp Gly
1               5                   10

<210> SEQ ID NO 28
<211> LENGTH: 9
<212> TYPE: PRT
<213> ORGANISM: Rattus norvegicus
```

<400> SEQUENCE: 28

Tyr Ile Thr Tyr Ser Gly Tyr Thr Ser
1               5

<210> SEQ ID NO 29
<211> LENGTH: 13
<212> TYPE: PRT
<213> ORGANISM: Rattus norvegicus

<400> SEQUENCE: 29

Ser Ile Asn His Gly Gly Tyr Ser Tyr Val Val Asp Ala
1               5                   10

<210> SEQ ID NO 30
<211> LENGTH: 109
<212> TYPE: PRT
<213> ORGANISM: Rattus norvegicus

<400> SEQUENCE: 30

Asp Val Gln Met Thr Gln Ser Pro Ser Ser Leu Ala Ala Ser Pro Gly
1               5                   10                  15

Glu Ser Val Ser Ile Ser Cys Arg Ala Thr Lys Ser Ile Gly Ile Tyr
            20                  25                  30

Leu Ala Trp Tyr Gln Gln Lys Pro Gly Lys Thr Phe Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Ser Leu Glu Pro
65                  70                  75                  80

Glu Asp Phe Gly Leu Tyr Phe Cys Gln Gln Phe Tyr Glu Asn Pro Phe
                85                  90                  95

Thr Phe Gly Ser Gly Thr Lys Leu Glu Ile Arg Arg Ala
            100                 105

<210> SEQ ID NO 31
<211> LENGTH: 327
<212> TYPE: DNA
<213> ORGANISM: Rattus norvegicus

<400> SEQUENCE: 31
gatgtccaga tgacccagtc tccgtcttct cttgctgcgt ctcctggaga aagtgtttcc      60
atcagttgca gggcaactaa gagcattggt atttatttag cctggtatca acagaaacct    120
gggaaaacat ttaagcttct tatctactct gggtcaactt gcaatctgg aactccatca     180 aggttcagtg gcagtgggtc tggtacagat ttcactctca ccatcagaag cctggagcct    240
gaagattttg gactctattt ctgtcaacag ttttatgaaa acccattcac gttcggctca    300
gggacgaagt tggaaataag acgggct                                        327

<210> SEQ ID NO 32
<211> LENGTH: 11
<212> TYPE: PRT
<213> ORGANISM: Rattus norvegicus

<400> SEQUENCE: 32

Arg Ala Thr Lys Ser Ile Gly Ile Tyr Leu Ala
1               5                   10

<210> SEQ ID NO 33

```
<211> LENGTH: 7
<212> TYPE: PRT
<213> ORGANISM: Rattus norvegicus

<400> SEQUENCE: 33

Ser Gly Ser Thr Leu Gln Ser
1               5

<210> SEQ ID NO 34
<211> LENGTH: 9
<212> TYPE: PRT
<213> ORGANISM: Rattus norvegicus

<400> SEQUENCE: 34

Gln Gln Phe Tyr Glu Asn Pro Phe Thr
1               5

<210> SEQ ID NO 35
<211> LENGTH: 121
<212> TYPE: PRT
<213> ORGANISM: Rattus norvegicus

<400> SEQUENCE: 35

Glu Val Gln Leu Gln Glu Ser Gly Pro Gly Leu Val Lys Pro Ser Gln
1               5                   10                  15

Ser Leu Ser Leu Thr Cys Ser Val Thr Asp Tyr Ser Ile Thr Thr Tyr
            20                  25                  30

Phe Trp Gly Trp Ile Arg Lys Phe Pro Gly Asn Lys Met Glu Trp Met
        35                  40                  45

Gly Tyr Met Ser Tyr Arg Gly Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Ala
                85                  90                  95

Arg Cys Pro Asn Tyr Gly Gly His Ser Leu Val Phe Asp Tyr Trp Gly
            100                 105                 110

Gln Gly Val Met Val Thr Val Ser Ser
        115                 120

<210> SEQ ID NO 36
<211> LENGTH: 363
<212> TYPE: DNA
<213> ORGANISM: Rattus norvegicus

<400> SEQUENCE: 36
gaggtgcagc ttcaggagtc aggacctggc cttgtgaaac cctcacagtc actctccctc        60
acctgttctg tcactgatta ctccatcact acttatttct ggggctggat ccggaagttc       120
ccaggaaata aaatggagtg gatgggatac atgagctacc gtggtggcac ttcctacaac       180
ccatctctca gagtcgaat ctccattact agagacacat cgaagaatca gttcttcctg        240
cagttgaact ctgtaactac tgaggacaca gccacatatt actgtgcaag atgccctaac       300
tacggagggc attcccttgt ttttgattac tggggccaag gagtcatggt cacagtgtcc       360
tca                                                                     363

<210> SEQ ID NO 37
<211> LENGTH: 10
<212> TYPE: PRT
<213> ORGANISM: Rattus norvegicus
```

<400> SEQUENCE: 37

Asp Tyr Ser Ile Thr Thr Tyr Phe Trp Gly
1               5                   10

<210> SEQ ID NO 38
<211> LENGTH: 9
<212> TYPE: PRT
<213> ORGANISM: Rattus norvegicus

<400> SEQUENCE: 38

Tyr Met Ser Tyr Arg Gly Gly Thr Ser
1               5

<210> SEQ ID NO 39
<211> LENGTH: 13
<212> TYPE: PRT
<213> ORGANISM: Rattus norvegicus

<400> SEQUENCE: 39

Cys Pro Asn Tyr Gly Gly His Ser Leu Val Phe Asp Tyr
1               5                   10

<210> SEQ ID NO 40
<211> LENGTH: 109
<212> TYPE: PRT
<213> ORGANISM: Rattus norvegicus

<400> SEQUENCE: 40

Asp Val Gln Met Thr Gln Ser Pro Ser Tyr Leu Ala Ala Ser Pro Gly
1               5                   10                  15

Glu Ser Val Ser Ile Ser Cys Lys Ala Thr Lys Ser Ile Ser Asn Tyr
            20                  25                  30

Leu Ala Trp Tyr Gln Gln Lys Pro Gly Glu Ala Tyr Lys Val Leu Ile
        35                  40                  45

Tyr Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Ser Leu Glu Pro
65                  70                  75                  80

Glu Asp Phe Gly Leu Tyr Ser Cys Gln Gln Tyr Tyr Glu Lys Pro Leu
                85                  90                  95

Thr Phe Gly Ser Gly Thr Lys Leu Glu Ile Lys Arg Ala
            100                 105

<210> SEQ ID NO 41
<211> LENGTH: 327
<212> TYPE: DNA
<213> ORGANISM: Rattus norvegicus

<400> SEQUENCE: 41
gatgtccaga tgacccagtc tccgtcttat cttgctgcgt ctcctggaga aagtgtttcc      60
atcagttgca aggcaactaa gagcattagt aattatttag cctggtatca acagaaacct     120
ggggaagcat ataaggttct tatctattct gggtcaactt tgcaatctgg aactccatca     180
aggttcagtg gcagtggatc tggtacagat ttcactctca ccatcagaag cctggagcct     240
gaagattttg gactctattc ctgtcaacag tattatgaaa aaccgctcac gttcggttct     300
gggaccaagc tggagatcaa acgggct                                         327

<210> SEQ ID NO 42

<210> SEQ ID NO 42
<211> LENGTH: 11
<212> TYPE: PRT
<213> ORGANISM: Rattus norvegicus

<400> SEQUENCE: 42

Lys Ala Thr Lys Ser Ile Ser Asn Tyr Leu Ala
1               5                   10

<210> SEQ ID NO 43
<211> LENGTH: 7
<212> TYPE: PRT
<213> ORGANISM: Rattus norvegicus

<400> SEQUENCE: 43

Ser Gly Ser Thr Leu Gln Ser
1               5

<210> SEQ ID NO 44
<211> LENGTH: 9
<212> TYPE: PRT
<213> ORGANISM: Rattus norvegicus

<400> SEQUENCE: 44

Gln Gln Tyr Tyr Glu Lys Pro Leu Thr
1               5

<210> SEQ ID NO 45
<211> LENGTH: 121
<212> TYPE: PRT
<213> ORGANISM: Rattus norvegicus

<400> SEQUENCE: 45

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Thr Tyr
            20                  25                  30

Tyr Trp Gly Trp Ile Arg Lys Phe Pro Gly Asn Lys Met Glu Trp Met
        35                  40                  45

Gly Tyr Ile Ser Tyr Ser Gly Arg Thr Ser Tyr Asn Pro Ser Leu Lys
    50                  55                  60

Ser Arg Met Ser Ile Thr Arg Asp Ala Ser Lys Asn Gln Phe Phe Leu
65                  70                  75                  80

Gln Leu Asn Ser Val Thr Thr Asp Asp Thr Ala Thr Tyr Tyr Cys Ala
                85                  90                  95

Arg Ser Pro Ile Asn His Gly Tyr Trp Tyr Phe Asp Phe Trp Gly
            100                 105                 110

Pro Gly Thr Met Val Thr Val Ser Ser
        115                 120

<210> SEQ ID NO 46
<211> LENGTH: 363
<212> TYPE: DNA
<213> ORGANISM: Rattus norvegicus

<400> SEQUENCE: 46
gaggtgcagc ttcaggagtc aggacctggc cttgtgaaac cctcacagtc actctccctc    60
acctgttctg tcactggtta ctccatcact acttattact ggggctggat ccggaagttc   120
ccaggaaata aaatggagtg gatggggtac ataagctaca gtggtcgcac tagttataac   180
ccatctctca aaagtcgaat gtccattact agagacgcat cgaagaatca gttcttccta   240

```
cagttgaact ctgtaactac tgacgacaca gccacatatt actgtgcaag atccccaatt    300
aaccacggag ggtactggta ctttgacttc tggggcccag gaaccatggt caccgtgtcc    360
tca                                                                 363
```

<210> SEQ ID NO 47
<211> LENGTH: 10
<212> TYPE: PRT
<213> ORGANISM: Rattus norvegicus

<400> SEQUENCE: 47

Gly Tyr Ser Ile Thr Thr Tyr Tyr Trp Gly
1               5                   10

<210> SEQ ID NO 48
<211> LENGTH: 9
<212> TYPE: PRT
<213> ORGANISM: Rattus norvegicus

<400> SEQUENCE: 48

Tyr Ile Ser Tyr Ser Gly Arg Thr Ser
1               5

<210> SEQ ID NO 49
<211> LENGTH: 13
<212> TYPE: PRT
<213> ORGANISM: Rattus norvegicus

<400> SEQUENCE: 49

Ser Pro Ile Asn His Gly Gly Tyr Trp Tyr Phe Asp Phe
1               5                   10

<210> SEQ ID NO 50
<211> LENGTH: 449
<212> TYPE: DNA
<213> ORGANISM: Artificial Sequence
<220> FEATURE:
<223> OTHER INFORMATION: DNA comprising DNA sequence coding for human
      light chain signal sequence and kappa chain constant region

<400> SEQUENCE: 50

```
gcctccggac tctagagcca ccatggtgct gcagacccag gtgttcatct ccctgctgct    60
gtggatctcc ggcgcgtacg gcgatatcgt gatgattaaa cgtacggtgg ccgcccctc    120 cgtgttcatc ttcccccct ccgacgagca gctgaagtcc ggcaccgcct ccgtggtgtg    180
cctgctgaat aacttctacc cagagaggc caaggtgcag tggaaggtgg acaacgccct    240
gcagtccggg aactcccagg agagcgtgac cgagcaggac agcaaggaca gcacctacag    300
cctgagcagc accctgaccc tgagcaaagc cgactacgag aagcacaagg tgtacgcctg    360
cgaggtgacc caccagggcc tgagctcccc cgtcaccaag agcttcaaca ggggggagtg    420
ttagggggcc gtttaaacgg gggaggcta                                     449
```

<210> SEQ ID NO 51
<211> LENGTH: 1132
<212> TYPE: DNA
<213> ORGANISM: Artificial Sequence
<220> FEATURE:
<223> OTHER INFORMATION: DNA comprising DNA sequence coding for human
      heavy chain signal sequence and IgG1 constant region

<400> SEQUENCE: 51

```
gcctccggac tctagagcca ccatgaaaca cctgtggttc ttcctcctgc tggtggcagc    60
```

```
tcccagatgg gtgctgagcc aggtgcaatt gtgcaggcgg ttagctcagc ctccaccaag    120
ggcccaagcg tcttccccct ggcaccctcc tccaagagca cctctggcgg cacagccgcc    180
ctgggctgcc tggtcaagga ctacttcccc gaacccgtga ccgtgagctg gaactcaggc    240
gccctgacca gcggcgtgca caccttcccc gctgtcctgc agtcctcagg actctactcc    300
ctcagcagcg tggtgaccgt gccctccagc agcttgggca cccagaccta catctgcaac    360
gtgaatcaca gcccagcaa caccaaggtg gacaagagag ttgagcccaa atcttgtgac    420
aaaactcaca catgcccacc ctgcccagca cctgaactcc tggggggacc ctcagtcttc    480
ctcttccccc caaaacccaa ggacaccctc atgatctccc ggacccctga ggtcacatgc    540
gtggtggtgg acgtgagcca cgaagaccct gaggtcaagt tcaactggta cgtggacggc    600
gtggaggtgc ataatgccaa gacaaagccc cgggaggagc agtacaacag cacgtaccgg    660
gtggtcagcg tcctcaccgt cctgcaccag gactggctga atggcaagga gtacaagtgc    720
aaggtctcca acaaagccct cccagccccc atcgagaaaa ccatctccaa agccaaaggc    780
cagccccggg aaccacaggt gtacaccctg cccccatccc gggaggagat gaccaagaac    840
caggtcagcc tgacctgcct ggtcaaaggc ttctatccca gcgacatcgc cgtggagtgg    900
gagagcaatg gccagcccga gaacaactac aagaccaccc tcccgtgct ggactccgac    960 ggctccttct tcctctacag caagctcacc gtggacaaga gcaggtggca gcagggcaac    1020
gtcttctcat gctccgtgat gcatgaggct ctgcacaacc actacaccca gaagagcctc    1080
tccctgtctc cggcaaatg agatatcggg cccgtttaaa cggggggaggc ta           1132
```

<210> SEQ ID NO 52
<211> LENGTH: 749
<212> TYPE: DNA
<213> ORGANISM: Artificial Sequence
<220> FEATURE:
<223> OTHER INFORMATION: DNA comprising DNA sequence coding for chG019 light chain

<400> SEQUENCE: 52

```
ccagcctccg gactctagag ccaccatggt gctgcagacc caggtgttca tcagcctgct     60
gctgtggatc agcggcgcct acggcgacat ccagatgacc cagagcccta gcctgctgag    120
cgccagcgtg ggcgatagag tgaccctgaa ctgcaaggcc agccagaaca tctacaagaa    180 cctggctgg tatcagcaga agctgggcga gggcccaag ctgctgatct acgacgccaa    240 cacccctgcag accggcatcc ccagcagatt ttctggcagc ggcagcggct ccgacttcac    300
cctgacaatc agcagcctgc agcccgagga cgtggccacc tacttttgcc agcagtacta    360
cagcggctgg gccttcggcg gcgtgaccaa cctggaactg aagagagccg tggccgctcc    420
ctccgtgttc atcttcccac ctagcgacga gcagctgaag tccggcacag cctctgtcgt    480
gtgcctgctg aacaacttct accccccgcga ggccaaggtg cagtggaagg tggacaatgc    540
cctgcagtct ggcaacagcc aggaaagcgt gaccgagcag gacagcaagg actccaccta    600
cagcctgagc agcaccctga ccctgagcaa ggccgactac gagaagcaca aggtgtacgc    660
ctgcgaagtg acccaccagg gcctgtctag ccccgtgacc aagagcttca ccggggcga    720 gtgttgagtt taaacggggg aggctaact                                      749
```

<210> SEQ ID NO 53
<211> LENGTH: 233
<212> TYPE: PRT
<213> ORGANISM: Artificial Sequence
<220> FEATURE:

<223> OTHER INFORMATION: amino acid sequesnce of chG019 light chain
full-length

<400> SEQUENCE: 53

```
Met Val Leu Gln Thr Gln Val Phe Ile Ser Leu Leu Leu Trp Ile Ser
1               5                   10                  15
Gly Ala Tyr Gly Asp Ile Gln Met Thr Gln Ser Pro Ser Leu Leu Ser
            20                  25                  30
Ala Ser Val Gly Asp Arg Val Thr Leu Asn Cys Lys Ala Ser Gln Asn
        35                  40                  45
Ile Tyr Lys Asn Leu Ala Trp Tyr Gln Gln Lys Leu Gly Glu Gly Pro
    50                  55                  60
Lys Leu Leu Ile Tyr Asp Ala Asn Thr Leu Gln Thr Gly Ile Pro Ser
65                  70                  75                  80
Arg Phe Ser Gly Ser Gly Ser Gly Ser Asp Phe Thr Leu Thr Ile Ser
                85                  90                  95
Ser Leu Gln Pro Glu Asp Val Ala Thr Tyr Phe Cys Gln Gln Tyr Tyr
            100                 105                 110
Ser Gly Trp Ala Phe Gly Gly Val Thr Asn Leu Glu Leu Lys Arg Ala
        115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys
225                 230
```

<210> SEQ ID NO 54
<211> LENGTH: 699
<212> TYPE: DNA
<213> ORGANISM: Artificial Sequence
<220> FEATURE:
<223> OTHER INFORMATION: nucleotide sequesnce of chG019 light chain
full-length

<400> SEQUENCE: 54

```
atggtgctgc agacccaggt gttcatcagc ctgctgctgt ggatcagcgg cgcctacggc      60
gacatccaga tgacccagag ccctagcctg ctgagcgcca gcgtgggcga tagagtgacc     120
ctgaactgca aggccagcca gaacatctac aagaacctgg cctggtatca gcagaagctg     180
ggcgagggcc ccaagctgct gatctacgac gccaacaccc tgcagaccgg catccccagc     240
agatttctct gcagcggcag cggctccgac ttcaccctga caatcagcag cctgcagccc     300
gaggacgtgg ccacctactt tgccagcag tactacagcg ctgggccttc ggcggcgtg      360
accaacctgg aactgaagag agccgtggcc gctccctccg tgttcatctt cccacctagc     420
gacgagcagc tgaagtccgg cacagcctct gtcgtgtgcc tgctgaacaa cttctacccc     480
cgcgaggcca aggtgcagtg gaaggtggac aatgccctgc agtctggcaa cagccaggaa     540
```

```
agcgtgaccg agcaggacag caaggactcc acctacagcc tgagcagcac cctgaccctg    600
agcaaggccg actacgagaa gcacaaggtg tacgcctgcg aagtgaccca ccagggcctg    660
tctagccccg tgaccaagag cttcaaccgg ggcgagtgt                           699
```

<210> SEQ ID NO 55
<211> LENGTH: 324
<212> TYPE: DNA
<213> ORGANISM: Artificial Sequence
<220> FEATURE:
<223> OTHER INFORMATION: nucleotide sequesnce of chG019 light chain
      variable region

<400> SEQUENCE: 55

```
gacatccaga tgacccagag ccctagcctg ctgagcgcca gcgtgggcga tagagtgacc     60
ctgaactgca aggccagcca gaacatctac aagaacctgg cctggtatca gcagaagctg    120
ggcgagggcc ccaagctgct gatctacgac gccaacaccc tgcagaccgg catccccagc    180 agatttctg gcagcggcag cggctccgac ttcaccctga caatcagcag cctgcagccc     240
gaggacgtgg ccacctactt ttgccagcag tactacagcg ctgggccttt cggcggcgtg    300
accaacctgg aactgaagag agcc                                            324
```

<210> SEQ ID NO 56
<211> LENGTH: 471
<212> TYPE: PRT
<213> ORGANISM: Artificial Sequence
<220> FEATURE:
<223> OTHER INFORMATION: amino acid sequesnce of chG019 heavy chain
      full-length

<400> SEQUENCE: 56

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Glu Leu Val Lys
            20                  25                  30

Pro Gly Ser Ser Val Lys Ile Ser Cys Lys Ala Ser Gly Tyr Thr Phe
        35                  40                  45

Thr Arg Asn Phe Met His Trp Ile Lys Gln Gln Pro Gly Asn Gly Leu
    50                  55                  60

Glu Trp Ile Gly Trp Ile Tyr Pro Gly Asp Gly Glu Thr Glu Tyr Asn
65                  70                  75                  80

Gln Lys Phe Asn Gly Lys Ala Thr Leu Thr Ala Asp Arg Ser Ser Ser
                85                  90                  95

Thr Ala Tyr Met Glu Leu Ser Arg Leu Thr Ser Glu Asp Ser Ala Val
            100                 105                 110

Tyr Phe Cys Ala Arg Gly Val Tyr Gly Gly Phe Ala Gly Gly Tyr Phe
        115                 120                 125

Asp Phe Trp Gly Gln Gly Val Met Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205
```

```
Val Val Thr Val Pro Ser Ser Ser Leu Gly Thr Gln Thr Tyr Ile Cys
    210                 215                 220
Asn Val Asn His Lys Pro Ser Asn Thr Lys Val Asp Lys Arg Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Glu Glu Met Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 57
<211> LENGTH: 1413
<212> TYPE: DNA
<213> ORGANISM: Artificial Sequence
<220> FEATURE:
<223> OTHER INFORMATION: nucleotide sequesnce of chG019 heavy chain
      full-length

<400> SEQUENCE: 57
atgaaacacc tgtggttctt cctcctgctg gtggcagctc ccagatgggt gctgagccag      60
gtgcagctgc agcagtctgg cgccgagctc gtgaagcctg gcagcagcgt gaagatcagc     120
tgcaaggcca gcggctacac cttcacccgg aacttcatgc actggatcaa gcagcagccc     180
ggcaacggcc tggaatggat cggctggatc tatcccggcg acggcgagac agagtacaac     240
cagaagttca cggcaaggc caccctgacc gccgacagaa gcagctccac cgcctacatg      300
gaactgagcc ggctgaccag cgaggacagc gccgtgtact tttgcgccag aggcgtgtac     360
ggcggcttcg ctggcggcta cttcgatttt tggggccagg gcgtgatggt caccgtcagc     420
tcagcctcca ccaagggccc aagcgtcttc cccctggcac cctcctccaa gagcacctct     480
ggcggcacag ccgccctggg ctgcctggtc aaggactact cccccgaacc cgtgaccgtg     540
```

```
agctggaact caggcgccct gaccagcggc gtgcacacct tccccgctgt cctgcagtcc    600
tcaggactct actccctcag cagcgtggtg accgtgccct ccagcagctt gggcacccag    660
acctacatct gcaacgtgaa tcacaagccc agcaacacca aggtggacaa gagagttgag    720
cccaaatctt gtgacaaaac tcacacatgc ccaccctgcc cagcacctga actcctgggg    780
ggaccctcag tcttcctctt ccccccaaaa cccaaggaca ccctcatgat ctcccggacc    840
cctgaggtca catgcgtggt ggtggacgtg agccacgaag accctgaggt caagttcaac    900
tggtacgtgg acggcgtgga ggtgcataat gccaagacaa agcccgggga ggagcagtac    960
aacagcacgt accgggtggt cagcgtcctc accgtcctgc accaggactg gctgaatggc   1020
aaggagtaca agtgcaaggt ctccaacaaa gccctcccag cccccatcga aaaaccatc    1080 tccaaagcca aggccagccc cgggaaccag cccgtctaca ccctgccccc atcccgggag   1140
gagatgacca gaaccaggt cagcctgacc tgcctggtca aaggcttcta tcccagcgac   1200
atcgccgtgg agtgggagag caatggccag cccgagaaca actacaagac cacccctccc   1260
gtgctggact ccgacggctc cttcttcctc tacagcaagc tcaccgtgga caagagcagg   1320
tggcagcagg gcaacgtctt ctcatgctcc gtgatgcatg aggctctgca caaccactac   1380
acccagaaga gcctctccct gtctcccggc aaa                                1413

<210> SEQ ID NO 58
<211> LENGTH: 122
<212> TYPE: PRT
<213> ORGANISM: Artificial Sequence
<220> FEATURE:
<223> OTHER INFORMATION: amino acid sequesnce of chG019 heavy chain
      variable region

<400> SEQUENCE: 58

Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Arg Asn
            20                  25                  30

Phe Met His Trp Ile Lys Gln Gln Pro Gly Asn Gly Leu Glu Trp Ile
        35                  40                  45

Gly Trp Ile Tyr Pro Gly Asp Gly Glu Thr Glu Tyr Asn Gln Lys Phe
    50                  55                  60

Asn Gly Lys Ala Thr Leu Thr Ala Asp Arg Ser Ser Ser Thr Ala Tyr
65                  70                  75                  80

Met Glu Leu Ser Arg Leu Thr Ser Glu Asp Ser Ala Val Tyr Phe Cys
                85                  90                  95

Ala Arg Gly Val Tyr Gly Gly Phe Ala Gly Gly Tyr Phe Asp Phe Trp
            100                 105                 110

Gly Gln Gly Val Met Val Thr Val Ser Ser
        115                 120

<210> SEQ ID NO 59
<211> LENGTH: 366
<212> TYPE: DNA
<213> ORGANISM: Artificial Sequence
<220> FEATURE:
<223> OTHER INFORMATION: nucleotide sequesnce of chG019 heavy chain
      variable region

<400> SEQUENCE: 59
caggtgcagc tgcagcagtc tggcgccgag ctcgtgaagc ctggcagcag cgtgaagatc    60
```

```
agctgcaagg ccagcggcta caccttcacc cggaacttca tgcactggat caagcagcag    120
cccggcaacg gcctggaatg gatcggctgg atctatcccg gcgacggcga gacagagtac    180
aaccagaagt tcaacggcaa ggccaccctg accgccgaca agcagctc caccgcctac     240 atggaactga gccggctgac cagcgaggac agcgccgtgt acttttgcgc cagaggcgtg    300
tacggcggct tcgctggcgg ctacttcgat ttttggggcc agggcgtgat ggtcaccgtc    360
agctca                                                              366
```

```
<210> SEQ ID NO 60
<211> LENGTH: 10
<212> TYPE: PRT
<213> ORGANISM: Artificial Sequence
<220> FEATURE:
<223> OTHER INFORMATION: amino acid sequesnce of chG019 CDRH2

<400> SEQUENCE: 60

Trp Ile Tyr Pro Gly Asp Gly Glu Thr Glu
1               5                   10

<210> SEQ ID NO 61
<211> LENGTH: 233
<212> TYPE: PRT
<213> ORGANISM: Artificial Sequence
<220> FEATURE:
<223> OTHER INFORMATION: amino acid sequesnce of hL02 light chain
      full-length

<400> SEQUENCE: 61

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Lys Ala Ser Gln Asn
            35                  40                  45

Ile Tyr Lys Asn Leu Ala Trp Tyr Gln Gln Lys Pro Gly Lys Ala Pro
        50                  55                  60

Lys Leu Leu Ile Tyr Asp Ala Asn Thr Leu Gln Thr Gly Val Pro Ser
65                  70                  75                  80

Arg Phe Ser Gly Ser Gly Ser Gly Ser Asp Phe Thr Leu Thr Ile Ser
                85                  90                  95

Ser Leu Gln Pro Glu Asp Phe Ala Thr Tyr Phe Cys Gln Gln Tyr Tyr
                100                 105                 110

Ser Gly Trp Ala Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
```

<210> SEQ ID NO 62
<211> LENGTH: 699
<212> TYPE: DNA
<213> ORGANISM: Artificial Sequence
<220> FEATURE:
<223> OTHER INFORMATION: nucleotide sequesnce of hL02 light chain full-length

<400> SEQUENCE: 62

```
atggtgctgc agacccaggt gttcatctcc ctgctgctgt ggatctccgg cgcgtacggc      60
gacatccaga tgacccagag ccctagcagc ctgagcgcca gcgtgggcga cagagtgacc     120
atcacatgca aggccagcca gaacatctac aagaacctgg cctggtatca gcagaagccc     180
ggcaaggccc ccaagctgct gatctacgac gccaacaccc tgcagaccgg cgtgcccagc     240
agatttctg gcagcggcag cggctccgac ttcaccctga caatcagcag cctgcagccc     300
gaggacttcg ccacctactt ttgccagcag tactacagcg gctgggcctt cggccagggc     360
accaaggtgg aaatcaagcg tacggtggcc gccccctccg tgttcatctt ccccccctcc     420
gacgagcagc tgaagtccgg caccgcctcc gtggtgtgcc tgctgaataa cttctacccc     480
agagaggcca aggtgcagtg gaaggtggac aacgccctgc agtccgggaa ctcccaggag     540
agcgtgaccg agcaggacag caaggacagc acctacagcc tgagcagcac cctgaccctg     600
agcaaagccg actacgagaa gcacaaggtg tacgcctgcg aggtgaccca ccagggcctg     660
agctcccccg tcaccaagag cttcaacagg ggggagtgt                            699
```

<210> SEQ ID NO 63
<211> LENGTH: 108
<212> TYPE: PRT
<213> ORGANISM: Artificial Sequence
<220> FEATURE:
<223> OTHER INFORMATION: amino acid sequesnce of hL02 light chain variable region

<400> SEQUENCE: 63

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asn Ile Tyr Lys Asn
            20                  25                  30
Leu Ala Trp Tyr Gln Gln Lys Pro Gly Lys Ala Pro Lys Leu Leu Ile
        35                  40                  45
Tyr Asp Ala Asn Thr Leu Gln Thr Gly Val Pro Ser Arg Phe Ser Gly
    50                  55                  60
Ser Gly Ser Gly Ser Asp Phe Thr Leu Thr Ile Ser Ser Leu Gln Pro
65                  70                  75                  80
Glu Asp Phe Ala Thr Tyr Phe Cys Gln Gln Tyr Tyr Ser Gly Trp Ala
                85                  90                  95
Phe Gly Gln Gly Thr Lys Val Glu Ile Lys Arg Thr
            100                 105
```

<210> SEQ ID NO 64
<211> LENGTH: 324
<212> TYPE: DNA
<213> ORGANISM: Artificial Sequence
<220> FEATURE:
<223> OTHER INFORMATION: nucleotide sequesnce of hL02 light chain variable region

<400> SEQUENCE: 64

-continued

```
gacatccaga tgacccagag ccctagcagc ctgagcgcca gcgtgggcga cagagtgacc      60
atcacatgca aggccagcca gaacatctac aagaacctgg cctggtatca gcagaagccc     120
ggcaaggccc ccaagctgct gatctacgac gccaacaccc tgcagaccgg cgtgcccagc     180
agattttctg gcagcggcag cggctccgac ttcaccctga caatcagcag cctgcagccc     240
gaggacttcg ccacctactt tgccagcag tactacagcg ctgggcctt cggccagggc      300 accaaggtgg aaatcaagcg tacg                                            324
```

<210> SEQ ID NO 65
<211> LENGTH: 233
<212> TYPE: PRT
<213> ORGANISM: Artificial Sequence
<220> FEATURE:
<223> OTHER INFORMATION: amino acid sequesnce of hL03 light chain full-length

<400> SEQUENCE: 65

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asn
        35                  40                  45

Ile Tyr Lys Asn Leu Ala Trp Tyr Gln Gln Lys Leu Gly Glu Gly Pro
    50                  55                  60

Lys Leu Leu Ile Tyr Asp Ala Asn Thr Leu Gln Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Tyr
            100                 105                 110

Ser Gly Trp Ala Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 66
<211> LENGTH: 699
<212> TYPE: DNA
<213> ORGANISM: Artificial Sequence
<220> FEATURE:
<223> OTHER INFORMATION: nucleotide sequesnce of hL03 light chain full-length

<400> SEQUENCE: 66

```
atggtgctgc agacccaggt gttcatctcc ctgctgctgt ggatctccgg cgcgtacggc    60
gacatccaga tgacccagag ccctagcagc ctgagcgcca gcgtgggcga cagagtgacc   120
atcacatgca aggccagcca gaacatctac aagaacctgg cctggtatca gcagaagctg   180
ggcgagggcc ccaagctgct gatctacgac gccaacaccc tgcagaccgg cgtgcccagc   240 agatttctg gcagcggctc cggcaccgac ttcaccctga caatcagcag cctgcagccc   300
gaggacttcg ccacctacta ctgccagcag tactacagcg gctgggcctt tggccagggc   360
accaaggtgg aaatcaagcg tacggtggcc gcccctccg tgttcatctt ccccccctcc    420
gacgagcagc tgaagtccgg caccgcctcc gtggtgtgcc tgctgaataa cttctacccc   480
agagaggcca aggtgcagtg gaaggtggac aacgccctgc agtccgggaa ctcccaggag   540
agcgtgaccg agcaggacag caaggacagc acctacagcc tgagcagcac cctgaccctg   600
agcaaagccg actacgagaa gcacaaggtg tacgcctgcg aggtgaccca ccagggcctg   660
agctcccccg tcaccaagag cttcaacagg ggggagtgt                          699
```

<210> SEQ ID NO 67
<211> LENGTH: 108
<212> TYPE: PRT
<213> ORGANISM: Artificial Sequence
<220> FEATURE:
<223> OTHER INFORMATION: amino acid sequesnce of hL03 light chain
      variable region

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Tyr Lys Asn
            20                  25                  30

Leu Ala Trp Tyr Gln Gln Lys Leu Gly Glu Gly Pro Lys Leu Leu Ile
        35                  40                  45

Tyr Asp Ala Asn Thr Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Gly Trp Ala
                85                  90                  95

Phe Gly Gln Gly Thr Lys Val Glu Ile Lys Arg Thr
            100                 105
```

<210> SEQ ID NO 68
<211> LENGTH: 324
<212> TYPE: DNA
<213> ORGANISM: Artificial Sequence
<220> FEATURE:
<223> OTHER INFORMATION: nucleotide sequesnce of hL03 light chain
      variable region

<400> SEQUENCE: 68

```
gacatccaga tgacccagag ccctagcagc ctgagcgcca gcgtgggcga cagagtgacc    60
atcacatgca aggccagcca gaacatctac aagaacctgg cctggtatca gcagaagctg   120
ggcgagggcc ccaagctgct gatctacgac gccaacaccc tgcagaccgg cgtgcccagc   180 agatttctg gcagcggctc cggcaccgac ttcaccctga caatcagcag cctgcagccc   240
gaggacttcg ccacctacta ctgccagcag tactacagcg gctgggcctt tggccagggc   300
accaaggtgg aaatcaagcg tacg                                          324
```

<210> SEQ ID NO 69
<211> LENGTH: 471
<212> TYPE: PRT
<213> ORGANISM: Artificial Sequence
<220> FEATURE:
<223> OTHER INFORMATION: amino acid sequesnce of hH01 heavy chain
full-length

<400> SEQUENCE: 69

```
Met Lys His Leu Trp Phe Phe Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Arg Asn Phe Met His Trp Val Arg Gln Ala Pro Gly Gln Gly Leu
    50                  55                  60

Glu Trp Met Gly Trp Ile Tyr Pro Gly Asp Gly Glu Thr Glu Tyr Ala
65                  70                  75                  80

Gln Lys Phe Gln Gly Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Val Tyr Gly Gly Phe Ala Gly Gly Tyr Phe
        115                 120                 125

Asp Phe Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
```

```
                355                 360                 365
Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 70
<211> LENGTH: 1413
<212> TYPE: DNA
<213> ORGANISM: Artificial Sequence
<220> FEATURE:
<223> OTHER INFORMATION: nucleotide sequesnce of hH01 heavy chain
      full-length

<400> SEQUENCE: 70
atgaaacacc tgtggttctt cctcctgctg gtggcagctc ccagatgggt gctgagcgaa      60
gtgcagctgg tgcagtctgg cgccgaagtg aagaaaccag cgccagcgt gaaggtgtcc     120 tgcaaggcca gcggctacac ctttacccgg aacttcatgc actgggtgcg ccaggctcca    180 ggccaggac tggaatggat gggctggatc tatcccggcg acggcgagac agagtacgcc     240
cagaaattcc agggcagagt gaccatcacc gccgacacca gcacctccac cgcctacatg    300
gaactgagca gcctgcggag cgaggacacc gccgtgtact attgtgccag aggcgtgtac    360
ggcggcttcg ctggcggcta cttcgatttt ggggccagg gcaccctcgt gaccgtcagc     420
tcagcctcca ccaagggccc aagcgtcttc cccctggcac cctcctccaa gagcacctct    480
ggcggcacag ccgccctggg ctgcctggtc aaggactact ccccgaacc cgtgaccgtg     540 agctggaact caggcgccct gaccagcggc gtgcacacct tcccgctgt cctgcagtcc     600 tcaggactct actccctcag cagcgtggtg accgtgccct ccagcagctt gggcacccag    660
acctacatct gcaacgtgaa tcacaagccc agcaacacca aggtggacaa gagagttgag    720
cccaaatctt gtgacaaaac tcacacatgc ccaccctgcc cagcacctga actcctgggg    780
ggaccctcag tcttcctctt ccccccaaaa cccaaggaca ccctcatgat ctcccggacc    840
cctgaggtca catgcgtggt ggtggacgtg agccacgaag accctgaggt caagttcaac    900
tggtacgtgg acggcgtgga ggtgcataat gccaagacaa agccccggga ggagcagtac    960
aacagcacgt accgggtggt cagcgtcctc accgtcctgc accaggactg gctgaatggc   1020
aaggagtaca agtgcaaggt ctccaacaaa gccctcccag ccccccatcga gaaaaccatc   1080 tccaaagcca aggccagcc ccgggaacca caggtgtaca ccctgccccc atcccgggag   1140
gagatgacca agaaccaggt cagcctgacc tgcctggtca aaggcttcta tcccagcgac   1200
atcgccgtgg agtgggagag caatggccag cccgagaaca actacaagac caccctccc   1260 gtgctggact ccgacggctc cttcttcctc tacagcaagc tcaccgtgga caagagcagg   1320
tggcagcagg gcaacgtctt ctcatgctcc gtgatgcatg aggctctgca caaccactac   1380
```

```
acccagaaga gcctctccct gtctcccggc aaa                                    1413
```

<210> SEQ ID NO 71
<211> LENGTH: 122
<212> TYPE: PRT
<213> ORGANISM: Artificial Sequence
<220> FEATURE:
<223> OTHER INFORMATION: amino acid sequesnce of hH01 heavy chain
      variable region

<400> SEQUENCE: 71

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Asn
            20                  25                  30

Phe Met His Trp Val Arg Gln Ala Pro Gly Gln Gly Leu Glu Trp Met
        35                  40                  45

Gly Trp Ile Tyr Pro Gly Asp Gly Glu Thr Glu Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Tyr Gly Gly Phe Ala Gly Tyr Phe Asp Phe Trp
            100                 105                 110

Gly Gln Gly Thr Leu Val Thr Val Ser Ser
        115                 120
```

<210> SEQ ID NO 72
<211> LENGTH: 366
<212> TYPE: DNA
<213> ORGANISM: Artificial Sequence
<220> FEATURE:
<223> OTHER INFORMATION: nucleotide sequesnce of hH01 heavy chain
      variable region

<400> SEQUENCE: 72

```
gaagtgcagc tggtgcagtc tggcgccgaa gtgaagaaac caggcgccag cgtgaaggtg      60
tcctgcaagg ccagcggcta cacctttacc cggaacttca tgcactgggt gcgccaggct     120
ccaggccagg gactggaatg gatgggctgg atctatcccg gcgacggcga gacagagtac     180
gcccagaaat tccagggcag agtgaccatc accgccgaca ccagcacctc caccgcctac     240
atggaactga gcagcctgcg gagcgaggac accgccgtgt actattgtgc cagaggcgtg     300
tacggcggct cgctggcgg ctacttcgat ttttgggggcc agggcaccct cgtgaccgtc     360
agctca                                                                366
```

<210> SEQ ID NO 73
<211> LENGTH: 471
<212> TYPE: PRT
<213> ORGANISM: Artificial Sequence
<220> FEATURE:
<223> OTHER INFORMATION: amino acid sequesnce of hH02 heavy chain
      full-length

<400> SEQUENCE: 73

```
Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30
```

```
Pro Gly Ala Ser Val Lys Val Ser Cys Lys Ala Ser Gly Tyr Thr Phe
         35                  40                  45

Thr Arg Asn Phe Met His Trp Val Arg Gln Ala Pro Gly Gln Gly Leu
     50                  55                  60

Glu Trp Met Gly Trp Ile Tyr Pro Gly Asp Gly Glu Thr Glu Tyr Asn
 65                  70                  75                  80

Gln Lys Phe Gln Gly Arg Val Thr Ile Thr Ala Asp Arg Ser Thr Ser
                 85                  90                  95

Thr Ala Tyr Met Glu Leu Ser Ser Leu Arg Ser Glu Asp Thr Ala Val
             100                 105                 110

Tyr Phe Cys Ala Arg Gly Val Tyr Gly Gly Phe Ala Gly Gly Tyr Phe
         115                 120                 125

Asp Phe Trp Gly Gln Gly Thr Leu Val Thr Val Ser Ser Ala Ser Thr
     130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                 165                 170                 175

Pro Val Thr Val Ser Trp Asn Ser Gly Ala Leu Thr Ser Gly Val His
             180                 185                 190

Thr Phe Pro Ala Val Leu Gln Ser Ser Gly Leu Tyr Ser Leu Ser Ser
         195                 200                 205

Val Val Thr Val Pro Ser Ser Ser Leu Gly Thr Gln Thr Tyr Ile Cys
     210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                 245                 250                 255

Glu Leu Leu Gly Gly Pro Ser Val Phe Leu Phe Pro Pro Lys Pro Lys
             260                 265                 270

Asp Thr Leu Met Ile Ser Arg Thr Pro Glu Val Thr Cys Val Val Val
         275                 280                 285

Asp Val Ser His Glu Asp Pro Glu Val Lys Phe Asn Trp Tyr Val Asp
     290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                 325                 330                 335

Trp Leu Asn Gly Lys Glu Tyr Lys Cys Lys Val Ser Asn Lys Ala Leu
             340                 345                 350

Pro Ala Pro Ile Glu Lys Thr Ile Ser Lys Ala Lys Gly Gln Pro Arg
         355                 360                 365

Glu Pro Gln Val Tyr Thr Leu Pro Pro Ser Arg Glu Glu Met Thr Lys
     370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                 405                 410                 415

Thr Thr Pro Pro Val Leu Asp Ser Asp Gly Ser Phe Phe Leu Tyr Ser
             420                 425                 430

Lys Leu Thr Val Asp Lys Ser Arg Trp Gln Gln Gly Asn Val Phe Ser
         435                 440                 445
```

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 74
<211> LENGTH: 1413
<212> TYPE: DNA
<213> ORGANISM: Artificial Sequence
<220> FEATURE:
<223> OTHER INFORMATION: nucleotide sequesnce of hH02 heavy chain
      full-length

<400> SEQUENCE: 74

| | | |
|---|---|---|
| atgaaacacc tgtggttctt cctcctgctg gtggcagctc ccagatgggt gctgagcgaa | 60 |
| gtgcagctgg tgcagtctgg cgccgaagtg aagaaaccag cgccagcgt gaaggtgtcc | 120 |
| tgcaaggcca gcggctacac ctttacccgg aacttcatgc actgggtgcg ccaggctcca | 180 |
| ggccagggac tggaatggat gggctggatc tatcccggcg acggcgagac agagtacaac | 240 |
| cagaaattcc agggcagagt gaccatcacc gccgacagaa gcaccagcac cgcctacatg | 300 |
| gaactgagca gcctgcggag cgaggatacc gccgtgtact tctgtgccag aggcgtgtac | 360 |
| ggcggcttcg ctggcggcta cttcgatttt tggggccagg gcaccctcgt gaccgtcagc | 420 |
| tcagcctcca ccaagggccc aagcgtcttc cccctggcac cctcctccaa gagcacctct | 480 |
| ggcggcacag ccgccctggg ctgcctggtc aaggactact tccccgaacc cgtgaccgtg | 540 |
| agctggaact caggcgccct gaccagcggc gtgcacacct tcccggctgt cctgcagtcc | 600 |
| tcaggactct actccctcag cagcgtggtg accgtgccct ccagcagctt gggcacccag | 660 |
| acctacatct gcaacgtgaa tcacaagccc agcaacacca aggtggacaa gagagttgag | 720 |
| cccaaatctt gtgacaaaac tcacacatgc ccaccctgcc cagcacctga actcctgggg | 780 |
| ggaccctcag tcttcctctt ccccccaaaa cccaaggaca cccctcatga tctcccggacc | 840 |
| cctgaggtca catgcgtggt ggtggacgtg agccacgaag accctgaggt caagttcaac | 900 |
| tggtacgtgg acggcgtgga ggtgcataat gccaagacaa agcccgggga ggagcagtac | 960 |
| aacagcacgt accgggtggt cagcgtcctc accgtcctgc accaggactg gctgaatggc | 1020 |
| aaggagtaca agtgcaaggt ctccaacaaa gccctcccag cccccatcga gaaaaccatc | 1080 |
| tccaaagcca aggccagcc ccgggaacca caggtgtaca ccctgccccc atcccgggag | 1140 |
| gagatgacca gaaccaggt cagcctgacc tgcctggtca aaggcttcta tcccagcgac | 1200 |
| atcgccgtgg agtgggagag caatggccag cccgagaaca actacaagac cacccctccc | 1260 |
| gtgctggact ccgacggctc cttcttcctc tacagcaagc tcaccgtgga caagagcagg | 1320 |
| tggcagcagg gcaacgtctt ctcatgctcc gtgatgcatg aggctctgca caaccactac | 1380 |
| acccagaaga gcctctccct gtctcccggc aaa | 1413 |

<210> SEQ ID NO 75
<211> LENGTH: 122
<212> TYPE: PRT
<213> ORGANISM: Artificial Sequence
<220> FEATURE:
<223> OTHER INFORMATION: amino acid sequesnce of hH02 heavy chain
      variable region

<400> SEQUENCE: 75

Glu Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Arg Asn
            20                  25                  30

Phe Met His Trp Val Arg Gln Ala Pro Gly Gln Gly Leu Glu Trp Met
        35                  40                  45

Gly Trp Ile Tyr Pro Gly Asp Gly Glu Thr Glu Tyr Asn Gln Lys Phe
    50                  55                  60

Gln Gly Arg Val Thr Ile Thr Ala Asp Arg Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Val Tyr Gly Gly Phe Ala Gly Gly Tyr Phe Asp Phe Trp
            100                 105                 110

Gly Gln Gly Thr Leu Val Thr Val Ser Ser
            115                 120
```

<210> SEQ ID NO 76
<211> LENGTH: 366
<212> TYPE: DNA
<213> ORGANISM: Artificial Sequence
<220> FEATURE:
<223> OTHER INFORMATION: nucleotide sequesnce of hH02 heavy chain
      variable region

<400> SEQUENCE: 76

```
gaagtgcagc tggtgcagtc tggcgccgaa gtgaagaaac aggcgccag cgtgaaggtg      60 tcctgcaagg ccagcggcta cacctttacc cggaacttca tgcactgggt gcgccaggct    120
ccaggccagg gactggaatg gatgggctgg atctatcccg gcgacggcga gacagagtac    180
aaccagaaat tccagggcag agtgaccatc accgccgaca agcaccag accgcctac       240 atggaactga gcagcctgcg gagcgaggat accgccgtgt acttctgtgc cagaggcgtg    300
tacggcggct cgctggcgg ctacttcgat ttttggggcc agggcaccct cgtgaccgtc     360
agctca                                                                366
```

<210> SEQ ID NO 77
<211> LENGTH: 471
<212> TYPE: PRT
<213> ORGANISM: Artificial Sequence
<220> FEATURE:
<223> OTHER INFORMATION: amino acid sequesnce of hH04 heavy chain
      full-length

<400> SEQUENCE: 77

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Arg Asn Phe Met His Trp Ile Arg Gln Ala Pro Gly Gln Gly Leu
    50                  55                  60

Glu Trp Met Gly Trp Ile Tyr Pro Gly Asp Gly Glu Thr Glu Tyr Ala
65                  70                  75                  80

Gln Lys Phe Gln Gly Arg Val Thr Leu Thr Ala Asp Arg Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Val Tyr Gly Gly Phe Ala Gly Gly Tyr Phe
```

```
            115                 120                 125
Asp Phe Trp Gly Gln Gly Thr Leu Val Thr Val Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 78
<211> LENGTH: 1413
<212> TYPE: DNA
<213> ORGANISM: Artificial Sequence
<220> FEATURE:
<223> OTHER INFORMATION: nucleotide sequesnce of hH04 heavy chain
      full-length

<400> SEQUENCE: 78
```

```
atgaaacacc tgtggttctt cctcctgctg gtggcagctc ccagatgggt gctgagccag      60
gtgcagctgg tgcagtctgg cgccgaagtg aagaaaccag gcgccagcgt gaaggtgtcc     120
tgcaaggcca gcggctacac ctttacccgg aacttcatgc actggatccg gcaggcccct     180
ggacagggcc tggaatggat gggctggatc tatcccggcg acggcgagac agagtacgcc     240
cagaaattcc agggcagagt gaccctgacc gccgacagaa gcaccagcac cgcctacatg     300
gaactgagca gcctgcggag cgaggacacc gccgtgtact attgtgccag aggcgtgtac     360
ggcggcttcg ctggcggcta cttcgatttt tggggccagg gcaccctcgt gaccgtcagc     420
tcagcctcca ccaagggccc aagcgtcttc cccctggcac cctcctccaa gagcacctct     480
ggcggcacag ccgccctggg ctgcctggtc aaggactact tccccgaacc cgtgaccgtg     540
agctggaact caggcgccct gaccagcggc gtgcacacct tcccgctgt cctgcagtcc     600
tcaggactct actccctcag cagcgtggtg accgtgccct ccagcagctt gggcacccag     660
acctacatct gcaacgtgaa tcacaagccc agcaacacca aggtggacaa gagagttgag     720
cccaaatctt gtgacaaaac tcacacatgc ccaccctgcc cagcacctga actcctgggg     780
ggaccctcag tcttcctctt ccccccaaaa cccaaggaca ccctcatgat ctcccggacc     840
cctgaggtca catgcgtggt ggtggacgtg agccacgaag accctgaggt caagttcaac     900
tggtacgtgg acggcgtgga ggtgcataat gccaagacaa agccccggga ggagcagtac     960
aacagcacgt accgggtggt cagcgtcctc accgtcctgc accaggactg gctgaatggc    1020
aaggagtaca agtgcaaggt ctccaacaaa gccctcccag cccccatcga gaaaaccatc    1080
tccaaagcca aggccagccc cgggaaccca caggtgtaca ccctgccccc atcccgggag    1140
gagatgacca agaaccaggt cagcctgacc tgcctggtca aaggcttcta tcccagcgac    1200
atcgccgtgg agtgggagag caatggccag ccggagaaca actacaagac cacccctccc    1260
gtgctggact ccgacggctc cttcttcctc tacagcaagc tcaccgtgga caagagcagg    1320
tggcagcagg gcaacgtctt ctcatgctcc gtgatgcatg aggctctgca caaccactac    1380
acccagaaga gcctctccct gtctcccggc aaa                                 1413
```

<210> SEQ ID NO 79  
<211> LENGTH: 122  
<212> TYPE: PRT  
<213> ORGANISM: Artificial Sequence  
<220> FEATURE:  
<223> OTHER INFORMATION: amino acid sequesnce of hH04 heavy chain variable region

<400> SEQUENCE: 79

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Asn
            20                  25                  30

Phe Met His Trp Ile Arg Gln Ala Pro Gly Gln Gly Leu Glu Trp Met
        35                  40                  45

Gly Trp Ile Tyr Pro Gly Asp Gly Glu Thr Glu Tyr Ala Gln Lys Phe
    50                  55                  60

Gln Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Tyr Gly Gly Phe Ala Gly Gly Tyr Phe Asp Phe Trp
            100                 105                 110
```

Gly Gln Gly Thr Leu Val Thr Val Ser Ser
            115                 120

<210> SEQ ID NO 80
<211> LENGTH: 366
<212> TYPE: DNA
<213> ORGANISM: Artificial Sequence
<220> FEATURE:
<223> OTHER INFORMATION: nucleotide sequesnce of hH04 heavy chain
      variable region

<400> SEQUENCE: 80
caggtgcagc tggtgcagtc tggcgccgaa gtgaagaaac caggcgccag cgtgaaggtg      60
tcctgcaagg ccagcggcta cacctttacc cggaacttca tgcactggat ccggcaggcc     120
cctggacagg gcctggaatg gatgggctgg atctatcccg cgacggcga gacagagtac     180 gcccagaaat tccagggcag agtgaccctg accgccgaca aagcaccag caccgcctac     240 atggaactga gcagcctgcg gagcgaggac accgccgtgt actattgtgc cagaggcgtg     300
tacggcggct cgctggcgg ctacttcgat ttttggggcc agggcaccct cgtgaccgtc     360
agctca                                                                366

<210> SEQ ID NO 81
<211> LENGTH: 235
<212> TYPE: PRT
<213> ORGANISM: Artificial Sequence
<220> FEATURE:
<223> OTHER INFORMATION: amino acid sequesnce of NOV0712 light chain
      full-length

<400> SEQUENCE: 81

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Ser
        35                  40                  45

Ile Ser Ser Tyr Leu Asn Trp Tyr Gln Gln Lys Pro Gly Lys Ala Pro
    50                  55                  60

Lys Leu Leu Ile Tyr Ala Val Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ser Gly
            100                 105                 110

Thr Phe Pro Pro Thr Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210             215                 220

Pro Val Thr Lys Ser Phe Asn Arg Gly Glu Cys
225             230                 235

<210> SEQ ID NO 82
<211> LENGTH: 705
<212> TYPE: DNA
<213> ORGANISM: Artificial Sequence
<220> FEATURE:
<223> OTHER INFORMATION: nucleotide sequesnce coding for amino acid
      sequence of sequence number 81

<400> SEQUENCE: 82
atggtgctgc agacccaggt gttcatctcc ctgctgctgt ggatctccgg cgcgtacggc     60
gacatccaga tgacccagag ccctagcagc ctgagcgcca gcgtgggcga cagagtgacc    120
atcacctgta gagccagcca gagcatcagc agctacctga actggtatca gcagaagccc    180
ggcaaggccc ccaaactgct gatctacgcc gtgtccacac tgcagagcgg cgtgcccagc    240 agatttctg gcagcggctc cggcaccgac ttcaccctga caatcagcag cctgcagccc    300
gaggacttcg ccacctacta ctgtcagcag tccggcaccc tcccccccac cacatttggc    360
cagggcacca aggtggaaat caagcgtacg gtggccgccc cctccgtgtt catcttcccc    420
ccctccgacg agcagctgaa gtccggcacc gcctccgtgg tgtgcctgct gaataacttc    480
taccccagag aggccaaggt gcagtggaag gtggacaacg ccctgcagtc cgggaactcc    540
caggagagcg tgaccgagca ggacagcaag gacagcacct acagcctgag cagcaccctg    600
accctgagca agccgactac gagaagcac aaggtgtacg cctgcgaggt gacccaccag    660
ggcctgagct cccccgtcac caagagcttc aacaggggg agtgt                    705

<210> SEQ ID NO 83
<211> LENGTH: 467
<212> TYPE: PRT
<213> ORGANISM: Artificial Sequence
<220> FEATURE:
<223> OTHER INFORMATION: amino acid sequesnce of NOV0712 heavy chain
      full-length

<400> SEQUENCE: 83

Met Lys His Leu Trp Phe Phe Leu Leu Leu Val Ala Ala Pro Arg Trp
1               5                   10                  15

Val Leu Ser Gln Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser His Gly Met His Trp Val Arg Gln Ala Pro Gly Lys Gly Leu
    50                  55                  60

Glu Trp Val Ser Val Ile Ser Gly Ser Gly Ser Asn Thr Gly Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gln Trp Gly Ser Tyr Ala Phe Asp Ser Trp Gly
        115                 120                 125

Gln Gly Thr Leu Val Thr Val Ser Ser Ala Ser Thr Lys Gly Pro Ser
    130                 135                 140

-continued

```
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
        180                 185                 190

Val Leu Gln Ser Ser Gly Leu Tyr Ser Leu Ser Ser Val Val Thr Val
    195                 200                 205

Pro Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 84
<211> LENGTH: 1401
<212> TYPE: DNA
<213> ORGANISM: Artificial Sequence
<220> FEATURE:
<223> OTHER INFORMATION: nucleotide sequesnce coding for amino acid
      sequence of sequence number 83

<400> SEQUENCE: 84
atgaaacacc tgtggttctt cctcctgctg gtggcagctc ccagatgggt gctgagccag      60
gtgcagctgc tggaatctgg cggaggactg gtgcagcctg gcggctctct gagactgtct     120
tgtgccgcca gcggcttcac cttcagcagc cacggaatgc actgggtgcg ccaggcccct     180
```

```
ggaaagggac tggaatgggt gtccgtgatc agcggcagcg gctccaatac cggctacgcc    240
gatagcgtga agggccggtt caccatcagc cgggacaaca gcaagaacac cctgtacctg    300
cagatgaaca gcctgcgggc cgaggacacc gccgtgtact attgtgccag acagtggggc    360
agctacgcct tcgattcttg gggccagggc accctcgtga ccgtcagctc agcctccacc    420
aagggcccaa gcgtcttccc cctggcaccc tcctccaaga gcacctctgg cggcacagcc    480
gccctgggct gcctggtcaa ggactacttc cccgaaccg tgaccgtgag ctggaactca     540
ggcgccctga ccagcggcgt gcacaccttc cccgctgtcc tgcagtcctc aggactctac    600
tccctcagca gcgtggtgac cgtgccctcc agcagcttgg gcacccagac ctacatctgc    660
aacgtgaatc acaagcccag caacaccaag gtggacaaga gagttgagcc caaatcttgt    720
gacaaaactc acacatgccc accctgccca gcacctgaac tcctgggggg accctcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccccgggagg agcagtacaa cagcacgtac    960
cgggtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
ggccagcccc gggaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atggccagcc cgagaacaac tacaagacca cccctcccgt gctggactcc   1260
gacggctcct tcttcctcta cagcaagctc accgtggaca gagcaggtg gcagcagggc    1320 aacgtcttct catgctccgt gatgcatgag gctctgcaca accactacac ccagaagagc   1380
ctctccctgt ctcccggcaa a                                              1401

<210> SEQ ID NO 85
<211> LENGTH: 34
<212> TYPE: DNA
<213> ORGANISM: Artificial Sequence
<220> FEATURE:
<223> OTHER INFORMATION: primer

<400> SEQUENCE: 85
caccatgaga acttaccgct acttcttgct gctc                                 34

<210> SEQ ID NO 86
<211> LENGTH: 30
<212> TYPE: DNA
<213> ORGANISM: Artificial Sequence
<220> FEATURE:
<223> OTHER INFORMATION: primer

<400> SEQUENCE: 86
ttaggagtct tgtcactgt ccactcctcc                                       30
```